| United States Patent [19] | [11] Patent Number: 4,802,908 |
| Hillemann | [45] Date of Patent: Feb. 7, 1989 |

[54] HERBICIDAL 2-(1H)-PYRAZINONES

[75] Inventor: Criag L. Hillemann, Wilmington, Del.

[73] Assignee: E. I. Du Pont de Nemours and Company, Wilmington, Del.

[21] Appl. No.: 6,822

[22] Filed: Jan. 22, 1987

[51] Int. Cl.⁴ .................... A01N 9/16; C07D 401/12; C07D 403/12
[52] U.S. Cl. ............................ 71/70; 71/91; 71/92; 71/93; 544/295; 544/405; 544/408
[58] Field of Search .................... 544/295, 405, 408; 71/90, 91, 92

[56] References Cited

U.S. PATENT DOCUMENTS

| 4,127,405 | 11/1978 | Levitt | 71/92 |
| 4,169,719 | 10/1979 | Levitt | 71/92 |
| 4,394,506 | 7/1983 | Levitt | 71/92 |
| 4,420,325 | 12/1983 | Sauers | 71/92 |
| 4,460,401 | 7/1984 | Sauers | 71/92 |
| 4,465,505 | 8/1984 | Wolf | 71/92 |
| 4,481,029 | 11/1984 | Levitt | 71/92 |
| 4,494,980 | 1/1985 | Shapiro | 71/92 |
| 4,511,392 | 4/1985 | Rorer | 71/90 |
| 4,514,211 | 4/1985 | Rorer | 71/92 |
| 4,586,950 | 5/1986 | Pasteris | 71/92 |
| 4,589,911 | 5/1986 | Ehrenfreund et al. | 71/92 |

FOREIGN PATENT DOCUMENTS

| 225881 | 1/1985 | Czechoslovakia . |
| 13480 | 3/1983 | European Pat. Off. . |
| 95925 | 12/1983 | European Pat. Off. . |
| 877223 | 9/1987 | South Africa . |

OTHER PUBLICATIONS

Varkonda et al., Chem. Abstracts, vol. 104, (1986), entry 125062u.

*Primary Examiner*—Donald G. Daus
*Assistant Examiner*—Cecilia Shen

[57] ABSTRACT

This invention relates to a novel class of 2-(1H)-pyrazinones and their use as herbicides and plant growth regulants.

35 Claims, No Drawings

HERBICIDAL 2-(1H)-PYRAZINONES

BACKGROUND OF THE INVENTION

Czechoslovakian Pat. No. 225,881 discloses herbicidal sulfonylureas of the formula

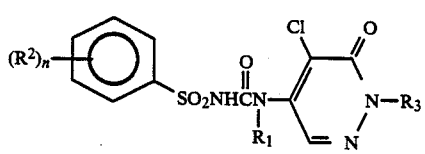

wherein $R_2$ is $CH_3$, $CF_3$ or $NO_2$.

U.S. Pat. No. 4,169,719 and U.S. Pat. No. 4,127,405 disclose, in part, herbicidal benzenesulfonylureas of the formulae

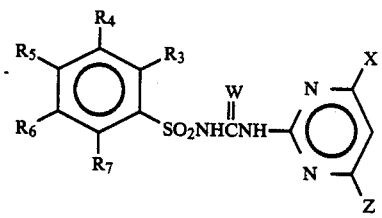

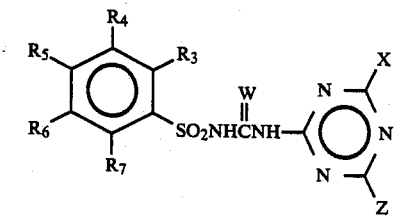

wherein
$R_3$ is H, F, Cl, Br, I, $C_1$-$C_4$ alkyl, $C_1$-$C_4$ alkoxy, $NO_2$, $CF_3$, CN, $S(O)_nCH_3$ or $S(O)_nCH_2CH_3$; and
$R_4$ is H, F, Cl, Br, $C_1$-$C_2$ alkyl or $C_1$-$C_2$ alkoxy.

U.S. Pat. No. 4,394,506 discloses, in part, herbicidal benzenesulfonylureas of the formula

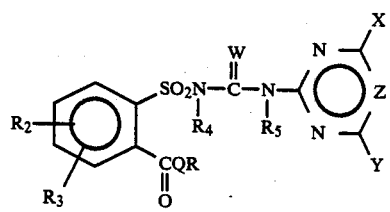

wherein Q is O, S or $NR_6$.

U.S. Pat. No. 4,420,325 discloses, in part, herbicidal benzylsulfonylureas of the formula

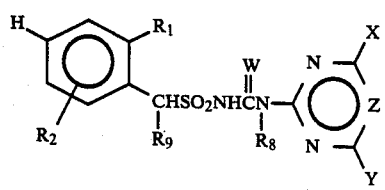

wherein $R_1$ is F, Cl, Br, $CF_3$, $C_1$-$C_3$ alkoxy, $C_1$-$C_3$ alkyl, $NO_2$, $CO_2R_4$, $SO_2R_5$, $SO_2NR_6R_7$, $SO_2N(OCH_3)CH_3$, $SO_2CH_2CF_3$ or $OSO_2R_5$.

U.S. Pat. No. 4,481,029 discloses, in part, herbicidal thiophenesulfonylureas of the formula

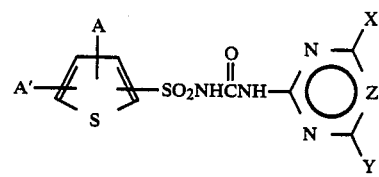

wherein
A' is H, Cl, Br, $C_1$-$C_4$ alkyl, $OCH_3$, $NO_2$ or $CF_3$;
A is $C(O)QR^I$ or $C(T)R^{II}$;
Q is O, S or $NR_6$; and
T is O or $=NOR^{III}$.

EP-A-13,480 discloses, in part, herbicidal pyridine sulfonylureas of the formula

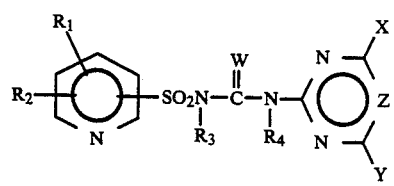

wherein $R_1$ is H, Cl, Br, F, $C_1$-$C_4$ alkyl, $C_1$-$C_4$ alkoxy, $C_1$-$C_4$ alkylthio, $NO_2$ or $CO_2R_5$.

EP-A-95,925 discloses, in part, herbicidal pyrazole sulfonylureas of the formula

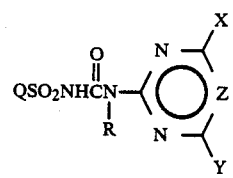

wherein

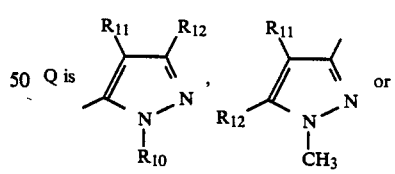

Q is

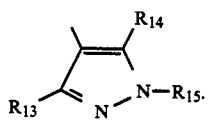

U.S. Pat. No. 4,511,392 and U.S. Pat. No. 4,465,505 disclose herbicidal benzenesulfonylureas where the ortho substituent is a 5-membered heterocycle.

U.S. Pat. No. 4,460,401 and U.S. Pat. No. 4,494,980 disclose herbicidal benzenesulfonylureas where the ortho substituent is a 5- or 6-membered heterocycle.

U.S. Pat. No. 4,514,211 discloses, in part, herbicidal sulfonylureas of the formula

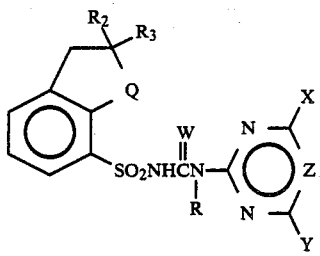

wherein Q is O, S, SO or $SO_2$.

U.S. Pat. No. 4,586,950 discloses, in part, herbicidal sulfonyluras of the formula

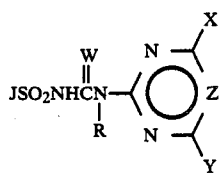

wherein J is

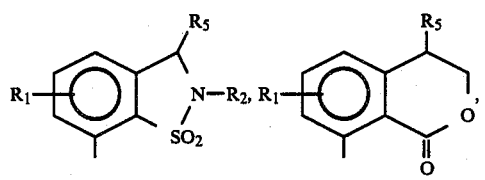

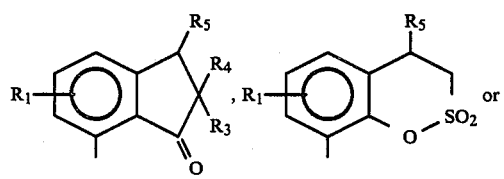

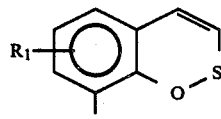

U.S. Pat. No. 4,589,911 discloses herbicidal sulfonylureas of the formula

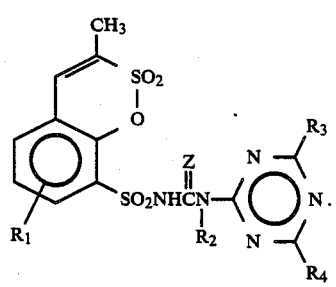

SUMMARY OF THE INVENTION

This application pertains to novel compounds of Formula I, agriculturally suitable compositions containing them and their method-of-use as preemergent and/or postemergent herbicides or plant growth regulants.

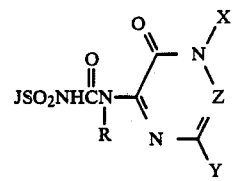

wherein

R is H or $CH_3$;

X is H, $C_1$-$C_3$ alkyl, $C_1$-$C_3$ alkoxy, $NH_2$, $NHCH_3$ or $N(CH_3)_2$;

Y is H, $C_1$-$C_3$ alkyl, $C_1$-$C_3$ alkoxy, $C_1$-$C_2$ alkylthio, Cl or Br;

Z is CH, N, CF, CCl or CBr;

J is

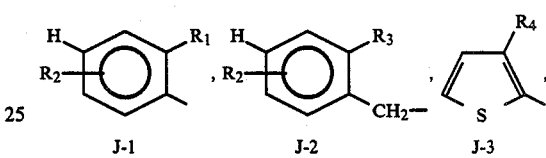

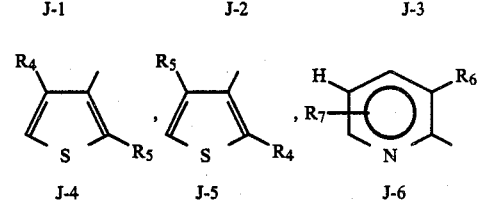

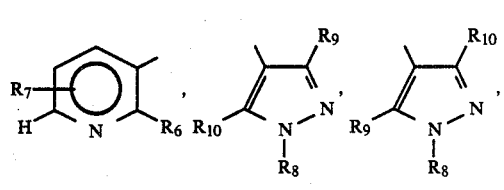

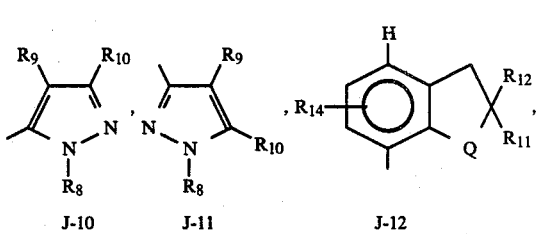

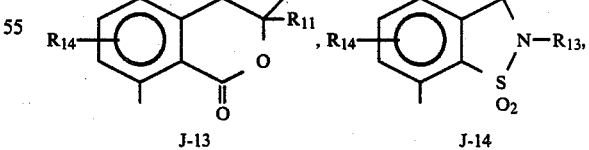

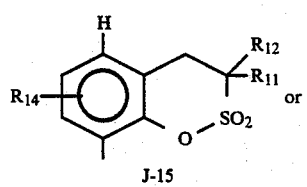

-continued

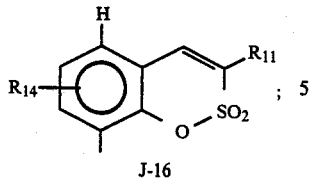
J-16

$R_1$ is F, Cl, Br, $NO_2$, $C_1$–$C_4$ alkyl, $C_1$–$C_4$ haloalkyl, $C_3$–$C_4$ cycloalkyl, $C_2$–$C_4$ haloalkenyl, $C_1$–$C_4$ alkoxy, $C_1$–$C_4$ haloalkoxy, $C_2$–$C_4$ alkoxyalkoxy, $CO_2R_a$, $C(O)NR_bR_c$, $SO_2NR_dR_e$, $S(O)_nR_f$, $C(O)R_g$, $CH_2CN$ or L;

$R_2$ is H, F, Cl, Br, CN, $CH_3$, $OCH_3$, $SCH_3$ or $OCF_2H$;

$R_3$ is Cl, $NO_2$, $CO_2CH_3$, $CO_2CH_2CH_3$, $SO_2N(CH_3)_2$, $SO_2CH_3$, $SO_2CH_2CH_3$, $OCH_3$, or $OCH_2CH_3$;

$R_a$ is $C_1$–$C_3$ alkyl optionally substituted by halogen, $C_1$–$C_2$ alkoxy or CN, allyl or propargyl;

$R_b$ is H, $C_1$–$C_3$ alkyl or $C_1$–$C_2$ alkoxy;

$R_c$ is $C_1$–$C_2$ alkyl;

$R_d$ is H, $C_1$–$C_3$ alkyl, $C_1$–$C_2$ alkoxy, allyl or cyclopropyl;

$R_e$ is H or $C_1$–$C_3$ alkyl;

$R_f$ is $C_1$–$C_3$ alkyl, $C_1$–$C_3$ haloalkyl, allyl or propargyl;

$R_g$ is $C_1$–$C_4$ alkyl, $C_1$–$C_4$ haloalkyl or $C_3$–$C_5$ cycloalkyl optionally substituted by halogen;

n is 0, 1 or 2;

L is

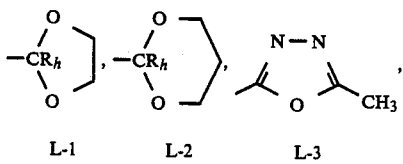
L-1  L-2  L-3

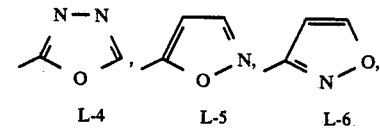
L-4  L-5  L-6

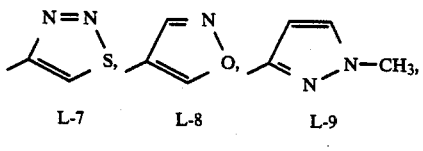
L-7  L-8  L-9

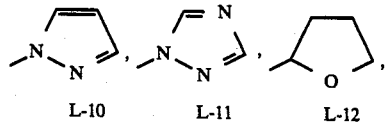
L-10  L-11  L-12

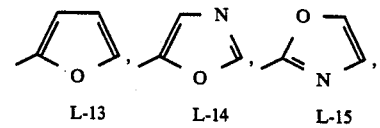
L-13  L-14  L-15

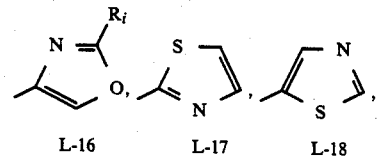
L-16  L-17  L-18

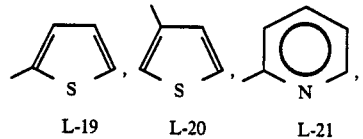
L-19  L-20  L-21

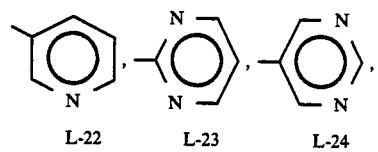
L-22  L-23  L-24

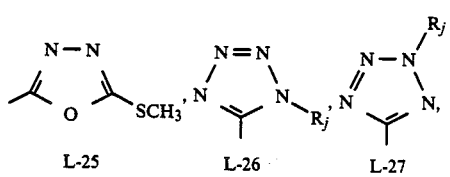
L-25  L-26  L-27

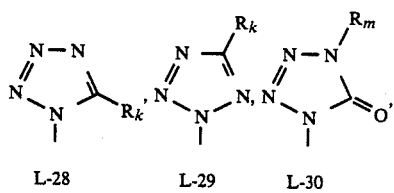
L-28  L-29  L-30

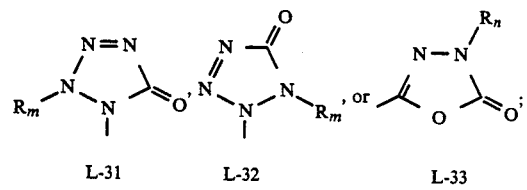
L-31  L-32  L-33

$R_h$ is H or $CH_3$;

$R_i$ is H or $CH_3$;

$R_j$ is H, $CH_3$ or $CH_2CH_3$;

$R_k$ is H, $CH_3$, $CH_2CH_3$, $OCH_3$, $OCH_2CH_3$, $SCH_3$ or $SCH_2CH_3$;

$R_m$ is H, $CH_3$ or $CH_2CH_3$;

$R_n$ is H or $CH_3$;

$R_4$ is $C_1$–$C_3$ alkyl, $C_1$–$C_2$ haloalkyl, $C_1$–$C_2$ alkoxy, $C_2$–$C_4$ haloalkenyl, F, Cl, Br, $NO_2$, $CO_2R_a$, $C(O)NR_bR_c$, $SO_2NR_dR_e$, $S(O)_nR_f$, $C(O)R_g$ or L;

$R_5$ is H, F, Cl, Br or $CH_3$;

$R_6$ is $C_1$–$C_3$ alkyl, $C_1$–$C_2$ alkoxy, $C_2$–$C_4$ haloalkenyl, F, Cl, Br, $CO_2R_a$, $C(O)NR_bR_c$, $SO_2NR_dR_e$, $S(O)_nR_f$, $C(O)R_g$ or L;

$R_7$ is H, F, Cl or $CH_3$;

$R_8$ is H or $C_1$–$C_3$ alkyl;

$R_9$ is $C_1$–$C_3$ alkyl, $C_1$–$C_2$ alkoxy, F, Cl, Br, $NO_2$, $CO_2R_a$, $SO_2NR_dR_e$, $S(O)_nR_f$, $OCF_2H$, $C(O)R_g$, $C_2$–$C_4$ haloalkenyl or L;

$R_{10}$ is H, Cl, F, Br, $C_1$–$C_3$ alkyl or $C_1$–$C_2$ alkoxy;

$R_{11}$ is H or $C_1$–$C_2$ alkyl;

$R_{12}$ is H or $C_1$–$C_2$ alkyl;

$R_{13}$ is H, $C_1$–$C_6$ alkyl, $C_1$–$C_4$ haloalkyl, $C_2$–$C_4$ alkoxyalkyl, $C_3$–$C_5$ cycloalkyl or $C_4$–$C_6$ cycloalkylalkyl;

$R_{14}$ is H, F, Cl, Br, CN, $CH_3$, $OCH_3$, $SCH_3$ or $OCF_2H$; and

Q is O, S, SO, $SO_2$ or C(O);

and their agriculturally suitable salts; provided that X and Y are not simultaneously H.

In the above definitions, the term "alkyl", used either alone or in compound words such as "haloalkyl", denotes straight chain or branched alkyl, e.g. methyl, ethyl, n-propyl, isopropyl or the different butyl, pentyl or hexyl isomers.

Alkoxy denotes methoxy, ethoxy, n-propyloxy, isopropyloxy and the different butyl isomers.

Alkenyl denotes straight chain or branched alkenes, e.g. vinyl, 1-propenyl, 2-propenyl, 3-propenyl and the different butenyl isomers.

Cycloalkyl denotes cyclopropyl or cyclobutyl.

The term "haloalkyl" denotes an alkyl group substituted by fluorine, chlorine, bromine or iodine.

In terms such as $C_2$-$C_4$ alkoxyalkoxy, the specified number of carbon atoms is meant to define the total number of carbon atoms in that substituent group. For example, $C_2$-$C_4$ alkoxyalkoxy would represent $OCH_2OCH_3$ through $O(CH_2)_3OCH_3$ or $OCH_2OCH_2CH_3$ and the various structural isomers embraced therein.

Preferred for reasons of their higher herbicidal activity, greater plant growth regulant activity or more favorable ease of synthesis are:
1. Compounds of Formula I wherein Z is CH.
2. Compounds of Preferred 1 where
    X is $CH_3$, $CH_2CH_3$, $OCH_3$ or $OCH_2CH_3$; and
    Y is $CH_3$, $CH_2CH_3$, $OCH_3$, $OCH_2CH_3$, $SCH_3$, $SCH_2CH_3$, Cl or Br.
3. Compounds of Preferred 2 where
    $R_1$ is Cl, $NO_2$, $CH_3$, $CH_2CH_3$, $C_1$-$C_2$ haloalkyl, cyclopropyl, $C_2$-$C_3$ haloalkenyl, $OCH_3$, $OCH_2CH_3$, $C_1$-$C_2$ haloalkoxy, $CO_2R_a$, $C(O)NR_bR_c$, $SO_2NR_dR_e$, $S(O)_nR_f$, $C(O)R_g$, $CH_2CN$ or L;
    $R_b$ is H, $CH_3$ or $OCH_3$;
    $R_c$ is $CH_3$;
    $R_d$ is H, $CH_3$ or $OCH_3$;
    $R_e$ is $CH_3$;
    $R_f$ is $CH_3$ or $CH_2CH_3$;
    $R_g$ is $CH_3$, $CH_2CH_3$ or cyclopropyl;
    n is 0 or 2;
    $R_4$ is $CH_3$, $CH_2CH_3$, Cl, Br, $NO_2$, $CO_2R_a$, $C(O)NR_bR_c$, $SO_2NR_dR_e$, $S(O)_nR_f$ or $C(O)R_g$;
    $R_5$ is H;
    $R_6$ is $CH_3$, $CH_2CH_3$, $OCH_3$, Cl, Br, $CO_2R_a$, $C(O)NR_bR_c$, $SO_2NR_dR_e$, $S(O)_nR_f$ or $C(O)R_g$;
    $R_7$ is H;
    $R_8$ is $CH_3$;
    $R_9$ is $CH_3$, $CH_2CH_3$, $OCH_3$, $OCH_2CH_3$, Cl, Br, $NO_2$, $CO_2R_a$, $SO_2NR_dR_e$ or $S(O)_nR_f$;
    $R_{10}$ is H, Cl, $CH_3$ or $OCH_3$; $R_{11}$ is H or $CH_3$; $R_{12}$ is H; and $R_{13}$ is H or $C_1$-$C_4$ alkyl.
4. Compounds of Preferred 3 where J is J-1.
5. Compounds of Preferred 3 where J is J-2.
6. Compounds of Preferred 3 where J is J-3.
7. Compounds of Preferred 3 where J is J-4.
8. Compounds of Preferred 3 where J is J-5.
9. Compounds of Preferred 3 where J is J-6.
10. Compounds of Preferred 3 where J is J-7.
11. Compounds of Preferred 3 where J is J-8.
12. Compounds of Preferred 3 where J is J-9.
13. Compounds of Preferred 3 where J is J-10.
14. Compounds of Preferred 3 where J is J-11.
15. Compounds of Preferred 3 where J is J-12.
16. Compounds of Preferred 3 where J is J-13.
17. Compounds of Preferred 3 where J is J-14.
18. Compounds of Preferred 3 where J is J-15.
19. Compounds of Preferred 3 where J is J-16.

Specifically preferred for reasons of greatest ease of synthesis and/or greatest herbicidal efficacy are:

2-[[(6-chloro-3,4-dihydro-4-methyl-3-oxo-2-pyrazinylamino)carbonylamino]sulfonyl]benzoic acid, methyl ester, m.p. 173°-176° C.; and 2-chloro-N-[(6-chloro-3,4-dihydro-4-methyl-3-oxo-2-pyrazinyl)aminocarbonyl]benzenesulfonamide, m.p. 208-210.

DETAILED DESCRIPTION OF THE INVENTION

Synthesis

The compounds of Formula I can be prepared by one or more of the following methods described below in Equations 1 to 5.

As shown in Equation 1 below, most compounds of Formula I can be prepared by reacting an appropriately substituted sulfonyl isocyanate of Formula (1) with an appropriate amino or alkylamino pyrazinone or triazinone of Formula (2).

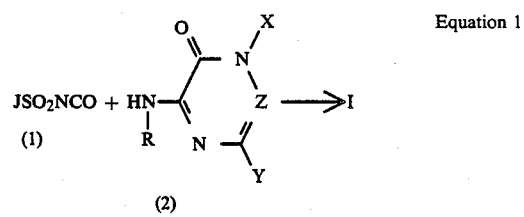

Equation 1 where J, R, X, Y and Z are as previously defined.

The reaction is best carried out in inert aprotic organic solvents such as dichloromethane, 1,2-dichloroethane, tetrahydrofuran, or acetonitrile, at a temperature between 20° and 85° C. The order of addition is not critical; however, it is often convenient to add the sulfonyl isocyanate or a solution of it in the reaction solvent to a stirred suspension of the amine.

Sulfonyl isocyanates (1) are generally prepared from the corresponding sulfonamides (3) (see Equations 17 and 18). In rare cases a sulfonamide may not be sufficiently stable to be useful as an intermediate. In these cases, as well as others, the requisite sulfonyl isocyanate (1) can be made and reacted with the heterocyclic amine (2) by treating the corresponding sulfonyl chloride with an isocyanate anion in the presence of the amine (see Equation 5 and accompanying discussion).

In some cases, the desired product is insoluble in the reaction solvent at ambient temperature and crystallizes from it in pure form. Products soluble in the reaction solvent are isolated by evaporation of the solvent. Compounds of Formula I then may be purified by trituration of the evaporation residue with solvents such as 1-chlorobutane or ethyl ether and filtration, by recrystallization from mixtures of solvents such as 1,2-dichloroethane, 1-chlorobutane, and heptane or by chromatography on silica gel.

Some of the compounds of Formula I can be prepared as shown in Equation 2. Reaction of a sulfonamide of Formula (3) with an appropriate methyl pyrazinonyl carbamate or methyl triazinonyl carbamate of Formula (4) in the presence of at least an equimolar amount of trimethylaluminum leads to compounds of Formula I.

Equation 2

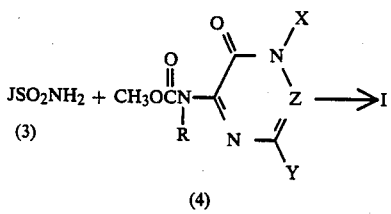

where J, R, X, Y and Z are as previously defined; however, for this method $R_2$, $R_3$, $R_4$, $R_6$ and $R_9$ cannot be $CO_2R_a$, $C(O)NR_bR_c$, $C(O)R_g$, L-1, or L-2, and J cannot be J-13.

The reaction of Equation 2 is best run in either dichloromethane or 1,2-dichloroethane solution at 20° to 85° C. for 10 to 96 hours under a nitrogen or argon atmosphere. The product can be isolated by addition of an aqueous acetic acid solution followed by extraction of the product into dichloromethane, or by filtration of a product of low solubility. The product can be purified by trituration with solvents such as 1-chlorobutane or ethyl ether, by recrystallization from mixtures of solvents such as 1,2-dichloroethane, 1-chlorobutane, and heptane, or by column chromatography on silica gel.

Many of the compounds of Formula I can be prepared by the procedures shown in Equation 3.

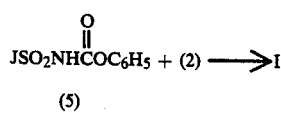

where J, R, X, Y and Z are as defined for Equation 2.

The reactions shown in Equation 3 are carried out by contacting phenylcarbamates of Formula (5) with the aminoheterocycles of Formula (2) in an inert organic solvent such as dioxane or tetrahydrofuran at temperatures of about 20°-100° C. for a period of about one-half to twenty-four hours. The product can be isolated by evaporation of the reaction solvent and purified by methods previously described.

Phenyl carbamates of Formula (5) can be prepared by the methods described, or modifications thereof known to those skilled in the art, in European Patent Application No. 44,808 published Jan. 27, 1982; or South African Patent Application No. 825042.

Alternatively, many of the compounds of Formula I can be prepared by the method described in Equation 4.

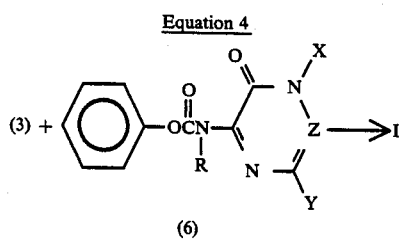

where J, R, X, Y and Z are as described for Equation 1, except that when $R_2$, $R_4$, $R_6$ or $R_9$ is $CO_2R_a$, $C(O)NR_bR_c$ or $C(O)R_g$, R must be H.

The reaction in Equation 4 can be carried out by contacting equimolar amounts of a sulfonamide of Formula (3) with a heterocyclic phenyl carbamate of Formula (6) in the presence of an equimolar amount of 1,8-diazabicyclo[5.4.0]undec-7-ene (DBU), by methods analogous to those described in South African Patent Application No. 830441. The phenyl carbamates of Formula (6) can be prepared (from the corresponding amines of Formula (2)) by methods, or modifications thereof known to those skilled in the art, described in South African Patent Application No. 825671 and South African Patent Application No. 825045.

Rarely sulfonamides of Formula (3) may not be of sufficient stability to be useful as starting materials in Equations 2 and 4, or as intermediates to the sulfonyl isocyanates (1) used in Equation 1 or sulfonyl carbamates (5) used in Equation 3. In these cases, as well as others, the sulfonyl isocyanates (1) can be made as unisolated intermediates by treating the corresponding sulfonyl chlorides of Formula (7) with isocyanate anion in the presence of the heterocyclic amine of Formula (2). The amines react with the sulfonyl isocyanates as they are formed to give the desired corresponding compounds of Formula I (Equation 5).

Equation 5

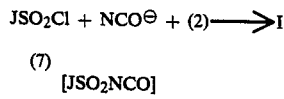

where J, R, X, Y and Z are as previously defined.

The reaction is best carried out by adding over one to six hours a solution of at least one equivalent of a tetraalkylammonium isocyanate, such as tetra-n-butylammonium isocyanate, in a suitable aprotic organic solvent, such as dichloromethane or tetrahydrofuran, to a well-stirred mixture of one equivalent of sulfonyl chloride (7) and at least one equivalent of heterocyclic amine (2) in a similar suitable organic solvent at 20°-40° C. The reaction mixture is then diluted with dichloromethane, washed with 1N sulfuric acid, and dried over sodium sulfate. Rotary evaporation of the solvent leaves the product of Formula I in crude form. This may be purified as has already been described for Equation 1.

Amino and alkylamino pyrazinones and triazinones of Formula (2) are made by one or more of the following methods.

Equation 6

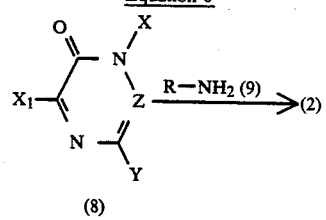

where
R, X, Y and Z are as initially defined; and
$X_1$ is Cl or Br.

A solution of halide (8) is reacted with at least two equivalents (only two equivalents when Z is N and Y is Cl or Br) of the amine (9) at a temperature of 20° to 100° C. for 2 to 36 hours. Solvents like aqueous dioxane which dissolves both halide (8) and amine (9) are especially useful.

The halides of Formula (8) where $Y=X_1$, may in turn be prepared by the method shown in Equation 7.

Equation 7

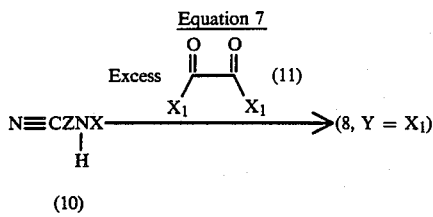

where $X_1$ and $Z$ are as previously defined. When $Z$ is CH, X is H, alkyl, alkoxy, $NH_2$, $NHCH_3$ or $N(CH_3)_2$, and when Z is N, X is H or alkyl.

In this method the cyanide (10) is treated with excess (typically 3-5 equivalents) of the oxalyl halide (11) using the general conditions described by J. Vekemans, C. Pallers-Wieers, and G. Hoornaert (*J. Heterocyclic Chem.*, 20, 919 (1983)).

Many of the halides of Formula (8) where Y is H, alkyl, or alkoxy can be prepared by the method described in Equation 8.

Equation 8

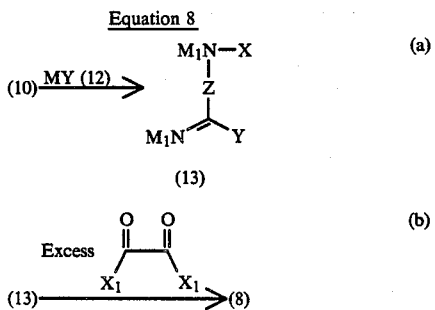

where
M is Li, Mg, Na or K;
$X_1$, X and Z are as defined for Equation 7; and
Y is H, alkyl, or alkoxy.
When Y is H, then MY (12) is $LiAlH(OC_2H_5)_3$. $M_1$ is M and Y is H or alkyl, and $M_1$ is H when Y is alkoxy.

In this method (Equation 8) the cyanide of Formula (10) is converted to the corresponding imine of Formula (13) by treatment with the nucleophilic reagent MY (12). When Y is alkoxy the transformation can be carried out by treating (10) with the appropriate alcohol (HY) in the presence of a catalytic amount of the alkoxide MY (12) or an acid using a variety of methods known in the art. See, for example, F. C. Schaefer and G. A. Peters, *J. Org. Chem.*, 26, 412 (1961) and H. Watanabe, Y. Kikugawa, and S. Yamada, *Chem. Pharm. Bull.*, 21, 465 (1973). The mixture is then neutralized and the solvent evaporated to leave the imine (13). When Y is alkyl the transformation can be carried out by treating the cyanide (10) with two equivalents of the appropriate Grignard or lithium reagent MY (12) in a hydrocarbon or ethereal solvent using a variety of methods well known in the art. For a review see C. A. Buehler and D. E. Pearson, *Survey or Organic Syntheses*, Wiley-Interscience, New York, 1970, pp. 717-718. When Y is H, the transformation can be effected by treating (10) with two equivalents of lithium triethoxyaluminohydride in ether. Alternatively, diisobutylaluminum hydride may often be substituted for the lithium triethoxyaluminohydride. These methods are reviewed in C. A. Buehler and D. E. Pearson *Survey of Organic Syntheses Volume* 2, Wiley-Interscience, New York, 1977, p. 500. Finally, the imines of Formula (13) are converted to the corresponding heterocycles of Formula (8) using methodology analogous to that referenced for the conversion (10) to (8, $Y=X_1$) in Equation 7 (Equation 8b).

The oxalyl halides of Formula (11) are commercially available, and the requisite cyanides of Formula (10) are either known in the art or may be made by a variety of methods known in the art. See for example, J. H. Boyer and J. Kooi, *J. Am. Chem. Soc.*, 98, 1099 (1976); M. S. Bloom, D. S. Breslow, and C. R. Hauser, *J. Am. Chem. Soc.*, 67, 539 (1945); H. Sakai, K. Ito and M. Sekiya, *Chem. Pharm. Bull.*, 21, 2257 (1973); M. Masui, M. Suzuki and C. Yijima, *J. Chem. Soc.*, 3958 (1964); K. Masuda, Y. Imashiro and T. Kaneko, *Chem. Pharm. Bull.*, 18, 128 (1970); and the references cited therein.

The halides (8, $X_1=Cl$) may be prepared in many cases from corresponding amines of Formula (2, R=H) as shown in Equation 9.

Equation 9

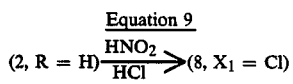

where X, Y and Z are as initially defined, except that X cannot be $NH_2$ or $NHCH_3$.

In this method a solution of the amine (2, R=H) in concentrated hydrochloric acid is treated with sodium nitrite solution to give the chloro compound (8, $X_1=Cl$) according to the general procedure of Bee and Rose (*J. Chem. Soc. C.*, 2031 (1966)). This route is especially useful when amines of Formula (2, R=H) are more readily prepared than the corresponding methylamines of Formula (2, $R=CH_3$).

The halides (8) where Z is CF, CCl or CBr are prepared from the corresponding halides (8) where Z is CH as shown in Equation 10.

Equation 10

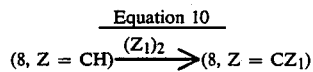

where
X, $X_1$ and Y are as defined for Equation 6; and
$Z_1$ is F, Cl or Br.

In this method a solution of (8, Z=CH) in a solvent inert to the reacting halogen is treated with one equivalent of the halogen (diluted with nitrogen when $Z_1$ is F) at a temperature of $-78°$ to 100° C. The mixture is then either heated to 100° C. to drive off the HZ by-product, or it is treated with a strong nonnucleophilic base like N,N-diisopropylethylamine to remove the $HZ_1$ by-product.

Many of the amino and alkylamino pyrazinones and triazinones of Formula (2) where X is alkyl or $NH_2$ can be prepared from the corresponding pyrazinones and triazinones of Formula (2) where X is H as shown in Equation 11.

Equation 11

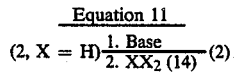

where R, Y and Z are as initially defined. X in the product (2) is alkyl or $NH_2$, and $X_2$ is Cl, Br, I,

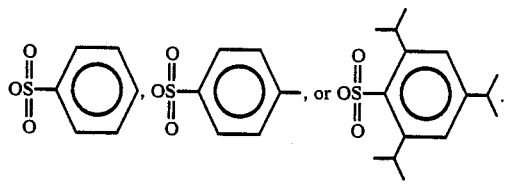

In this method a solution or suspension of (2, X=H) is converted by treatment with one equivalent of a strong base to the corresponding salt. Representative base-solvent combinations include methyllithium in tetrahydrofuran and sodium hydride in both this solvent and in N,N-dimethylformamide. The reaction is conducted between 20° and 60° C. The solution or suspension of the derived salt is then treated at 0°–60° C. with one equivalent of the alkylating or aminating agent $XX_2$ (14). When X is alkyl, $X_2$ is preferred to be I so as to maximize N-alkylation. When X is $NH_2$, $X_2$ is preferred to be 2,4,6-trimethylbenzenesulfonate or 2,4,6-triisopropylbenzenesulfonate. The requisite alkylating and aminating reagents are known in the art, and many of them are commercially available. After evaporation of the solvent the crude products of Formula (2) can be purified by recrystallization or chromatography on silica gel. Compounds of Formula (2) where X is $NH_2$ may be methylated to give corresponding compounds (2) where X is $NHCH_3$ or $N(CH_3)_2$ by a variety of general methods known in the art.

Many of the aminopyrazinones of Formula (2) where R is H, X is H, Y is H or alkyl, and Z is CH can be prepared via the route described by G. Palamidassi for the case where Y is $CH_3$ (see *Farmaco Ed. Sci.*, 18, 557 (1963) and British Pat. No. 922,725 (*Chem. Abstracts*, 59, 10076h (1963)).

Some of the amino and methylaminotriazinones of Formula (2) where X is H, Y is H, alkyl or alkoxy and Z is N may be prepared from the known 3,5,6-trichloro-1,2,4-triazine (15) as shown in Equation 12.

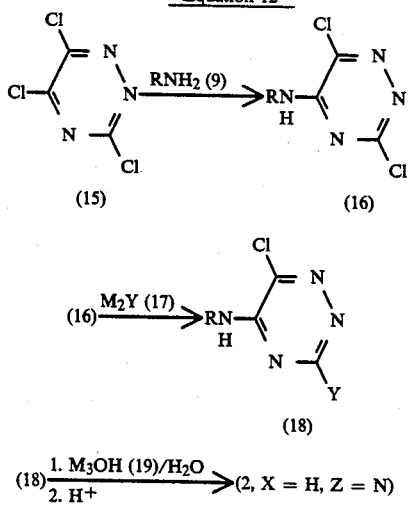

Equation 12 where
R is H or $CH_3$;
$M_2$ is Li, Mg, Na, K, Zn, Cd, Cu, or represents a combination of these elements;

Y is alkoxy, alkyl, alkylthio or H (Y in (17) is a hydridoaluminate species when Y is H in (18); and
$M_3$ is Li, Na or K.
$M_2$ is $M_3$ when Y is alkoxy or alkylthio.

In this method the trichloro compound (15) is aminated to give (16) using the procedure described by H. Neunhoeffer and B. Lehmann for the reaction of (15) with dimethylamine (see *Chem. Ber.*, 109, 1113 (1976)) (Equation 12a).

Reaction conditions used in the next step (Equation 12b) depend upon the nature of Y. When Y is alkoxy, a solution of (16) in the appropriate alcohol HY and/or an inert solvent like benzene or tetrahydrofuran is treated with one equivalent of the alkoxide $M_2Y$ (17) at 0°–40° C. Evaporation of the solvent leaves a crude product that can be purified by recrystallization or chromatography on silica gel.

When Y is alkylthio, a solution of (16) in an inert solvent like tetrahydrofuran or glyme is treated with one equivalent of the thiolate (17) at −50° to 30° C. Evaporation of the solvent leaves a crude product that can be purified by recrystallization or chromatography on silica gel.

When Y is alkyl, the reaction is conducted by reacting a solution or suspension of (16) in an ethereal solvent with one of a variety of alkyl-lithium, alkyl magnesium, alkyl zinc, alkyl cadmium, or cuprate reagents known in the art either in the presence or absence of a palladium-based coupling catalyst. (For a couple of recent references to reactions of alkyl magnesium and alkyl zinc reagents in the presence of a palladium-based coupling catalyst see T. Hayashi, M. Konishi, Y. Kobori, M. Kumada, T. Higuchi, K. Hirotsu, *J. Am. Chem. Soc.*, 106, 158 (1984) and E.-I. Negishi, H. Matsushita, M. Kobayashi, C. L. Rand, *Tetrahedron Lett.*, 24, 3823 (1983)). When Y is H, the reaction is similarly conducted by reacting a solution on suspension of (16) with one of a variety of hydridoaluminate reagents known in the art. The crude products (18) obtained upon evaporation of solvent are purified by recrystallization or chromatography on silica gel.

Finally a solution or suspension of (18) in water is treated with one equivalent of the hydroxide (19) at 40°–100° C. The solution is then cooled to room temperature and neutralized with a strong acid like concentrated hydrochloric acid. Evaporation of the water leaves (2, X=H, Z=N) contaminated with a little inorganic salt. If desired, the salt can be removed from (2, X=H, Z=N) by recrystallization or column chromatography (Equation 12c). The X substituent of these compounds (2, X=H, Z=N) can be elaborated as described in Equation 11.

Many of the amino and methylamino triazinones of Formula (2) where X is H, Y is H, alkyl, alkoxy, or alkylthio, and Z is N can be prepared via the route described by H. Neunhoeffer and H. Hammann for the case where R is $NH_2$ and Y is phenyl, employing modifications known to those trained in the art (see *Liebig's Ann. Chem.*, 283, (1984)). The X substituent of these compounds (2, Z=N) can then be elaborated as described in Equation 11.

Some of the amino and methylamino pyrazinones and triazinones of Formula (2) where Y is alkoxy or alkyl and most of the amino and methylamino pyrazinones and triazinones of Formula (2) where Y is alkylthio can be prepared from the corresponding pyrazinones and triazinones where Y is Cl or Br as shown in Equation 13.

Equation 13

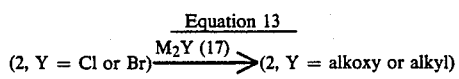

where
R, X and Z are as initially defined; and
$M_2$ and Y are as described for Equation 12.

The reaction conditions depend upon the nature of Y. When Y is alkoxy, a solution or suspension of (2, Y=Cl or Br) in the appropriate alcohol HY or an unreactive polar solvent like N,N-dimethylformamide is treated with at least one equivalent of the alkoxide $M_2Y$ (17) at a temperature of 80° to 200° C. Such elevated temperatures may necessitate performing the reaction at above ambient pressure. In some cases the presence of a cyclic polyether like 18-crown-6 or a long chain polyester may prove helpful. When Y is alkylthio, a solution or suspension of (2, Y=Cl or Br) in a unreactive solvent like N,N-dimethylformamide is treated with at least one equivalent of the thiolate $M_2Y$ (17) at a temperature of 80° to 150° C. When Y is alkyl the reaction is conducted as already described for Equation 12b regarding the case where Y is alkyl. The products (2, Y=alkoxy, alkylthio or alkyl) are isolated by evaporation of the solvent and purified by recrystallization or chromatography on silica gel.

Finally, most of the amino and methylamino pyrazinones and triazinones of Formula (2) where Y is H can be prepared from the corresponding pyrazinones and triazinones where Y is Cl or Br as shown in Equation 14.

Equation 14

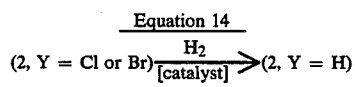

where R, X and Z are as initially defined.

The reaction is carried out by treating the appropriate halide (2, Y=Cl or Br) with hydrogen in the presence of a catalyst. For specific examples of this type of reaction see H. Neunhoeffer and B. Lehmann, *Chem. Ber.*, 109, 1113 (1976) and for a general review see P. N. Rylander, *Catalytic Hydrogenation in Organic Syntheses*, Academic Press, New York, 1979.

Heterocyclic intermediates of Formula (4) are made from the corresponding free heterocycles (2, R=H) by the following method.

Equation 15

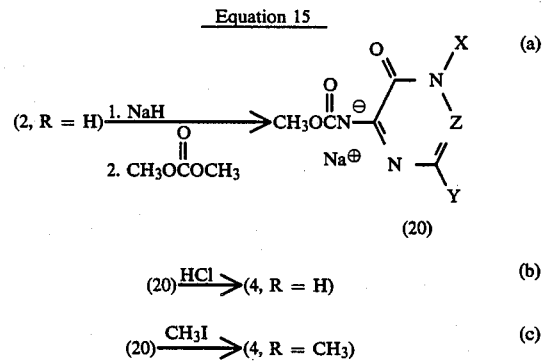

where X, Y and Z are as initially defined.

In this method, a solution or slurry of the appropriate heterocycle (2, R=H) in a suitable aprotic solvent (e.g., tetrahydrofuran, dioxane, glyme) at 0°-30° C. is treated with two equivalents of sodium hydride. After gas evolution ceases, the reaction mixture is treated with one equivalent of dimethyl carbonate and stirred at 20°-30° C. for 8 to 24 hours to provide a suspension of the sodium salt (20) (Equation 15a).

Sufficient concentrated hydrochloric acid is then added to bring the pH to 4. The mixture is saturated with sodium chloride and filtered. The organic layer is separated away from the aqueous layer, dried over magnesium sulfate, and filtered. Evaporation of the solvent leaves the carbamate (4, R=H) (Equation 15b).

Alternatively, the reaction mixture containing (20) formed in Equation 15a is treated with at least two equivalents of iodomethane and then heated at 60°-80° C. for 8 to 24 hours. The mixture is cooled and filtered, and the solvent is evaporated. The residue is taken up in dichloromethane, washed with water, and the solvent is evaporated, leaving the N-methyl carbamate (4, R=CH$_3$) (Equation 15c).

In some cases heterocycles of Formula (2) may be more easily prepared with R being H than with R being CH$_3$. Many heterocycles (2, R=CH$_3$) can be prepared from the corresponding heterocycles (2, R=H) by using the method disclosed in Equation 9 followed by the method disclosed in Equation 6 or by using the method described in Equation 16 below.

Equation 16

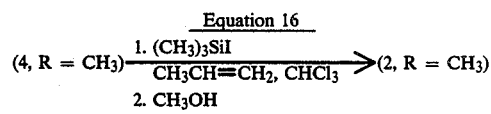

where X, Y and Z are as defined in Equation 15.

In this method, the carbamate (4, R=CH$_3$) prepared from (2, R=H) (Equations 15a and 15c) is dissolved in anhydrous, alcohol-free chloroform saturated with propylene gas. Slightly more than one equivalent (typically 1.1-1.2 equivalents) of iodotrimethylsilane is added and the stirred solution is heated at 50°-60° C. for 2 to 4 hours. The mixture is cooled and two equivalents of methanol is added. The solvent is evaporated and the residue is taken up in methanol. The mixture is carefully neutralized with 10% sodium methoxide in methanol, and then the solvent is evaporated. The residue is triturated with ice-water. If a precipitate forms, it is filtered out, rinsed with ice-water and dried to provide (2, R=CH$_3$). If no precipitate forms, the solution is saturated with sodium chloride and extracted with ethyl acetate. Evaporation of the solvent leaves the heterocycle (2, R=CH$_3$).

Sulfonyl isocyanates (1) are prepared from the corresponding sulfonamides (3) by one of the following two general methods.

Equation 17

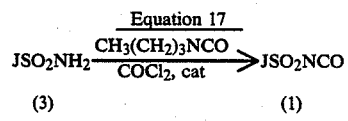

where J is as previously defined.

The sulfonamide (3) and an alkyl isocyanate (e.g., n-butyl isocyanate) in xylene or other solvent boiling above 135° C. are mixed in the presence or absence of a catalytic amount of 1,4-diaza[2.2.2]bicyclooctane (DABCO) and heated to 135°-140° C. After 5-60 minutes phosgene is slowly added to the heated mixture at such a rate that the temperature remains between 133° and 135° C. When the consumption of phosgene has ceased, the mixture is cooled and filtered to remove insoluble material. Finally, the solvent, alkyl isocyanate, and excess phosgene are evaporated, leaving the sulfonyl isocyanate (1).

If desired, the alkyl isocyanate-sulfonamide adduct can be made and isolated before reaction with the phosgene. In this case the sulfonamide (5), alkyl isocyanate, and anhydrous base (e.g., K₂CO₃) in a polar, aprotic solvent (e.g. acetone, butanone, or acetonitrile) are mixed and heated under reflux for 1 to 6 hours. The reaction mixture is then diluted with water, and the pH is adjusted to about 3 with acid (e.g. HCl, H₂SO₄). The adduct is filtered out and dried, and then reacted with phosgene as described above. This procedure modification is especially useful when sulfonamide (3) is high melting and has low solubility in the phosgenation solvent.

Sulfonyl isocyanates (1) can also be prepared by the following method.

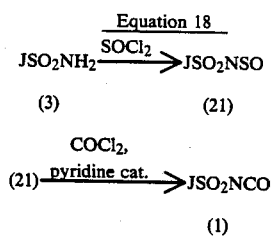

Equation 18 where J is as previously defined.

The sulfonamide (3) is heated at reflux in an excess of thionyl chloride. The reaction is continued until the sulfonamide protons are no longer detectable in the proton magnetic resonance spectrum. From 16 hours to 5 days is typically sufficient for complete conversion to the thionylamide (21) (Equation 18a).

The thionyl chloride is evaporated and the residue is treated with an inert solvent (e.g. toluene) containing at least one equivalent (typically 2–3 equivalents) of phosgene. A catalytic amount of pyridine (typically 0.1 equivalent) is added, and the mixture is heated to about 60°–140° C., with 80°–100° preferred. Conversion to the isocyanate (1) is usually substantially complete within 15 minutes to 3 hours (Equation 18b). The mixture is then cooled and filtered, and the solvent is evaporated, leaving the sulfonyl isocyanate (1).

The preparation of sulfonamides from ammonia and sulfonyl chlorides is widely reported in the literature, e.g. Crossley et al., *J. Am. Chem. Soc.*, 60, 2223 (1938).

Certain sulfonyl chlorides are best prepared by chlorosulfonation of a substituted benzene, naphthalene, or thiophene in tetrachloromethane according to the teachings of H. T. Clarke et al., *Org. Synth. Coll.*, Vol. 1, 2nd Ed. 1941, p. 85. Other sulfonyl chlorides can be made by diazotization of the appropriate amine with sodium nitrite in hydrochloric acid, followed by reaction of the diazonium salt with sulfur dioxide and cuprous or cupric chloride in acetic acid according to the teachings of H. L. Yale and F. Sowinski, *J. Org. Chem.*, 25, 1824 (1960) and of H. Meerwein et al., *Chem. Ber.*, 90, 841 (1957).

Reference to the following patents and applications are suggested for further details regarding the preparation of the sulfonamides (3) and sulfonyl isocyanates (1): U.S. Pat. No. 4,169,719; U.S. Pat. No. 4,127,405; U.S. Pat. No. 4,394,506; U.S. Pat. No. 4,420,325; U.S. Pat. No. 4,481,029; EP-A-No. 13,480; EP-A-No. 95,925; U.S. Pat. No. 4,511,392; U.S. Pat. No. 4,465,505; U.S. Pat. No. 4,460,401; U.S. Pat. No. 4,494,980; U.S. Pat. No. 4,514,211; U.S. Pat. No. 4,586,950; and U.S. Pat. No. 4,589,911.

The following examples further illustrate the synthesis of this invention.

EXAMPLE 1

3,5-Dichloro-1-methyl-2(1H)-pyrazinone

Methylaminoacetonitrile hydrochloride (159.78 g, 1.50 mol) was added in one portion to a solution of oxalyl chloride (654.3 mL, 7.50 mol) in anhydrous chlorobenzene (2000 mL). The mixture was heated at 80° C. for 8 hours. The solvent was then rotary evaporated, and the residue was taken up in CH₂Cl₂ and preabsorbed onto silica gel. Flash chromatography using 6:3:1 dichloromethane-hexanes-ether solvent mixture as eluant gave a partially purified product that was further purified by chromatography on silica·gel using a 8:1:1 dichloromethane-hexane-ether solvent mixture as eluant. Finally, crystallization from a mixture of ether, 1-chlorobutane; and hexanes furnished the product as a pale yellow, dense crystalline powder melting at 65°–67°. The yield of 3,5-dichloro-1-methyl-2(1H)-pyrazinone was 101.60 g.

PMR (CDCl₃, 200 MHz); δ 7.26 (s, 1H, Het-H); 3.60 (s, 3H, N—CH₃). IR (Nujol mull): 1660 (s, C=O) cm⁻¹.

EXAMPLE 2

3-Amino-5-chloro-1-methyl-2(1H)-pyrazinone

A solution of 3,5-dichloro-1-methyl-2(1H)-pyrazinone (7.16 g, 0.040 mol) in dioxane (120 mL) was treated with a concentrated aqueous solution of ammonia (28%, 16 mL, 0.24 mol). After stirring at room temperature for three days a suspension of solid had formed. The solid was collected, rinsed with a little water, ether, and hexanes and air dried. The product, 3-amino-5-chloro-1-methyl-2(1H)-pyrazinone, was obtained as a white crystalline powder (4.81 g) melting above 250° C.

PMR (DMSO-d₆, 200 MHz): δ 7.16 (broad s, 2H, NH₂); 6.99 (s, 1H, Het-H); 3.34 (s, 3H, N—CH₃).

IR (Nujol mull): 3310 (w, NH); 3170 (w, NH); 1660 (s, C=O) cm⁻¹.

EXAMPLE 3

Methyl 2-[[(6-Chloro-3,4-dihydro-4-methyl-3-oxo-2-pyrazinylamino)carbonylamino]sulfonyl]benzoate To a mixture of 3-amino-5-chloro-1-methyl-2(1H)-pyrazinone (0.40 g, 0.0025 mol) in anhydrous 1,2-dichloroethane (4 mL) under nitrogen was added a solution of 2-carbomethoxybenzenesulfonyl isocyanate (0.84 g, 0.0035 mol) in anhydrous 1,2-dichloromethane (3 mL). The mixture was heated at reflux for 2 hours. The solvent was rotary evaporated, and the residue was purified by chromatography on a column of silica gel using a solvent mixture of 1:1 hexanes-acetone containing a little acetic acid as eluant. Rotary evaporation of the appropriate fractions left 0.34 g of methyl 2-[[(6-chloro-3,4-dihydro-4-methyl-3-oxo-2-pyrazinylamino)carbonylamino]sulfonyl]benzoate as a crystalline powder melting at 173°–176° C.

PMR (CDCl₃, 200 MHz): δ 11.52 (broad s, 1H, SO₂NHCO); 8.40 (broad s, 2H, C(O)NHHet and aryl H ortho to SO₂); 7.69 (broad s, 3H, other aryl H's); 6.96 (s, 1H, Het-H); 3.99 (s, 3H, OCH₃); 3.55 (s, 3H, N—CH₃). IR (Nujol mull): 3240 (w, NH); 1745 (s, C=O); 1705 (s, C=O); 1670 (s, C=O) cm⁻¹.

EXAMPLE 4

Phenyl (6-chloro-3,4-dihydro-4-methyl-3-oxopyrazin-2-yl)carbamate

A mixture of 3-amino-5-chloro-1-methyl-2(1H)-pyrazinone (11.17 g, 0.070 mol) in anhydrous N,N-dimethylformamide (90 mL) was treated with oil-free sodium hydride (3.4 g, 0.154 mol). After stirring at room temperature for 1 hour, the mixture was cooled with the aid of a dry ice-acetone bath while a solution of diphenyl carbonate (16.49 g, 0.077 mol) in N,N-dimethylformamide (60 mL) was added as rapidly as possible. A wet ice bath was substituted for the dry ice bath, and the reaction mixture was stirred at approximately 0° C. for 3 hours. The mixture was allowed to briefly warm to room temperature, and was then poured into a stirred mixture of ice (350 g), concentrated hydrochloric acid (42 mL); dichloromethane (318 mL), and tetrahydrofuran (32 mL). The layers were separated, and the aqueous layer was extracted with 10:1 dichloromethane-tetrahydrofuran (5×100 mL). The combined organic solutions were dried (Na₂SO₄), and the solvent was rotary evaporated. After the residue was taken up in toluene, further rotary evaporation left a tan solid. This solid was taken up in dichloromethane, absorbed onto silica gel and then chromatographed using a 5:1 mixture of dichloromethane-ether as eluant. Rotary evaporation of the appropriate fractions left 9.70 g of phenyl (6-chloro-3,4-dihydro-4-methyl-3-oxopyrazin-2-yl)carbamate as a crystalline solid melting at 175°–177° C.

PMR (CDCl₃, 200 MHz): δ8.74 (broad s, 1H, NH); 7.20–7.45 (m, 5H, aryl H's); 6.96 (s, 1H, Het-H); 3.58 (s, 3H, N—CH₃). IR (Nujol mull): 3320 (w, NH); 1770 (s, C=O); 1640 (vs, C=O) cm⁻¹.

EXAMPLE 5

N′-[(6-Chloro-3,4-dihydro-4-methyl-3-oxopyrazin-2-yl)aminocarbonyl]-N,N-dimethyl-1,2-benzenedisulfonamide 1,8-Diazabicyclo[5.4.0]undec-7-ene (0.30 mL, 2.00 mmol) was added dropwise over two minutes to a mixture of N,N-dimethyl-1,2-benzenedisulfonamide (0.53 g, 2.00 mmol) and phenyl (6-chloro-3,4-dihydro-4-methyl-3-oxopyrazin-2-yl)carbamate (0.56 g, 2.00 mmol) in anhydrous acetonitrile (20 mL) under nitrogen. After 3 hours at room temperature, glacial acetic acid (0.12 mL, 2.10 mmol) was added. The solvent was rotary evaporated and the residue was chromatographed on a column of silica gel using a solvent mixture of 1:1 dichloromethane-ether containing 2 mL/L acetic acid as eluant. The appropriate fractions were evaporated to leave 0.76 g of N′-[(6-chloro-3,4-dihydro-4-methyl-3-oxopyrazin-2-yl)aminocarbonyl]-N,N-dimethyl-1,2-benzenedisulfonamide as a crystalline solid melting at 227°–230° C.

PMR (CDCl₃, 200 MHz; δ11.90 (slightly broadened s, 1H, SO₂NHCO); 8.58 (m, 1H, Aryl-H ortho to bridge); 8.33 (slightly broadened s, bH, C(O)NH-Het); 8.13 (m, 1H, Aryl-H ortho to SO₂N(CH₃)₂); 7.78 (m, 2H, other aryl H's); 6.94 (s, 1H, Het-H), 3.55 (s, 3H, NCH₃ on Het); 2.94 (s, 6H, N(CH₃)₂). IR (Nujol mull): 1710 (s, C=O); 1670 (s, C=O) cm⁻¹.

Using the procedures and examples shown above, the compounds in Tables 1–16 can be prepared.

TABLE 1

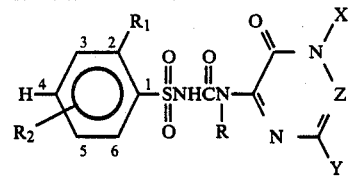

| R | R₁ | R₂ | X | Y | Z | m.p. (°C.) |
|---|---|---|---|---|---|---|
| H | CO₂CH₃ | H | H | OCH₃ | CH | |
| H | CO₂CH₃ | H | CH₃ | Cl | CH | 173–176 |
| H | CO₂CH₃ | H | CH₃ | Br | CH | 205–207 |
| H | CO₂CH₃ | H | CH₃ | OCH₃ | CH | |
| H | CO₂CH₃ | H | CH₃ | OCH₂CH₃ | CH | |
| H | CO₂CH₃ | H | CH₃ | O(CH₂)₂CH₃ | CH | |
| H | CO₂CH₃ | H | CH₃ | CH₃ | CH | |
| H | CO₂CH₃ | H | CH₃ | CH₂CH₃ | CH | |
| H | CO₂CH₃ | H | CH₃ | (CH₂)₂CH₃ | CH | |
| H | CO₂CH₃ | H | CH₂CH₃ | Cl | CH | 166–168 |
| H | CO₂CH₃ | H | CH₂CH₃ | OCH₃ | CH | |
| H | CO₂CH₃ | H | (CH₂)₂CH₃ | Cl | CH | |
| H | CO₂CH₃ | H | (CH₂)₂CH₃ | OCH₃ | CH | |
| H | CO₂CH₃ | H | OCH₃ | H | CH | |
| H | CO₂CH₃ | H | OCH₃ | CH₃ | CH | |
| H | CO₂CH₃ | H | OCH₃ | CH₂CH₃ | CH | |
| H | CO₂CH₃ | H | OCH₃ | (CH₂)₂CH₃ | CH | |
| H | CO₂CH₃ | H | OCH₃ | OCH₃ | CH | |
| H | CO₂CH₃ | H | OCH₃ | OCH₂CH₃ | CH | |
| H | CO₂CH₃ | H | OCH₃ | O(CH₂)₂CH₃ | CH | |
| H | CO₂CH₃ | H | OCH₃ | Cl | CH | |
| H | CO₂CH₃ | H | OCH₃ | Br | CH | |
| H | CO₂CH₃ | H | OCH₂CH₃ | Cl | CH | |
| H | CO₂CH₃ | H | OCH₂CH₃ | CH₃ | CH | |
| H | CO₂CH₃ | H | OCH₂CH₃ | OCH₃ | CH | |
| H | CO₂CH₃ | H | O(CH₂)₂CH₃ | Cl | CH | |

TABLE 1-continued

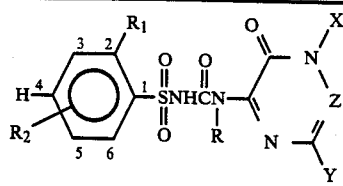

| R | R₁ | R₂ | X | Y | Z | m.p. (°C.) |
|---|---|---|---|---|---|---|
| H | CO₂CH₃ | H | O(CH₂)₂CH₃ | CH₃ | CH | |
| H | CO₂CH₃ | H | O(CH₂)₂CH₃ | OCH₃ | CH | |
| H | CO₂CH₃ | H | NH₂ | Cl | CH | |
| H | CO₂CH₃ | H | NH₂ | CH₃ | CH | |
| H | CO₂CH₃ | H | NH₂ | OCH₃ | CH | |
| H | CO₂CH₃ | H | NHCH₃ | Cl | CH | |
| H | CO₂CH₃ | H | NHCH₃ | CH₃ | CH | |
| H | CO₂CH₃ | H | NHCH₃ | OCH₃ | CH | |
| H | CO₂CH₃ | H | N(CH₃)₂ | Cl | CH | |
| H | CO₂CH₃ | H | N(CH₃)₂ | CH₃ | CH | |
| H | CO₂CH₃ | H | N(CH₃)₂ | OCH₃ | CH | |
| H | CO₂CH₃ | H | NHCH₃ | OCH₂CH₃ | CH | |
| CH₃ | CO₂CH₃ | H | CH₃ | Cl | CH | |
| CH₃ | CO₂CH₃ | H | OCH₃ | Cl | CH | |
| CH₃ | CO₂CH₃ | H | CH₃ | OCH₃ | CH | |
| CH₃ | CO₂CH₃ | H | OCH₃ | CH₃ | CH | |
| CH₃ | CO₂CH₃ | H | OCH₃ | OCH₃ | CH | |
| H | CO₂CH₃ | H | CH₃ | Cl | CF | |
| H | CO₂CH₃ | H | CH₃ | OCH₃ | CF | |
| H | CO₂CH₃ | H | OCH₃ | OCH₃ | CF | |
| H | CO₂CH₃ | H | OCH₃ | CH₃ | CF | |
| H | CO₂CH₃ | H | CH₃ | Cl | CCl | |
| H | CO₂CH₃ | H | CH₃ | OCH₃ | CCl | |
| H | CO₂CH₃ | H | CH₃ | Br | CBr | |
| H | CO₂CH₃ | H | CH₃ | Cl | CBr | |
| H | CO₂CH₃ | H | CH₃ | OCH₃ | CBr | |
| H | CO₂CH₃ | H | H | OCH₃ | N | |
| H | CO₂CH₃ | H | CH₃ | Cl | N | |
| H | CO₂CH₃ | H | CH₃ | Br | N | |
| H | CO₂CH₃ | H | CH₃ | OCH₃ | N | |
| H | CO₂CH₃ | H | CH₃ | OCH₂CH₃ | N | |
| H | CO₂CH₃ | H | CH₃ | O(CH₂)₂CH₃ | N | |
| H | CO₂CH₃ | H | CH₃ | CH₃ | N | |
| H | CO₂CH₃ | H | CH₃ | CH₂CH₃ | N | |
| H | CO₂CH₃ | H | CH₃ | (CH₂)₂CH₃ | N | |
| H | CO₂CH₃ | H | CH₂CH₃ | Cl | N | |
| H | CO₂CH₃ | H | CH₂CH₃ | OCH₃ | N | |
| H | CO₂CH₃ | H | (CH₂)₂CH₃ | Cl | N | |
| H | CO₂CH₃ | H | (CH₂)₂CH₃ | OCH₃ | N | |
| H | CO₂CH₃ | H | OCH₃ | H | N | |
| H | CO₂CH₃ | H | OCH₃ | CH₃ | N | |
| H | CO₂CH₃ | H | OCH₃ | CH₂CH₃ | N | |
| H | CO₂CH₃ | H | OCH₃ | (CH₂)₂CH₃ | N | |
| H | CO₂CH₃ | H | OCH₃ | OCH₃ | N | |
| H | CO₂CH₃ | H | OCH₃ | OCH₂CH₃ | N | |
| H | CO₂CH₃ | H | OCH₃ | O(CH₂)₂CH₃ | N | |
| H | CO₂CH₃ | H | OCH₃ | Cl | N | |
| H | CO₂CH₃ | H | OCH₃ | Br | N | |
| H | CO₂CH₃ | H | OCH₂CH₃ | Cl | N | |
| H | CO₂CH₃ | H | H | SCH₃ | CH | |
| H | CO₂CH₃ | H | CH₃ | SCH₂CH₃ | CH | |
| H | CO₂CH₃ | H | CH₂CH₃ | SCH₃ | CH | |
| H | CO₂CH₃ | H | (CH₂)₂CH₃ | SCH₃ | CH | |
| H | CO₂CH₃ | H | OCH₃ | SCH₃ | CH | |
| H | CO₂CH₃ | H | OCH₃ | SCH₂CH₃ | CH | |
| H | CO₂CH₃ | H | O(CH₂)₂CH₃ | SCH₃ | CH | |
| H | CO₂CH₃ | H | N(CH₃)₂ | SCH₃ | CH | |
| H | CO₂CH₃ | H | OCH₂CH₃ | CH₃ | N | |
| H | CO₂CH₃ | H | OCH₂CH₃ | OCH₃ | N | |
| H | CO₂CH₃ | H | O(CH₂)₂CH₃ | Cl | N | |
| H | CO₂CH₃ | H | O(CH₂)₂CH₃ | CH₃ | N | |
| H | CO₂CH₃ | H | O(CH₂)₂CH₃ | OCH₃ | N | |
| H | CO₂CH₃ | H | NH₂ | Cl | N | |
| H | CO₂CH₃ | H | NH₂ | CH₃ | N | |
| H | CO₂CH₃ | H | NH₂ | OCH₃ | N | |
| H | CO₂CH₃ | H | NHCH₃ | Cl | N | |
| H | CO₂CH₃ | H | NHCH₃ | CH₃ | N | |
| H | CO₂CH₃ | H | NHCH₃ | OCH₃ | N | |
| H | CO₂CH₃ | H | N(CH₃)₂ | Cl | N | |
| H | CO₂CH₃ | H | N(CH₃)₂ | CH₃ | N | |
| H | CO₂CH₃ | H | N(CH₃)₂ | OCH₃ | N | |

TABLE 1-continued

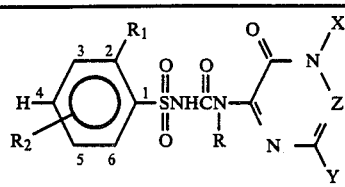

| R | R₁ | R₂ | X | Y | Z | m.p. (°C.) |
|---|---|---|---|---|---|---|
| H | CO₂CH₃ | H | NHCH₃ | OCH₂CH₃ | N | |
| CH₃ | CO₂CH₃ | H | CH₃ | Cl | N | |
| CH₃ | CO₂CH₃ | H | OCH₃ | Cl | N | |
| CH₃ | CO₂CH₃ | H | CH₃ | OCH₃ | N | |
| CH₃ | CO₂CH₃ | H | CH₂CH₃ | OCH₃ | N | |
| CH₃ | CO₂CH₃ | H | OCH₃ | CH₃ | N | |
| CH₃ | CO₂CH₃ | H | OCH₃ | OCH₃ | N | |
| H | CO₂CH₃ | 5-F | OCH₃ | Cl | CH | |
| H | CO₂CH₃ | 3-Cl | CH₃ | CH₃ | CH | |
| H | CO₂CH₃ | 5-Br | CH₃ | OCH₃ | CH | |
| H | CO₂CH₃ | 5-CN | OCH₃ | CH₃ | CH | |
| H | CO₂CH₃ | 6-CH₃ | CH₃ | Cl | Cl | |
| H | CO₂CH₃ | 5-OCH₃ | CH₃ | OCH₃ | N | |
| H | CO₂CH₃ | 5-SCH₃ | CH₃ | OCH₂CH₃ | N | |
| H | CO₂CH₃ | 5-OCF₂H | OCH₃ | Cl | CH | |
| H | CO₂CH₃ | 6-F | CH₃ | CH₃ | CH | |
| H | CO₂CH₃ | H | CH₃ | SCH₃ | CH | 165–167 |
| H | CO₂CH₃ | H | CH₃ | SCH₃ | N | |
| H | CO₂CH₃ | H | CH₃ | SCH₂CH₃ | N | |
| H | CO₂CH₃ | H | CH₂CH₃ | SCH₃ | N | |
| H | CO₂CH₃ | H | (CH₂)₂CH₃ | SCH₃ | N | |
| H | CO₂CH₃ | H | OCH₃ | SCH₃ | N | |
| H | CO₂CH₃ | H | OCH₃ | SCH₂CH₃ | N | |
| H | CO₂CH₃ | H | O(CH₂)₂CH₃ | SCH₃ | N | |
| H | CO₂CH₃ | H | N(CH₃)₂ | SCH₃ | N | |
| H | CO₂CH₃ | 5-Cl | CH₃ | OCH₃ | CH | |
| H | CO₂CH₃ | 6-Br | OCH₃ | CH₃ | CH | |
| H | CO₂CH₃ | 5-OCH₃ | CH₃ | Cl | CH | 230–240 |
| H | CO₂CH₃ | 3-CH₃ | CH₃ | OCH₃ | N | |
| H | CO₂CH₃ | 3-F | CH₃ | OCH₂CH₃ | N | |
| H | CO₂CH₃ | 6-Cl | OCH₂CH₃ | CH₃ | CH | |
| H | CO₂CH₃ | 3-SCH₃ | OCH₃ | OCH₃ | CH | |
| H | CO₂CH₃ | 5-F | CH₂CH₃ | OCH₃ | CH | |
| H | CO₂CH₃ | 5-CH₃ | CH₃ | Br | CH | |
| H | CO₂CH₃ | 5-SCH₃ | CH₃ | OCH₂CH₃ | CH | |
| H | CO₂CH₃ | 5-OCF₂H | CH₃ | CH₂CH₃ | CH | |
| H | CO₂CH₂CH₃ | H | OCH₃ | Cl | CH | |
| H | CO₂CH₂CH₃ | H | CH₃ | CH₃ | CH | |
| H | CO₂CH₂CH₃ | H | CH₃ | OCH₃ | CH | |
| H | CO₂CH₂CH₃ | H | OCH₃ | CH₃ | CH | |
| H | CO₂CH₂CH₃ | H | CH₃ | Cl | CH | |
| H | CO₂CH₂CH₃ | H | CH₃ | OCH₃ | CH | |
| H | CO₂CH₂CH₃ | H | CH₃ | OCH₃ | N | |
| H | CO₂CH₂CH₃ | H | CH₃ | OCH₂CH₃ | N | |
| H | CO₂CH₂CH₃ | H | OCH₂CH₃ | CH₃ | CH | |
| H | CO₂CH₂CH₃ | H | OCH₃ | OCH₃ | CH | |
| H | CO₂CH₂CH₃ | H | CH₂CH₃ | OCH₃ | CH | |
| H | CO₂CH₂CH₃ | H | CH₃ | Br | CH | |
| H | CO₂CH₂CH₃ | H | CH₃ | OCH₂CH₃ | CH | |
| H | CO₂CH₂CH₃ | H | CH₃ | CH₂CH₃ | CH | |
| H | CO₂CH₂CH=CH₃ | H | OCH₃ | Cl | CH | |
| H | CO₂CH₂C≡CH | H | CH₃ | CH₃ | CH | |
| H | CO₂CH(CH₃)₂ | H | CH₃ | OCH₃ | CH | |
| H | CO₂(CH₂)₂CH₃ | H | OCH₃ | CH₃ | CH | |
| H | CO₂(CH₂)₂OCH₃ | H | CH₃ | Cl | CH | |
| H | CO₂(CH₂)₂OCH₂CH₃ | H | CH₃ | OCH₃ | N | |
| H | CO₂CH₂OCH₃ | H | CH₃ | OCH₂CH₃ | N | |
| H | CO₂(CH₂)₂Cl | H | OCH₂CH₃ | CH₃ | CH | |
| H | CO₂(CH₂)₂F | H | OCH₃ | OCH₃ | CH | |
| H | CO₂(CH₂)₂Br | H | CH₂CH₃ | OCH₃ | CH | |
| H | CO₂(CH₂)₂I | H | CH₃ | Br | CH | |
| H | CO₂CH₂CF₃ | H | CH₃ | OCH₂CH₃ | CH | |
| H | CO₂CH₂CH₂CN | H | CH₃ | CH₂CH₃ | CH | |
| CH₃ | CO₂CH₂CH₃ | H | OCH₃ | Cl | CH | |
| H | CO₂CH₂CH₃ | 5-OCH₃ | CH₃ | OCH₃ | CH | |
| H | F | H | OCH₃ | CH₃ | CH | |
| H | Cl | H | CH₃ | OCH₂CH₃ | N | |
| H | Br | H | CH₃ | OCH₃ | N | |
| H | NO₂ | H | CH₃ | Cl | CH | |
| H | CH₃ | H | OCH₃ | CH₃ | CH | |
| H | CH₂CH₃ | H | CH₃ | OCH₃ | CH | |

TABLE 1-continued

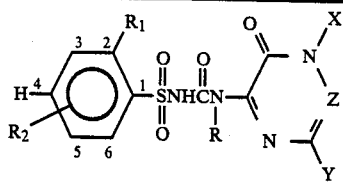

| R | R₁ | R₂ | X | Y | Z | m.p. (°C.) |
|---|---|---|---|---|---|---|
| H | (CH₂)₂CH₃ | H | CH₃ | CH₃ | CH | |
| H | (CH₂)₃CH₃ | H | OCH₃ | Cl | CH | |
| H | CH(CH₃)₂ | H | OCH₂CH₃ | CH₃ | CH | |
| H | CF₃ | H | OCH₃ | OCH₃ | CH | |
| H | (CH₂)₂F | H | CH₂CH₃ | OCH₃ | CH | |
| H | (CH₂)₂Br | H | CH₃ | Br | CH | |
| H | CF₂H | H | CH₃ | OCH₂CH₃ | CH | |
| H | (CH₂)₃Cl | H | CH₃ | CH₂CH₃ | CH | |
| H | Cl | H | CH₃ | Cl | CH | 208–210 |
| H | Cl | H | CH₂CH₃ | Cl | CH | 184–187 |
| H | cyclopropyl | H | OCH₃ | Cl | CH | |
| H | cyclobutyl | H | CH₃ | CH₃ | CH | |
| H | CH=CF₂ | H | CH₃ | OCH₃ | CH | |
| H | CCl=CCl₂ | H | OCH₃ | CH₃ | CH | |
| H | CH₂CH=CHCCl₃ | H | CH₃ | Cl | CH | |
| H | CH=CHCl | H | CH₃ | OCH₃ | N | |
| H | CH=CHI | H | CH₃ | OCH₂CH₃ | N | |
| H | CH=CBr₂ | H | OCH₂CH₃ | CH₃ | CH | |
| H | CF=CFH | H | OCH₃ | OCH₃ | CH | |
| H | CH₂CH=CF₂ | H | CH₂CH₃ | OCH₃ | CH | |
| H | CH=CHCF₃ | H | CH₃ | Br | CH | |
| H | CF=CFCH₃ | H | CH₃ | OCH₂CH₃ | H | |
| H | OCH₃ | H | CH₃ | CH₂CH₃ | CH | |
| H | OCH₃ | 5-CH₃ | OCH₃ | Cl | CH | |
| H | OCH₂CH₃ | H | CH₃ | CH₃ | CH | |
| H | O(CH₂)₂CH₃ | H | CH₃ | OCH₃ | CH | |
| H | O(CH₂)₃CH₃ | H | OCH₃ | CH₃ | CH | |
| H | OCH(CH₃)₂ | H | CH₃ | Cl | CH | |
| H | OCF₂H | H | CH₃ | OCH₃ | N | |
| H | OCF₂CF₂H | H | CH₃ | OCH₂CH₃ | N | |
| H | O(CH₂)₂CCl₂H | H | OCH₃ | Cl | CH | |
| H | O(CH₂)₄I | H | CH₃ | CH₃ | CH | |
| H | OCH₂OCH₃ | H | CH₃ | OCH₃ | CH | |
| H | O(CH₂)₂OCH₃ | H | OCH₃ | CH₃ | CH | |
| H | O(CH₂)₂OCH₂CH₃ | H | CH₃ | Cl | CH | |
| H | O(CH₂)₃OCH₃ | H | CH₃ | OCH₃ | N | |
| H | C(O)N(CH₃)₂ | H | CH₃ | OCH₂CH₃ | N | |
| H | C(O)NHCH₂CH₃ | H | OCH₃ | Cl | CH | |
| H | C(O)N(CH₃)OCH₃ | H | CH₃ | CH₃ | CH | |
| H | C(O)NHOCH₃ | H | CH₃ | OCH₃ | CH | |
| H | C(O)NH(CH₂)₂CH₃ | H | OCH₃ | CH₃ | CH | |
| H | SO₂N(CH₃)₂ | H | CH₃ | Cl | CH | 227–230 |
| H | CO₂CH₃ | 5-Cl | CH₃ | Cl | CH | 227–230 |
| H | SO₂NH—cyclopropyl | H | OCH₃ | Cl | CH | |
| CH₃ | SO₂N(CH₃)₂ | H | CH₃ | CH₃ | CH | |
| H | SO₂N(CH₃)₂ | 3-CH₃ | CH₃ | OCH₃ | CH | |
| H | SO₂N(CH₃)CH₂CH=CH₂ | H | OCH₃ | CH₃ | CH | |
| H | SO₂N((CH₂)₂CH₃)₂ | H | CH₃ | Cl | CH | |
| H | SO₂NH₂ | H | CH₃ | OCH₃ | N | |
| H | C(O)N(CH₃)₂ | 5-OCH₃ | CH₃ | Cl | CH | 190–195 |
| H | SO₂N(CH₃)OCH₃ | H | CH₃ | OCH₂CH₃ | N | |
| H | SO₂N(CH₃)OCH₂CH₃ | H | OCH₂CH₃ | CH₃ | CH | |
| H | SCH₃ | H | OCH₃ | OCH₃ | CH | |
| H | SCH₂CH=CH₃ | H | CH₂CH₃ | OCH₃ | CH | |
| H | SCH₂C≡CH₃ | H | CH₃ | Br | CH | |
| H | S(CH₂)₂CH₃ | H | CH₃ | OCH₂CH₃ | CH | |
| H | S(O)CH₃ | H | CH₃ | CH₂CH₃ | CH | |
| H | SCF₂H | H | OCH₃ | Cl | CH | |
| H | SCF₂CF₂H | H | CH₃ | CH₃ | CH | |
| H | S(CH₂)₂Cl | H | CH₃ | OCH₃ | CH | |
| H | S(CH₂)₂I | H | OCH₃ | CH₃ | CH | |
| H | S(CH₂)₃Br | H | CH₃ | Cl | CH | |
| H | S(O)CF₂CF₂H | H | CH₃ | OCH₃ | N | |
| H | S(O)(CH₂)₂I | H | CH₃ | OCH₂CH₃ | N | |
| H | S(O)₂CH₃ | H | OCH₃ | Cl | CH | |
| H | S(O)₂CH₂CH₃ | H | CH₃ | CH₃ | CH | |
| H | S(O)₂CH₂CH=CH₂ | H | CH₃ | OCH₃ | CH | |
| H | S(O)₂CH₂C≡CH | H | OCH₃ | CH₃ | CH | |
| H | S(O)₂CF₂H | H | CH₃ | Cl | CH | |
| H | S(O)₂CF₂CF₂H | H | CH₃ | OCH₃ | N | |
| H | S(O)₂(CH₂)₂I | H | CH₃ | OCH₂CH₃ | N | |

TABLE 1-continued

| R | R₁ | R₂ | X | Y | Z | m.p. (°C.) |
|---|---|---|---|---|---|---|
| H | C(O)CH₃ | H | OCH₃ | Cl | CH | |
| H | C(O)(CH₂)₃CH₃ | H | CH₃ | CH₃ | CH | |
| H | C(O)CH₂CH₃ | H | CH₃ | OCH₃ | CH | |
| H | C(O)—cyclo-C₃H₅ | H | OCH₃ | CH₃ | CH | |
| H | C(O)—cyclo-C₄H₇ | H | CH₃ | Cl | CH | |
| H | S(O)₂CH₃ | H | CH₃ | Cl | CH | 230–240 |
| H | C(O)—cyclo-C₅H₉ | H | OCH₃ | Cl | CH | |
| H | C(O)—cyclo-C₃F₅ | H | CH₃ | CH₃ | CH | |
| H | C(O)CF₃ | H | CH₃ | OCH₃ | CH | |
| H | C(O)(CH₂)₃CCl₂H | H | OCH₃ | CH₃ | CH | |
| H | C(O)(CH₂)₄F | H | CH₃ | Cl | CH | |
| H | C(O)—cyclo-(CHCH₂CCl₂) | H | CH₃ | OCH₃ | N | |
| H | CH₂CN | H | CH₃ | OCH₂CH₃ | N | |
| H | L-1, R$_h$ = H | H | OCH₂CH₃ | CH₃ | CH | |
| H | L-1, R$_h$ = CH₃ | H | OCH₃ | OCH₃ | CH | |
| H | L-2, R$_h$ = H | H | CH₂CH₃ | OCH₃ | CH | |
| H | L-2, R$_h$ = CH₃ | H | CH₃ | Br | CH | |
| H | L-3 | H | CH₃ | OCH₂CH₃ | CH | |
| H | L-4 | H | CH₃ | CH₂CH₃ | CH | |
| H | L-5 | H | OCH₃ | Cl | CH | |
| H | L-6 | H | CH₃ | CH₃ | CH | |
| H | L-7 | H | CH₃ | OCH₃ | CH | |
| H | L-8 | H | OCH₃ | CH₃ | CH | |
| H | L-9 | H | CH₃ | Cl | CH | |
| H | L-10 | H | CH₃ | OCH₃ | N | |
| H | L-11 | H | CH₃ | OCH₂CH₃ | N | |
| H | L-12 | H | OCH₃ | Cl | CH | |
| H | L-13 | H | CH₃ | CH₃ | CH | |
| H | L-14 | H | CH₃ | OCH₃ | CH | |
| H | L-15 | H | OCH₃ | CH₃ | CH | |
| H | L-16, R$_i$ = H | H | CH₃ | Cl | CH | |
| H | L-16, R$_i$ = CH₃ | H | CH₃ | OCH₃ | N | |
| H | L-17 | H | CH₃ | OCH₂CH₃ | N | |
| H | L-18 | H | OCH₃ | Cl | CH | |
| H | L-19 | H | CH₃ | CH₃ | CH | |
| H | L-20 | H | CH₃ | OCH₃ | CH | |
| H | L-21 | H | OCH₃ | CH₃ | CH | |
| H | L-22 | H | CH₃ | Cl | CH | |
| H | L-23 | H | OCH₃ | Cl | CH | |
| H | L-24 | H | CH₃ | CH₃ | CH | |
| H | L-25 | H | CH₃ | OCH₃ | CH | |
| H | L-26, R$_j$ = H | H | OCH₃ | CH₃ | CH | |
| H | L-26, R$_j$ = CH₃ | H | CH₃ | Cl | CH | |
| H | L-26, R$_j$ = CH₂CH₃ | H | CH₃ | OCH₃ | N | |
| H | L-27, R$_j$ = H | H | CH₃ | OCH₂CH₃ | N | |
| H | L-27, R$_j$ = CH₃ | H | OCH₂CH₃ | CH₃ | CH | |
| H | L-27, R$_j$ = CH₂CH₃ | H | OCH₃ | OCH₃ | CH | |
| H | L-28, R$_k$ = H | H | CH₂CH₃ | OCH₃ | CH | |
| H | L-28, R$_k$ = CH₃ | H | CH₃ | Br | CH | |
| H | L-28, R$_k$ = CH₂CH₃ | H | CH₃ | OCH₂CH₃ | CH | |
| H | L-28, R$_k$ = OCH₃ | H | CH₃ | CH₂CH₃ | CH | |
| H | L-28, R$_k$ = OCH₂CH₃ | H | OCH₃ | Cl | CH | |
| H | L-28, R$_k$ = SCH₃ | H | CH₃ | CH₃ | CH | |
| H | L-28, R$_k$ = SCH₂CH₃ | H | CH₃ | OCH₃ | CH | |
| H | L-29, R$_k$ = H | H | OCH₃ | CH₃ | CH | |
| H | L-29, R$_k$ = CH₃ | H | CH₃ | Cl | CH | |
| H | L-29, R$_k$ = CH₂CH₃ | H | CH₃ | OCH₃ | N | |
| H | L-29, R$_k$ = OCH₃ | H | CH₃ | OCH₂CH₃ | N | |
| H | L-29, R$_k$ = OCH₂CH₃ | H | OCH₃ | Cl | CH | |
| H | L-29, R$_k$ = SCH₃ | H | CH₃ | CH₃ | CH | |
| H | L-29, R$_k$ = SCH₂CH₃ | H | CH₃ | OCH₃ | CH | |
| H | L-30, R$_m$ = H | H | OCH₃ | CH₃ | CH | |
| H | L-30, R$_m$ = CH₃ | H | CH₃ | Cl | CH | |
| H | L-30, R$_m$ = CH₂CH₃ | H | CH₃ | OCH₃ | N | |
| H | L-31, R$_m$ = H | H | CH₃ | OCH₂CH₃ | N | |
| H | L-31, R$_m$ = CH₃ | H | OCH₃ | Cl | CH | |
| H | L-31, R$_m$ = CH₂CH₃ | H | CH₃ | CH₃ | CH | |
| H | L-32, R$_m$ = H | H | CH₃ | OCH₃ | CH | |
| H | L-32, R$_m$ = CH₃ | H | OCH₃ | CH₃ | CH | |
| H | L-32, R$_m$ = CH₂CH₃ | H | CH₃ | Cl | CH | |
| H | L-33, R$_n$ = H | H | CH₃ | CH₃ | N | |

TABLE 1-continued

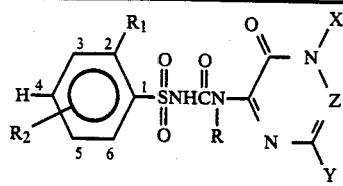

| R | R₁ | R₂ | X | Y | Z | m.p. (°C.) |
|---|---|---|---|---|---|---|
| H | L-33, $R_n$ = CH₃ | H | CH₃ | OCH₃ | CH | |

TABLE 2

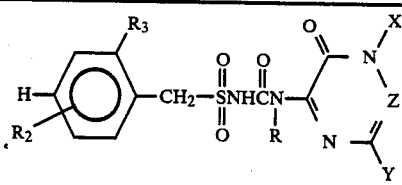

| R | R₃ | R₂ | X | Y | Z | m.p. (°C.) |
|---|---|---|---|---|---|---|
| H | CO₂CH₃ | H | H | OCH₃ | CH | |
| H | CO₂CH₃ | H | CH₃ | Cl | CH | |
| H | CO₂CH₃ | H | CH₃ | Br | CH | |
| H | CO₂CH₃ | H | CH₃ | OCH₃ | CH | |
| H | CO₂CH₃ | H | CH₃ | OCH₂CH₃ | CH | |
| H | CO₂CH₃ | H | CH₃ | O(CH₂)₂CH₃ | CH | |
| H | CO₂CH₃ | H | CH₃ | CH₃ | CH | |
| H | CO₂CH₃ | H | CH₃ | CH₂CH₃ | CH | |
| H | CO₂CH₃ | H | CH₃ | (CH₂)₂CH₃ | CH | |
| H | CO₂CH₃ | H | CH₂CH₃ | Cl | CH | |
| H | CO₂CH₃ | H | CH₂CH₃ | OCH₃ | CH | |
| H | CO₂CH₃ | H | (CH₂)₂CH₃ | Cl | CH | |
| H | CO₂CH₃ | H | (CH₂)₂CH₃ | OCH₃ | CH | |
| H | CO₂CH₃ | H | OCH₃ | H | CH | |
| H | CO₂CH₃ | H | OCH₃ | CH₃ | CH | |
| H | CO₂CH₃ | H | OCH₃ | CH₂CH₃ | CH | |
| H | CO₂CH₃ | H | OCH₃ | (CH₂)₂CH₃ | CH | |
| H | CO₂CH₃ | H | OCH₃ | OCH₃ | CH | |
| H | CO₂CH₃ | H | OCH₃ | OCH₂CH₃ | CH | |
| H | CO₂CH₃ | H | OCH₃ | O(CH₂)₂CH₃ | CH | |
| H | CO₂CH₃ | H | CH₃ | O(CH₂)₂CH₃ | CH | |
| H | CO₂CH₃ | H | OCH₃ | SCH₃ | CH | |
| H | CO₂CH₃ | H | CH₃ | SCH₃ | CH | |
| H | CO₂CH₃ | H | CH₃ | SCH₂CH₃ | CH | |
| H | CO₂CH₃ | H | CH₃ | SCH₃ | N | |
| H | CO₂CH₃ | H | OCH₃ | Cl | CH | |
| H | CO₂CH₃ | H | OCH₃ | Br | CH | |
| H | CO₂CH₃ | H | OCH₂CH₃ | Cl | CH | |
| H | CO₂CH₃ | H | OCH₂CH₃ | CH₃ | CH | |
| H | CO₂CH₃ | H | OCH₂CH₃ | OCH₃ | CH | |
| H | CO₂CH₃ | H | O(CH₂)₂CH₃ | Cl | CH | |
| H | CO₂CH₃ | H | O(CH₂)₂CH₃ | CH₃ | CH | |
| H | CO₂CH₃ | H | O(CH₂)₂CH₃ | OCH₃ | CH | |
| H | CO₂CH₃ | H | NH₂ | Cl | CH | |
| H | CO₂CH₃ | H | NH₂ | CH₃ | CH | |
| H | CO₂CH₃ | H | NH₂ | OCH₃ | CH | |
| H | CO₂CH₃ | H | NHCH₃ | Cl | CH | |
| H | CO₂CH₃ | H | NHCH₃ | CH₃ | CH | |
| H | CO₂CH₃ | H | NHCH₃ | OCH₃ | CH | |
| H | CO₂CH₃ | H | N(CH₃)₂ | Cl | CH | |
| H | CO₂CH₃ | H | N(CH₃)₂ | CH₃ | CH | |
| H | CO₂CH₃ | H | N(CH₃)₂ | OCH₃ | CH | |
| H | CO₂CH₃ | H | NHCH₃ | OCH₂CH₃ | CH | |
| CH₃ | CO₂CH₃ | H | CH₃ | Cl | CH | |
| CH₃ | CO₂CH₃ | H | OCH₃ | Cl | CH | |
| CH₃ | CO₂CH₃ | H | CH₃ | OCH₃ | CH | |
| CH₃ | CO₂CH₃ | H | OCH₃ | CH₃ | CH | |
| CH₃ | CO₂CH₃ | H | OCH₃ | OCH₃ | CH | |
| H | CO₂CH₃ | H | CH₃ | Cl | CF | |
| H | CO₂CH₃ | H | CH₃ | OCH₃ | CF | |
| H | CO₂CH₃ | H | OCH₃ | OCH₃ | CF | |
| H | CO₂CH₃ | H | OCH₃ | CH₃ | CF | |
| H | CO₂CH₃ | H | CH₃ | Cl | CCl | |
| H | CO₂CH₃ | H | CH₃ | OCH₃ | CCl | |
| H | CO₂CH₃ | H | CH₃ | Br | CBr | |
| H | CO₂CH₃ | H | CH₃ | Cl | CBr | |

TABLE 2-continued

| R | R₃ | R₂ | X | Y | Z | m.p. (°C.) |
|---|---|---|---|---|---|---|
| H | CO₂CH₃ | H | CH₃ | OCH₃ | CBr | |
| H | CO₂CH₃ | H | H | OCH₃ | N | |
| H | CO₂CH₃ | H | CH₃ | Cl | N | |
| H | CO₂CH₃ | H | CH₃ | Br | N | |
| H | CO₂CH₃ | H | CH₃ | OCH₃ | N | |
| H | CO₂CH₃ | H | CH₃ | OCH₂CH₃ | N | |
| H | CO₂CH₃ | H | CH₃ | O(CH₂)₂CH₃ | N | |
| H | CO₂CH₃ | H | CH₃ | CH₃ | N | |
| H | CO₂CH₃ | H | CH₃ | CH₂CH₃ | N | |
| H | CO₂CH₃ | H | CH₃ | (CH₂)₂CH₃ | N | |
| H | CO₂CH₃ | H | CH₂CH₃ | Cl | N | |
| H | CO₂CH₃ | H | CH₂CH₃ | OCH₃ | N | |
| H | CO₂CH₃ | H | (CH₂)₂CH₃ | Cl | N | |
| H | CO₂CH₃ | H | (CH₂)₂CH₃ | OCH₃ | N | |
| H | CO₂CH₃ | H | OCH₃ | H | N | |
| H | CO₂CH₃ | H | OCH₃ | CH₃ | N | |
| H | CO₂CH₃ | H | OCH₃ | CH₂CH₃ | N | |
| H | CO₂CH₃ | H | OCH₃ | (CH₂)₂CH₃ | N | |
| H | CO₂CH₃ | H | OCH₃ | OCH₃ | N | |
| H | CO₂CH₃ | H | OCH₃ | OCH₂CH₃ | N | |
| H | CO₂CH₃ | H | OCH₃ | O(CH₂)₂CH₃ | N | |
| H | CO₂CH₃ | H | OCH₃ | Cl | N | |
| H | CO₂CH₃ | H | OCH₃ | Br | N | |
| H | CO₂CH₃ | H | OCH₂CH₃ | Cl | N | |
| H | CO₂CH₃ | H | OCH₂CH₃ | CH₃ | N | |
| H | CO₂CH₃ | H | OCH₂CH₃ | OCH₃ | N | |
| H | CO₂CH₃ | H | O(CH₂)₂CH₃ | Cl | N | |
| H | CO₂CH₃ | H | O(CH₂)₂CH₃ | CH₃ | N | |
| H | CO₂CH₃ | H | O(CH₂)₂CH₃ | OCH₃ | N | |
| H | CO₂CH₃ | H | NH₂ | Cl | N | |
| H | CO₂CH₃ | H | NH₂ | CH₃ | N | |
| H | CO₂CH₃ | H | NH₂ | OCH₃ | N | |
| H | CO₂CH₃ | H | NHCH₃ | Cl | N | |
| H | CO₂CH₃ | H | NHCH₃ | CH₃ | N | |
| H | CO₂CH₃ | H | NHCH₃ | OCH₃ | N | |
| H | CO₂CH₃ | H | N(CH₃)₂ | Cl | N | |
| H | CO₂CH₃ | H | N(CH₃)₂ | CH₃ | N | |
| H | CO₂CH₃ | H | N(CH₃)₂ | OCH₃ | N | |
| H | CO₂CH₃ | H | NHCH₃ | OCH₂CH₃ | N | |
| CH₃ | CO₂CH₃ | H | CH₃ | Cl | N | |
| CH₃ | CO₂CH₃ | H | OCH₃ | Cl | N | |
| CH₃ | CO₂CH₃ | H | CH₃ | OCH₃ | N | |
| CH₃ | CO₂CH₃ | H | CH₂CH₃ | OCH₃ | N | |
| CH₃ | CO₂CH₃ | H | OCH₃ | CH₃ | N | |
| CH₃ | CO₂CH₃ | H | OCH₃ | OCH₃ | N | |
| H | Cl | H | OCH₃ | Cl | CH | |
| H | NO₂ | H | CH₃ | CH₃ | CH | |
| H | CO₂CH₂CH₃ | H | CH₃ | OCH₃ | CH | |
| H | SO₂N(CH₃)₂ | H | OCH₃ | CH₃ | CH | |
| H | SO₂CH₃ | H | CH₃ | Cl | CH | |
| H | SO₂CH₂CH₃ | H | CH₃ | OCH₃ | N | |
| H | OCH₃ | H | CH₃ | OCH₂CH₃ | N | |
| H | OCH₂CH₃ | H | OCH₂CH₃ | CH₃ | CH | |
| H | CO₂CH₃ | 3-F | OCH₃ | OCH₃ | CH | |
| H | CO₂CH₃ | 5-Br | CH₂CH₃ | OCH₃ | CH | |
| H | CO₂CH₃ | 5-CN | CH₃ | Br | CH | |
| H | CO₂CH₃ | 6-CH₃ | CH₃ | OCH₂CH₃ | CH | |
| H | CO₂CH₃ | 5-OCH₃ | CH₃ | CH₃CH₂ | CH | |
| H | CO₂CH₃ | 5-SCH₃ | OCH₃ | Cl | CH | |
| H | CO₂CH₃ | 5-OCF₂H | CH₃ | CH₃ | CH | |

TABLE 3

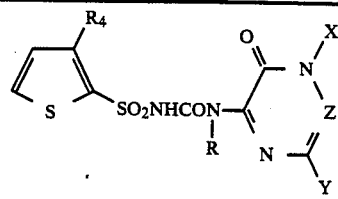

| R | R₄ | X | Y | Z | m.p. (°C.) |
|---|---|---|---|---|---|
| H | CO₂CH₃ | H | OCH₃ | CH | |
| H | CO₂CH₃ | CH₃ | Cl | CH | 230–233 (d) |
| H | CO₂CH₃ | CH₃ | Br | CH | |
| H | CO₂CH₃ | CH₃ | OCH₃ | CH | |
| H | CO₂CH₃ | CH₃ | OCH₂CH₃ | CH | |
| H | CO₂CH₃ | CH₃ | O(CH₂)₂CH₃ | CH | |
| H | CO₂CH₃ | CH₃ | CH₃ | CH | |
| H | CO₂CH₃ | CH₃ | CH₂CH₃ | CH | |
| H | CO₂CH₃ | CH₃ | (CH₂)₂CH₃ | CH | |
| H | CO₂CH₃ | CH₂CH₃ | Cl | CH | |
| H | CO₂CH₃ | CH₂CH₃ | OCH₃ | CH | |
| H | CO₂CH₃ | (CH₂)₂CH₃ | Cl | CH | |
| H | CO₂CH₃ | (CH₂)₂CH₃ | OCH₃ | CH | |
| H | CO₂CH₃ | OCH₃ | H | CH | |
| H | CO₂CH₃ | OCH₃ | CH₃ | CH | |
| H | CO₂CH₃ | OCH₃ | CH₂CH₃ | CH | |
| H | CO₂CH₃ | OCH₃ | (CH₂)₂CH₃ | CH | |
| H | CO₂CH₃ | OCH₃ | OCH₃ | CH | |
| H | CO₂CH₃ | OCH₃ | OCH₂CH₃ | CH | |
| H | CO₂CH₃ | OCH₃ | O(CH₂)₂CH₃ | CH | |
| H | CO₂CH₃ | H | SCH₃ | CH | |
| H | CO₂CH₃ | CH₃ | SCH₃ | CH | |
| H | CO₂CH₃ | OCH₃ | SCH₃ | CH | |
| H | CO₂CH₃ | CH₃ | SCH₂CH₃ | CH | |
| H | CO₂CH₃ | CH₃ | SCH₃ | N | |
| H | CO₂CH₃ | N(CH₃)₂ | SCH₃ | N | |
| H | CO₂CH₃ | OCH₃ | Cl | CH | |
| H | CO₂CH₃ | OCH₃ | Br | CH | |
| H | CO₂CH₃ | OCH₂CH₃ | Cl | CH | |
| H | CO₂CH₃ | OCH₂CH₃ | CH₃ | CH | |
| H | CO₂CH₃ | OCH₂CH₃ | OCH₃ | CH | |
| H | CO₂CH₃ | O(CH₂)₂CH₃ | Cl | CH | |
| H | CO₂CH₃ | O(CH₂)₂CH₃ | CH₃ | CH | |
| H | CO₂CH₃ | O(CH₂)₂CH₃ | OCH₃ | CH | |
| H | CO₂CH₃ | NH₂ | Cl | CH | |
| H | CO₂CH₃ | NH₂ | CH₃ | CH | |
| H | CO₂CH₃ | NH₂ | OCH₃ | CH | |
| H | CO₂CH₃ | NHCH₃ | Cl | CH | |
| H | CO₂CH₃ | NHCH₃ | CH₃ | CH | |
| H | CO₂CH₃ | NHCH₃ | OCH₃ | CH | |
| H | CO₂CH₃ | N(CH₃)₂ | Cl | CH | |
| H | CO₂CH₃ | N(CH₃)₂ | CH₃ | CH | |
| H | CO₂CH₃ | N(CH₃)₂ | OCH₃ | CH | |
| H | CO₂CH₃ | NHCH₃ | OCH₂CH₃ | CH | |
| CH₃ | CO₂CH₃ | CH₃ | Cl | CH | |
| CH₃ | CO₂CH₃ | OCH₃ | Cl | CH | |
| CH₃ | CO₂CH₃ | CH₃ | OCH₃ | CH | |
| CH₃ | CO₂CH₃ | OCH₃ | CH₃ | CH | |
| CH₃ | CO₂CH₃ | OCH₃ | OCH₃ | CH | |
| H | CO₂CH₃ | CH₃ | Cl | CF | |
| H | CO₂CH₃ | CH₃ | OCH₃ | CF | |
| H | CO₂CH₃ | OCH₃ | OCH₃ | CF | |
| H | CO₂CH₃ | OCH₃ | CH₃ | CF | |
| H | CO₂CH₃ | CH₃ | Cl | CCl | |
| H | CO₂CH₃ | CH₃ | OCH₃ | CCl | |
| H | CO₂CH₃ | CH₃ | Br | CBr | |
| H | CO₂CH₃ | CH₃ | Cl | CBr | |
| H | CO₂CH₃ | CH₃ | OCH₃ | CBr | |
| H | CO₂CH₃ | H | OCH₃ | N | |
| H | CO₂CH₃ | CH₃ | Cl | N | |
| H | CO₂CH₃ | CH₃ | Br | N | |
| H | CO₂CH₃ | CH₃ | OCH₃ | N | |
| H | CO₂CH₃ | CH₃ | OCH₂CH₃ | N | |
| H | CO₂CH₃ | CH₃ | O(CH₂)₂CH₃ | N | |
| H | CO₂CH₃ | CH₃ | CH₃ | N | |
| H | CO₂CH₃ | CH₃ | CH₂CH₃ | N | |
| H | CO₂CH₃ | CH₃ | (CH₂)₂CH₃ | N | |
| H | CO₂CH₃ | CH₂CH₃ | Cl | N | |
| H | CO₂CH₃ | CH₂CH₃ | OCH₃ | N | |
| H | CO₂CH₃ | (CH₂)₂CH₃ | Cl | N | |
| H | CO₂CH₃ | (CH₂)₂CH₃ | OCH₃ | N | |

TABLE 3-continued

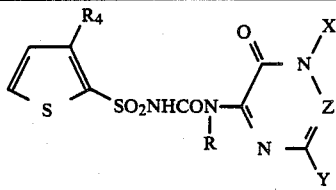

| R | R4 | X | Y | Z | m.p. (°C.) |
|---|----|---|---|---|------------|
| H | CO2CH3 | OCH3 | H | N | |
| H | CO2CH3 | OCH3 | CH3 | N | |
| H | CO2CH3 | OCH3 | CH2CH3 | N | |
| H | CO2CH3 | OCH3 | (CH2)2CH3 | N | |
| H | CO2CH3 | OCH3 | OCH3 | N | |
| H | CO2CH3 | OCH3 | OCH2CH3 | N | |
| H | CO2CH3 | OCH3 | O(CH2)2CH3 | N | |
| H | CO2CH3 | OCH3 | Cl | N | |
| H | CO2CH3 | OCH3 | Br | N | |
| H | CO2CH3 | OCH2CH3 | Cl | N | |
| H | CO2CH3 | OCH2CH3 | CH3 | N | |
| H | CO2CH3 | OCH2CH3 | OCH3 | N | |
| H | CO2CH3 | O(CH2)2CH3 | Cl | N | |
| H | CO2CH3 | O(CH2)2CH3 | CH3 | N | |
| H | CO2CH3 | O(CH2)2CH3 | OCH3 | N | |
| H | CO2CH3 | NH2 | Cl | N | |
| H | CO2CH3 | NH2 | CH3 | N | |
| H | CO2CH3 | NH2 | OCH3 | N | |
| H | CO2CH3 | NHCH3 | Cl | N | |
| H | CO2CH3 | NHCH3 | CH3 | N | |
| H | CO2CH3 | NHCH3 | OCH3 | N | |
| H | CO2CH3 | N(CH3)2 | Cl | N | |
| H | CO2CH3 | N(CH3)2 | CH3 | N | |
| H | CO2CH3 | N(CH3)2 | OCH3 | N | |
| H | CO2CH3 | NHCH3 | OCH2CH3 | N | |
| CH3 | CO2CH3 | CH3 | Cl | N | |
| CH3 | CO2CH3 | OCH3 | Cl | N | |
| CH3 | CO2CH3 | CH3 | OCH3 | N | |
| CH3 | CO2CH3 | CH2CH3 | OCH3 | N | |
| CH3 | CO2CH3 | OCH3 | CH3 | N | |
| CH3 | CO2CH3 | OCH3 | OCH3 | N | |
| H | CO2CH3 | OCH3 | Cl | CH | |
| H | CO2CH3 | CH3 | CH3 | CH | |
| H | CO2CH3 | CH3 | OCH3 | CH | |
| H | CO2CH3 | OCH3 | CH3 | CH | |
| H | CO2CH3 | CH3 | Cl | Cl | |
| H | CO2CH3 | CH3 | OCH3 | N | |
| H | CO2CH3 | CH3 | OCH2CH3 | N | |
| H | CO2CH3 | OCH3 | Cl | CH | |
| H | CO2CH3 | CH3 | CH3 | CH | |
| H | CO2CH3 | CH3 | OCH3 | CH | |
| H | CO2CH3 | OCH3 | CH3 | CH | |
| H | CO2CH3 | CH3 | Cl | CH | |
| H | CO2CH3 | CH3 | OCH3 | N | |
| H | CO2CH3 | CH3 | OCH2CH3 | N | |
| H | CO2CH3 | OCH2CH3 | CH3 | CH | |
| H | CO2CH3 | OCH3 | OCH3 | CH | |
| H | CO2CH3 | CH2CH3 | OCH3 | CH | |
| H | CO2CH3 | CH3 | Br | CH | |
| H | CO2CH3 | CH3 | OCH2CH3 | CH | |
| H | CO2CH3 | CH3 | CH2CH3 | CH | |
| H | CO2CH2CH3 | OCH3 | Cl | CH | |
| H | CO2CH2CH3 | CH3 | CH3 | CH | |
| H | CO2CH2CH3 | CH3 | OCH3 | CH | |
| H | CO2CH2CH3 | OCH3 | CH3 | CH | |
| H | CO2CH2CH3 | CH3 | Cl | CH | |
| H | CO2CH2CH3 | CH3 | OCH3 | CH | |
| H | CO2CH2CH3 | CH3 | OCH3 | N | |
| H | CO2CH2CH3 | CH3 | OCH2CH3 | N | |
| H | CO2CH2CH3 | OCH2CH3 | CH3 | CH | |
| H | CO2CH2CH3 | OCH3 | OCH3 | CH | |
| H | CO2CH2CH3 | CH2CH3 | OCH3 | CH | |
| H | CO2CH2CH3 | CH3 | Br | CH | |
| H | CO2CH2CH3 | CH3 | OCH2CH3 | CH | |
| H | CO2CH2CH3 | CH3 | CH2CH3 | CH | |
| H | CO2CH2CH=CH3 | OCH3 | Cl | CH | |
| H | CO2CH2C≡CH | CH3 | CH3 | CH | |
| H | CO2CH(CH3)2 | CH3 | OCH3 | CH | |
| H | CO2(CH2)2CH3 | OCH3 | CH3 | CH | |
| H | CO2(CH2)2OCH3 | CH3 | Cl | CH | |
| H | CO2(CH2)2OCH2CH3 | CH3 | OCH3 | N | |

TABLE 3-continued

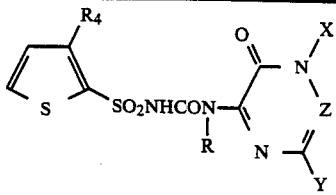

| R | R4 | X | Y | Z | m.p. (°C.) |
|---|---|---|---|---|---|
| H | CO2CH2OCH3 | CH3 | OCH2CH3 | N | |
| H | CO2(CH2)2Cl | OCH2CH3 | CH3 | CH | |
| H | CO2(CH2)2F | OCH3 | OCH3 | CH | |
| H | CO2(CH2)2Br | CH2CH3 | OCH3 | CH | |
| H | CO2(CH2)2I | CH3 | Br | CH | |
| H | CO2CH2CF3 | CH3 | OCH2CH3 | CH | |
| H | CO2CH2CH2CN | CH3 | CH2CH3 | CH | |
| CH3 | CO2CH2CH3 | OCH3 | Cl | CH | |
| H | CO2CH2CH3 | CH3 | OCH3 | CH | |
| H | F | OCH3 | CH3 | CH | |
| H | Cl | CH3 | OCH2CH3 | N | |
| H | Br | CH3 | OCH3 | N | |
| H | NO2 | CH3 | Cl | CH | |
| H | CH3 | OCH3 | CH3 | CH | |
| H | CH2CH3 | CH3 | OCH3 | CH | |
| H | (CH2)2CH3 | CH3 | CH3 | CH | |
| H | CH(CH3)2 | OCH2CH3 | CH3 | CH | |
| H | CF3 | OCH3 | OCH3 | CH | |
| H | (CH2)2F | CH2CH3 | OCH3 | CH | |
| H | (CH2)2Br | CH3 | Br | CH | |
| H | CF2H | CH3 | OCH2CH3 | CH | |
| H | CH=CF2 | CH3 | OCH3 | CH | |
| H | CCl=CCl2 | OCH3 | CH3 | CH | |
| H | CH2CH=CHCCl3 | CH3 | Cl | CH | |
| H | CH=CHCl | CH3 | OCH3 | N | |
| H | CH=CHI | CH3 | OCH2CH3 | N | |
| H | CH=CBr2 | OCH2CH3 | CH3 | CH | |
| H | CF=CFH | OCH3 | OCH3 | CH | |
| H | CH2CH=CF2 | CH2CH3 | OCH3 | CH | |
| H | CH=CHCF3 | CH3 | Br | CH | |
| H | CF=CFCH3 | CH3 | OCH2CH3 | H | |
| H | OCH3 | CH3 | CH2CH3 | CH | |
| H | OCH3 | OCH3 | Cl | CH | |
| H | OCH2CH3 | CH3 | CH3 | CH | |
| H | C(O)N(CH3)2 | CH3 | OCH2CH3 | N | |
| H | C(O)NHCH2CH3 | OCH3 | Cl | CH | |
| H | C(O)N(CH3)OCH3 | CH3 | CH3 | CH | |
| H | C(O)NHOCH2CH3 | CH3 | OCH3 | CH | |
| H | C(O)NH(CH2)2CH3 | OCH3 | CH3 | CH | |
| H | SO2N(CH3)2 | CH3 | Cl | CH | |
| H | SO2NH—cyclopropyl | OCH3 | Cl | CH | |
| CH3 | SO2N(CH3)2 | CH3 | CH3 | CH | |
| H | SO2N(CH3)2 | CH3 | OCH3 | CH | |
| H | SO2N(CH3)CH2CH=CH2 | OCH3 | CH3 | CH | |
| H | SO2N((CH2)2CH3)2 | CH3 | Cl | CH | |
| H | SO2NH2 | CH3 | OCH3 | N | |
| H | SO2N(CH3)OCH3 | CH3 | OCH2CH3 | N | |
| H | SO2N(CH3)OCH2CH3 | OCH2CH3 | CH3 | CH | |
| H | SCH3 | OCH3 | OCH3 | CH | |
| H | SCH2CH=CH3 | CH2CH3 | OCH3 | CH | |
| H | SCH2C≡CH3 | CH3 | Br | CH | |
| H | S(CH2)2CH3 | CH3 | OCH2CH3 | CH | |
| H | S(O)CH3 | CH3 | CH2CH3 | CH | |
| H | SCF2H | OCH3 | Cl | CH | |
| H | SCF2CF2H | CH3 | CH3 | CH | |
| H | S(CH2)2Cl | CH3 | OCH3 | CH | |
| H | S(CH2)2I | OCH3 | CH3 | CH | |
| H | S(CH2)3Br | CH3 | Cl | CH | |
| H | S(O)CF2CF2H | CH3 | OCH3 | N | |
| H | S(O)(CH2)2I | CH3 | OCH2CH3 | N | |
| H | S(O)2CH3 | OCH3 | Cl | CH | |
| H | S(O)2CH2CH3 | CH3 | CH3 | CH | |
| H | S(O)2CH2CH=CH2 | CH3 | OCH3 | CH | |
| H | S(O)2CH2C≡CH | OCH3 | CH3 | CH | |
| H | S(O)2CF2H | CH3 | Cl | CH | |
| H | S(O)2CF2CF2H | CH3 | OCH3 | N | |
| H | S(O)2(CH2)2I | CH3 | OCH2CH3 | N | |
| H | C(O)CH3 | OCH3 | Cl | CH | |
| H | C(O)(CH2)3CH3 | CH3 | CH3 | CH | |
| H | C(O)CH2CH3 | CH3 | OCH3 | CH | |
| H | C(O)—cyclo-C3H5 | OCH3 | CH3 | CH | |

TABLE 3-continued

| R | R4 | X | Y | Z | m.p. (°C.) |
|---|---|---|---|---|---|
| H | C(O)—cyclo-C4H7 | CH3 | Cl | CH | |
| H | C(O)—cyclo-C5H9 | OCH3 | Cl | CH | |
| H | C(O)—cyclo-C3F5 | CH3 | CH3 | CH | |
| H | C(O)CF3 | CH3 | OCH3 | CH | |
| H | C(O)(CH2)3CCl2H | OCH3 | CH3 | CH | |
| H | C(O)(CH2)4F | CH3 | Cl | CH | |
| H | C(O)—cyclo-(CHCH2CCl2) | CH3 | OCH3 | N | |
| H | L-1, $R_h$ = H | OCH2CH3 | CH3 | CH | |
| H | L-1, $R_h$ = CH3 | OCH3 | OCH3 | CH | |
| H | L-2, $R_h$ = H | CH2CH3 | OCH3 | CH | |
| H | L-2, $R_h$ = CH3 | CH3 | Br | CH | |
| H | L-3 | CH3 | OCH2CH3 | CH | |
| H | L-4 | CH3 | CH2CH3 | CH | |
| H | L-5 | OCH3 | Cl | CH | |
| H | L-6 | CH3 | CH3 | CH | |
| H | L-7 | CH3 | OCH3 | CH | |
| H | L-8 | OCH3 | CH3 | CH | |
| H | L-9 | CH3 | Cl | CH | |
| H | L-10 | CH3 | OCH3 | N | |
| H | L-11 | CH3 | OCH2CH3 | N | |
| H | L-12 | OCH3 | Cl | CH | |
| H | L-13 | CH3 | CH3 | CH | |
| H | L-14 | CH3 | OCH3 | CH | |
| H | L-15 | OCH3 | CH3 | CH | |
| H | L-16, $R_i$ = H | CH3 | Cl | CH | |
| H | L-16, $R_i$ = CH3 | CH3 | OCH3 | N | |
| H | L-17 | CH3 | OCH2CH3 | N | |
| H | L-18 | OCH3 | Cl | CH | |
| H | L-19 | CH3 | CH3 | CH | |
| H | L-20 | CH3 | OCH3 | CH | |
| H | L-21 | OCH3 | CH3 | CH | |
| H | L-22 | CH3 | Cl | CH | |
| H | L-23 | OCH3 | Cl | CH | |
| H | L-24 | CH3 | CH3 | CH | |
| H | L-25 | CH3 | OCH3 | CH | |
| H | L-26, $R_j$ = H | OCH3 | CH3 | CH | |
| H | L-26, $R_j$ = CH3 | CH3 | Cl | CH | |
| H | L-26, $R_j$ = CH2CH3 | CH3 | OCH3 | N | |
| H | L-27, $R_j$ = H | CH3 | OCH2CH3 | N | |
| H | L-27, $R_j$ = CH3 | OCH2CH3 | CH3 | CH | |
| H | L-27, $R_j$ = CH2CH3 | OCH3 | OCH3 | CH | |
| H | L-28, $R_k$ = H | CH2CH3 | OCH3 | CH | |
| H | L-28, $R_k$ = CH3 | CH3 | Br | CH | |
| H | L-28, $R_k$ = CH2CH3 | CH3 | OCH2CH3 | CH | |
| H | L-28, $R_k$ = OCH3 | CH3 | CH2CH3 | CH | |
| H | L-28, $R_k$ = OCH2CH3 | OCH3 | Cl | CH | |
| H | L-28, $R_k$ = SCH3 | CH3 | CH3 | CH | |
| H | L-28, $R_k$ = SCH2CH3 | CH3 | OCH3 | CH | |
| H | L-29, $R_k$ = H | OCH3 | CH3 | CH | |
| H | L-29, $R_k$ = CH3 | CH3 | Cl | CH | |
| H | L-29, $R_k$ = CH2CH3 | CH3 | OCH3 | N | |
| H | L-29, $R_k$ = OCH3 | CH3 | OCH2CH3 | N | |
| H | L-29, $R_k$ = OCH2CH3 | OCH3 | Cl | CH | |
| H | L-29, $R_k$ = SCH3 | CH3 | CH3 | CH | |
| H | L-29, $R_k$ = SCH2CH3 | CH3 | OCH3 | CH | |
| H | L-30, $R_m$ = H | OCH3 | CH3 | CH | |
| H | L-30, $R_m$ = CH3 | CH3 | Cl | CH | |
| H | L-30, $R_m$ = CH2CH3 | CH3 | OCH3 | N | |
| H | L-31, $R_m$ = H | CH3 | OCH2CH3 | N | |
| H | L-31, $R_m$ = CH3 | OCH3 | Cl | CH | |
| H | L-31, $R_m$ = CH2CH3 | OCH3 | CH3 | CH | |
| H | L-32, $R_m$ = H | CH3 | OCH3 | CH | |
| H | L-32, $R_m$ = CH3 | OCH3 | CH3 | CH | |
| H | L-32, $R_m$ = CH2CH3 | CH3 | Cl | CH | |
| H | L-33, $R_n$ = H | CH3 | CH3 | N | |
| H | L-33, $R_n$ = CH3 | CH3 | OCH3 | CH | |

TABLE 4

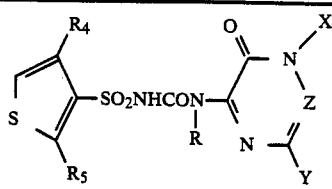

| R | R₄ | R₅ | X | Y | Z | m.p. (°C.) |
|---|---|---|---|---|---|---|
| H | CO₂CH₃ | H | H | OCH₃ | CH | |
| H | CO₂CH₃ | H | CH₃ | Cl | CH | |
| H | CO₂CH₃ | H | CH₃ | Br | CH | |
| H | CO₂CH₃ | H | CH₃ | OCH₃ | CH | |
| H | CO₂CH₃ | H | CH₃ | OCH₂CH₃ | CH | |
| H | CO₂CH₃ | H | CH₃ | O(CH₂)₂CH₃ | CH | |
| H | CO₂CH₃ | H | CH₃ | CH₃ | CH | |
| H | CO₂CH₃ | H | CH₃ | CH₂CH₃ | CH | |
| H | CO₂CH₃ | H | CH₃ | (CH₂)₂CH₃ | CH | |
| H | CO₂CH₃ | H | CH₂CH₃ | Cl | CH | |
| H | CO₂CH₃ | H | CH₂CH₃ | OCH₃ | CH | |
| H | CO₂CH₃ | H | (CH₂)₂CH₃ | Cl | CH | |
| H | CO₂CH₃ | H | (CH₂)₂CH₃ | OCH₃ | CH | |
| H | CO₂CH₃ | H | OCH₃ | H | CH | |
| H | CO₂CH₃ | H | OCH₃ | CH₃ | CH | |
| H | CO₂CH₃ | H | OCH₃ | CH₂CH₃ | CH | |
| H | CO₂CH₃ | H | OCH₃ | (CH₂)₂CH₃ | CH | |
| H | CO₂CH₃ | H | OCH₃ | OCH₃ | CH | |
| H | CO₂CH₃ | H | OCH₃ | OCH₂CH₃ | CH | |
| H | CO₂CH₃ | H | OCH₃ | O(CH₂)₂CH₃ | CH | |
| H | CO₂CH₃ | H | CH₃ | SCH₃ | CH | |
| H | CO₂CH₃ | H | CH₃ | SCH₃ | N | |
| H | CO₂CH₃ | H | OCH₃ | SCH₃ | CH | |
| H | CO₂CH₃ | H | CH₃ | SCH₂CH₃ | CH | |
| H | CO₂CH₃ | H | NHCH₃ | SCH₃ | N | |
| H | CO₂CH₃ | H | CH₂CH₃ | SCH₃ | CH | |
| H | CO₂CH₃ | H | OCH₃ | Cl | CH | |
| H | CO₂CH₃ | H | OCH₃ | Br | CH | |
| H | CO₂CH₃ | H | OCH₂CH₃ | Cl | CH | |
| H | CO₂CH₃ | H | OCH₂CH₃ | CH₃ | CH | |
| H | CO₂CH₃ | H | OCH₂CH₃ | OCH₃ | CH | |
| H | CO₂CH₃ | H | O(CH₂)₂CH₃ | Cl | CH | |
| H | CO₂CH₃ | H | O(CH₂)₂CH₃ | CH₃ | CH | |
| H | CO₂CH₃ | H | O(CH₂)₂CH₃ | OCH₃ | CH | |
| H | CO₂CH₃ | H | NH₂ | Cl | CH | |
| H | CO₂CH₃ | H | NH₂ | CH₃ | CH | |
| H | CO₂CH₃ | H | NH₂ | OCH₃ | CH | |
| H | CO₂CH₃ | H | NHCH₃ | Cl | CH | |
| H | CO₂CH₃ | H | NHCH₃ | CH₃ | CH | |
| H | CO₂CH₃ | H | NHCH₃ | OCH₃ | CH | |
| H | CO₂CH₃ | H | N(CH₃)₂ | Cl | CH | |
| H | CO₂CH₃ | H | N(CH₃)₂ | CH₃ | CH | |
| H | CO₂CH₃ | H | N(CH₃)₂ | OCH₃ | CH | |
| H | CO₂CH₃ | H | NHCH₃ | OCH₂CH₃ | CH | |
| CH₃ | CO₂CH₃ | H | CH₃ | Cl | CH | |
| CH₃ | CO₂CH₃ | H | OCH₃ | Cl | CH | |
| CH₃ | CO₂CH₃ | H | CH₃ | OCH₃ | CH | |
| CH₃ | CO₂CH₃ | H | OCH₃ | CH₃ | CH | |
| CH₃ | CO₂CH₃ | H | OCH₃ | OCH₃ | CH | |
| H | CO₂CH₃ | H | CH₃ | Cl | CF | |
| H | CO₂CH₃ | H | CH₃ | OCH₃ | CF | |
| H | CO₂CH₃ | H | OCH₃ | OCH₃ | CF | |
| H | CO₂CH₃ | H | OCH₃ | CH₃ | CF | |
| H | CO₂CH₃ | H | CH₃ | Cl | CCl | |
| H | CO₂CH₃ | H | CH₃ | OCH₃ | CCl | |
| H | CO₂CH₃ | H | CH₃ | Br | CBr | |
| H | CO₂CH₃ | H | CH₃ | Cl | CBr | |
| H | CO₂CH₃ | H | CH₃ | OCH₃ | CBr | |
| H | CO₂CH₃ | H | H | OCH₃ | N | |
| H | CO₂CH₃ | H | CH₃ | Cl | N | |
| H | CO₂CH₃ | H | CH₃ | Br | N | |
| H | CO₂CH₃ | H | CH₃ | OCH₃ | N | |
| H | CO₂CH₃ | H | CH₃ | OCH₂CH₃ | N | |
| H | CO₂CH₃ | H | CH₃ | O(CH₂)₂CH₃ | N | |
| H | CO₂CH₃ | H | CH₃ | CH₃ | N | |
| H | CO₂CH₃ | H | CH₃ | CH₂CH₃ | N | |
| H | CO₂CH₃ | H | CH₃ | (CH₂)₂CH₃ | N | |
| H | CO₂CH₃ | H | CH₂CH₃ | Cl | N | |
| H | CO₂CH₃ | H | CH₂CH₃ | OCH₃ | N | |
| H | CO₂CH₃ | H | (CH₂)₂CH₃ | Cl | N | |
| H | CO₂CH₃ | H | (CH₂)₂CH₃ | OCH₃ | N | |

TABLE 4-continued

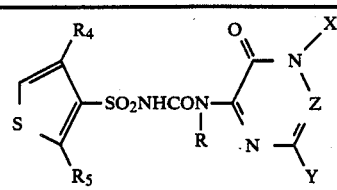

| R | R4 | R5 | X | Y | Z | m.p. (°C.) |
|---|---|---|---|---|---|---|
| H | CO2CH3 | H | OCH3 | H | N | |
| H | CO2CH3 | H | OCH3 | CH3 | N | |
| H | CO2CH3 | H | OCH3 | CH2CH3 | N | |
| H | CO2CH3 | H | OCH3 | (CH2)2CH3 | N | |
| H | CO2CH3 | H | OCH3 | OCH3 | N | |
| H | CO2CH3 | H | OCH3 | OCH2CH3 | N | |
| H | CO2CH3 | H | OCH3 | O(CH2)2CH3 | N | |
| H | CO2CH3 | H | OCH3 | Cl | N | |
| H | CO2CH3 | H | OCH3 | Br | N | |
| H | CO2CH3 | H | OCH2CH3 | Cl | N | |
| H | CO2CH3 | H | OCH2CH3 | CH3 | N | |
| H | CO2CH3 | H | OCH2CH3 | OCH3 | N | |
| H | CO2CH3 | H | O(CH2)2CH3 | Cl | N | |
| H | CO2CH3 | H | O(CH2)2CH3 | CH3 | N | |
| H | CO2CH3 | H | O(CH2)2CH3 | OCH3 | N | |
| H | CO2CH3 | H | NH2 | Cl | N | |
| H | CO2CH3 | H | NH2 | CH3 | N | |
| H | CO2CH3 | H | NH2 | OCH3 | N | |
| H | CO2CH3 | H | NHCH3 | Cl | N | |
| H | CO2CH3 | H | NHCH3 | CH3 | N | |
| H | CO2CH3 | H | NHCH3 | OCH3 | N | |
| H | CO2CH3 | H | N(CH3)2 | Cl | N | |
| H | CO2CH3 | H | N(CH3)2 | CH3 | N | |
| H | CO2CH3 | H | N(CH3)2 | OCH3 | N | |
| H | CO2CH3 | H | NHCH3 | OCH2CH3 | N | |
| CH3 | CO2CH3 | H | CH3 | Cl | N | |
| CH3 | CO2CH3 | H | OCH3 | Cl | N | |
| CH3 | CO2CH3 | H | CH3 | OCH3 | N | |
| CH3 | CO2CH3 | H | CH2CH3 | OCH3 | N | |
| CH3 | CO2CH3 | H | OCH3 | CH3 | N | |
| CH3 | CO2CH3 | H | OCH3 | OCH3 | N | |
| H | CO2CH3 | F | OCH3 | Cl | CH | |
| H | CO2CH3 | Cl | CH3 | CH3 | CH | |
| H | CO2CH3 | Br | CH3 | OCH3 | CH | |
| H | CO2CH3 | CH3 | CH3 | Cl | Cl | |
| H | CO2CH3 | F | CH3 | CH3 | CH | |
| H | CO2CH3 | Cl | CH3 | OCH3 | CH | |
| H | CO2CH3 | Br | OCH3 | CH3 | CH | |
| H | CO2CH3 | CH3 | CH3 | OCH3 | N | |
| H | CO2CH3 | F | CH3 | OCH2CH3 | N | |
| H | CO2CH3 | Cl | OCH2CH3 | CH3 | CH | |
| H | CO2CH3 | F | CH2CH3 | OCH3 | CH | |
| H | CO2CH3 | CH3 | CH3 | Br | CH | |
| H | CO2CH2CH3 | H | OCH3 | Cl | CH | |
| H | CO2CH2CH3 | H | CH3 | CH3 | CH | |
| H | CO2CH2CH3 | H | CH3 | OCH3 | CH | |
| H | CO2CH2CH3 | H | OCH3 | CH3 | CH | |
| H | CO2CH2CH3 | H | CH3 | Cl | CH | |
| H | CO2CH2CH3 | H | CH3 | OCH3 | CH | |
| H | CO2CH2CH3 | H | CH3 | OCH3 | N | |
| H | CO2CH2CH3 | H | CH3 | OCH2CH3 | N | |
| H | CO2CH2CH3 | H | OCH2CH3 | CH3 | CH | |
| H | CO2CH2CH3 | H | OCH3 | OCH3 | CH | |
| H | CO2CH2CH3 | H | CH2CH3 | OCH3 | CH | |
| H | CO2CH2CH3 | H | CH3 | Br | CH | |
| H | CO2CH2CH3 | H | CH3 | OCH2CH3 | CH | |
| H | CO2CH2CH3 | H | CH3 | CH2CH3 | CH | |
| H | CO2CH2CH=CH3 | H | OCH3 | Cl | CH | |
| H | CO2CH2C≡CH | H | CH3 | CH3 | CH | |
| H | CO2CH(CH3)2 | H | CH3 | OCH3 | CH | |
| H | CO2(CH2)2CH3 | H | OCH3 | CH3 | CH | |
| H | CO2(CH2)2OCH3 | H | CH3 | Cl | CH | |
| H | CO2(CH2)2OCH2CH3 | H | CH3 | OCH3 | N | |
| H | CO2CH2OCH3 | H | CH3 | OCH2CH3 | N | |
| H | CO2(CH2)2Cl | H | OCH2CH3 | CH3 | CH | |
| H | CO2(CH2)2F | H | OCH3 | OCH3 | CH | |
| H | CO2(CH2)2Br | H | CH2CH3 | OCH3 | CH | |
| H | CO2(CH2)2I | H | CH3 | Br | CH | |
| H | CO2CH2CF3 | H | CH3 | OCH2CH3 | CH | |
| H | CO2CH2CH2CN | H | CH3 | CH2CH3 | CH | |
| CH3 | CO2CH2CH3 | H | OCH3 | Cl | CH | |

TABLE 4-continued

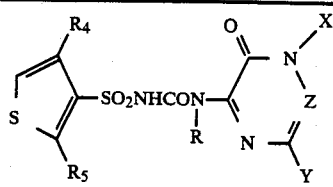

| R | R4 | R5 | X | Y | Z | m.p. (°C.) |
|---|---|---|---|---|---|---|
| H | CO$_2$CH$_2$CH$_3$ | OCH$_3$ | CH$_3$ | OCH$_3$ | CH | |
| H | F | H | OCH$_3$ | CH$_3$ | CH | |
| H | Cl | H | CH$_3$ | OCH$_2$CH$_3$ | N | |
| H | Br | H | CH$_3$ | OCH$_3$ | N | |
| H | NO$_2$ | H | CH$_3$ | Cl | CH | |
| H | CH$_3$ | H | OCH$_3$ | CH$_3$ | CH | |
| H | CH$_2$CH$_3$ | H | CH$_3$ | OCH$_3$ | CH | |
| H | (CH$_2$)$_2$CH$_3$ | H | CH$_3$ | CH$_3$ | CH | |
| H | CH(CH$_3$)$_2$ | H | OCH$_2$CH$_3$ | CH$_3$ | CH | |
| H | CF$_3$ | H | OCH$_3$ | OCH$_3$ | CH | |
| H | (CH$_2$)$_2$F | H | CH$_2$CH$_3$ | OCH$_3$ | CH | |
| H | (CH$_2$)$_2$Br | H | CH$_3$ | Br | CH | |
| H | CF$_2$H | H | CH$_3$ | OCH$_2$CH$_3$ | CH | |
| H | CH=CF$_2$ | H | CH$_3$ | OCH$_3$ | CH | |
| H | CCl=CCl$_2$ | H | OCH$_3$ | CH$_3$ | CH | |
| H | CH$_2$CH=CHCCl$_2$ | H | CH$_3$ | Cl | CH | |
| H | CH=CHCl | H | CH$_3$ | OCH$_3$ | N | |
| H | CH=CHI | H | CH$_3$ | OCH$_2$CH$_3$ | N | |
| H | CH=CBr$_2$ | H | OCH$_2$CH$_3$ | CH$_3$ | CH | |
| H | CF=CFH | H | OCH$_3$ | OCH$_3$ | CH | |
| H | CH$_2$CH=CF$_2$ | H | CH$_2$CH$_3$ | OCH$_3$ | CH | |
| H | CH=CHCF$_3$ | H | CH$_3$ | Br | CH | |
| H | CF=CFCH$_3$ | H | CH$_3$ | OCH$_2$CH$_3$ | H | |
| H | OCH$_3$ | H | CH$_3$ | CH$_2$CH$_3$ | CH | |
| H | OCH$_3$ | Cl | OCH$_3$ | Cl | CH | |
| H | OCH$_2$CH$_3$ | H | CH$_3$ | CH$_3$ | CH | |
| H | C(O)N(CH$_3$)$_2$ | H | CH$_3$ | OCH$_2$CH$_3$ | N | |
| H | C(O)NHCH$_2$CH$_3$ | H | OCH$_3$ | Cl | CH | |
| H | C(O)N(CH$_3$)OCH$_3$ | H | CH$_3$ | CH$_3$ | CH | |
| H | C(O)NHOCH$_2$CH$_3$ | H | CH$_3$ | OCH$_3$ | CH | |
| H | C(O)NH(CH$_2$)$_2$CH$_3$ | H | OCH$_3$ | CH$_3$ | CH | |
| H | SO$_2$N(CH$_3$)$_2$ | H | CH$_3$ | Cl | CH | |
| H | SO$_2$NH—cyclopropyl | H | OCH$_3$ | Cl | CH | |
| CH$_3$ | SO$_2$N(CH$_3$)$_2$ | H | CH$_3$ | CH$_3$ | CH | |
| H | SO$_2$N(CH$_3$)$_2$ | CH$_3$ | CH$_3$ | OCH$_3$ | CH | |
| H | SO$_2$N(CH$_3$)CH$_2$CH=CH$_2$ | H | OCH$_3$ | CH$_3$ | CH | |
| H | SO$_2$N((CH$_2$)$_2$CH$_3$)$_2$ | H | CH$_3$ | Cl | CH | |
| H | SO$_2$NH$_2$ | H | CH$_3$ | OCH$_3$ | N | |
| H | SO$_2$N(CH$_3$)OCH$_3$ | H | CH$_3$ | OCH$_2$CH$_3$ | N | |
| H | SO$_2$N(CH$_3$)OCH$_2$CH$_3$ | H | OCH$_2$CH$_3$ | CH$_3$ | CH | |
| H | SCH$_3$ | H | OCH$_3$ | OCH$_3$ | CH | |
| H | SCH$_2$CH=CH$_3$ | H | CH$_2$CH$_3$ | OCH$_3$ | CH | |
| H | SCH$_2$C≡CH$_3$ | H | CH$_2$ | Br | CH | |
| H | S(CH$_2$)$_2$CH$_3$ | H | CH$_3$ | OCH$_2$CH$_3$ | CH | |
| H | S(O)CH$_3$ | H | CH$_3$ | CH$_2$CH$_3$ | CH | |
| H | SCF$_2$H | H | OCH$_3$ | Cl | CH | |
| H | SCF$_2$CF$_2$H | H | CH$_3$ | CH$_3$ | CH | |
| H | S(CH$_2$)$_2$Cl | H | CH$_3$ | OCH$_3$ | CH | |
| H | S(CH$_2$)$_2$I | H | OCH$_3$ | CH$_3$ | CH | |
| H | S(CH$_2$)$_3$Br | H | CH$_3$ | Cl | CH | |
| H | S(O)CF$_2$CF$_2$H | H | CH$_3$ | OCH$_3$ | N | |
| H | S(O)(CH$_2$)$_2$I | H | CH$_3$ | OCH$_2$CH$_3$ | N | |
| H | S(O)$_2$CH$_3$ | H | OCH$_3$ | Cl | CH | |
| H | S(O)$_2$CH$_2$CH$_3$ | H | CH$_3$ | CH$_3$ | CH | |
| H | S(O)$_2$CH$_2$CH=CH$_2$ | H | CH$_3$ | OCH$_3$ | CH | |
| H | S(O)$_2$CH$_2$C≡CH | H | OCH$_3$ | CH$_3$ | CH | |
| H | S(O)$_2$CF$_2$H | H | CH$_3$ | Cl | CH | |
| H | S(O)$_2$CF$_2$CF$_2$H | H | CH$_3$ | OCH$_3$ | N | |
| H | S(O)$_2$(CH$_2$)$_2$I | H | CH$_3$ | OCH$_2$CH$_3$ | N | |
| H | C(O)CH$_3$ | H | OCH$_3$ | Cl | CH | |
| H | C(O)(CH$_2$)$_3$CH$_3$ | H | CH$_3$ | CH$_3$ | CH | |
| H | C(O)CH$_2$CH$_3$ | H | CH$_3$ | OCH$_3$ | CH | |
| H | C(O)—cyclo-C$_3$H$_5$ | H | OCH$_3$ | CH$_3$ | CH | |
| H | C(O)—cyclo-C$_4$H$_7$ | H | CH$_3$ | Cl | CH | |
| H | C(O)—cyclo-C$_5$H$_9$ | H | OCH$_3$ | Cl | CH | |
| H | C(O)—cyclo-C$_3$F$_5$ | H | CH$_3$ | CH$_3$ | CH | |
| H | C(O)CF$_3$ | H | CH$_3$ | OCH$_3$ | CH | |
| H | C(O)(CH$_2$)$_3$CCl$_2$H | H | OCH$_3$ | CH$_3$ | CH | |
| H | C(O)(CH$_2$)$_4$F | H | CH$_3$ | Cl | CH | |
| H | C(O)—cyclo-(CHCH$_2$CCl$_2$) | H | CH$_3$ | OCH$_3$ | N | |
| H | L-1, R$_h$ = H | H | OCH$_2$CH$_3$ | CH$_3$ | CH | |

TABLE 4-continued

| R | R$_4$ | R$_5$ | X | Y | Z | m.p. (°C.) |
|---|---|---|---|---|---|---|
| H | L-1, R$_h$ = CH$_3$ | H | OCH$_3$ | OCH$_3$ | CH | |
| H | L-2, R$_h$ = H | H | CH$_2$CH$_3$ | OCH$_3$ | CH | |
| H | L-2, R$_h$ = CH$_3$ | H | CH$_3$ | Br | CH | |
| H | L-3 | H | CH$_3$ | OCH$_2$CH$_3$ | CH | |
| H | L-4 | H | CH$_3$ | CH$_2$CH$_3$ | CH | |
| H | L-5 | H | OCH$_3$ | Cl | CH | |
| H | L-6 | H | CH$_3$ | CH$_3$ | CH | |
| H | L-7 | H | CH$_3$ | OCH$_3$ | CH | |
| H | L-8 | H | OCH$_3$ | CH$_3$ | CH | |
| H | L-9 | H | OCH$_3$ | Cl | CH | |
| H | L-10 | H | CH$_3$ | OCH$_3$ | N | |
| H | L-11 | H | CH$_3$ | OCH$_2$CH$_3$ | N | |
| H | L-12 | H | OCH$_3$ | Cl | CH | |
| H | L-13 | H | CH$_3$ | CH$_3$ | CH | |
| H | L-14 | H | CH$_3$ | OCH$_3$ | CH | |
| H | L-15 | H | OCH$_3$ | CH$_3$ | CH | |
| H | L-16, R$_i$ = H | H | CH$_3$ | Cl | CH | |
| H | L-16, R$_i$ = CH$_3$ | H | CH$_3$ | OCH$_3$ | N | |
| H | L-17 | H | CH$_3$ | OCH$_2$CH$_3$ | N | |
| H | L-18 | H | OCH$_3$ | Cl | CH | |
| H | L-19 | H | CH$_3$ | CH$_3$ | CH | |
| H | L-20 | H | CH$_3$ | OCH$_3$ | CH | |
| H | L-21 | H | OCH$_3$ | CH$_3$ | CH | |
| H | L-22 | H | CH$_3$ | Cl | CH | |
| H | L-23 | H | OCH$_3$ | Cl | CH | |
| H | L-24 | H | CH$_3$ | CH$_3$ | CH | |
| H | L-25 | H | CH$_3$ | OCH$_3$ | CH | |
| H | L-26, R$_j$ = H | H | OCH$_3$ | CH$_3$ | CH | |
| H | L-26, R$_j$ = CH$_3$ | H | CH$_3$ | Cl | CH | |
| H | L-26, R$_j$ = CH$_2$CH$_3$ | H | CH$_3$ | OCH$_3$ | N | |
| H | L-27, R$_j$ = H | H | CH$_3$ | OCH$_2$CH$_3$ | N | |
| H | L-27, R$_j$ = CH$_3$ | H | OCH$_2$CH$_3$ | CH$_3$ | CH | |
| H | L-27, R$_j$ = CH$_2$CH$_3$ | H | OCH$_3$ | OCH$_3$ | CH | |
| H | L-28, R$_k$ = H | H | CH$_2$CH$_3$ | OCH$_3$ | CH | |
| H | L-28, R$_k$ = CH$_3$ | H | CH$_3$ | Br | CH | |
| H | L-28, R$_k$ = CH$_2$CH$_3$ | H | CH$_3$ | OCH$_2$CH$_3$ | CH | |
| H | L-28, R$_k$ = OCH$_3$ | H | CH$_3$ | CH$_2$CH$_3$ | CH | |
| H | L-28, R$_k$ = OCH$_2$CH$_3$ | H | OCH$_3$ | Cl | CH | |
| H | L-28, R$_k$ = SCH$_3$ | H | CH$_3$ | CH$_3$ | CH | |
| H | L-28, R$_k$ = SCH$_2$CH$_3$ | H | CH$_3$ | OCH$_3$ | CH | |
| H | L-29, R$_k$ = H | H | OCH$_3$ | CH$_3$ | CH | |
| H | L-29, R$_k$ = CH$_3$ | H | CH$_3$ | Cl | CH | |
| H | L-29, R$_k$ = CH$_2$CH$_3$ | H | CH$_3$ | OCH$_3$ | N | |
| H | L-29, R$_k$ = OCH$_3$ | H | CH$_3$ | OCH$_2$CH$_3$ | N | |
| H | L-29, R$_k$ = OCH$_2$CH$_3$ | H | OCH$_3$ | Cl | CH | |
| H | L-29, R$_k$ = SCH$_3$ | H | CH$_3$ | CH$_3$ | CH | |
| H | L-29, R$_k$ = SCH$_2$CH$_3$ | H | CH$_3$ | OCH$_3$ | CH | |
| H | L-30, R$_m$ = H | H | OCH$_3$ | CH$_3$ | CH | |
| H | L-30, R$_m$ = CH$_3$ | H | CH$_3$ | Cl | CH | |
| H | L-30, R$_m$ = CH$_2$CH$_3$ | H | CH$_3$ | OCH$_3$ | N | |
| H | L-31, R$_m$ = H | H | CH$_3$ | OCH$_2$CH$_3$ | N | |
| H | L-31, R$_m$ = CH$_3$ | H | OCH$_3$ | Cl | CH | |
| H | L-31, R$_m$ = CH$_2$CH$_3$ | H | CH$_3$ | CH$_3$ | CH | |
| H | L-32, R$_m$ = H | H | CH$_3$ | OCH$_3$ | CH | |
| H | L-32, R$_m$ = CH$_3$ | H | OCH$_3$ | CH$_3$ | CH | |
| H | L-32, R$_m$ = CH$_2$CH$_3$ | H | CH$_3$ | Cl | CH | |
| H | L-33, R$_n$ = H | H | CH$_3$ | CH$_3$ | N | |
| H | L-33, R$_n$ = CH$_3$ | H | CH$_3$ | OCH$_3$ | CH | |

TABLE 5

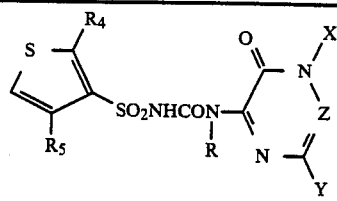

| R | R₄ | R₅ | X | Y | Z | m.p. (°C.) |
|---|---|---|---|---|---|---|
| H | CO₂CH₃ | H | H | OCH₃ | CH | |
| H | CO₂CH₃ | H | CH₃ | Cl | CH | |
| H | CO₂CH₃ | H | CH₃ | Br | CH | |
| H | CO₂CH₃ | H | CH₃ | OCH₃ | CH | |
| H | CO₂CH₃ | H | CH₃ | OCH₂CH₃ | CH | |
| H | CO₂CH₃ | H | CH₃ | O(CH₂)₂CH₃ | CH | |
| H | CO₂CH₃ | H | CH₃ | CH₃ | CH | |
| H | CO₂CH₃ | H | CH₃ | CH₂CH₃ | CH | |
| H | CO₂CH₃ | H | CH₃ | (CH₂)₂CH₃ | CH | |
| H | CO₂CH₃ | H | CH₂CH₃ | Cl | CH | |
| H | CO₂CH₃ | H | CH₂CH₃ | OCH₃ | CH | |
| H | CO₂CH₃ | H | (CH₂)₂CH₃ | Cl | CH | |
| H | CO₂CH₃ | H | (CH₂)₂CH₃ | OCH₃ | CH | |
| H | CO₂CH₃ | H | OCH₃ | H | CH | |
| H | CO₂CH₃ | H | OCH₃ | CH₃ | CH | |
| H | CO₂CH₃ | H | OCH₃ | CH₂CH₃ | CH | |
| H | CO₂CH₃ | H | OCH₃ | (CH₂)₂CH₃ | CH | |
| H | CO₂CH₃ | H | OCH₃ | OCH₃ | CH | |
| H | CO₂CH₃ | H | OCH₃ | OCH₂CH₃ | CH | |
| H | CO₂CH₃ | H | OCH₃ | O(CH₂)₂CH₃ | CH | |
| H | CO₂CH₃ | H | CH₃ | SCH₃ | CH | |
| H | CO₂CH₃ | H | H | SCH₃ | CH | |
| H | CO₂CH₃ | H | CH₃ | SCH₃ | N | |
| H | CO₂CH₃ | H | OCH₃ | SCH₃ | CH | |
| H | CO₂CH₃ | H | OCH₃ | SCH₃ | N | |
| H | CO₂CH₃ | H | NH₂ | SCH₃ | N | |
| H | CO₂CH₃ | H | CH₃ | SCH₂CH₃ | CH | |
| H | CO₂CH₃ | H | OCH₃ | Cl | CH | |
| H | CO₂CH₃ | H | OCH₃ | Br | CH | |
| H | CO₂CH₃ | H | OCH₂CH₃ | Cl | CH | |
| H | CO₂CH₃ | H | OCH₂CH₃ | CH₃ | CH | |
| H | CO₂CH₃ | H | OCH₂CH₃ | OCH₃ | CH | |
| H | CO₂CH₃ | H | O(CH₂)₂CH₃ | Cl | CH | |
| H | CO₂CH₃ | H | O(CH₂)₂CH₃ | CH₃ | CH | |
| H | CO₂CH₃ | H | O(CH₂)₂CH₃ | OCH₃ | CH | |
| H | CO₂CH₃ | H | NH₂ | Cl | CH | |
| H | CO₂CH₃ | H | NH₂ | CH₃ | CH | |
| H | CO₂CH₃ | H | NH₂ | OCH₃ | CH | |
| H | CO₂CH₃ | H | NHCH₃ | Cl | CH | |
| H | CO₂CH₃ | H | NHCH₃ | CH₃ | CH | |
| H | CO₂CH₃ | H | NHCH₃ | OCH₃ | CH | |
| H | CO₂CH₃ | H | N(CH₃)₂ | Cl | CH | |
| H | CO₂CH₃ | H | N(CH₃)₂ | CH₃ | CH | |
| H | CO₂CH₃ | H | N(CH₃)₂ | OCH₃ | CH | |
| H | CO₂CH₃ | H | NHCH₃ | OCH₂CH₃ | CH | |
| CH₃ | CO₂CH₃ | H | CH₃ | Cl | CH | |
| CH₃ | CO₂CH₃ | H | OCH₃ | Cl | CH | |
| CH₃ | CO₂CH₃ | H | CH₃ | OCH₃ | CH | |
| CH₃ | CO₂CH₃ | H | OCH₃ | CH₃ | CH | |
| CH₃ | CO₂CH₃ | H | OCH₃ | OCH₃ | CH | |
| H | CO₂CH₃ | H | CH₃ | Cl | CF | |
| H | CO₂CH₃ | H | CH₃ | OCH₃ | CF | |
| H | CO₂CH₃ | H | OCH₃ | OCH₃ | CF | |
| H | CO₂CH₃ | H | OCH₃ | CH₃ | CF | |
| H | CO₂CH₃ | H | CH₃ | Cl | CCl | |
| H | CO₂CH₃ | H | CH₃ | OCH₃ | CCl | |
| H | CO₂CH₃ | H | CH₃ | Br | CBr | |
| H | CO₂CH₃ | H | CH₃ | Cl | CBr | |
| H | CO₂CH₃ | H | CH₃ | OCH₃ | CBr | |
| H | CO₂CH₃ | H | H | OCH₃ | N | |
| H | CO₂CH₃ | H | CH₃ | Cl | N | |
| H | CO₂CH₃ | H | CH₃ | Br | N | |
| H | CO₂CH₃ | H | CH₃ | OCH₃ | N | |
| H | CO₂CH₃ | H | CH₃ | OCH₂CH₃ | N | |
| H | CO₂CH₃ | H | CH₃ | O(CH₂)₂CH₃ | N | |
| H | CO₂CH₃ | H | CH₃ | CH₃ | N | |
| H | CO₂CH₃ | H | CH₃ | CH₂CH₃ | N | |
| H | CO₂CH₃ | H | CH₃ | (CH₂)₂CH₃ | N | |
| H | CO₂CH₃ | H | CH₂CH₃ | Cl | N | |
| H | CO₂CH₃ | H | CH₂CH₃ | OCH₃ | N | |
| H | CO₂CH₃ | H | (CH₂)₂CH₃ | Cl | N | |

TABLE 5-continued

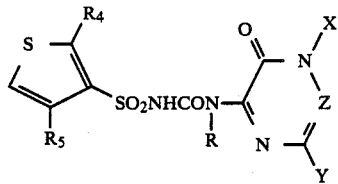

| R | R4 | R5 | X | Y | Z | m.p. (°C.) |
|---|---|---|---|---|---|---|
| H | CO2CH3 | H | (CH2)2CH3 | OCH3 | N | |
| H | CO2CH3 | H | OCH3 | H | N | |
| H | CO2CH3 | H | OCH3 | CH3 | N | |
| H | CO2CH3 | H | OCH3 | CH2CH3 | N | |
| H | CO2CH3 | H | OCH3 | (CH2)2CH3 | N | |
| H | CO2CH3 | H | OCH3 | OCH3 | N | |
| H | CO2CH3 | H | OCH3 | OCH2CH3 | N | |
| H | CO2CH3 | H | OCH3 | O(CH2)2CH3 | N | |
| H | CO2CH3 | H | OCH3 | Cl | N | |
| H | CO2CH3 | H | OCH3 | Br | N | |
| H | CO2CH3 | H | OCH2CH3 | Cl | N | |
| H | CO2CH3 | H | OCH2CH3 | CH3 | N | |
| H | CO2CH3 | H | OCH2CH3 | OCH3 | N | |
| H | CO2CH3 | H | O(CH2)2CH3 | Cl | N | |
| H | CO2CH3 | H | O(CH2)2CH3 | CH3 | N | |
| H | CO2CH3 | H | O(CH2)2CH3 | OCH3 | N | |
| H | CO2CH3 | H | NH2 | Cl | N | |
| H | CO2CH3 | H | NH2 | CH3 | N | |
| H | CO2CH3 | H | NH2 | OCH3 | N | |
| H | CO2CH3 | H | NHCH3 | Cl | N | |
| H | CO2CH3 | H | NHCH3 | CH3 | N | |
| H | CO2CH3 | H | NHCH3 | OCH3 | N | |
| H | CO2CH3 | H | N(CH3)2 | Cl | N | |
| H | CO2CH3 | H | N(CH3)2 | CH3 | N | |
| H | CO2CH3 | H | N(CH3)2 | OCH3 | N | |
| H | CO2CH3 | H | NHCH3 | OCH2CH3 | N | |
| CH3 | CO2CH3 | H | CH3 | Cl | N | |
| CH3 | CO2CH3 | H | OCH3 | Cl | N | |
| CH3 | CO2CH3 | H | CH3 | OCH3 | N | |
| CH3 | CO2CH3 | H | CH2CH3 | OCH3 | N | |
| CH3 | CO2CH3 | H | OCH3 | CH3 | N | |
| CH3 | CO2CH3 | H | OCH3 | OCH3 | N | |
| H | CO2CH3 | F | OCH3 | Cl | CH | |
| H | CO2CH3 | Cl | CH3 | CH3 | CH | |
| H | CO2CH3 | Br | CH3 | OCH3 | CH | |
| H | CO2CH3 | CH3 | CH3 | Cl | Cl | |
| H | CO2CH3 | F | CH3 | CH3 | CH | |
| H | CO2CH3 | Cl | CH3 | OCH3 | CH | |
| H | CO2CH3 | Br | OCH3 | CH3 | CH | |
| H | CO2CH3 | CH3 | CH3 | OCH3 | N | |
| H | CO2CH3 | F | CH3 | OCH2CH3 | N | |
| H | CO2CH3 | Cl | OCH2CH3 | CH3 | CH | |
| H | CO2CH3 | F | CH2CH3 | OCH3 | CH | |
| H | CO2CH3 | CH3 | CH3 | Br | CH | |
| H | CO2CH2CH3 | H | OCH3 | Cl | CH | |
| H | CO2CH2CH3 | H | CH3 | CH3 | CH | |
| H | CO2CH2CH3 | H | CH3 | OCH3 | CH | |
| H | CO2CH2CH3 | H | OCH3 | CH3 | CH | |
| H | CO2CH2CH3 | H | CH3 | Cl | CH | |
| H | CO2CH2CH3 | H | CH3 | OCH3 | CH | |
| H | CO2CH2CH3 | H | CH3 | OCH3 | N | |
| H | CO2CH2CH3 | H | CH3 | OCH2CH3 | N | |
| H | CO2CH2CH3 | H | OCH2CH3 | CH3 | CH | |
| H | CO2CH2CH3 | H | OCH3 | OCH3 | CH | |
| H | CO2CH2CH3 | H | CH2CH3 | OCH3 | CH | |
| H | CO2CH2CH3 | H | CH3 | Br | CH | |
| H | CO2CH2CH3 | H | CH3 | OCH2CH3 | CH | |
| H | CO2CH2CH3 | H | CH3 | CH2CH3 | CH | |
| H | CO2CH2CH=CH3 | H | OCH3 | Cl | CH | |
| H | CO2CH2C≡CH | H | CH3 | CH3 | CH | |
| H | CO2CH(CH3)2 | H | CH3 | OCH3 | CH | |
| H | CO2(CH2)2CH3 | H | OCH3 | CH3 | CH | |
| H | CO2(CH2)2OCH3 | H | CH3 | Cl | CH | |
| H | CO2(CH2)2OCH2CH3 | H | CH3 | OCH3 | N | |
| H | CO2CH2OCH3 | H | CH3 | OCH2CH3 | N | |
| H | CO2(CH2)2Cl | H | OCH2CH3 | CH3 | CH | |
| H | CO2(CH3)2F | H | OCH3 | OCH3 | CH | |
| H | CO2(CH2)2Br | H | CH2CH3 | OCH3 | CH | |
| H | CO2(CH2)2I | H | CH3 | Br | CH | |
| H | CO2CH2CF3 | H | CH3 | OCH2CH3 | CH | |
| H | CO2CH2CH2CN | H | CH3 | CH2CH3 | CH | |

TABLE 5-continued

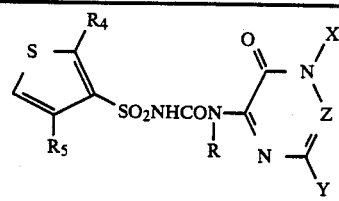

| R | R4 | R5 | X | Y | Z | m.p. (°C.) |
|---|---|---|---|---|---|---|
| CH3 | CO2CH2CH3 | H | OCH3 | Cl | CH | |
| H | CO2CH2CH3 | CH3 | CH3 | OCH3 | CH | |
| H | F | H | OCH3 | CH3 | CH | |
| H | Cl | H | CH3 | OCH2CH3 | N | |
| H | Br | H | CH3 | OCH3 | N | |
| H | NO2 | H | CH3 | Cl | CH | |
| H | CH3 | H | OCH3 | CH3 | CH | |
| H | CH2CH3 | H | CH3 | OCH3 | CH | |
| H | (CH2)2CH3 | H | CH3 | CH3 | CH | |
| H | CH(CH3)2 | H | OCH2CH3 | CH3 | CH | |
| H | CF3 | H | OCH3 | OCH3 | CH | |
| H | (CH2)2F | H | CH2CH3 | OCH3 | CH | |
| H | (CH2)2Br | H | CH3 | Br | CH | |
| H | CF2H | H | CH3 | OCH2CH3 | CH | |
| H | CH=CF2 | H | CH3 | OCH3 | CH | |
| H | CCl=CCl2 | H | OCH3 | CH3 | CH | |
| H | CH2CH=CHCCl3 | H | CH3 | Cl | CH | |
| H | CH=CHCl | H | CH3 | OCH3 | N | |
| H | CH=CHI | H | CH3 | OCH2CH3 | N | |
| H | CH=CBr2 | H | OCH2CH3 | CH3 | CH | |
| H | CF=CFH | H | OCH3 | OCH3 | CH | |
| H | CH2CH=CF2 | H | CH2CH3 | OCH3 | CH | |
| H | CH=CHCF3 | H | CH3 | Br | CH | |
| H | CF=CFCH3 | H | CH3 | OCH2CH3 | H | |
| H | OCH3 | H | CH3 | CH2CH3 | CH | |
| H | OCH3 | Cl | OCH3 | Cl | CH | |
| H | OCH2CH3 | H | CH3 | CH3 | CH | |
| H | C(O)N(CH3)2 | H | CH3 | OCH2CH3 | N | |
| H | C(O)NHCH2CH3 | H | OCH3 | Cl | CH | |
| H | C(O)N(CH3)OCH3 | H | CH3 | CH3 | CH | |
| H | C(O)NHOCH2CH3 | H | CH3 | OCH3 | CH | |
| H | C(O)NH(CH2)2CH3 | H | OCH3 | CH3 | CH | |
| H | SO2N(CH3)2 | H | CH3 | Cl | CH | 195–198 |
| H | C(O)N(CH3)2 | H | CH3 | Cl | CH | 200–210 (d) |
| H | SO2NH—cyclopropyl | H | OCH3 | Cl | CH | |
| CH3 | SO2N(CH3)2 | H | CH3 | CH3 | CH | |
| H | SO2N(CH3)2 | CH3 | CH3 | OCH3 | CH | |
| H | SO2N(CH3)CH2CH=CH2 | H | OCH3 | CH3 | CH | |
| H | SO2N((CH2)2CH3)2 | H | CH3 | Cl | CH | |
| H | SO2NH2 | H | CH3 | OCH3 | N | |
| H | SO2N(CH3)OCH3 | H | CH3 | OCH2CH3 | N | |
| H | SO2N(CH3)OCH2CH3 | H | OCH2CH3 | CH3 | CH | |
| H | SCH3 | H | OCH3 | OCH3 | CH | |
| H | SCH2CH=CH3 | H | CH2CH3 | OCH3 | CH | |
| H | SCH2C≡CH3 | H | CH3 | Br | CH | |
| H | S(CH2)2CH3 | H | CH3 | OCH2CH3 | CH | |
| H | S(O)CH3 | H | CH3 | CH2CH3 | CH | |
| H | SCF2H | H | OCH3 | Cl | CH | |
| H | SCF2CF2H | H | CH3 | CH3 | CH | |
| H | S(CH2)2Cl | H | CH3 | OCH3 | CH | |
| H | S(CH2)2I | H | OCH3 | CH3 | CH | |
| H | S(CH2)3Br | H | CH3 | Cl | CH | |
| H | S(O)CF2CF2H | H | CH3 | OCH3 | N | |
| H | S(O)(CH2)2I | H | CH3 | OCH2CH3 | N | |
| H | S(O)2CH3 | H | OCH3 | Cl | CH | |
| H | S(O)2CH2CH3 | H | CH3 | CH3 | CH | |
| H | S(O)2CH2CH=CH2 | H | CH3 | OCH3 | CH | |
| H | S(O)2CH2C≡CH | H | OCH3 | CH3 | CH | |
| H | S(O)2CF2H | H | CH3 | Cl | CH | |
| H | S(O)2CF2CF2H | H | CH3 | OCH3 | N | |
| H | S(O)2(CH2)2I | H | CH3 | OCH2CH3 | N | |
| H | C(O)CH3 | H | OCH3 | Cl | CH | |
| H | C(O)(CH2)3CH3 | H | CH3 | CH3 | CH | |
| H | C(O)CH2CH3 | H | CH3 | OCH3 | CH | |
| H | C(O)—cyclo-C3H5 | H | OCH3 | CH3 | CH | |
| H | C(O)—cyclo-C4H7 | H | CH3 | Cl | CH | |
| H | C(O)—cyclo-C5H9 | H | OCH3 | Cl | CH | |
| H | C(O)—cyclo-C3F5 | H | CH3 | CH3 | CH | |
| H | C(O)CF3 | H | CH3 | OCH3 | CH | |
| H | C(O)(CH2)3CCl2H | H | OCH3 | CH3 | CH | |
| H | C(O)(CH2)4F | H | CH3 | Cl | CH | |

TABLE 5-continued

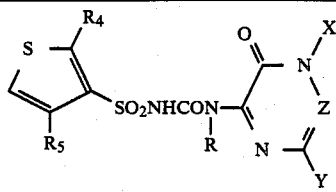

| R | R4 | R5 | X | Y | Z | m.p. (°C.) |
|---|---|---|---|---|---|---|
| H | C(O)—cyclo-(CHCH2CCl2) | H | CH3 | OCH3 | N | |
| H | L-1, $R_h$ = H | H | OCH2CH3 | CH3 | CH | |
| H | L-1, $R_h$ = CH3 | H | OCH3 | OCH3 | CH | |
| H | L-2, $R_h$ = H | H | CH2CH3 | OCH3 | CH | |
| H | L-2, $R_h$ = CH3 | H | CH3 | Br | CH | |
| H | L-3 | H | CH3 | OCH2CH3 | CH | |
| H | L-4 | H | CH3 | CH2CH3 | CH | |
| H | L-5 | H | OCH3 | Cl | CH | |
| H | L-6 | H | CH3 | CH3 | CH | |
| H | L-7 | H | CH3 | OCH3 | CH | |
| H | L-8 | H | OCH3 | CH3 | CH | |
| H | L-9 | H | CH3 | Cl | CH | |
| H | L-10 | H | CH3 | OCH3 | N | |
| H | L-11 | H | CH3 | OCH2CH3 | N | |
| H | L-12 | H | OCH3 | Cl | CH | |
| H | L-13 | H | CH3 | CH3 | CH | |
| H | L-14 | H | CH3 | OCH3 | CH | |
| H | L-15 | H | OCH3 | CH3 | CH | |
| H | L-16, $R_i$ = H | H | CH3 | Cl | CH3 | |
| H | L-16, $R_i$ = CH3 | H | CH3 | OCH3 | N | |
| H | L-17 | H | CH3 | OCH2CH3 | N | |
| H | L-18 | H | OCH3 | Cl | CH | |
| H | L-19 | H | CH3 | CH3 | CH | |
| H | L-20 | H | CH3 | OCH3 | CH | |
| H | L-21 | H | OCH3 | CH3 | CH | |
| H | L-22 | H | CH3 | Cl | CH | |
| H | L-23 | H | OCH3 | Cl | CH | |
| H | L-24 | H | CH3 | CH3 | CH | |
| H | L-25 | H | CH3 | OCH3 | CH | |
| H | L-26, $R_j$ = H | H | OCH3 | CH3 | CH | |
| H | L-26, $R_j$ = CH3 | H | CH3 | Cl | CH | |
| H | L-26, $R_j$ = CH2CH3 | H | CH3 | OCH3 | N | |
| H | L-27, $R_j$ = H | H | CH3 | OCH2CH3 | N | |
| H | L-27, $R_j$ = CH3 | H | OCH2CH3 | CH3 | CH | |
| H | L-27, $R_j$ = CH2CH3 | H | OCH3 | OCH3 | CH | |
| H | L-28, $R_k$ = H | H | CH2CH3 | OCH3 | CH | |
| H | L-28, $R_k$ = CH3 | H | CH3 | Br | CH | |
| H | L-28, $R_k$ = CH2CH3 | H | CH3 | OCH2CH3 | CH | |
| H | L-28, $R_k$ = OCH3 | H | CH3 | CH2CH3 | CH | |
| H | L-28, $R_k$ = OCH2CH3 | H | OCH3 | Cl | CH | |
| H | L-28, $R_k$ = SCH3 | H | CH3 | CH3 | CH | |
| H | L-28, $R_k$ = SCH2CH3 | H | CH3 | OCH3 | CH | |
| H | L-29, $R_k$ = H | H | OCH3 | CH3 | CH | |
| H | L-29, $R_k$ = CH3 | H | CH3 | Cl | CH | |
| H | L-29, $R_k$ = CH2CH3 | H | CH3 | OCH3 | N | |
| H | L-29, $R_k$ = OCH3 | H | CH3 | OCH2CH3 | N | |
| H | L-29, $R_k$ = OCH2CH3 | H | OCH3 | Cl | CH | |
| H | L-29, $R_k$ = SCH3 | H | CH3 | CH3 | CH | |
| H | L-29, $R_k$ = SCH2CH3 | H | CH3 | OCH3 | CH | |
| H | L-30, $R_m$ = H | H | OCH3 | CH3 | CH | |
| H | L-30, $R_m$ = CH3 | H | CH3 | Cl | CH | |
| H | L-30, $R_m$ = CH2CH3 | H | CH3 | OCH3 | N | |
| H | L-31, $R_m$ = H | H | CH3 | OCH2CH3 | N | |
| H | L-31, $R_m$ = CH3 | H | OCH3 | Cl | CH | |
| H | L-31, $R_m$ = CH2CH3 | H | CH3 | CH3 | CH | |
| H | L-32, $R_m$ = H | H | CH3 | OCH3 | CH | |
| H | L-32, $R_m$ = CH3 | H | OCH3 | CH3 | CH | |
| H | L-32, $R_m$ = CH2CH3 | H | CH3 | Cl | CH | |
| H | L-33, $R_n$ = H | H | CH3 | CH3 | N | |
| H | L-33, $R_n$ = CH3 | H | CH3 | OCH3 | CH | |

TABLE 6

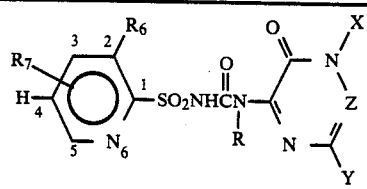

| R | R6 | R7 | X | Y | Z | m.p. (°C.) |
|---|---|---|---|---|---|---|
| H | CO2CH3 | H | H | OCH3 | CH | |
| H | CO2CH3 | H | CH3 | Cl | CH | |
| H | CO2CH3 | H | CH3 | Br | CH | |
| H | CO2CH3 | H | CH3 | OCH3 | CH | |
| H | CO2CH3 | H | CH3 | OCH2CH3 | CH | |
| H | CO2CH3 | H | CH3 | O(CH2)2CH3 | CH | |
| H | CO2CH3 | H | CH3 | CH3 | CH | |
| H | CO2CH3 | H | CH3 | CH2CH3 | CH | |
| H | CO2CH3 | H | CH3 | (CH2)2CH3 | CH | |
| H | CO2CH3 | H | CH2CH3 | Cl | CH | |
| H | CO2CH3 | H | CH2CH3 | OCH3 | CH | |
| H | CO2CH3 | H | (CH2)2CH3 | Cl | CH | |
| H | CO2CH3 | H | (CH2)2CH3 | OCH3 | CH | |
| H | CO2CH3 | H | OCH3 | H | CH | |
| H | CO2CH3 | H | OCH3 | CH3 | CH | |
| H | CO2CH3 | H | OCH3 | CH2CH3 | CH | |
| H | CO2CH3 | H | OCH3 | (CH2)2CH3 | CH | |
| H | CO2CH3 | H | OCH3 | OCH3 | CH | |
| H | CO2CH3 | H | OCH3 | OCH2CH3 | CH | |
| H | CO2CH3 | H | OCH3 | O(CH2)2CH3 | CH | |
| H | CO2CH3 | H | CH3 | SCH3 | CH | |
| H | CO2CH3 | H | OCH3 | SCH3 | CH | |
| H | CO2CH3 | H | OCH3 | SCH2CH3 | CH | |
| H | CO2CH3 | H | CH2CH3 | SCH3 | CH | |
| H | CO2CH3 | H | CH3 | SCH3 | N | |
| H | CO2CH3 | H | N(CH3)2 | SCH3 | CH | |
| H | CO2CH3 | H | OCH3 | Cl | CH | |
| H | CO2CH3 | H | OCH3 | Br | CH | |
| H | CO2CH3 | H | OCH2CH3 | Cl | CH | |
| H | CO2CH3 | H | OCH2CH3 | CH3 | CH | |
| H | CO2CH3 | H | OCH2CH3 | OCH3 | CH | |
| H | CO2CH3 | H | O(CH2)2CH3 | Cl | CH | |
| H | CO2CH3 | H | O(CH2)2CH3 | CH3 | CH | |
| H | CO2CH3 | H | O(CH2)2CH3 | OCH3 | CH | |
| H | CO2CH3 | H | NH2 | Cl | CH | |
| H | CO2CH3 | H | NH2 | CH3 | CH | |
| H | CO2CH3 | H | NH2 | OCH3 | CH | |
| H | CO2CH3 | H | NHCH3 | Cl | CH | |
| H | CO2CH3 | H | NHCH3 | CH3 | CH | |
| H | CO2CH3 | H | NHCH3 | OCH3 | CH | |
| H | CO2CH3 | H | N(CH3)2 | Cl | CH | |
| H | CO2CH3 | H | N(CH3)2 | CH3 | CH | |
| H | CO2CH3 | H | N(CH3)2 | OCH3 | CH | |
| H | CO2CH3 | H | NHCH3 | OCH2CH3 | CH | |
| CH3 | CO2CH3 | H | CH3 | Cl | CH | |
| CH3 | CO2CH3 | H | OCH3 | Cl | CH | |
| CH3 | CO2CH3 | H | CH3 | OCH3 | CH | |
| CH3 | CO2CH3 | H | OCH3 | CH3 | CH | |
| CH3 | CO2CH3 | H | OCH3 | OCH3 | CH | |
| H | CO2CH3 | H | CH3 | Cl | CF | |
| H | CO2CH3 | H | CH3 | OCH3 | CF | |
| H | CO2CH3 | H | OCH3 | OCH3 | CF | |
| H | CO2CH3 | H | OCH3 | CH3 | CF | |
| H | CO2CH3 | H | CH3 | Cl | CCl | |
| H | CO2CH3 | H | CH3 | OCH3 | CCl | |
| H | CO2CH3 | H | CH3 | Br | CBr | |
| H | CO2CH3 | H | CH3 | Cl | CBr | |
| H | CO2CH3 | H | CH3 | OCH3 | CBr | |
| H | CO2CH3 | H | H | OCH3 | N | |
| H | CO2CH3 | H | CH3 | Cl | N | |
| H | CO2CH3 | H | CH3 | Br | N | |
| H | CO2CH3 | H | CH3 | OCH3 | N | |
| H | CO2CH3 | H | CH3 | OCH2CH3 | N | |
| H | CO2CH3 | H | CH3 | O(CH2)2CH3 | N | |
| H | CO2CH3 | H | CH3 | CH3 | N | |
| H | CO2CH3 | H | CH3 | CH2CH3 | N | |
| H | CO2CH3 | H | CH3 | (CH2)2CH3 | N | |
| H | CO2CH3 | H | CH2CH3 | Cl | N | |
| H | CO2CH3 | H | CH2CH3 | OCH3 | N | |
| H | CO2CH3 | H | (CH2)2CH3 | Cl | N | |
| H | CO2CH3 | H | (CH2)2CH3 | OCH3 | N | |

TABLE 6-continued

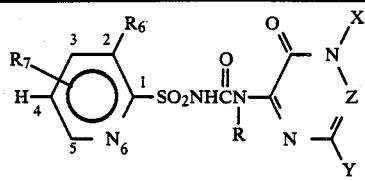

| R | R6 | R7 | X | Y | Z | m.p. (°C.) |
|---|---|---|---|---|---|---|
| H | CO2CH3 | H | OCH3 | H | N | |
| H | CO2CH3 | H | OCH3 | CH3 | N | |
| H | CO2CH3 | H | OCH3 | CH2CH3 | N | |
| H | CO2CH3 | H | OCH3 | (CH2)2CH3 | N | |
| H | CO2CH3 | H | OCH3 | OCH3 | N | |
| H | CO2CH3 | H | OCH3 | OCH2CH3 | N | |
| H | CO2CH3 | H | OCH3 | O(CH2)2CH3 | N | |
| H | CO2CH3 | H | OCH3 | Cl | N | |
| H | CO2CH3 | H | OCH3 | Br | N | |
| H | CO2CH3 | H | OCH2CH3 | Cl | N | |
| H | CO2CH3 | H | OCH2CH3 | CH3 | N | |
| H | CO2CH3 | H | OCH2CH3 | OCH3 | N | |
| H | CO2CH3 | H | O(CH2)2CH3 | Cl | N | |
| H | CO2CH3 | H | O(CH2)2CH3 | CH3 | N | |
| H | CO2CH3 | H | O(CH2)2CH3 | OCH3 | N | |
| H | CO2CH3 | H | NH2 | Cl | N | |
| H | CO2CH3 | H | NH2 | CH3 | N | |
| H | CO2CH3 | H | NH2 | OCH3 | N | |
| H | CO2CH3 | H | NHCH3 | Cl | N | |
| H | CO2CH3 | H | NHCH3 | CH3 | N | |
| H | CO2CH3 | H | NHCH3 | OCH3 | N | |
| H | CO2CH3 | H | N(CH3)2 | Cl | N | |
| H | CO2CH3 | H | N(CH3)2 | CH3 | N | |
| H | CO2CH3 | H | N(CH3)2 | OCH3 | N | |
| H | CO2CH3 | H | NHCH3 | OCH2CH3 | N | |
| CH3 | CO2CH3 | H | CH3 | Cl | N | |
| CH3 | CO2CH3 | H | OCH3 | Cl | N | |
| CH3 | CO2CH3 | H | CH3 | OCH3 | N | |
| CH3 | CO2CH3 | H | CH2CH3 | OCH3 | N | |
| CH3 | CO2CH3 | H | OCH3 | CH3 | N | |
| CH3 | CO2CH3 | H | OCH3 | OCH3 | N | |
| H | CO2CH3 | 5-F | OCH3 | Cl | CH | |
| H | CO2CH3 | 3-Cl | CH3 | CH3 | CH | |
| H | CO2CH3 | 5-Cl | CH3 | OCH3 | CH | |
| H | CO2CH3 | 3-CH3 | CH3 | OCH3 | N | |
| H | CO2CH3 | 3-F | CH3 | OCH2CH3 | N | |
| H | CO2CH3 | 5-F | CH2CH3 | OCH3 | CH | |
| H | CO2CH3 | 5-CH3 | CH3 | Br | CH | |
| H | CO2CH2CH3 | H | OCH3 | Cl | CH | |
| H | CO2CH2CH3 | H | CH3 | CH3 | CH | |
| H | CO2CH2CH3 | H | CH3 | OCH3 | CH | |
| H | CO2CH2CH3 | H | OCH3 | CH3 | CH | |
| H | CO2CH2CH3 | H | CH3 | Cl | CH | |
| H | CO2CH2CH3 | H | CH3 | OCH3 | CH | |
| H | CO2CH2CH3 | H | CH3 | OCH3 | N | |
| H | CO2CH2CH3 | H | CH3 | OCH2CH3 | N | |
| H | CO2CH2CH3 | H | OCH2CH3 | CH3 | CH | |
| H | CO2CH2CH3 | H | OCH3 | OCH3 | CH | |
| H | CO2CH2CH3 | H | CH2CH3 | OCH3 | CH | |
| H | CO2CH2CH3 | H | CH3 | Br | CH | |
| H | CO2CH2CH3 | H | CH3 | OCH2CH3 | CH | |
| H | CO2CH2CH3 | H | CH3 | CH2CH3 | CH | |
| H | CO2CH2CH=CH3 | H | OCH3 | Cl | CH | |
| H | CO2CH2C≡CH | H | CH3 | CH3 | CH | |
| H | CO2CH(CH3)2 | H | CH3 | OCH3 | CH | |
| H | CO2(CH2)2CH3 | H | OCH3 | CH3 | CH | |
| H | CO2(CH2)2OCH3 | H | CH3 | Cl | CH | |
| H | CO2(CH2)2OCH2CH3 | H | CH3 | OCH3 | N | |
| H | CO2CH2OCH3 | H | CH3 | OCH2CH3 | N | |
| H | CO2(CH2)2Cl | H | OCH2CH3 | CH3 | CH | |
| H | CO2(CH2)2F | H | OCH3 | OCH3 | CH | |
| H | CO2(CH2)2Br | H | CH2CH3 | OCH3 | CH | |
| H | CO2(CH2)2I | H | CH3 | Br | CH | |
| H | CO2CH2CF3 | H | CH3 | OCH2CH3 | CH | |
| H | CO2CH2CH2CN | H | CH3 | CH2CH3 | CH | |
| CH3 | CO2CH2CH3 | H | OCH3 | Cl | CH | |
| H | CO2CH2CH3 | 3-CH3 | CH3 | OCH3 | CH | |
| H | F | H | OCH3 | CH3 | CH | |
| H | Cl | H | CH3 | OCH2CH3 | N | |
| H | Br | H | CH3 | OCH3 | N | |
| H | CH3 | H | OCH3 | CH3 | CH | |

TABLE 6-continued

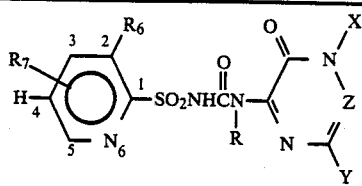

| R | R6 | R7 | X | Y | Z | m.p. (°C.) |
|---|---|---|---|---|---|---|
| H | CH2CH3 | H | CH3 | OCH3 | CH | |
| H | (CH2)2CH3 | H | CH3 | CH3 | CH | |
| H | CH(CH3)2 | H | OCH2CH3 | CH3 | CH | |
| H | CH=CF2 | H | CH3 | OCH3 | CH | |
| H | CCl=CCl2 | H | OCH3 | CH3 | CH | |
| H | CH2CH=CHCCl3 | H | CH3 | Cl | CH | |
| H | CH=CHCl | H | CH3 | OCH3 | N | |
| H | CH=CHI | H | CH3 | OCH2CH3 | N | |
| H | CH=CBr2 | H | OCH2CH3 | CH3 | CH | |
| H | CF=CFH | H | OCH3 | OCH3 | CH | |
| H | CH2CH=CF2 | H | CH2CH3 | OCH3 | CH | |
| H | CH=CHCF3 | H | CH3 | Br | CH | |
| H | CF=CFCH3 | H | CH3 | OCH2CH3 | H | |
| H | OCH3 | H | CH3 | CH2CH3 | CH | |
| H | OCH3 | 3-Cl | OCH3 | Cl | CH | |
| H | OCH2CH3 | H | CH3 | CH3 | CH | |
| H | C(O)N(CH3)2 | H | CH3 | OCH2CH3 | N | |
| H | C(O)NHCH2CH3 | H | OCH3 | Cl | CH | |
| H | C(O)N(CH3)OCH3 | H | CH3 | CH3 | CH | |
| H | C(O)NHOCH2CH3 | H | OCH3 | OCH3 | CH | |
| H | C(O)NH(CH2)2CH3 | H | OCH3 | CH3 | CH | |
| H | SO2N(CH3)2 | H | CH3 | Cl | CH | |
| H | SO2NH—cyclopropyl | H | OCH3 | Cl | CH | |
| CH3 | SO2N(CH3)2 | H | CH3 | CH3 | CH | |
| H | SO2N(CH3)2 | 3-CH3 | CH3 | OCH3 | CH | |
| H | SO2N(CH3)CH2CH=CH2 | H | OCH3 | CH3 | CH | |
| H | SO2N((CH2)2CH3)2 | H | CH3 | Cl | CH | |
| H | SO2NH2 | H | CH3 | OCH3 | N | |
| H | SO2N(CH3)OCH3 | H | CH3 | OCH2CH3 | N | |
| H | SO2N(CH3)OCH2CH3 | H | OCH2CH3 | CH3 | CH | |
| H | SCH3 | H | OCH3 | OCH3 | CH | |
| H | SCH2CH=CH3 | H | CH2CH3 | OCH3 | CH | |
| H | SCH2C≡CH3 | H | CH3 | Br | CH | |
| H | S(CH2)2CH3 | H | CH3 | OCH2CH3 | CH | |
| H | S(O)CH3 | H | CH3 | CH2CH3 | CH | |
| H | SCF2H | H | OCH3 | Cl | CH | |
| H | SCF2CF2H | H | CH3 | CH3 | CH | |
| H | S(CH2)2Cl | H | CH3 | OCH3 | CH | |
| H | S(CH2)2I | H | OCH3 | CH3 | CH | |
| H | S(CH2)3Br | H | CH3 | Cl | CH | |
| H | S(O)CF2CF2H | H | CH3 | OCH3 | N | |
| H | S(O)(CH2)2I | H | CH3 | OCH2CH3 | N | |
| H | S(O)2CH3 | H | OCH3 | Cl | CH | |
| H | S(O)2CH2CH3 | H | CH3 | CH3 | CH | |
| H | S(O)2CH2CH=CH2 | H | CH3 | OCH3 | CH | |
| H | S(O)2CH2C≡CH | H | OCH3 | CH3 | CH | |
| H | S(O)2CF2H | H | CH3 | Cl | CH | |
| H | S(O)2CF2CF2H | H | CH3 | OCH3 | N | |
| H | S(O)2(CH2)2I | H | CH3 | OCH2CH3 | N | |
| H | C(O)CH3 | H | OCH3 | Cl | CH | |
| H | C(O)(CH2)3CH3 | H | CH3 | CH3 | CH | |
| H | C(O)CH2CH3 | H | CH3 | OCH3 | CH | |
| H | C(O)—cyclo-C3H5 | H | OCH3 | CH3 | CH | |
| H | C(O)—cyclo-C4H7 | H | CH3 | Cl | CH | |
| H | C(O)—cyclo-C5H9 | H | OCH3 | Cl | CH | |
| H | C(O)—cyclo-C3F5 | H | CH3 | CH3 | CH | |
| H | C(O)CF3 | H | CH3 | OCH3 | CH | |
| H | C(O)(CH2)3CCl2H | H | OCH3 | CH3 | CH | |
| H | C(O)(CH2)4F | H | CH3 | Cl | CH | |
| H | C(O)—cyclo-(CHCH2CCl2) | H | CH3 | OCH3 | N | |
| H | L-1, Rh=H | H | OCH2CH3 | CH3 | CH | |
| H | L-1, Rh=CH3 | H | OCH3 | OCH3 | CH | |
| H | L-2, Rh=H | H | CH2CH3 | OCH3 | CH | |
| H | L-2, Rh=CH3 | H | CH3 | Br | CH | |
| H | L-3 | H | CH3 | OCH2CH3 | CH | |
| H | L-4 | H | CH3 | CH2CH3 | CH | |
| H | L-5 | H | OCH3 | Cl | CH | |
| H | L-6 | H | CH3 | CH3 | CH | |
| H | L-7 | H | CH3 | OCH3 | CH | |
| H | L-8 | H | OCH3 | CH3 | CH | |
| H | L-9 | H | CH3 | Cl | CH | |

TABLE 6-continued

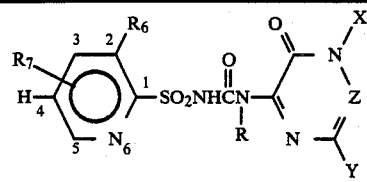

| R | R6 | R7 | X | Y | Z | m.p. (°C.) |
|---|---|---|---|---|---|---|
| H | L-10 | H | $CH_3$ | $OCH_3$ | N | |
| H | L-11 | H | $CH_3$ | $OCH_2CH_3$ | N | |
| H | L-12 | H | $OCH_3$ | Cl | CH | |
| H | L-13 | H | $CH_3$ | $CH_3$ | CH | |
| H | L-14 | H | $CH_3$ | $OCH_3$ | CH | |
| H | L-15 | H | $OCH_3$ | $CH_3$ | CH | |
| H | L-16, $R_i$=H | H | $CH_3$ | Cl | CH | |
| H | L-16, $R_i$=$CH_3$ | H | $CH_3$ | $OCH_3$ | N | |
| H | L-17 | H | $CH_3$ | $OCH_2CH_3$ | N | |
| H | L-18 | H | $OCH_3$ | Cl | CH | |
| H | L-19 | H | $CH_3$ | $CH_3$ | CH | |
| H | L-20 | H | $CH_3$ | $OCH_3$ | CH | |
| H | L-21 | H | $OCH_3$ | $CH_3$ | CH | |
| H | L-22 | H | $CH_3$ | Cl | CH | |
| H | L-23 | H | $OCH_3$ | Cl | CH | |
| H | L-24 | H | $CH_3$ | $CH_3$ | CH | |
| H | L-25 | H | $CH_3$ | $OCH_3$ | CH | |
| H | L-26, $R_j$=H | H | $OCH_3$ | $CH_3$ | CH | |
| H | L-26, $R_j$=$CH_3$ | H | $CH_3$ | Cl | CH | |
| H | L-26, $R_j$=$CH_2CH_3$ | H | $CH_3$ | $OCH_3$ | N | |
| H | L-27, $R_j$=H | H | $CH_3$ | $OCH_2CH_3$ | N | |
| H | L-27, $R_j$=$CH_3$ | H | $OCH_2CH_3$ | $CH_3$ | CH | |
| H | L-27, $R_j$=$CH_2CH_3$ | H | $OCH_3$ | $OCH_3$ | CH | |
| H | L-28, $R_k$=H | H | $CH_2CH_3$ | $OCH_3$ | CH | |
| H | L-28, $R_k$=$CH_3$ | H | $CH_3$ | Br | CH | |
| H | L-28, $R_k$=$CH_2CH_3$ | H | $CH_3$ | $OCH_2CH_3$ | CH | |
| H | L-28, $R_k$=$OCH_3$ | H | $CH_3$ | $CH_2CH_3$ | CH | |
| H | L-28, $R_k$=$OCH_2CH_3$ | H | $OCH_3$ | Cl | CH | |
| H | L-28, $R_k$=$SCH_3$ | H | $CH_3$ | $CH_3$ | CH | |
| H | L-28, $R_k$=$SCH_2CH_3$ | H | $CH_3$ | $OCH_3$ | CH | |
| H | L-29, $R_k$=H | H | $OCH_3$ | $CH_3$ | CH | |
| H | L-29, $R_k$=$CH_3$ | H | $CH_3$ | Cl | CH | |
| H | L-29, $R_k$=$CH_2CH_3$ | H | $CH_3$ | $OCH_3$ | N | |
| H | L-29, $R_k$=$OCH_3$ | H | $CH_3$ | $OCH_2CH_3$ | N | |
| H | L-29, $R_k$=$OCH_2CH_3$ | H | $OCH_3$ | Cl | CH | |
| H | L-29, $R_k$=$SCH_3$ | H | $CH_3$ | $CH_3$ | CH | |
| H | L-29, $R_k$=$SCH_2CH_3$ | H | $CH_3$ | $OCH_3$ | CH | |
| H | L-30, $R_m$=H | H | $OCH_3$ | $CH_3$ | CH | |
| H | L-30, $R_m$=$CH_3$ | H | $CH_3$ | Cl | CH | |
| H | L-30, $R_m$=$CH_2CH_3$ | H | $CH_3$ | $OCH_3$ | N | |
| H | L-31, $R_m$=H | H | $CH_3$ | $OCH_2CH_3$ | N | |
| H | L-31, $R_m$=$CH_3$ | H | $OCH_3$ | Cl | CH | |
| H | L-31, $R_m$=$CH_2CH_3$ | H | $CH_3$ | $CH_3$ | CH | |
| H | L-32, $R_m$=H | H | $CH_3$ | $OCH_3$ | CH | |
| H | L-32, $R_m$=$CH_3$ | H | $OCH_3$ | $CH_3$ | CH | |
| H | L-32, $R_m$=$CH_2CH_3$ | H | $CH_3$ | Cl | CH | |
| H | L-33, $R_n$=H | H | $CH_3$ | $CH_3$ | N | |
| H | L-33, $R_n$=$CH_3$ | H | $CH_3$ | $OCH_3$ | CH | |

TABLE 7

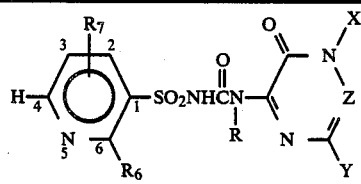

| R | R6 | R7 | X | Y | Z | m.p. (°C.) |
|---|---|---|---|---|---|---|
| H | $CO_2CH_3$ | H | H | $OCH_3$ | CH | |
| H | $CO_2CH_3$ | H | $CH_3$ | Cl | CH | |
| H | $CO_2CH_3$ | H | $CH_3$ | Br | CH | |
| H | $CO_2CH_3$ | H | $CH_3$ | $OCH_3$ | CH | |
| H | $CO_2CH_3$ | H | $CH_3$ | $OCH_2CH_3$ | CH | |
| H | $CO_2CH_3$ | H | $CH_3$ | $O(CH_2)_2CH_3$ | CH | |
| H | $CO_2CH_3$ | H | $CH_3$ | $CH_3$ | CH | |
| H | $CO_2CH_3$ | H | $CH_3$ | $CH_2CH_3$ | CH | |
| H | $CO_2CH_3$ | H | $CH_3$ | $(CH_2)_2CH_3$ | CH | |

TABLE 7-continued

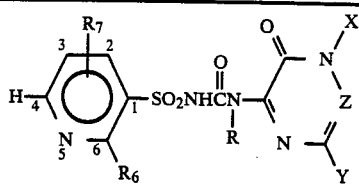

| R | $R_6$ | $R_7$ | X | Y | Z | m.p. (°C.) |
|---|---|---|---|---|---|---|
| H | $CO_2CH_3$ | H | $CH_2CH_3$ | Cl | CH | |
| H | $CO_2CH_3$ | H | $CH_2CH_3$ | $OCH_3$ | CH | |
| H | $CO_2CH_3$ | H | $(CH_2)_2CH_3$ | Cl | CH | |
| H | $CO_2CH_3$ | H | $(CH_2)_2CH_3$ | $OCH_3$ | CH | |
| H | $CO_2CH_3$ | H | $OCH_3$ | H | CH | |
| H | $CO_2CH_3$ | H | $OCH_3$ | $CH_3$ | CH | |
| H | $CO_2CH_3$ | H | $OCH_3$ | $CH_2CH_3$ | CH | |
| H | $CO_2CH_3$ | H | $OCH_3$ | $(CH_2)_2CH_3$ | CH | |
| H | $CO_2CH_3$ | H | $OCH_3$ | $OCH_3$ | CH | |
| H | $CO_2CH_3$ | H | $OCH_3$ | $OCH_2CH_3$ | CH | |
| H | $CO_2CH_3$ | H | $OCH_3$ | $O(CH_2)_2CH_3$ | CH | |
| H | $CO_2CH_3$ | H | $CH_3$ | $SCH_3$ | CH | |
| H | $CO_2CH_3$ | H | $OCH_3$ | $SCH_3$ | CH | |
| H | $CO_2CH_3$ | H | $N(CH_3)_2$ | $SCH_3$ | N | |
| H | $CO_2CH_3$ | H | $CH_3$ | $SCH_2CH_3$ | CH | |
| H | $CO_2CH_3$ | H | $CH_2CH_3$ | $SCH_3$ | CH | |
| H | $CO_2CH_3$ | H | $CH_3$ | $SCH_3$ | N | |
| H | $CO_2CH_3$ | H | $OCH_3$ | Cl | CH | |
| H | $CO_2CH_3$ | H | $OCH_3$ | Br | CH | |
| H | $CO_2CH_3$ | H | $OCH_2CH_3$ | Cl | CH | |
| H | $CO_2CH_3$ | H | $OCH_2CH_3$ | $CH_3$ | CH | |
| H | $CO_2CH_3$ | H | $OCH_2CH_3$ | $OCH_3$ | CH | |
| H | $CO_2CH_3$ | H | $O(CH_2)_2CH_3$ | Cl | CH | |
| H | $CO_2CH_3$ | H | $O(CH_2)_2CH_3$ | $CH_3$ | CH | |
| H | $CO_2CH_3$ | H | $O(CH_2)_2CH_3$ | $OCH_3$ | CH | |
| H | $CO_2CH_3$ | H | $NH_2$ | Cl | CH | |
| H | $CO_2CH_3$ | H | $NH_2$ | $CH_3$ | CH | |
| H | $CO_2CH_3$ | H | $NH_2$ | $OCH_3$ | CH | |
| H | $CO_2CH_3$ | H | $NHCH_3$ | Cl | CH | |
| H | $CO_2CH_3$ | H | $NHCH_3$ | $CH_3$ | CH | |
| H | $CO_2CH_3$ | H | $NHCH_3$ | $OCH_3$ | CH | |
| H | $CO_2CH_3$ | H | $N(CH_3)_2$ | Cl | CH | |
| H | $CO_2CH_3$ | H | $N(CH_3)_2$ | $CH_3$ | CH | |
| H | $CO_2CH_3$ | H | $N(CH_3)_2$ | $OCH_3$ | CH | |
| H | $CO_2CH_3$ | H | $NHCH_3$ | $OCH_2CH_3$ | CH | |
| $CH_3$ | $CO_2CH_3$ | H | $CH_3$ | Cl | CH | |
| $CH_3$ | $CO_2CH_3$ | H | $OCH_3$ | Cl | CH | |
| $CH_3$ | $CO_2CH_3$ | H | $CH_3$ | $OCH_3$ | CH | |
| $CH_3$ | $CO_2CH_3$ | H | $OCH_3$ | $CH_3$ | CH | |
| $CH_3$ | $CO_2CH_3$ | H | $OCH_3$ | $OCH_3$ | CH | |
| H | $CO_2CH_3$ | H | $CH_3$ | Cl | CF | |
| H | $CO_2CH_3$ | H | $CH_3$ | $OCH_3$ | CF | |
| H | $CO_2CH_3$ | H | $OCH_3$ | $OCH_3$ | CF | |
| H | $CO_2CH_3$ | H | $OCH_3$ | $CH_3$ | CF | |
| H | $CO_2CH_3$ | H | $CH_3$ | Cl | CCl | |
| H | $CO_2CH_3$ | H | $CH_3$ | $OCH_3$ | CCl | |
| H | $CO_2CH_3$ | H | $CH_3$ | Br | CBr | |
| H | $CO_2CH_3$ | H | $CH_3$ | Cl | CBr | |
| H | $CO_2CH_3$ | H | $CH_3$ | $OCH_3$ | CBr | |
| H | $CO_2CH_3$ | H | H | $OCH_3$ | N | |
| H | $CO_2CH_3$ | H | $CH_3$ | Cl | N | |
| H | $CO_2CH_3$ | H | $CH_3$ | Br | N | |
| H | $CO_2CH_3$ | H | $CH_3$ | $OCH_3$ | N | |
| H | $CO_2CH_3$ | H | $CH_3$ | $OCH_2CH_3$ | N | |
| H | $CO_2CH_3$ | H | $CH_3$ | $O(CH_2)_2CH_3$ | N | |
| H | $CO_2CH_3$ | H | $CH_3$ | $CH_3$ | N | |
| H | $CO_2CH_3$ | H | $CH_3$ | $CH_2CH_3$ | N | |
| H | $CO_2CH_3$ | H | $CH_3$ | $(CH_2)_2CH_3$ | N | |
| H | $CO_2CH_3$ | H | $CH_2CH_3$ | Cl | N | |
| H | $CO_2CH_3$ | H | $CH_2CH_3$ | $OCH_3$ | N | |
| H | $CO_2CH_3$ | H | $(CH_2)_2CH_3$ | Cl | N | |
| H | $CO_2CH_3$ | H | $(CH_2)_2CH_3$ | $OCH_3$ | N | |
| H | $CO_2CH_3$ | H | $OCH_3$ | H | N | |
| H | $CO_2CH_3$ | H | $OCH_3$ | $CH_3$ | N | |
| H | $CO_2CH_3$ | H | $OCH_3$ | $CH_2CH_3$ | N | |
| H | $CO_2CH_3$ | H | $OCH_3$ | $(CH_2)_2CH_3$ | N | |
| H | $CO_2CH_3$ | H | $OCH_3$ | $OCH_3$ | N | |
| H | $CO_2CH_3$ | H | $OCH_3$ | $OCH_2CH_3$ | N | |
| H | $CO_2CH_3$ | H | $OCH_3$ | $O(CH_2)_2CH_3$ | N | |
| H | $CO_2CH_3$ | H | $OCH_3$ | Cl | N | |
| H | $CO_2CH_3$ | H | $OCH_3$ | Br | N | |

TABLE 7-continued

| R | R₆ | R₇ | X | Y | Z | m.p. (°C.) |
|---|---|---|---|---|---|---|
| H | CO₂CH₃ | H | OCH₂CH₃ | Cl | N | |
| H | CO₂CH₃ | H | OCH₂CH₃ | CH₃ | N | |
| H | CO₂CH₃ | H | OCH₂CH₃ | OCH₃ | N | |
| H | CO₂CH₃ | H | O(CH₂)₂CH₃ | Cl | N | |
| H | CO₂CH₃ | H | O(CH₂)₂CH₃ | CH₃ | N | |
| H | CO₂CH₃ | H | O(CH₂)₂CH₃ | OCH₃ | N | |
| H | CO₂CH₃ | H | NH₂ | Cl | N | |
| H | CO₂CH₃ | H | NH₂ | CH₃ | N | |
| H | CO₂CH₃ | H | NH₂ | OCH₃ | N | |
| H | CO₂CH₃ | H | NHCH₃ | Cl | N | |
| H | CO₂CH₃ | H | NHCH₃ | CH₃ | N | |
| H | CO₂CH₃ | H | NHCH₃ | OCH₃ | N | |
| H | CO₂CH₃ | H | N(CH₃)₂ | Cl | N | |
| H | CO₂CH₃ | H | N(CH₃)₂ | CH₃ | N | |
| H | CO₂CH₃ | H | N(CH₃)₂ | OCH₃ | N | |
| H | CO₂CH₃ | H | NHCH₃ | OCH₂CH₃ | N | |
| CH₃ | CO₂CH₃ | H | CH₃ | Cl | N | |
| CH₃ | CO₂CH₃ | H | OCH₃ | Cl | N | |
| CH₃ | CO₂CH₃ | H | CH₃ | OCH₃ | N | |
| CH₃ | CO₂CH₃ | H | CH₂CH₃ | OCH₃ | N | |
| CH₃ | CO₂CH₃ | H | OCH₃ | CH₃ | N | |
| CH₃ | CO₂CH₃ | H | OCH₃ | OCH₃ | N | |
| H | CO₂CH₃ | 2-F | OCH₃ | Cl | CH | |
| H | CO₂CH₃ | 3-Cl | CH₃ | CH₃ | CH | |
| H | CO₂CH₃ | 2-Cl | CH₃ | OCH₃ | CH | |
| H | CO₂CH₃ | 3-CH₃ | CH₃ | OCH₃ | N | |
| H | CO₂CH₃ | 3-F | CH₃ | OCH₂CH₃ | N | |
| H | CO₂CH₃ | 2-F | CH₂CH₃ | OCH₃ | CH | |
| H | CO₂CH₃ | 2-CH₃ | CH₃ | Br | CH | |
| H | CO₂CH₂CH₃ | H | OCH₃ | Cl | CH | |
| H | CO₂CH₂CH₃ | H | CH₃ | CH₃ | CH | |
| H | CO₂CH₂CH₃ | H | CH₃ | OCH₃ | CH | |
| H | CO₂CH₂CH₃ | H | OCH₃ | CH₃ | CH | |
| H | CO₂CH₂CH₃ | H | CH₃ | Cl | CH | |
| H | CO₂CH₂CH₃ | H | CH₃ | OCH₃ | CH | |
| H | CO₂CH₂CH₃ | H | CH₃ | OCH₃ | N | |
| H | CO₂CH₂CH₃ | H | CH₃ | OCH₂CH₃ | N | |
| H | CO₂CH₂CH₃ | H | OCH₂CH₃ | CH₃ | CH | |
| H | CO₂CH₂CH₃ | H | OCH₃ | OCH₃ | CH | |
| H | CO₂CH₂CH₃ | H | CH₂CH₃ | OCH₃ | CH | |
| H | CO₂CH₂CH₃ | H | CH₃ | Br | CH | |
| H | CO₂CH₂CH₃ | H | CH₃ | OCH₂CH₃ | CH | |
| H | CO₂CH₂CH₃ | H | CH₃ | CH₂CH₃ | CH | |
| H | CO₂CH₂CH=CH₃ | H | OCH₃ | Cl | CH | |
| H | CO₂CH₂C≡CH | H | CH₃ | CH₃ | CH | |
| H | CO₂CH(CH₃)₂ | H | CH₃ | OCH₃ | CH | |
| H | CO₂(CH₂)₂CH₃ | H | OCH₃ | CH₃ | CH | |
| H | CO₂(CH₂)₂OCH₃ | H | CH₃ | Cl | CH | |
| H | CO₂(CH₂)₂OCH₂CH₃ | H | CH₃ | OCH₃ | N | |
| H | CO₂CH₂OCH₃ | H | CH₃ | OCH₂CH₃ | N | |
| H | CO₂(CH₂)₂Cl | H | OCH₂CH₃ | CH₃ | CH | |
| H | CO₂(CH₂)₂F | H | OCH₃ | OCH₃ | CH | |
| H | CO₂(CH₂)₂Br | H | CH₂CH₃ | OCH₃ | CH | |
| H | CO₂(CH₂)₂I | H | CH₃ | Br | CH | |
| H | CO₂CH₂CF₃ | H | CH₃ | OCH₂CH₃ | CH | |
| H | CO₂CH₂CH₂CN | H | CH₃ | CH₂CH₃ | CH | |
| CH₃ | CO₂CH₂CH₃ | H | OCH₃ | Cl | CH | |
| H | CO₂CH₂CH₃ | 3-CH₃ | CH₃ | OCH₃ | CH | |
| H | F | H | OCH₃ | CH₃ | CH | |
| H | Cl | H | CH₃ | OCH₂CH₃ | N | |
| H | Br | H | CH₃ | OCH₃ | N | |
| H | CH₃ | H | OCH₃ | CH₃ | CH | |
| H | CH₂CH₃ | H | CH₃ | OCH₃ | CH | |
| H | (CH₂)₂CH₃ | H | CH₃ | CH₃ | CH | |
| H | CH(CH₃)₂ | H | OCH₂CH₃ | CH₃ | CH | |
| H | CH=CF₂ | H | CH₃ | OCH₃ | CH | |
| H | CCl=CCl₂ | H | OCH₃ | CH₃ | CH | |
| H | CH₂CH=CHCCl₃ | H | CH₃ | Cl | CH | |
| H | CH=CHCl | H | CH₃ | OCH₃ | N | |
| H | CH=CHI | H | CH₃ | OCH₂CH₃ | N | |
| H | CH=CBr₂ | H | OCH₂CH₃ | CH₃ | CH | |

TABLE 7-continued

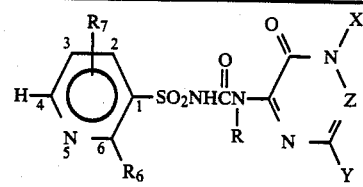

| R | R₆ | R₇ | X | Y | Z | m.p. (°C.) |
|---|---|---|---|---|---|---|
| H | CF=CFH | H | OCH₃ | OCH₃ | CH | |
| H | CH₂CH=CF₂ | H | CH₂CH₃ | OCH₃ | CH | |
| H | CH=CHCF₃ | H | CH₃ | Br | CH | |
| H | CF=CFCH₃ | H | CH₃ | OCH₂CH₃ | H | |
| H | OCH₃ | H | CH₃ | CH₂CH₃ | CH | |
| H | OCH₃ | 3-Cl | OCH₃ | Cl | CH | |
| H | OCH₂CH₃ | H | CH₃ | CH₃ | CH | |
| H | C(O)N(CH₃)₂ | H | CH₃ | OCH₂CH₃ | N | |
| H | C(O)NHCH₂CH₃ | H | OCH₃ | Cl | CH | |
| H | C(O)N(CH₃)OCH₃ | H | CH₃ | CH₃ | CH | |
| H | C(O)NHOCH₂CH₃ | H | CH₃ | OCH₃ | CH | |
| H | C(O)NH(CH₂)₂CH₃ | H | OCH₃ | CH₃ | CH | |
| H | SO₂N(CH₃)₂ | H | CH₃ | Cl | CH | |
| H | SO₂NH—cyclopropyl | H | OCH₃ | Cl | CH | |
| CH₃ | SO₂N(CH₃)₂ | H | CH₃ | CH₃ | CH | |
| H | SO₂N(CH₃)₂ | 3-CH₃ | CH₃ | OCH₃ | CH | |
| H | SO₂N(CH₃)CH₂CH=CH₂ | H | OCH₃ | CH₃ | CH | |
| H | SO₂N((CH₂)₂CH₃)₂ | H | CH₃ | Cl | CH | |
| H | SO₂NH₂ | H | CH₃ | OCH₃ | N | |
| H | SO₂N(CH₃)OCH₃ | H | CH₃ | OCH₂CH₃ | N | |
| H | SO₂N(CH₃)OCH₂CH₃ | H | OCH₂CH₃ | CH₃ | CH | |
| H | SCH₃ | H | OCH₃ | OCH₃ | CH | |
| H | SCH₂CH=CH₃ | H | CH₂CH₃ | OCH₃ | CH | |
| H | SCH₂C≡CH₃ | H | CH₃ | Br | CH | |
| H | S(CH₂)₂CH₃ | H | CH₃ | OCH₂CH₃ | CH | |
| H | S(O)CH₃ | H | CH₃ | CH₂CH₃ | CH | |
| H | SCF₂H | H | OCH₃ | Cl | CH | |
| H | SCF₂CF₂H | H | CH₃ | CH₃ | CH | |
| H | S(CH₂)₂Cl | H | CH₃ | OCH₃ | CH | |
| H | S(CH₂)₂I | H | OCH₃ | CH₃ | CH | |
| H | S(CH₂)₃Br | H | CH₃ | Cl | CH | |
| H | S(O)CF₂CF₂H | H | CH₃ | OCH₃ | N | |
| H | S(O)(CH₂)₂I | H | CH₃ | OCH₂CH₃ | N | |
| H | S(O)₂CH₃ | H | OCH₃ | Cl | CH | |
| H | S(O)₂CH₂CH₃ | H | CH₃ | CH₃ | CH | |
| H | S(O)₂CH₂CH=CH₂ | H | CH₃ | OCH₃ | CH | |
| H | S(O)₂CH₂C≡CH | H | OCH₃ | CH₃ | CH | |
| H | S(O)₂CF₂H | H | CH₃ | Cl | CH | |
| H | S(O)₂CF₂CF₂H | H | CH₃ | OCH₃ | N | |
| H | S(O)₂(CH₂)₂I | H | CH₃ | OCH₂CH₃ | N | |
| H | C(O)CH₃ | H | OCH₃ | Cl | CH | |
| H | C(O)(CH₂)₃CH₃ | H | CH₃ | CH₃ | CH | |
| H | C(O)CH₂CH₃ | H | CH₃ | OCH₃ | CH | |
| H | C(O)—cyclo-C₃H₅ | H | OCH₃ | CH₃ | CH | |
| H | C(O)—cyclo-C₄H₇ | H | CH₃ | Cl | CH | |
| H | C(O)—cyclo-C₅H₉ | H | OCH₃ | Cl | CH | |
| H | C(O)—cyclo-C₃F₅ | H | CH₃ | CH₃ | CH | |
| H | C(O)CF₃ | H | CH₃ | OCH₃ | CH | |
| H | C(O)(CH₂)₃CCl₂H | H | OCH₃ | CH₃ | CH | |
| H | C(O)(CH₂)₄F | H | CH₃ | Cl | CH | |
| H | C(O)—cyclo-(CHCH₂CCl₂) | H | CH₃ | OCH₃ | N | |
| H | L-1, Rₕ = H | H | OCH₂CH₃ | CH₃ | CH | |
| H | L-1, Rₕ = CH₃ | H | OCH₃ | OCH₃ | CH | |
| H | L-2, Rₕ = H | H | CH₂CH₃ | OCH₃ | CH | |
| H | L-2, Rₕ = CH₃ | H | CH₃ | Br | CH | |
| H | L-3 | H | CH₃ | OCH₂CH₃ | CH | |
| H | L-4 | H | CH₃ | CH₂CH₃ | CH | |
| H | L-5 | H | OCH₃ | Cl | CH | |
| H | L-6 | H | CH₃ | CH₃ | CH | |
| H | L-7 | H | CH₃ | OCH₃ | CH | |
| H | L-8 | H | OCH₃ | CH₃ | CH | |
| H | L-9 | H | CH₃ | Cl | CH | |
| H | L-10 | H | CH₃ | OCH₃ | N | |
| H | L-11 | H | CH₃ | OCH₂CH₃ | N | |
| H | L-12 | H | OCH₃ | Cl | CH | |
| H | L-13 | H | CH₃ | CH₃ | CH | |
| H | L-14 | H | CH₃ | OCH₃ | CH | |
| H | L-15 | H | OCH₃ | CH₃ | CH | |
| H | L-16, Rᵢ = H | H | CH₃ | Cl | CH | |
| H | L-16, Rᵢ = CH₃ | H | CH₃ | OCH₃ | N | |
| H | L-17 | H | CH₃ | OCH₂CH₃ | N | |

TABLE 7-continued

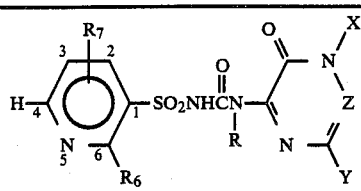

| R | R6 | R7 | X | Y | Z | m.p. (°C.) |
|---|---|---|---|---|---|---|
| H | L-18 | H | OCH3 | Cl | CH | |
| H | L-19 | H | CH3 | CH3 | CH | |
| H | L-20 | H | CH3 | OCH3 | CH | |
| H | L-21 | H | OCH3 | CH3 | CH | |
| H | L-22 | H | CH3 | Cl | CH | |
| H | L-23 | H | OCH3 | Cl | CH | |
| H | L-24 | H | CH3 | CH3 | CH | |
| H | L-25 | H | CH3 | OCH3 | CH | |
| H | L-26, $R_j$ = H | H | OCH3 | CH3 | CH | |
| H | L-26, $R_j$ = CH3 | H | CH3 | Cl | CH | |
| H | L-26, $R_j$ = CH2CH3 | H | CH3 | OCH3 | N | |
| H | L-27, $R_j$ = H | H | CH3 | OCH2CH3 | N | |
| H | L-27, $R_j$ = CH3 | H | OCH2CH3 | CH3 | CH | |
| H | L-27, $R_j$ = CH2CH3 | H | OCH3 | OCH3 | CH | |
| H | L-28, $R_k$ = H | H | CH2CH3 | OCH3 | CH | |
| H | L-28, $R_k$ = CH3 | H | CH3 | Br | CH | |
| H | L-28, $R_k$ = CH2CH3 | H | CH3 | OCH2CH3 | CH | |
| H | L-28, $R_k$ = OCH3 | H | CH3 | CH2CH3 | CH | |
| H | L-28, $R_k$ = OCH2CH3 | H | OCH3 | Cl | CH | |
| H | L-28, $R_k$ = SCH3 | H | CH3 | CH3 | CH | |
| H | L-28, $R_k$ = SCH2CH3 | H | CH3 | OCH3 | CH | |
| H | L-29, $R_k$ = H | H | OCH3 | CH3 | CH | |
| H | L-29, $R_k$ = CH3 | H | CH3 | Cl | CH | |
| H | L-29, $R_k$ = CH2CH3 | H | CH3 | OCH3 | N | |
| H | L-29, $R_k$ = OCH3 | H | CH3 | OCH2CH3 | N | |
| H | L-29, $R_k$ = OCH2CH3 | H | OCH3 | Cl | CH | |
| H | L-29, $R_k$ = SCH3 | H | CH3 | CH3 | CH | |
| H | L-29, $R_k$ = SCH2CH3 | H | CH3 | OCH3 | CH | |
| H | L-30, $R_m$ = H | H | OCH3 | CH3 | CH | |
| H | L-30, $R_m$ = CH3 | H | CH3 | Cl | CH | |
| H | L-30, $R_m$ = CH2CH3 | H | CH3 | OCH3 | N | |
| H | L-31, $R_m$ = H | H | CH3 | OCH2CH3 | N | |
| H | L-31, $R_m$ = CH3 | H | OCH3 | Cl | CH | |
| H | L-31, $R_m$ = CH2CH3 | H | CH3 | CH3 | CH | |
| H | L-32, $R_m$ = H | H | CH3 | OCH3 | CH | |
| H | L-32, $R_m$ = CH3 | H | OCH3 | CH3 | CH | |
| H | L-32, $R_m$ = CH2CH3 | H | CH3 | Cl | CH | |
| H | L-33, $R_n$ = H | H | CH3 | CH3 | N | |
| H | L-33, $R_n$ = CH3 | H | CH3 | OCH3 | CH | |

TABLE 8

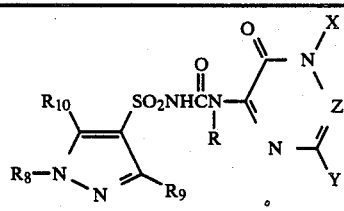

| R | R8 | R9 | R10 | X | Y | Z | m.p. (°C.) |
|---|---|---|---|---|---|---|---|
| H | CH3 | CO2CH3 | H | H | OCH3 | CH | |
| H | CH3 | CO2CH3 | H | CH3 | Cl | CH | |
| H | CH3 | CO2CH3 | H | CH3 | Br | CH | |
| H | CH3 | CO2CH3 | H | CH3 | OCH3 | CH | |
| H | CH3 | CO2CH3 | H | CH3 | OCH2CH3 | CH | |
| H | CH3 | CO2CH3 | H | CH3 | O(CH2)2CH3 | CH | |
| H | CH3 | CO2CH3 | H | CH3 | CH3 | CH | |
| H | CH3 | CO2CH3 | H | CH3 | CH2CH3 | CH | |
| H | CH3 | CO2CH3 | H | CH3 | (CH2)2CH3 | CH | |
| H | CH3 | CO2CH3 | H | CH2CH3 | Cl | CH | |
| H | CH3 | CO2CH3 | H | CH2CH3 | OCH3 | CH | |
| H | CH3 | CO2CH3 | H | (CH2)2CH3 | Cl | CH | |
| H | CH3 | CO2CH3 | H | (CH2)2CH3 | OCH3 | CH | |
| H | CH3 | CO2CH3 | H | OCH3 | H | CH | |
| H | CH3 | CO2CH3 | H | OCH3 | CH3 | CH | |
| H | CH3 | CO2CH3 | H | OCH3 | CH2CH3 | CH | |
| H | CH3 | CO2CH3 | H | OCH3 | (CH2)2CH3 | CH | |

TABLE 8-continued

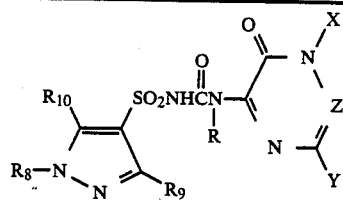

| R | R8 | R9 | R10 | X | Y | Z | m.p. (°C.) |
|---|---|---|---|---|---|---|---|
| H | CH3 | CO2CH3 | H | OCH3 | OCH3 | CH | |
| H | CH3 | CO2CH3 | H | OCH3 | OCH2CH3 | CH | |
| H | CH3 | CO2CH3 | H | OCH3 | O(CH2)2CH3 | CH | |
| H | CH3 | CO2CH3 | H | CH3 | SCH3 | CH | |
| H | CH3 | CO2CH3 | H | CH2CH3 | SCH3 | CH | |
| H | CH3 | CO2CH3 | H | OCH3 | SCH3 | CH | |
| H | CH3 | CO2CH3 | H | CH3 | SCH3 | N | |
| H | CH3 | CO2CH3 | H | OCH2CH3 | SCH3 | CH | |
| H | CH3 | CO2CH3 | H | CH3 | SCH2CH3 | CH | |
| H | CH3 | CO2CH3 | H | OCH3 | Cl | CH | |
| H | CH3 | CO2CH3 | H | OCH3 | Br | CH | |
| H | CH3 | CO2CH3 | H | OCH2CH3 | Cl | CH | |
| H | CH3 | CO2CH3 | H | OCH2CH3 | CH3 | CH | |
| H | CH3 | CO2CH3 | H | OCH2CH3 | OCH3 | CH | |
| H | CH3 | CO2CH3 | H | O(CH2)2CH3 | Cl | CH | |
| H | CH3 | CO2CH3 | H | O(CH2)2CH3 | CH3 | CH | |
| H | CH3 | CO2CH3 | H | O(CH2)2CH3 | OCH3 | CH | |
| H | CH3 | CO2CH3 | H | NH2 | Cl | CH | |
| H | CH3 | CO2CH3 | H | NH2 | CH3 | CH | |
| H | CH3 | CO2CH3 | H | NH2 | OCH3 | CH | |
| H | CH3 | CO2CH3 | H | NHCH3 | Cl | CH | |
| H | CH3 | CO2CH3 | H | NHCH3 | CH3 | CH | |
| H | CH3 | CO2CH3 | H | NHCH3 | OCH3 | CH | |
| H | CH3 | CO2CH3 | H | N(CH3)2 | Cl | CH | |
| H | CH3 | CO2CH3 | H | N(CH3)2 | CH3 | CH | |
| H | CH3 | CO2CH3 | H | N(CH3)2 | OCH3 | CH | |
| H | CH3 | CO2CH3 | H | NHCH3 | OCH2CH3 | CH | |
| CH3 | CH3 | CO2CH3 | H | CH3 | Cl | CH | |
| CH3 | CH3 | CO2CH3 | H | OCH3 | Cl | CH | |
| CH3 | CH3 | CO2CH3 | H | CH3 | OCH3 | CH | |
| CH3 | CH3 | CO2CH3 | H | OCH3 | CH3 | CH | |
| CH3 | CH3 | CO2CH3 | H | OCH3 | OCH3 | CH | |
| H | CH3 | CO2CH3 | H | CH3 | Cl | CF | |
| H | CH3 | CO2CH3 | H | CH3 | OCH3 | CF | |
| H | CH3 | CO2CH3 | H | OCH3 | OCH3 | CF | |
| H | CH3 | CO2CH3 | H | OCH3 | CH3 | CF | |
| H | CH3 | CO2CH3 | H | CH3 | Cl | CCl | |
| H | CH3 | CO2CH3 | H | CH3 | OCH3 | CCl | |
| H | CH3 | CO2CH3 | H | CH3 | Br | CBr | |
| H | CH3 | CO2CH3 | H | CH3 | Cl | CBr | |
| H | CH3 | CO2CH3 | H | CH3 | OCH3 | CBr | |
| H | CH3 | CO2CH3 | H | H | OCH3 | N | |
| H | CH3 | CO2CH3 | H | CH3 | Cl | N | |
| H | CH3 | CO2CH3 | H | CH3 | Br | N | |
| H | CH3 | CO2CH3 | H | CH3 | OCH3 | N | |
| H | CH3 | CO2CH3 | H | CH3 | OCH2CH3 | N | |
| H | CH3 | CO2CH3 | H | CH3 | O(CH2)2CH3 | N | |
| H | CH3 | CO2CH3 | H | CH3 | CH3 | N | |
| H | CH3 | CO2CH3 | H | CH3 | CH2CH3 | N | |
| H | CH3 | CO2CH3 | H | CH3 | (CH2)2CH3 | N | |
| H | CH3 | CO2CH3 | H | CH2CH3 | Cl | N | |
| H | CH3 | CO2CH3 | H | CH2CH3 | OCH3 | N | |
| H | CH3 | CO2CH3 | H | (CH2)2CH3 | Cl | N | |
| H | CH3 | CO2CH3 | H | (CH2)2CH3 | OCH3 | N | |
| H | CH3 | CO2CH3 | H | OCH3 | H | N | |
| H | CH3 | CO2CH3 | H | OCH3 | CH3 | N | |
| H | CH3 | CO2CH3 | H | OCH3 | CH2CH3 | N | |
| H | CH3 | CO2CH3 | H | OCH3 | (CH2)2CH3 | N | |
| H | CH3 | CO2CH3 | H | OCH3 | OCH3 | N | |
| H | CH3 | CO2CH3 | H | OCH3 | OCH2CH3 | N | |
| H | CH3 | CO2CH3 | H | OCH3 | O(CH2)2CH3 | N | |
| H | CH3 | CO2CH3 | H | OCH3 | Cl | N | |
| H | CH3 | CO2CH3 | H | OCH3 | Br | N | |
| H | CH3 | CO2CH3 | H | OCH2CH3 | Cl | N | |
| H | CH3 | CO2CH3 | H | OCH2CH3 | CH3 | N | |
| H | CH3 | CO2CH3 | H | OCH2CH3 | OCH3 | N | |
| H | CH3 | CO2CH3 | H | O(CH2)2CH3 | Cl | N | |
| H | CH3 | CO2CH3 | H | O(CH2)2CH3 | CH3 | N | |
| H | CH3 | CO2CH3 | H | O(CH2)2CH3 | OCH3 | N | |
| H | CH3 | CO2CH3 | H | NH2 | Cl | N | |
| H | CH3 | CO2CH3 | H | NH2 | CH3 | N | |

TABLE 8-continued

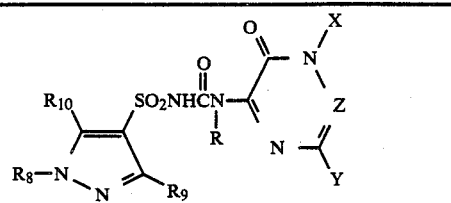

| R | R8 | R9 | R10 | X | Y | Z | m.p. (°C.) |
|---|---|---|---|---|---|---|---|
| H | CH3 | CO2CH3 | H | NH2 | OCH3 | N | |
| H | CH3 | CO2CH3 | H | NHCH3 | Cl | N | |
| H | CH3 | CO2CH3 | H | NHCH3 | CH3 | N | |
| H | CH3 | CO2CH3 | H | NHCH3 | OCH3 | N | |
| H | CH3 | CO2CH3 | H | N(CH3)2 | Cl | N | |
| H | CH3 | CO2CH3 | H | N(CH3)2 | CH3 | N | |
| H | CH3 | CO2CH3 | H | N(CH3)2 | OCH3 | N | |
| H | CH3 | CO2CH3 | H | NHCH3 | OCH2CH3 | N | |
| CH3 | CH3 | CO2CH3 | H | CH3 | Cl | N | |
| CH3 | CH3 | CO2CH3 | H | OCH3 | Cl | N | |
| CH3 | CH3 | CO2CH3 | H | CH3 | OCH3 | N | |
| CH3 | CH3 | CO2CH3 | H | CH2CH3 | OCH3 | N | |
| CH3 | CH3 | CO2CH3 | H | OCH3 | CH3 | N | |
| CH3 | CH3 | CO2CH3 | H | OCH3 | OCH3 | N | |
| H | CH3 | CO2CH3 | Cl | OCH3 | Cl | CH | |
| H | CH3 | CO2CH3 | F | CH3 | CH3 | CH | |
| H | CH3 | CO2CH3 | Br | CH3 | OCH3 | CH | |
| H | CH3 | CO2CH3 | CH3 | OCH3 | CH3 | CH | |
| H | CH3 | CO2CH3 | CH2CH3 | CH3 | Cl | Cl | |
| H | CH3 | CO2CH3 | (CH2)2CH3 | CH3 | OCH3 | N | |
| H | CH3 | CO2CH3 | CH(CH3)2 | CH3 | OCH2CH3 | N | |
| H | CH3 | CO2CH3 | Br | OCH3 | Cl | CH | |
| H | CH3 | CO2CH3 | OCH3 | CH3 | CH3 | CH | |
| H | CH3 | CO2CH3 | OCH2CH3 | CH3 | OCH3 | CH | |
| H | CH3 | CO2CH2CH3 | H | OCH3 | Cl | CH | |
| H | CH3 | CO2CH2CH3 | H | CH3 | CH3 | CH | |
| H | CH3 | CO2CH2CH3 | H | CH3 | OCH3 | CH | |
| H | CH3 | CO2CH2CH3 | H | OCH3 | CH3 | CH | |
| H | CH3 | CO2CH2CH3 | H | CH3 | Cl | CH | |
| H | CH3 | CO2CH2CH3 | H | CH3 | OCH3 | CH | |
| H | CH3 | CO2CH2CH3 | H | CH3 | OCH3 | N | |
| H | CH3 | CO2CH2CH3 | H | CH3 | OCH2CH3 | N | |
| H | CH3 | CO2CH2CH3 | H | OCH2CH3 | CH3 | CH | |
| H | CH3 | CO2CH2CH3 | H | OCH3 | OCH3 | CH | |
| H | CH3 | CO2CH2CH3 | H | CH2CH3 | OCH3 | CH | |
| H | CH3 | CO2CH2CH3 | H | CH3 | Br | CH | |
| H | CH3 | CO2CH2CH3 | H | CH3 | OCH2CH3 | CH | |
| H | CH3 | CO2CH2CH3 | H | CH3 | CH2CH3 | CH | |
| H | CH3 | CO2CH2CH=CH3 | H | OCH3 | Cl | CH | |
| H | CH3 | CO2CH2C≡CH | H | CH3 | CH3 | CH | |
| H | CH3 | CO2CH(CH3)2 | H | OCH3 | OCH3 | CH | |
| H | CH3 | CO2(CH2)2CH3 | H | OCH3 | CH3 | CH | |
| H | CH3 | CO2(CH2)2OCH3 | H | CH3 | Cl | CH | |
| H | CH3 | CO2(CH2)2OCH2CH3 | H | CH3 | OCH3 | N | |
| H | CH3 | CO2CH2OCH3 | H | CH3 | OCH2CH3 | N | |
| H | CH3 | CO2(CH2)2Cl | H | OCH2CH3 | CH3 | CH | |
| H | CH3 | CO2(CH2)2F | H | OCH3 | OCH3 | CH | |
| H | CH3 | CO2(CH2)2Br | H | CH2CH3 | OCH3 | CH | |
| H | CH3 | CO2(CH2)2I | H | CH3 | Br | CH | |
| H | CH3 | CO2CH2CF3 | H | CH3 | OCH2CH3 | CH | |
| H | CH3 | CO2CH2CH2CN | H | CH3 | CH2CH3 | CH | |
| CH3 | CH3 | CO2CH2CH3 | H | OCH3 | Cl | CH | |
| H | CH3 | CO2CH2CH3 | OCH3 | CH3 | OCH3 | CH | |
| H | CH3 | F | H | OCH3 | CH3 | CH | |
| H | CH3 | Cl | H | CH3 | OCH2CH3 | N | |
| H | CH3 | Br | H | CH3 | OCH3 | N | |
| H | CH3 | NO2 | H | CH3 | Cl | CH | |
| H | CH3 | CH3 | H | OCH3 | CH3 | CH | |
| H | CH3 | CH2CH3 | H | CH3 | OCH3 | CH | |
| H | CH3 | (CH2)2CH3 | H | CH3 | CH3 | CH | |
| H | CH3 | CH(CH3)2 | H | OCH2CH3 | CH3 | CH | |
| H | CH3 | CH=CF2 | H | CH3 | OCH3 | CH | |
| H | CH3 | CCl=CCl2 | H | OCH3 | CH3 | CH | |
| H | CH3 | CH2CH=CHCCl3 | H | CH3 | Cl | CH | |
| H | CH3 | CH=CHCl | H | CH3 | OCH3 | N | |
| H | CH3 | CH=CHI | H | CH3 | OCH2CH3 | N | |
| H | CH3 | CH=CBr2 | H | OCH2CH3 | CH3 | CH | |
| H | CH3 | CF=CFH | H | OCH3 | OCH3 | CH | |
| H | CH3 | CH2CH=CF2 | H | CH2CH3 | OCH3 | CH | |
| H | CH3 | CH=CHCF3 | H | CH3 | Br | CH | |
| H | CH3 | CF=CFCH3 | H | CH3 | OCH2CH3 | H | |

TABLE 8-continued

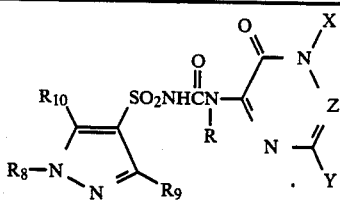

| R | $R_8$ | $R_9$ | $R_{10}$ | X | Y | Z | m.p. (°C.) |
|---|---|---|---|---|---|---|---|
| H | $CH_3$ | $OCH_3$ | H | $CH_3$ | $CH_2CH_3$ | CH | |
| H | $CH_3$ | $OCH_3$ | $CH_3$ | $OCH_3$ | Cl | CH | |
| H | $CH_3$ | $OCH_2CH_3$ | H | $CH_3$ | $CH_3$ | CH | |
| H | $CH_3$ | $C(O)N(CH_3)_2$ | H | $CH_3$ | $OCH_2CH_3$ | N | |
| H | $CH_3$ | $C(O)NHCH_2CH_3$ | H | $OCH_3$ | Cl | CH | |
| H | $CH_3$ | $C(O)N(CH_3)OCH_3$ | H | $CH_3$ | $CH_3$ | CH | |
| H | $CH_3$ | $C(O)NHOCH_2CH_3$ | H | $CH_3$ | $OCH_3$ | CH | |
| H | $CH_3$ | $C(O)NH(CH_2)_2CH_3$ | H | $OCH_3$ | $CH_3$ | CH | |
| H | $CH_3$ | $SO_2N(CH_3)_2$ | H | $CH_3$ | Cl | CH | |
| H | $CH_3$ | $SO_2NH$—cyclopropyl | H | $OCH_3$ | Cl | CH | |
| $CH_3$ | $CH_3$ | $SO_2N(CH_3)_2$ | H | $CH_3$ | $CH_3$ | CH | |
| H | $CH_3$ | $SO_2N(CH_3)_2$ | $CH_3$ | $CH_3$ | $OCH_3$ | CH | |
| H | $CH_3$ | $SO_2N(CH_3)CH_2CH=CH_2$ | H | $OCH_3$ | $CH_3$ | CH | |
| H | $CH_3$ | $SO_2N((CH_2)_2CH_3)_2$ | H | $CH_3$ | Cl | CH | |
| H | $CH_3$ | $SO_2NH_2$ | H | $CH_3$ | $OCH_3$ | N | |
| H | $CH_3$ | $SO_2N(CH_3)OCH_3$ | H | $CH_3$ | $OCH_2CH_3$ | N | |
| H | $CH_3$ | $SO_2N(CH_3)OCH_2CH_3$ | H | $OCH_2CH_3$ | $CH_3$ | CH | |
| H | $CH_3$ | $SCH_3$ | H | $OCH_3$ | $OCH_3$ | CH | |
| H | $CH_3$ | $SCH_2CH=CH_3$ | H | $CH_2CH_3$ | $OCH_3$ | CH | |
| H | $CH_3$ | $SCH_2C\equiv CH_3$ | H | $CH_3$ | Br | CH | |
| H | $CH_3$ | $S(CH_2)_2CH_3$ | H | $CH_3$ | $OCH_2CH_3$ | CH | |
| H | $CH_3$ | $S(O)CH_3$ | H | $CH_3$ | $CH_2CH_3$ | CH | |
| H | $CH_3$ | $SCF_2H$ | H | $OCH_3$ | Cl | CH | |
| H | $CH_3$ | $SCF_2CF_2H$ | H | $CH_3$ | $CH_3$ | CH | |
| H | $CH_3$ | $S(CH_2)_2Cl$ | H | $CH_3$ | $OCH_3$ | CH | |
| H | $CH_3$ | $S(CH_2)_2I$ | H | $OCH_3$ | $CH_3$ | CH | |
| H | $CH_3$ | $S(CH_2)_3Br$ | H | $CH_3$ | Cl | CH | |
| H | $CH_3$ | $S(O)CF_2CF_2H$ | H | $CH_3$ | $OCH_3$ | N | |
| H | $CH_3$ | $S(O)(CH_2)_2I$ | H | $CH_3$ | $OCH_2CH_3$ | N | |
| H | $CH_3$ | $S(O)_2CH_3$ | H | $OCH_3$ | Cl | CH | |
| H | $CH_3$ | $S(O)_2CH_2CH_3$ | H | $CH_3$ | $CH_3$ | CH | |
| H | $CH_3$ | $S(O)_2CH_2CH=CH_2$ | H | $CH_3$ | $OCH_3$ | CH | |
| H | $CH_3$ | $S(O)_2CH_2C\equiv CH$ | H | $OCH_3$ | $CH_3$ | CH | |
| H | $CH_3$ | $S(O)_2CF_2H$ | H | $CH_3$ | Cl | CH | |
| H | $CH_3$ | $S(O)_2CF_2CF_2H$ | H | $CH_3$ | $OCH_3$ | N | |
| H | $CH_3$ | $S(O)_2(CH_2)_2I$ | H | $CH_3$ | $OCH_2CH_3$ | N | |
| H | $CH_3$ | $C(O)CH_3$ | H | $OCH_3$ | Cl | CH | |
| H | $CH_3$ | $C(O)(CH_2)_3CH_3$ | H | $CH_3$ | $CH_3$ | CH | |
| H | $CH_3$ | $C(O)CH_2CH_3$ | H | $CH_3$ | $OCH_3$ | CH | |
| H | $CH_3$ | $C(O)$—cyclo-$C_3H_5$ | H | $OCH_3$ | $CH_3$ | CH | |
| H | $CH_3$ | $C(O)$—cyclo-$C_4H_7$ | H | $CH_3$ | Cl | CH | |
| H | $CH_3$ | $C(O)$—cyclo-$C_5H_9$ | H | $OCH_3$ | Cl | CH | |
| H | $CH_3$ | $C(O)$—cyclo-$C_3F_5$ | H | $CH_3$ | $CH_3$ | CH | |
| H | $CH_3$ | $C(O)CF_3$ | H | $CH_3$ | $OCH_3$ | CH | |
| H | $CH_3$ | $C(O)(CH_2)_3CCl_2H$ | H | $OCH_3$ | $CH_3$ | CH | |
| H | $CH_3$ | $C(O)(CH_2)_4F$ | H | $CH_3$ | Cl | CH | |
| H | $CH_3$ | $C(O)$—cycylo-$(CHCH_2CCl_2)$ | H | $CH_3$ | $OCH_3$ | N | |
| H | $CH_3$ | $OCF_2H$ | H | $CH_3$ | $OCH_2CH_3$ | N | |
| H | $CH_3$ | L-1, $R_h$ = H | H | $OCH_2CH_3$ | $CH_3$ | CH | |
| H | $CH_3$ | L-1, $R_h$ = $CH_3$ | H | $OCH_3$ | $OCH_3$ | CH | |
| H | $CH_3$ | L-2, $R_h$ = H | H | $CH_2CH_3$ | $OCH_3$ | CH | |
| H | $CH_3$ | L-2, $R_h$ = $CH_3$ | H | $CH_3$ | Br | CH | |
| H | $CH_3$ | L-3 | H | $CH_3$ | $OCH_2CH_3$ | CH | |
| H | $CH_3$ | L-4 | H | $CH_3$ | $CH_2CH_3$ | CH | |
| H | $CH_3$ | L-5 | H | $OCH_3$ | Cl | CH | |
| H | $CH_3$ | L-6 | H | $CH_3$ | $CH_3$ | CH | |
| H | $CH_3$ | L-7 | H | $CH_3$ | $OCH_3$ | CH | |
| H | $CH_3$ | L-8 | H | $OCH_3$ | $CH_3$ | CH | |
| H | $CH_3$ | L-9 | H | $CH_3$ | Cl | CH | |
| H | $CH_3$ | L-10 | H | $CH_3$ | $OCH_3$ | N | |
| H | $CH_3$ | L-11 | H | $CH_3$ | $OCH_2CH_3$ | N | |
| H | $CH_3$ | L-12 | H | $OCH_3$ | Cl | CH | |
| H | $CH_3$ | L-13 | H | $CH_3$ | $CH_3$ | CH | |
| H | $CH_3$ | L-14 | H | $CH_3$ | $OCH_3$ | CH | |
| H | $CH_3$ | L-15 | H | $OCH_3$ | $CH_3$ | CH | |
| H | $CH_3$ | L-16, $R_i$ = H | H | $CH_3$ | Cl | CH | |
| H | $CH_3$ | L-16, $R_i$ = $CH_3$ | H | $CH_3$ | $OCH_3$ | N | |
| H | $CH_3$ | L-17 | H | $CH_3$ | $OCH_2CH_3$ | N | |
| H | $CH_3$ | L-18 | H | $OCH_3$ | Cl | CH | |
| H | $CH_3$ | L-19 | H | $CH_3$ | $CH_3$ | CH | |
| H | $CH_3$ | L-20 | H | $CH_3$ | $OCH_3$ | CH | |

TABLE 8-continued

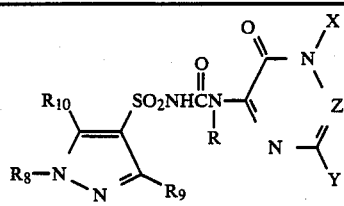

| R | R8 | R9 | R10 | X | Y | Z | m.p. (°C.) |
|---|---|---|---|---|---|---|---|
| H | CH3 | L-21 | H | OCH3 | CH3 | CH | |
| H | CH3 | L-22 | H | CH3 | Cl | CH | |
| H | CH3 | L-23 | H | OCH3 | Cl | CH | |
| H | CH3 | L-24 | H | CH3 | CH3 | CH | |
| H | CH3 | L-25 | H | CH3 | OCH3 | CH | |
| H | CH3 | L-26, $R_j$ = H | H | OCH3 | CH3 | CH | |
| H | CH3 | L-26, $R_j$ = CH3 | H | CH3 | Cl | CH | |
| H | CH3 | L-26, $R_j$ = CH2CH3 | H | CH3 | OCH3 | N | |
| H | CH3 | L-27, $R_j$ = H | H | CH3 | OCH2CH3 | N | |
| H | CH3 | L-27, $R_j$ = CH3 | H | OCH2CH3 | CH3 | CH | |
| H | CH3 | L-27, $R_j$ = CH2CH3 | H | OCH3 | OCH3 | CH | |
| H | CH3 | L-28, $R_k$ = H | H | CH2CH3 | OCH3 | CH | |
| H | CH3 | L-28, $R_k$ = CH3 | H | CH3 | Br | CH | |
| H | CH3 | L-28, $R_k$ = CH2CH3 | H | CH3 | OCH2CH3 | CH | |
| H | CH3 | L-28, $R_k$ = OCH3 | H | CH3 | CH2CH3 | CH | |
| H | CH3 | L-28, $R_k$ = OCH2CH3 | H | OCH3 | Cl | CH | |
| H | CH3 | L-28, $R_k$ = SCH3 | H | CH3 | CH3 | CH | |
| H | CH3 | L-28, $R_k$ = SCH2CH3 | H | CH3 | OCH3 | CH | |
| H | CH3 | L-29, $R_k$ = H | H | OCH3 | CH3 | CH | |
| H | CH3 | L-29, $R_k$ = CH3 | H | CH3 | Cl | CH | |
| H | CH3 | L-29, $R_k$ = CH2CH3 | H | CH3 | OCH3 | N | |
| H | CH3 | L-29, $R_k$ = OCH3 | H | CH3 | OCH2CH3 | N | |
| H | CH3 | L-29, $R_k$ = OCH2CH3 | H | OCH3 | Cl | CH | |
| H | CH3 | L-29, $R_k$ = SCH3 | H | CH3 | CH3 | CH | |
| H | CH3 | L-29, $R_k$ = SCH2CH3 | H | CH3 | OCH3 | CH | |
| H | CH3 | L-30, $R_m$ = H | H | OCH3 | CH3 | CH | |
| H | CH3 | L-30, $R_m$ = CH3 | H | CH3 | Cl | CH | |
| H | CH3 | L-30, $R_m$ = CH2CH3 | H | CH3 | OCH3 | N | |
| H | CH3 | L-31, $R_m$ = H | H | CH3 | OCH2CH3 | N | |
| H | CH3 | L-31, $R_m$ = CH3 | H | OCH3 | Cl | CH | |
| H | CH3 | L-31, $R_m$ = CH2CH3 | H | CH3 | CH3 | CH | |
| H | CH3 | L-32, $R_m$ = H | H | CH3 | OCH3 | CH | |
| H | CH3 | L-32, $R_m$ = CH3 | H | OCH3 | CH3 | CH | |
| H | CH3 | L-32, $R_m$ = CH2CH3 | H | CH3 | Cl | CH | |
| H | CH3 | L-33, $R_n$ = H | H | CH3 | CH3 | N | |
| H | CH3 | L-33, $R_n$ = CH3 | H | CH3 | OCH3 | CH | |
| H | H | CO2CH3 | H | OCH3 | Cl | CH | |
| H | CH2CH3 | CO2CH3 | H | CH3 | CH3 | CH | |
| H | (CH2)2CH3 | CO2CH3 | H | CH3 | OCH3 | CH | |
| H | H | CO2CH2CH3 | H | OCH3 | CH3 | CH | |
| H | CH2CH3 | CO2CH2CH3 | H | CH3 | Cl | CH | |
| H | (CH2)2CH3 | CO2CH2CH3 | H | CH3 | OCH3 | N | |
| CH3 | CH2CH3 | CO2CH3 | H | CH3 | OCH2CH3 | N | |
| CH3 | (CH2)2CH3 | CO2CH3 | H | OCH2CH3 | CH3 | CH | |
| CH3 | H | CO2CH3 | H | OCH3 | OCH3 | CH | |
| H | H | CO2CH3 | H | CH2CH3 | OCH3 | CH | |
| H | CH2CH3 | CO2CH3 | H | CH3 | Br | CH | |
| H | (CH2)2CH3 | CO2CH3 | H | CH3 | OCH2CH3 | CH | |
| H | H | CO2CH3 | H | CH3 | CH2CH3 | CH | |
| H | CH2CH3 | CO2CH3 | H | OCH3 | Cl | CH | |
| H | H | SO2N(CH3)2 | H | CH3 | CH3 | CH | |
| H | CH2CH3 | CH3 | H | CH3 | OCH3 | CH | |
| H | H | Br | H | OCH3 | CH3 | CH | |
| H | CH2CH3 | SO2CH3 | H | CH3 | Cl | CH | |
| H | H | OCF2H | H | CH3 | OCH3 | N | |
| H | (CH2)2CH3 | OCH3 | H | CH3 | OCH2CH3 | N | |
| H | CH(CH3)2 | CO2CH3 | H | OCH3 | Cl | CH | |

TABLE 9

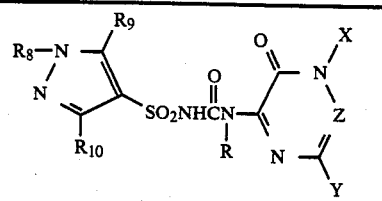

| R | $R_8$ | $R_9$ | $R_{10}$ | X | Y | Z | m.p. (°C.) |
|---|---|---|---|---|---|---|---|
| H | $CH_3$ | $CO_2CH_3$ | H | H | $OCH_3$ | CH | |
| H | $CH_3$ | $CO_2CH_3$ | H | $CH_3$ | Cl | CH | |
| H | $CH_3$ | $CO_2CH_3$ | H | $CH_3$ | Br | CH | |
| H | $CH_3$ | $CO_2CH_3$ | H | $CH_3$ | $OCH_3$ | CH | |
| H | $CH_3$ | $CO_2CH_3$ | H | $CH_3$ | $OCH_2CH_3$ | CH | |
| H | $CH_3$ | $CO_2CH_3$ | H | $CH_3$ | $O(CH_2)_2CH_3$ | CH | |
| H | $CH_3$ | $CO_2CH_3$ | H | $CH_3$ | $CH_3$ | CH | |
| H | $CH_3$ | $CO_2CH_3$ | H | $CH_3$ | $CH_2CH_3$ | CH | |
| H | $CH_3$ | $CO_2CH_3$ | H | $CH_3$ | $(CH_2)_2CH_3$ | CH | |
| H | $CH_3$ | $CO_2CH_3$ | H | $CH_2CH_3$ | Cl | CH | |
| H | $CH_3$ | $CO_2CH_3$ | H | $CH_2CH_3$ | $OCH_3$ | CH | |
| H | $CH_3$ | $CO_2CH_3$ | H | $(CH_2)_2CH_3$ | Cl | CH | |
| H | $CH_3$ | $CO_2CH_3$ | H | $(CH_2)_2CH_3$ | $OCH_3$ | CH | |
| H | $CH_3$ | $CO_2CH_3$ | H | $OCH_3$ | H | CH | |
| H | $CH_3$ | $CO_2CH_3$ | H | $OCH_3$ | $CH_3$ | CH | |
| H | $CH_3$ | $CO_2CH_3$ | H | $OCH_3$ | $CH_2CH_3$ | CH | |
| H | $CH_3$ | $CO_2CH_3$ | H | $OCH_3$ | $(CH_2)_2CH_3$ | CH | |
| H | $CH_3$ | $CO_2CH_3$ | H | $OCH_3$ | $OCH_3$ | CH | |
| H | $CH_3$ | $CO_2CH_3$ | H | $OCH_3$ | $OCH_2CH_3$ | CH | |
| H | $CH_3$ | $CO_2CH_3$ | H | $OCH_3$ | $O(CH_2)_2CH_3$ | CH | |
| H | $CH_3$ | $CO_2CH_3$ | H | $CH_3$ | $SCH_3$ | CH | |
| H | $CH_3$ | $CO_2CH_3$ | H | $CH_3$ | $SCH_3$ | N | |
| H | $CH_3$ | $CO_2CH_3$ | H | $CH_3$ | $SCH_2CH_3$ | N | |
| H | $CH_3$ | $CO_2CH_3$ | H | $OCH_3$ | $SCH_3$ | CH | |
| H | $CH_3$ | $CO_2CH_3$ | H | $N(CH_3)_2$ | $SCH_3$ | CH | |
| H | $CH_3$ | $CO_2CH_3$ | H | $NHCH_3$ | $SCH_3$ | N | |
| H | $CH_3$ | $CO_2CH_3$ | H | $OCH_3$ | Cl | CH | |
| H | $CH_3$ | $CO_2CH_3$ | H | $OCH_3$ | Br | CH | |
| H | $CH_3$ | $CO_2CH_3$ | H | $OCH_2CH_3$ | Cl | CH | |
| H | $CH_3$ | $CO_2CH_3$ | H | $OCH_2CH_3$ | $CH_3$ | CH | |
| H | $CH_3$ | $CO_2CH_3$ | H | $OCH_2CH_3$ | $OCH_3$ | CH | |
| H | $CH_3$ | $CO_2CH_3$ | H | $O(CH_2)_2CH_3$ | Cl | CH | |
| H | $CH_3$ | $CO_2CH_3$ | H | $O(CH_2)_2CH_3$ | $CH_3$ | CH | |
| H | $CH_3$ | $CO_2CH_3$ | H | $O(CH_2)_2CH_3$ | $OCH_3$ | CH | |
| H | $CH_3$ | $CO_2CH_3$ | H | $NH_2$ | Cl | CH | |
| H | $CH_3$ | $CO_2CH_3$ | H | $NH_2$ | $CH_3$ | CH | |
| H | $CH_3$ | $CO_2CH_3$ | H | $NH_2$ | $OCH_3$ | CH | |
| H | $CH_3$ | $CO_2CH_3$ | H | $NHCH_3$ | Cl | CH | |
| H | $CH_3$ | $CO_2CH_3$ | H | $NHCH_3$ | $CH_3$ | CH | |
| H | $CH_3$ | $CO_2CH_3$ | H | $NHCH_3$ | $OCH_3$ | CH | |
| H | $CH_3$ | $CO_2CH_3$ | H | $N(CH_3)_2$ | Cl | CH | |
| H | $CH_3$ | $CO_2CH_3$ | H | $N(CH_3)_2$ | $CH_3$ | CH | |
| H | $CH_3$ | $CO_2CH_3$ | H | $N(CH_3)_2$ | $OCH_3$ | CH | |
| H | $CH_3$ | $CO_2CH_3$ | H | $NHCH_3$ | $OCH_2CH_3$ | CH | |
| $CH_3$ | $CH_3$ | $CO_2CH_3$ | H | $CH_3$ | Cl | CH | |
| $CH_3$ | $CH_3$ | $CO_2CH_3$ | H | $OCH_3$ | Cl | CH | |
| $CH_3$ | $CH_3$ | $CO_2CH_3$ | H | $CH_3$ | $OCH_3$ | CH | |
| $CH_3$ | $CH_3$ | $CO_2CH_3$ | H | $OCH_3$ | $CH_3$ | CH | |
| $CH_3$ | $CH_3$ | $CO_2CH_3$ | H | $OCH_3$ | $OCH_3$ | CH | |
| H | $CH_3$ | $CO_2CH_3$ | H | $CH_3$ | Cl | CF | |
| H | $CH_3$ | $CO_2CH_3$ | H | $CH_3$ | $OCH_3$ | CF | |
| H | $CH_3$ | $CO_2CH_3$ | H | $OCH_3$ | $OCH_3$ | CF | |
| H | $CH_3$ | $CO_2CH_3$ | H | $OCH_3$ | $CH_3$ | CF | |
| H | $CH_3$ | $CO_2CH_3$ | H | $CH_3$ | Cl | CCl | |
| H | $CH_3$ | $CO_2CH_3$ | H | $CH_3$ | $OCH_3$ | CCl | |
| H | $CH_3$ | $CO_2CH_3$ | H | $CH_3$ | Br | CBr | |
| H | $CH_3$ | $CO_2CH_3$ | H | $CH_3$ | Cl | CBr | |
| H | $CH_3$ | $CO_2CH_3$ | H | $CH_3$ | $OCH_3$ | CBr | |
| H | $CH_3$ | $CO_2CH_3$ | H | H | $OCH_3$ | N | |
| H | $CH_3$ | $CO_2CH_3$ | H | $CH_3$ | Cl | N | |
| H | $CH_3$ | $CO_2CH_3$ | H | $CH_3$ | Br | N | |
| H | $CH_3$ | $CO_2CH_3$ | H | $CH_3$ | $OCH_3$ | N | |
| H | $CH_3$ | $CO_2CH_3$ | H | $CH_3$ | $OCH_2CH_3$ | N | |
| H | $CH_3$ | $CO_2CH_3$ | H | $CH_3$ | $O(CH_2)_2CH_3$ | N | |
| H | $CH_3$ | $CO_2CH_3$ | H | $CH_3$ | $CH_3$ | N | |
| H | $CH_3$ | $CO_2CH_3$ | H | $CH_3$ | $CH_2CH_3$ | N | |
| H | $CH_3$ | $CO_2CH_3$ | H | $CH_3$ | $(CH_2)_2CH_3$ | N | |
| H | $CH_3$ | $CO_2CH_3$ | H | $CH_2CH_3$ | Cl | N | |
| H | $CH_3$ | $CO_2CH_3$ | H | $CH_2CH_3$ | $OCH_3$ | N | |
| H | $CH_3$ | $CO_2CH_3$ | H | $(CH_2)_2CH_3$ | Cl | N | |
| H | $CH_3$ | $CO_2CH_3$ | H | $(CH_2)_2CH_3$ | $OCH_3$ | N | |

TABLE 9-continued

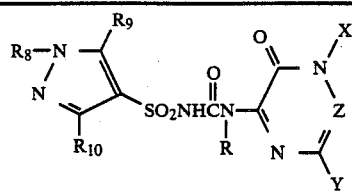

| R | R8 | R9 | R10 | X | Y | Z | m.p. (°C.) |
|---|----|----|-----|---|---|---|------------|
| H | CH3 | CO2CH3 | H | OCH3 | H | N | |
| H | CH3 | CO2CH3 | H | OCH3 | CH3 | N | |
| H | CH3 | CO2CH3 | H | OCH3 | CH2CH3 | N | |
| H | CH3 | CO2CH3 | H | OCH3 | (CH2)2CH3 | N | |
| H | CH3 | CO2CH3 | H | OCH3 | OCH3 | N | |
| H | CH3 | CO2CH3 | H | OCH3 | OCH2CH3 | N | |
| H | CH3 | CO2CH3 | H | OCH3 | O(CH2)2CH3 | N | |
| H | CH3 | CO2CH3 | H | OCH3 | Cl | N | |
| H | CH3 | CO2CH3 | H | OCH3 | Br | N | |
| H | CH3 | CO2CH3 | H | OCH2CH3 | Cl | N | |
| H | CH3 | CO2CH3 | H | OCH2CH3 | OCH3 | N | |
| H | CH3 | CO2CH3 | H | O(CH2)2CH3 | Cl | N | |
| H | CH3 | CO2CH3 | H | O(CH2)2CH3 | CH3 | N | |
| H | CH3 | CO2CH3 | H | O(CH2)2CH3 | OCH3 | N | |
| H | CH3 | CO2CH3 | H | NH2 | Cl | N | |
| H | CH3 | CO2CH3 | H | NH2 | CH3 | N | |
| H | CH3 | CO2CH3 | H | NH2 | OCH3 | N | |
| H | CH3 | CO2CH3 | H | NHCH3 | Cl | N | |
| H | CH3 | CO2CH3 | H | NHCH3 | CH3 | N | |
| H | CH3 | CO2CH3 | H | NHCH3 | OCH3 | N | |
| H | CH3 | CO2CH3 | H | N(CH3)2 | Cl | N | |
| H | CH3 | CO2CH3 | H | N(CH3)2 | CH3 | N | |
| H | CH3 | CO2CH3 | H | N(CH3)2 | OCH3 | N | |
| H | CH3 | CO2CH3 | H | NHCH3 | OCH2CH3 | N | |
| CH3 | CH3 | CO2CH3 | H | CH3 | Cl | N | |
| CH3 | CH3 | CO2CH3 | H | OCH3 | Cl | N | |
| CH3 | CH3 | CO2CH3 | H | CH3 | OCH3 | N | |
| CH3 | CH3 | CO2CH3 | H | CH2CH3 | OCH3 | N | |
| CH3 | CH3 | CO2CH3 | H | OCH3 | CH3 | N | |
| CH3 | CH3 | CO2CH3 | H | OCH3 | OCH3 | N | |
| H | CH3 | CO2CH3 | Cl | OCH3 | Cl | CH | |
| H | CH3 | CO2CH3 | F | CH3 | CH3 | CH | |
| H | CH3 | CO2CH3 | Br | CH3 | OCH3 | CH | |
| H | CH3 | CO2CH3 | CH3 | OCH3 | CH3 | CH | |
| H | CH3 | CO2CH3 | CH2CH3 | CH3 | Cl | Cl | |
| H | CH3 | CO2CH3 | (CH2)2CH3 | CH3 | OCH3 | N | |
| H | CH3 | CO2CH3 | CH(CH3)2 | CH3 | OCH2CH3 | N | |
| H | CH3 | CO2CH3 | Br | OCH3 | Cl | CH | |
| H | CH3 | CO2CH3 | OCH3 | CH3 | CH3 | CH | |
| H | CH3 | CO2CH3 | OCH2CH3 | CH3 | OCH3 | CH | |
| H | CH3 | CO2CH2CH3 | H | OCH3 | Cl | CH | |
| H | CH3 | CO2CH2CH3 | H | CH3 | CH3 | CH | |
| H | CH3 | CO2CH2CH3 | H | CH3 | OCH3 | CH | |
| H | CH3 | CO2CH2CH3 | H | OCH3 | CH3 | CH | |
| H | CH3 | CO2CH2CH3 | H | CH3 | Cl | CH | |
| H | CH3 | CO2CH2CH3 | H | CH3 | OCH3 | CH | |
| H | CH3 | CO2CH2CH3 | H | CH3 | OCH3 | N | |
| H | CH3 | CO2CH2CH3 | H | CH3 | OCH2CH3 | N | |
| H | CH3 | CO2CH2CH3 | H | OCH2CH3 | CH3 | CH | |
| H | CH3 | CO2CH2CH3 | H | OCH3 | OCH3 | CH | |
| H | CH3 | CO2CH2CH3 | H | CH2CH3 | OCH3 | CH | |
| H | CH3 | CO2CH2CH3 | H | CH3 | Br | CH | |
| H | CH3 | CO2CH2CH3 | H | CH3 | OCH2CH3 | CH | |
| H | CH3 | CO2CH2CH3 | H | CH3 | CH2CH3 | CH | |
| H | CH3 | CO2CH2CH=CH3 | H | OCH3 | Cl | CH | |
| H | CH3 | CO2CH2C≡CH | H | CH3 | CH3 | CH | |
| H | CH3 | CO2CH(CH3)2 | H | CH3 | OCH3 | CH | |
| H | CH3 | CO2(CH2)2CH3 | H | OCH3 | CH3 | CH | |
| H | CH3 | CO2(CH2)2OCH3 | H | CH3 | Cl | CH | |
| H | CH3 | CO2(CH2)2OCH2CH3 | H | CH3 | OCH3 | N | |
| H | CH3 | CO2CH2OCH3 | H | CH3 | OCH2CH3 | N | |
| H | CH3 | CO2(CH2)2Cl | H | OCH2CH3 | CH3 | CH | |
| H | CH3 | CO2(CH2)2F | H | OCH3 | OCH3 | CH | |
| H | CH3 | CO2(CH2)2Br | H | CH2CH3 | OCH3 | CH | |
| H | CH3 | CO2(CH2)2I | H | CH3 | Br | CH | |
| H | CH3 | CO2CH2CF3 | H | CH3 | OCH2CH3 | CH | |
| H | CH3 | CO2CH2CH2CN | H | CH3 | CH2CH3 | CH | |
| CH3 | CH3 | CO2CH2CH3 | H | OCH3 | Cl | CH | |
| H | CH3 | CO2CH2CH3 | OCH3 | CH3 | OCH3 | CH | |
| H | CH3 | F | H | OCH3 | CH3 | CH | |

TABLE 9-continued

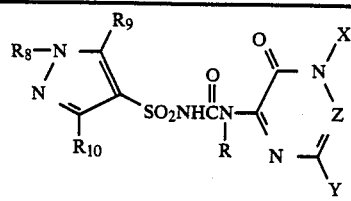

| R | R8 | R9 | R10 | X | Y | Z | m.p. (°C.) |
|---|----|----|-----|---|---|---|------------|
| H | CH3 | Cl | H | CH3 | OCH2CH3 | N | |
| H | CH3 | Br | H | CH3 | OCH3 | N | |
| H | CH3 | NO2 | H | CH3 | Cl | CH | |
| H | CH3 | CH3 | H | OCH3 | CH3 | CH | |
| H | CH3 | CH2CH3 | H | CH3 | OCH3 | CH | |
| H | CH3 | (CH2)2CH3 | H | CH3 | CH3 | CH | |
| H | CH3 | CH(CH3)2 | H | OCH2CH3 | CH3 | CH | |
| H | CH3 | CH=CF2 | H | CH3 | OCH3 | CH | |
| H | CH3 | CCl=CCl2 | H | OCH3 | CH3 | CH | |
| H | CH3 | CH2CH=CHCCl3 | H | CH3 | Cl | CH | |
| H | CH3 | CH=CHCl | H | CH3 | OCH3 | N | |
| H | CH3 | CH=CHI | H | CH3 | OCH2CH3 | N | |
| H | CH3 | CH=CBr2 | H | OCH2CH3 | CH3 | CH | |
| H | CH3 | CF=CFH | H | OCH3 | OCH3 | CH | |
| H | CH3 | CH2CH=CF2 | H | CH2CH3 | OCH3 | CH | |
| H | CH3 | CH=CHCF3 | H | CH3 | Br | CH | |
| H | CH3 | CF=CFCH3 | H | CH3 | OCH2CH3 | H | |
| H | CH3 | OCH3 | H | CH3 | CH2CH3 | CH | |
| H | CH3 | OCH3 | CH3 | OCH3 | Cl | CH | |
| H | CH3 | OCH2CH3 | H | CH3 | CH3 | CH | |
| H | CH3 | C(O)N(CH3)2 | H | CH3 | OCH2CH3 | N | |
| H | CH3 | C(O)NHCH2CH3 | H | OCH3 | Cl | CH | |
| H | CH3 | C(O)N(CH3)OCH3 | H | CH3 | CH3 | CH | |
| H | CH3 | C(O)NHOCH2CH3 | H | CH3 | OCH3 | CH | |
| H | CH3 | C(O)NH(CH2)2CH3 | H | OCH3 | CH3 | CH | |
| H | CH3 | SO2N(CH3)2 | H | CH3 | Cl | CH | |
| H | CH3 | SO2NH—cyclopropyl | H | OCH3 | Cl | CH | |
| CH3 | CH3 | SO2N(CH3)2 | H | CH3 | CH3 | CH | |
| H | CH3 | SO2N(CH3)2 | CH3 | CH3 | OCH3 | CH | |
| H | CH3 | SO2N(CH3)CH2CH=CH2 | H | OCH3 | CH3 | CH | |
| H | CH3 | SO2N((CH2)2CH3)2 | H | CH3 | Cl | CH | |
| H | CH3 | SO2NH2 | H | CH3 | OCH3 | N | |
| H | CH3 | SO2N(CH3)OCH3 | H | CH3 | OCH2CH3 | N | |
| H | CH3 | SO2N(CH3)OCH2CH3 | H | OCH2CH3 | CH3 | CH | |
| H | CH3 | SCH3 | H | OCH3 | OCH3 | CH | |
| H | CH3 | SCH2CH=CH3 | H | CH2CH3 | OCH3 | CH | |
| H | CH3 | SCH2C≡CH3 | H | CH3 | Br | CH | |
| H | CH3 | S(CH2)2CH3 | H | CH3 | OCH2CH3 | CH | |
| H | CH3 | S(O)CH3 | H | CH3 | CH2CH3 | CH | |
| H | CH3 | SCF2H | H | OCH3 | Cl | CH | |
| H | CH3 | SCF2CF2H | H | CH3 | CH3 | CH | |
| H | CH3 | S(CH2)2Cl | H | CH3 | OCH3 | CH | |
| H | CH3 | S(CH2)2I | H | OCH3 | CH3 | CH | |
| H | CH3 | S(CH2)3Br | H | CH3 | Cl | CH | |
| H | CH3 | S(O)CF2CF2H | H | CH3 | OCH3 | N | |
| H | CH3 | S(O)(CH2)2I | H | CH3 | OCH2CH3 | N | |
| H | CH3 | S(O)2CH3 | H | OCH3 | Cl | CH | |
| H | CH3 | S(O)2CH2CH3 | H | CH3 | CH3 | CH | |
| H | CH3 | S(O)2CH2CH=CH2 | H | CH3 | OCH3 | CH | |
| H | CH3 | S(O)2CH2C≡CH | H | OCH3 | CH3 | CH | |
| H | CH3 | S(O)2CF2H | H | CH3 | Cl | CH | |
| H | CH3 | S(O)2CF2CF2H | H | CH3 | OCH3 | N | |
| H | CH3 | S(O)2(CH2)2I | H | CH3 | OCH2CH3 | N | |
| H | CH3 | C(O)CH3 | H | OCH3 | Cl | CH | |
| H | CH3 | C(O)(CH2)3CH3 | H | CH3 | CH3 | CH | |
| H | CH3 | C(O)CH2CH3 | H | CH3 | OCH3 | CH | |
| H | CH3 | C(O)—cyclo-C3H5 | H | OCH3 | CH3 | CH | |
| H | CH3 | C(O)—cyclo-C4H7 | H | CH3 | Cl | CH | |
| H | CH3 | C(O)—cyclo-C5H9 | H | OCH3 | Cl | CH | |
| H | CH3 | C(O)—cyclo-C3F5 | H | CH3 | CH3 | CH | |
| H | CH3 | C(O)CF3 | H | CH3 | OCH3 | CH | |
| H | CH3 | C(O)(CH2)3CCl2H | H | OCH3 | CH3 | CH | |
| H | CH3 | C(O)(CH2)4F | H | CH3 | Cl | CH | |
| H | CH3 | C(O)—cyclo-(CHCH2CCl2) | H | CH3 | OCH3 | N | |
| H | CH3 | OCF2H | H | CH3 | OCH2CH3 | N | |
| H | CH3 | L-1, Rh = H | H | OCH2CH3 | CH3 | CH | |
| H | CH3 | L-1, Rh = CH3 | H | OCH3 | OCH3 | CH | |
| H | CH3 | L-2, Rh = H | H | CH2CH3 | OCH3 | CH | |
| H | CH3 | L-2, Rh = CH3 | H | CH3 | Br | CH | |
| H | CH3 | L-3 | H | CH3 | OCH2CH3 | CH | |
| H | CH3 | L-4 | H | CH3 | CH2CH3 | CH | |

TABLE 9-continued

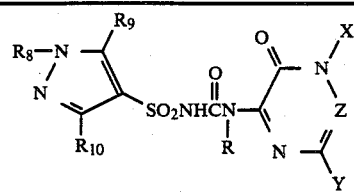

| R | R₈ | R₉ | R₁₀ | X | Y | Z | m.p. (°C.) |
|---|---|---|---|---|---|---|---|
| H | CH₃ | L-5 | H | OCH₃ | Cl | CH | |
| H | CH₃ | L-6 | H | CH₃ | CH₃ | CH | |
| H | CH₃ | L-7 | H | CH₃ | OCH₃ | CH | |
| H | CH₃ | L-8 | H | OCH₃ | CH₃ | CH | |
| H | CH₃ | L-9 | H | CH₃ | Cl | CH | |
| H | CH₃ | L-10 | H | CH₃ | OCH₃ | N | |
| H | CH₃ | L-11 | H | CH₃ | OCH₂CH₃ | N | |
| H | CH₃ | L-12 | H | OCH₃ | Cl | CH | |
| H | CH₃ | L-13 | H | CH₃ | CH₃ | CH | |
| H | CH₃ | L-14 | H | CH₃ | OCH₃ | CH | |
| H | CH₃ | L-15 | H | OCH₃ | CH₃ | CH | |
| H | CH₃ | L-16, Rᵢ = H | H | CH₃ | Cl | CH | |
| H | CH₃ | L-16, Rᵢ = CH₃ | H | CH₃ | OCH₃ | N | |
| H | CH₃ | L-17 | H | CH₃ | OCH₂CH₃ | N | |
| H | CH₃ | L-18 | H | OCH₃ | Cl | CH | |
| H | CH₃ | L-19 | H | CH₃ | CH₃ | CH | |
| H | CH₃ | L-20 | H | CH₃ | OCH₃ | CH | |
| H | CH₃ | L-21 | H | OCH₃ | CH₃ | CH | |
| H | CH₃ | L-22 | H | CH₃ | Cl | CH | |
| H | CH₃ | L-23 | H | OCH₃ | Cl | CH | |
| H | CH₃ | L-24 | H | CH₃ | CH₃ | CH | |
| H | CH₃ | L-25 | H | CH₃ | OCH₃ | CH | |
| H | CH₃ | L-26, Rⱼ = H | H | OCH₃ | CH₃ | CH | |
| H | CH₃ | L-26, Rⱼ = CH₃ | H | CH₃ | Cl | CH | |
| H | CH₃ | L-26, Rⱼ = CH₂CH₃ | H | CH₃ | OCH₃ | N | |
| H | CH₃ | L-27, Rⱼ = H | H | CH₃ | OCH₂CH₃ | N | |
| H | CH₃ | L-27, Rⱼ = CH₃ | H | OCH₂CH₃ | CH₃ | CH | |
| H | CH₃ | L-27, Rⱼ = CH₂CH₃ | H | OCH₃ | OCH₃ | CH | |
| H | CH₃ | L-28, Rₖ = H | H | CH₂CH₃ | OCH₃ | CH | |
| H | CH₃ | L-28, Rₖ = CH₃ | H | CH₃ | Br | CH | |
| H | CH₃ | L-28, Rₖ = CH₂CH₃ | H | CH₃ | OCH₂CH₃ | CH | |
| H | CH₃ | L-28, Rₖ = OCH₃ | H | CH₃ | CH₂CH₃ | CH | |
| H | CH₃ | L-28, Rₖ = OCH₂CH₃ | H | OCH₃ | Cl | CH | |
| H | CH₃ | L-28, Rₖ = SCH₃ | H | CH₃ | CH₃ | CH | |
| H | CH₃ | L-28, Rₖ = SCH₂CH₃ | H | CH₃ | OCH₃ | CH | |
| H | CH₃ | L-29, Rₖ = H | H | OCH₃ | CH₃ | CH | |
| H | CH₃ | L-29, Rₖ = CH₃ | H | CH₃ | Cl | CH | |
| H | CH₃ | L-29, Rₖ = CH₂CH₃ | H | CH₃ | OCH₃ | N | |
| H | CH₃ | L-29, Rₖ = OCH₃ | H | CH₃ | OCH₂CH₃ | N | |
| H | CH₃ | L-29, Rₖ = OCH₂CH₃ | H | OCH₃ | Cl | CH | |
| H | CH₃ | L-29, Rₖ = SCH₃ | H | CH₃ | CH₃ | CH | |
| H | CH₃ | L-29, Rₖ = SCH₂CH₃ | H | CH₃ | OCH₃ | CH | |
| H | CH₃ | L-30, Rₘ = H | H | OCH₃ | CH₃ | CH | |
| H | CH₃ | L-30, Rₘ = CH₃ | H | CH₃ | Cl | CH | |
| H | CH₃ | L-30, Rₘ = CH₂CH₃ | H | CH₃ | OCH₃ | N | |
| H | CH₃ | L-31, Rₘ = H | H | CH₃ | OCH₂CH₃ | N | |
| H | CH₃ | L-31, Rₘ = CH₃ | H | OCH₃ | Cl | CH | |
| H | CH₃ | L-31, Rₘ = CH₂CH₃ | H | CH₃ | CH₃ | CH | |
| H | CH₃ | L-32, Rₘ = H | H | CH₃ | OCH₃ | CH | |
| H | CH₃ | L-32, Rₘ = CH₃ | H | OCH₃ | CH₃ | CH | |
| H | CH₃ | L-32, Rₘ = CH₂CH₃ | H | CH₃ | Cl | CH | |
| H | CH₃ | L-33, Rₙ = H | H | CH₃ | CH₃ | N | |
| H | CH₃ | L-33, Rₙ = CH₃ | H | CH₃ | OCH₃ | CH | |
| H | H | CO₂CH₃ | H | OCH₃ | Cl | CH | |
| H | CH₂CH₃ | CO₂CH₃ | H | CH₃ | CH₃ | CH | |
| H | (CH₂)₂CH₃ | CO₂CH₃ | H | CH₃ | OCH₃ | CH | |
| H | H | CO₂CH₂CH₃ | H | OCH₃ | CH₃ | CH | |
| H | CH₂CH₃ | CO₂CH₂CH₃ | H | CH₃ | Cl | CH | |
| H | (CH₂)₂CH₃ | CO₂CH₂CH₃ | H | CH₃ | OCH₃ | N | |
| CH₃ | CH₂CH₃ | CO₂CH₃ | H | CH₃ | OCH₂CH₃ | N | |
| CH₃ | (CH₂)₂CH₃ | CO₂CH₃ | H | OCH₂CH₃ | CH₃ | CH | |
| CH₃ | H | CO₂CH₃ | H | OCH₃ | OCH₃ | CH | |
| H | H | CO₂CH₃ | H | CH₂CH₃ | OCH₃ | CH | |
| H | CH₂CH₃ | CO₂CH₃ | H | CH₃ | Br | CH | |
| H | (CH₂)₂CH₃ | CO₂CH₃ | H | CH₃ | OCH₂CH₃ | CH | |
| H | H | CO₂CH₃ | H | CH₃ | CH₂CH₃ | CH | |
| H | CH₂CH₃ | CO₂CH₃ | H | OCH₃ | Cl | CH | |
| H | H | SO₂N(CH₃)₂ | H | CH₃ | CH₃ | CH | |
| H | CH₂CH₃ | CH₃ | H | CH₃ | OCH₃ | CH | |
| H | H | Br | H | OCH₃ | CH₃ | CH | |
| H | CH₂CH₃ | SO₂CH₃ | H | CH₃ | Cl | CH | |

TABLE 10-continued

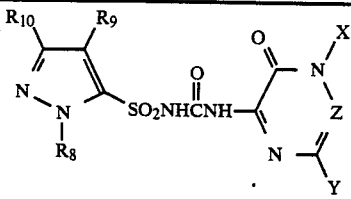

| R | $R_8$ | $R_9$ | $R_{10}$ | X | Y | Z | m.p. (°C.) |
|---|---|---|---|---|---|---|---|
| H | $CH_3$ | $CO_2CH_3$ | H | $CH_3$ | Cl | CCl | |
| H | $CH_3$ | $CO_2CH_3$ | H | $CH_3$ | $OCH_3$ | CCl | |
| H | $CH_3$ | $CO_2CH_3$ | H | $CH_3$ | Br | CBr | |
| H | $CH_3$ | $CO_2CH_3$ | H | $CH_3$ | $OCH_3$ | CBr | |
| H | $CH_3$ | $CO_2CH_3$ | H | H | $OCH_3$ | N | |
| H | $CH_3$ | $CO_2CH_3$ | H | $CH_3$ | Cl | N | |
| H | $CH_3$ | $CO_2CH_3$ | H | $CH_3$ | Br | N | |
| H | $CH_3$ | $CO_2CH_3$ | H | $CH_3$ | $OCH_3$ | N | |
| H | $CH_3$ | $CO_2CH_3$ | H | $CH_3$ | $OCH_2CH_3$ | N | |
| H | $CH_3$ | $CO_2CH_3$ | H | $CH_3$ | $O(CH_2)_2CH_3$ | N | |
| H | $CH_3$ | $CO_2CH_3$ | H | $CH_3$ | $CH_3$ | N | |
| H | $CH_3$ | $CO_2CH_3$ | H | $CH_3$ | $CH_2CH_3$ | N | |
| H | $CH_3$ | $CO_2CH_3$ | H | $CH_3$ | $(CH_2)_2CH_3$ | N | |
| H | $CH_3$ | $CO_2CH_3$ | H | $CH_2CH_3$ | Cl | N | |
| H | $CH_3$ | $CO_2CH_3$ | H | $CH_2CH_3$ | $OCH_3$ | N | |
| H | $CH_3$ | $CO_2CH_3$ | H | $(CH_2)_2CH_3$ | Cl | N | |
| H | $CH_3$ | $CO_2CH_3$ | H | $(CH_2)_2CH_3$ | $OCH_3$ | N | |
| H | $CH_3$ | $CO_2CH_3$ | H | $OCH_3$ | H | N | |
| H | $CH_3$ | $CO_2CH_3$ | H | $OCH_3$ | $CH_3$ | N | |
| H | $CH_3$ | $CO_2CH_3$ | H | $OCH_3$ | $CH_2CH_3$ | N | |
| H | $CH_3$ | $CO_2CH_3$ | H | $OCH_3$ | $(CH_2)_2CH_3$ | N | |
| H | $CH_3$ | $CO_2CH_3$ | H | $OCH_3$ | $OCH_3$ | N | |
| H | $CH_3$ | $CO_2CH_3$ | H | $OCH_3$ | $OCH_2CH_3$ | N | |
| H | $CH_3$ | $CO_2CH_3$ | H | $OCH_3$ | $O(CH_2)_2CH_3$ | N | |
| H | $CH_3$ | $CO_2CH_3$ | H | $OCH_3$ | Cl | N | |
| H | $CH_3$ | $CO_2CH_3$ | H | $OCH_3$ | Br | N | |
| H | $CH_3$ | $CO_2CH_3$ | H | $OCH_2CH_3$ | Cl | N | |
| H | $CH_3$ | $CO_2CH_3$ | H | $OCH_2CH_3$ | $CH_3$ | N | |
| H | $CH_3$ | $CO_2CH_3$ | H | $OCH_2CH_3$ | $OCH_3$ | N | |
| H | $CH_3$ | $CO_2CH_3$ | H | $O(CH_2)_2CH_3$ | Cl | N | |
| H | $CH_3$ | $CO_2CH_3$ | H | $O(CH_2)_2CH_3$ | $CH_3$ | N | |
| H | $CH_3$ | $CO_2CH_3$ | H | $O(CH_2)_2CH_3$ | $OCH_3$ | N | |
| H | $CH_3$ | $CO_2CH_3$ | H | $NH_2$ | Cl | N | |
| H | $CH_3$ | $CO_2CH_3$ | H | $NH_2$ | $CH_3$ | N | |
| H | $CH_3$ | $CO_2CH_3$ | H | $NH_2$ | $OCH_3$ | N | |
| H | $CH_3$ | $CO_2CH_3$ | H | $NHCH_3$ | Cl | N | |
| H | $CH_3$ | $CO_2CH_3$ | H | $NHCH_3$ | $CH_3$ | N | |
| H | $CH_3$ | $CO_2CH_3$ | H | $NHCH_3$ | $OCH_3$ | N | |
| H | $CH_3$ | $CO_2CH_3$ | H | $N(CH_3)_2$ | Cl | N | |
| H | $CH_3$ | $CO_2CH_3$ | H | $N(CH_3)_2$ | $CH_3$ | N | |
| H | $CH_3$ | $CO_2CH_3$ | H | $N(CH_3)_2$ | $OCH_3$ | N | |
| H | $CH_3$ | $CO_2CH_3$ | H | $NHCH_3$ | $OCH_2CH_3$ | N | |
| $CH_3$ | $CH_3$ | $CO_2CH_3$ | H | $CH_3$ | Cl | N | |
| $CH_3$ | $CH_3$ | $CO_2CH_3$ | H | $OCH_3$ | Cl | N | |
| $CH_3$ | $CH_3$ | $CO_2CH_3$ | H | $CH_3$ | $OCH_3$ | N | |
| $CH_3$ | $CH_3$ | $CO_2CH_3$ | H | $CH_2CH_3$ | $OCH_3$ | N | |
| $CH_3$ | $CH_3$ | $CO_2CH_3$ | H | $OCH_3$ | $CH_3$ | N | |
| $CH_3$ | $CH_3$ | $CO_2CH_3$ | H | $OCH_3$ | $OCH_3$ | N | |
| H | $CH_3$ | $CO_2CH_3$ | Cl | $OCH_3$ | Cl | CH | |
| H | $CH_3$ | $CO_2CH_3$ | F | $CH_3$ | $CH_3$ | CH | |
| H | $CH_3$ | $CO_2CH_3$ | Br | $CH_3$ | $OCH_3$ | CH | |
| H | $CH_3$ | $CO_2CH_3$ | $CH_3$ | $OCH_3$ | $CH_3$ | CH | |
| H | $CH_3$ | $CO_2CH_3$ | $CH_2CH_3$ | $CH_3$ | Cl | Cl | |
| H | $CH_3$ | $CO_2CH_3$ | $(CH_2)_2CH_3$ | $CH_3$ | $OCH_3$ | N | |
| H | $CH_3$ | $CO_2CH_3$ | $CH(CH_3)_2$ | $CH_3$ | $OCH_2CH_3$ | N | |
| H | $CH_3$ | $CO_2CH_3$ | Br | $OCH_3$ | Cl | CH | |
| H | $CH_3$ | $CO_2CH_3$ | $OCH_3$ | $CH_3$ | $CH_3$ | CH | |
| H | $CH_3$ | $CO_2CH_3$ | $OCH_2CH_3$ | $CH_3$ | $OCH_3$ | CH | |
| H | $CH_3$ | $CO_2CH_2CH_3$ | H | $OCH_3$ | Cl | CH | |
| H | $CH_3$ | $CO_2CH_2CH_3$ | H | $CH_3$ | $CH_3$ | CH | |
| H | $CH_3$ | $CO_2CH_2CH_3$ | H | $CH_3$ | $OCH_3$ | CH | |
| H | $CH_3$ | $CO_2CH_2CH_3$ | H | $OCH_3$ | $CH_3$ | CH | |
| H | $CH_3$ | $CO_2CH_2CH_3$ | H | $CH_3$ | Cl | CH | |
| H | $CH_3$ | $CO_2CH_2CH_3$ | H | $CH_3$ | $OCH_3$ | N | |
| H | $CH_3$ | $CO_2CH_2CH_3$ | H | $CH_3$ | $OCH_2CH_3$ | N | |
| H | $CH_3$ | $CO_2CH_2CH_3$ | H | $OCH_2CH_3$ | $CH_3$ | CH | |
| H | $CH_3$ | $CO_2CH_2CH_3$ | H | $OCH_3$ | $OCH_3$ | CH | |
| H | $CH_3$ | $CO_2CH_2CH_3$ | H | $CH_2CH_3$ | $OCH_3$ | CH | |
| H | $CH_3$ | $CO_2CH_2CH_3$ | H | $CH_3$ | Br | CH | |

TABLE 9-continued

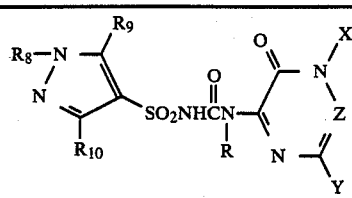

| R | $R_8$ | $R_9$ | $R_{10}$ | X | Y | Z | m.p. (°C.) |
|---|---|---|---|---|---|---|---|
| H | H | $OCF_2H$ | H | $CH_3$ | $OCH_3$ | N | |
| H | $(CH_2)_2CH_3$ | $OCH_3$ | H | $CH_3$ | $OCH_2CH_3$ | N | |
| H | $CH(CH_3)_2$ | $CO_2CH_3$ | H | $OCH_3$ | Cl | CH | |

TABLE 10

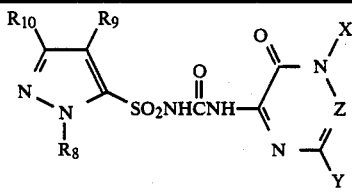

| R | $R_8$ | $R_9$ | $R_{10}$ | X | Y | Z | m.p. (°C.) |
|---|---|---|---|---|---|---|---|
| H | $CH_3$ | $CO_2CH_3$ | H | H | $OCH_3$ | CH | |
| H | $CH_3$ | $CO_2CH_3$ | H | $CH_3$ | Cl | CH | >250 |
| H | $CH_3$ | $CO_2CH_3$ | H | $CH_3$ | Br | CH | |
| H | $CH_3$ | $CO_2CH_3$ | H | $CH_3$ | $OCH_3$ | CH | |
| H | $CH_3$ | $CO_2CH_3$ | H | $CH_3$ | $OCH_2CH_3$ | CH | |
| H | $CH_3$ | $CO_2CH_3$ | H | $CH_3$ | $O(CH_2)_2CH_3$ | CH | |
| H | $CH_3$ | $CO_2CH_3$ | H | $CH_3$ | $CH_3$ | CH | |
| H | $CH_3$ | $CO_2CH_3$ | H | $CH_3$ | $CH_2CH_3$ | CH | |
| H | $CH_3$ | $CO_2CH_3$ | H | $CH_3$ | $(CH_2)_2CH_3$ | CH | |
| H | $CH_3$ | $CO_2CH_3$ | H | $CH_2CH_3$ | Cl | CH | |
| H | $CH_3$ | $CO_2CH_3$ | H | $CH_2CH_3$ | $OCH_3$ | CH | |
| H | $CH_3$ | $CO_2CH_3$ | H | $(CH_2)_2CH_3$ | Cl | CH | |
| H | $CH_3$ | $CO_2CH_3$ | H | $(CH_2)_2CH_3$ | $OCH_3$ | CH | |
| H | $CH_3$ | $CO_2CH_3$ | H | $OCH_3$ | H | CH | |
| H | $CH_3$ | $CO_2CH_3$ | H | $OCH_3$ | $CH_3$ | CH | |
| H | $CH_3$ | $CO_2CH_3$ | H | $OCH_3$ | $CH_2CH_3$ | CH | |
| H | $CH_3$ | $CO_2CH_3$ | H | $OCH_3$ | $(CH_2)_2CH_3$ | CH | |
| H | $CH_3$ | $CO_2CH_3$ | H | $OCH_3$ | $OCH_3$ | CH | |
| H | $CH_3$ | $CO_2CH_3$ | H | $OCH_3$ | $OCH_2CH_3$ | CH | |
| H | $CH_3$ | $CO_2CH_3$ | H | $OCH_3$ | $O(CH_2)_2CH_3$ | CH | |
| H | $CH_3$ | $CO_2CH_3$ | H | $CH_3$ | $SCH_3$ | CH | |
| H | $CH_3$ | $CO_2CH_3$ | H | $OCH_3$ | $SCH_3$ | CH | |
| H | $CH_3$ | $CO_2CH_3$ | H | $CH_3$ | $SCH_3$ | N | |
| H | $CH_3$ | $CO_2CH_3$ | H | $NH_2$ | $SCH_3$ | N | |
| H | $CH_3$ | $CO_2CH_3$ | H | $CH_3$ | $SCH_2CH_3$ | CH | |
| H | $CH_3$ | $CO_2CH_3$ | H | $CH_2CH_3$ | $SCH_3$ | CH | |
| H | $CH_3$ | $CO_2CH_3$ | H | $OCH_3$ | Cl | CH | |
| H | $CH_3$ | $CO_2CH_3$ | H | $OCH_3$ | Br | CH | |
| H | $CH_3$ | $CO_2CH_3$ | H | $OCH_2CH_3$ | Cl | CH | |
| H | $CH_3$ | $CO_2CH_3$ | H | $OCH_2CH_3$ | $CH_3$ | CH | |
| H | $CH_3$ | $CO_2CH_3$ | H | $OCH_2CH_3$ | $OCH_3$ | CH | |
| H | $CH_3$ | $CO_2CH_3$ | H | $O(CH_2)_2CH_3$ | Cl | CH | |
| H | $CH_3$ | $CO_2CH_3$ | H | $O(CH_2)_2CH_3$ | $CH_3$ | CH | |
| H | $CH_3$ | $CO_2CH_3$ | H | $O(CH_2)_2CH_3$ | $OCH_3$ | CH | |
| H | $CH_3$ | $CO_2CH_3$ | H | $NH_2$ | Cl | CH | |
| H | $CH_3$ | $CO_2CH_3$ | H | $NH_2$ | $CH_3$ | CH | |
| H | $CH_3$ | $CO_2CH_3$ | H | $NH_2$ | $OCH_3$ | CH | |
| H | $CH_3$ | $CO_2CH_3$ | H | $NHCH_3$ | Cl | CH | |
| H | $CH_3$ | $CO_2CH_3$ | H | $NHCH_3$ | $CH_3$ | CH | |
| H | $CH_3$ | $CO_2CH_3$ | H | $NHCH_3$ | $OCH_3$ | CH | |
| H | $CH_3$ | $CO_2CH_3$ | H | $N(CH_3)_2$ | Cl | CH | |
| H | $CH_3$ | $CO_2CH_3$ | H | $N(CH_3)_2$ | $CH_3$ | CH | |
| H | $CH_3$ | $CO_2CH_3$ | H | $N(CH_3)_2$ | $OCH_3$ | CH | |
| H | $CH_3$ | $CO_2CH_3$ | H | $NHCH_3$ | $OCH_2CH_3$ | CH | |
| $CH_3$ | $CH_3$ | $CO_2CH_3$ | H | $CH_3$ | Cl | CH | |
| $CH_3$ | $CH_3$ | $CO_2CH_3$ | H | $OCH_3$ | Cl | CH | |
| $CH_3$ | $CH_3$ | $CO_2CH_3$ | H | $CH_3$ | $OCH_3$ | CH | |
| $CH_3$ | $CH_3$ | $CO_2CH_3$ | H | $OCH_3$ | $CH_3$ | CH | |
| $CH_3$ | $CH_3$ | $CO_2CH_3$ | H | $OCH_3$ | $OCH_3$ | CH | |
| H | $CH_3$ | $CO_2CH_3$ | H | $CH_3$ | Cl | CF | |
| H | $CH_3$ | $CO_2CH_3$ | H | $CH_3$ | $OCH_3$ | CF | |
| H | $CH_3$ | $CO_2CH_3$ | H | $OCH_3$ | $OCH_3$ | CF | |
| H | $CH_3$ | $CO_2CH_3$ | H | $OCH_3$ | $CH_3$ | CF | |

TABLE 10-continued

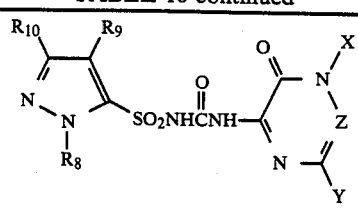

| R | R8 | R9 | R10 | X | Y | Z | m.p. (°C.) |
|---|---|---|---|---|---|---|---|
| H | CH3 | CO2CH2CH3 | H | CH3 | OCH2CH3 | CH | |
| H | CH3 | CO2CH2CH3 | H | CH3 | CH2CH3 | CH | |
| H | CH3 | CO2CH2CH=CH3 | H | OCH3 | Cl | CH | |
| H | CH3 | CO2CH2C≡CH | H | CH3 | CH3 | CH | |
| H | CH3 | CO2CH(CH3)2 | H | CH3 | OCH3 | CH | |
| H | CH3 | CO2(CH2)2CH3 | H | OCH3 | CH3 | CH | |
| H | CH3 | CO2(CH2)2OCH3 | H | CH3 | Cl | CH | |
| H | CH3 | CO2(CH2)2OCH2CH3 | H | CH3 | OCH3 | N | |
| H | CH3 | CO2CH2OCH3 | H | CH3 | OCH2CH3 | N | |
| H | CH3 | CO2(CH2)2Cl | H | OCH2CH3 | CH3 | CH | |
| H | CH3 | CO2(CH2)2F | H | OCH3 | OCH3 | CH | |
| H | CH3 | CO2(CH2)2Br | H | CH2CH3 | OCH3 | CH | |
| H | CH3 | CO2(CH2)2I | H | CH3 | Br | CH | |
| H | CH3 | CO2CH2CF3 | H | CH3 | OCH2CH3 | CH | |
| H | CH3 | CO2CH2CH2CN | H | CH3 | CH2CH3 | CH | |
| CH3 | CH3 | CO2CH2CH3 | H | OCH3 | Cl | CH | |
| H | CH3 | CO2CH2CH3 | OCH3 | CH3 | OCH3 | CH | |
| H | CH3 | F | H | OCH3 | CH3 | CH | |
| H | CH3 | Cl | H | CH3 | OCH2CH3 | N | |
| H | CH3 | Br | H | CH3 | OCH3 | N | |
| H | CH3 | NO2 | H | CH3 | Cl | CH | |
| H | CH3 | CH3 | H | OCH3 | CH3 | CH | |
| H | CH3 | CH2CH3 | H | CH3 | OCH3 | CH | |
| H | CH3 | (CH2)2CH3 | H | CH3 | CH3 | CH | |
| H | CH3 | CH(CH3)2 | H | OCH2CH3 | CH3 | CH | |
| H | CH3 | CH=CF2 | H | CH3 | OCH3 | CH | |
| H | CH3 | CCl=CCl2 | H | OCH3 | CH3 | CH | |
| H | CH3 | CH2CH=CHCCl3 | H | CH3 | Cl | CH | |
| H | CH3 | CH=CHCl | H | CH3 | OCH3 | N | |
| H | CH3 | CH=CHI | H | CH3 | OCH2CH3 | N | |
| H | CH3 | CH=CBr2 | H | OCH2CH3 | CH3 | CH | |
| H | CH3 | CF=CFH | H | OCH3 | OCH3 | CH | |
| H | CH3 | CH2CH=CF2 | H | CH2CH3 | OCH3 | CH | |
| H | CH3 | CH=CHCF3 | H | CH3 | Br | CH | |
| H | CH3 | CF=CFCH3 | H | CH3 | OCH2CH3 | H | |
| H | CH3 | OCH3 | H | CH3 | CH2CH3 | CH | |
| H | CH3 | OCH3 | CH3 | OCH3 | Cl | CH | |
| H | CH3 | OCH2CH3 | H | CH3 | CH3 | CH | |
| H | CH3 | C(O)N(CH3)2 | H | CH3 | OCH2CH3 | N | |
| H | CH3 | C(O)NHCH2CH3 | H | OCH3 | Cl | CH | |
| H | CH3 | C(O)N(CH3)OCH3 | H | CH3 | CH3 | CH | |
| H | CH3 | C(O)NHOCH2CH3 | H | CH3 | OCH3 | CH | |
| H | CH3 | C(O)NH(CH2)2CH3 | H | OCH3 | CH3 | CH | |
| H | CH3 | SO2N(CH3)2 | H | CH3 | Cl | CH | |
| H | CH3 | SO2NH—cyclopropyl | H | OCH3 | Cl | CH | |
| CH3 | CH3 | SO2N(CH3)2 | H | CH3 | CH3 | CH | |
| H | CH3 | SO2N(CH3)2 | CH3 | CH3 | OCH3 | CH | |
| H | CH3 | SO2N(CH3)CH2CH=CH2 | H | OCH3 | CH3 | CH | |
| H | CH3 | SO2N((CH2)2CH3)2 | H | CH3 | Cl | CH | |
| H | CH3 | SO2NH2 | H | CH3 | OCH3 | N | |
| H | CH3 | SO2N(CH3)OCH3 | H | CH3 | OCH2CH3 | N | |
| H | CH3 | SO2N(CH3)OCH2CH3 | H | OCH2CH3 | CH3 | CH | |
| H | CH3 | SCH3 | H | OCH3 | OCH3 | CH | |
| H | CH3 | SCH2CH=CH3 | H | CH2CH3 | OCH3 | CH | |
| H | CH3 | SCH2C≡CH3 | H | CH3 | Br | CH | |
| H | CH3 | S(CH2)2CH3 | H | CH3 | OCH2CH3 | CH | |
| H | CH3 | S(O)CH3 | H | CH3 | CH2CH3 | CH | |
| H | CH3 | SCF2H | H | OCH3 | Cl | CH | |
| H | CH3 | SCF2CF2H | H | CH3 | CH3 | CH | |
| H | CH3 | S(CH2)2Cl | H | CH3 | OCH3 | CH | |
| H | CH3 | S(CH2)2I | H | CH3 | CH3 | CH | |
| H | CH3 | S(CH2)3Br | H | CH3 | Cl | CH | |
| H | CH3 | S(O)CF2CF2H | H | CH3 | OCH3 | N | |
| H | CH3 | S(O)(CH2)2I | H | CH3 | OCH2CH3 | N | |
| H | CH3 | S(O)2CH3 | H | OCH3 | Cl | CH | |
| H | CH3 | S(O)2CH2CH3 | H | CH3 | CH3 | CH | |
| H | CH3 | S(O)2CH2CH=CH2 | H | CH3 | OCH3 | CH | |
| H | CH3 | S(O)2CH2C≡CH | H | OCH3 | CH3 | CH | |
| H | CH3 | S(O)2CF2H | H | CH3 | Cl | CH | |
| H | CH3 | S(O)2CF2CF2H | H | CH3 | OCH3 | N | |
| H | CH3 | S(O)2(CH2)2I | H | CH3 | OCH2CH3 | N | |

TABLE 10-continued

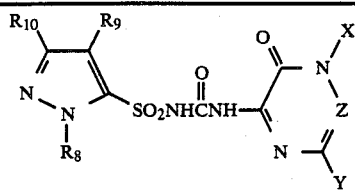

| R | R8 | R9 | R10 | X | Y | Z | m.p. (°C.) |
|---|---|---|---|---|---|---|---|
| H | CH3 | C(O)CH3 | H | OCH3 | Cl | CH | |
| H | CH3 | C(O)(CH2)3CH3 | H | CH3 | CH3 | CH | |
| H | CH3 | C(O)CH2CH3 | H | CH3 | OCH3 | CH | |
| H | CH3 | C(O)—cyclo-C3H5 | H | OCH3 | CH3 | CH | |
| H | CH3 | C(O)—cyclo-C4H7 | H | CH3 | Cl | CH | |
| H | CH3 | C(O)—cyclo-C5H9 | H | OCH3 | Cl | CH | |
| H | CH3 | C(O)—cyclo-C3F5 | H | CH3 | CH3 | CH | |
| H | CH3 | C(O)CF3 | H | CH3 | OCH3 | CH | |
| H | CH3 | C(O)(CH2)3CCl2H | H | OCH3 | CH3 | CH | |
| H | CH3 | C(O)(CH2)4F | H | CH3 | Cl | CH | |
| H | CH3 | C(O)—cyclo-(CHCH2CCl2) | H | CH3 | OCH3 | N | |
| H | CH3 | OCF2H | H | CH3 | OCH2CH3 | N | |
| H | CH3 | L-1, Rh = H | H | OCH2CH3 | CH3 | CH | |
| H | CH3 | L-1, Rh = CH3 | H | OCH3 | OCH3 | CH | |
| H | CH3 | L-2, Rh = H | H | CH2CH3 | OCH3 | CH | |
| H | CH3 | L-2, Rh = CH3 | H | CH3 | Br | CH | |
| H | CH3 | L-3 | H | CH3 | OCH2CH3 | CH | |
| H | CH3 | L-4 | H | CH3 | CH2CH3 | CH | |
| H | CH3 | L-5 | H | OCH3 | Cl | CH | |
| H | CH3 | L-6 | H | CH3 | CH3 | CH | |
| H | CH3 | L-7 | H | CH3 | OCH3 | CH | |
| H | CH3 | L-8 | H | OCH3 | CH3 | CH | |
| H | CH3 | L-9 | H | CH3 | Cl | CH | |
| H | CH3 | L-10 | H | CH3 | OCH3 | N | |
| H | CH3 | L-11 | H | CH3 | OCH2CH3 | N | |
| H | CH3 | L-12 | H | OCH3 | Cl | CH | |
| H | CH3 | L-13 | H | CH3 | CH3 | CH | |
| H | CH3 | L-14 | H | CH3 | OCH3 | CH | |
| H | CH3 | L-15 | H | OCH3 | CH3 | CH | |
| H | CH3 | L-16, Ri = H | H | CH3 | Cl | CH | |
| H | CH3 | L-16, Ri = CH3 | H | CH3 | OCH3 | N | |
| H | CH3 | L-17 | H | CH3 | OCH2CH3 | N | |
| H | CH3 | L-18 | H | OCH3 | Cl | CH | |
| H | CH3 | L-19 | H | CH3 | CH3 | CH | |
| H | CH3 | L-20 | H | CH3 | OCH3 | CH | |
| H | CH3 | L-21 | H | OCH3 | CH3 | CH | |
| H | CH3 | L-22 | H | CH3 | Cl | CH | |
| H | CH3 | L-23 | H | OCH3 | Cl | CH | |
| H | CH3 | L-24 | H | CH3 | CH3 | CH | |
| H | CH3 | L-25 | H | CH3 | OCH3 | CH | |
| H | CH3 | L-26, Rj = H | H | OCH3 | CH3 | CH | |
| H | CH3 | L-26, Rj = CH3 | H | CH3 | Cl | CH | |
| H | CH3 | L-26, Rj = CH2CH3 | H | CH3 | OCH3 | N | |
| H | CH3 | L-27, Rj = H | H | CH3 | OCH2CH3 | N | |
| H | CH3 | L-27, Rj = CH3 | H | OCH2CH3 | CH3 | CH | |
| H | CH3 | L-27, Rj = CH2CH3 | H | OCH3 | OCH3 | CH | |
| H | CH3 | L-28, Rk = H | H | CH2CH3 | OCH3 | CH | |
| H | CH3 | L-28, Rk = CH3 | H | CH3 | Br | CH | |
| H | CH3 | L-28, Rk = CH2CH3 | H | CH3 | OCH2CH3 | CH | |
| H | CH3 | L-28, Rk = OCH3 | H | CH3 | CH2CH3 | CH | |
| H | CH3 | L-28, Rk = OCH2CH3 | H | OCH3 | Cl | CH | |
| H | CH3 | L-28, Rk = SCH3 | H | CH3 | CH3 | CH | |
| H | CH3 | L-28, Rk = SCH2CH3 | H | CH3 | OCH3 | CH | |
| H | CH3 | L-29, Rk = H | H | OCH3 | CH3 | CH | |
| H | CH3 | L-29, Rk = CH3 | H | CH3 | Cl | CH | |
| H | CH3 | L-29, Rk = CH2CH3 | H | CH3 | OCH3 | N | |
| H | CH3 | L-29, Rk = OCH3 | H | CH3 | OCH2CH3 | N | |
| H | CH3 | L-29, Rk = OCH2CH3 | H | OCH3 | Cl | CH | |
| H | CH3 | L-29, Rk = SCH3 | H | CH3 | CH3 | CH | |
| H | CH3 | L-29, Rk = SCH2CH3 | H | CH3 | OCH3 | CH | |
| H | CH3 | L-30, Rm = H | H | OCH3 | CH3 | CH | |
| H | CH3 | L-30, Rm = CH3 | H | CH3 | Cl | CH | |
| H | CH3 | L-30, Rm = CH2CH3 | H | CH3 | OCH3 | N | |
| H | CH3 | L-31, Rm = H | H | CH3 | OCH2CH3 | N | |
| H | CH3 | L-31, Rm = CH3 | H | OCH3 | Cl | CH | |
| H | CH3 | L-31, Rm = CH2CH3 | H | CH3 | CH3 | CH | |
| H | CH3 | L-32, Rm = H | H | CH3 | OCH3 | CH | |
| H | CH3 | L-32, Rm = CH3 | H | OCH3 | CH3 | CH | |
| H | CH3 | L-32, Rm = CH2CH3 | H | CH3 | Cl | CH | |
| H | CH3 | L-33, Rn = H | H | CH3 | CH3 | N | |
| H | CH3 | L-33, Rn = CH3 | H | CH3 | OCH3 | CH | |

TABLE 10-continued

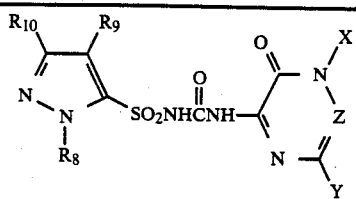

| R | R8 | R9 | R10 | X | Y | Z | m.p. (°C.) |
|---|---|---|---|---|---|---|---|
| H | H | CO2CH3 | H | OCH3 | Cl | CH | |
| H | CH2CH3 | CO2CH3 | H | CH3 | CH3 | CH | |
| H | (CH2)2CH3 | CO2CH3 | H | CH3 | OCH3 | CH | |
| H | H | CO2CH2CH3 | H | OCH3 | CH3 | CH | |
| H | CH2CH3 | CO2CH2CH3 | H | CH3 | Cl | CH | |
| H | (CH2)2CH3 | CO2CH2CH3 | H | CH3 | OCH3 | N | |
| CH3 | CH2CH3 | CO2CH3 | H | CH3 | OCH2CH3 | N | |
| CH3 | (CH2)2CH3 | CO2CH3 | H | OCH2CH3 | CH3 | CH | |
| CH3 | H | CO2CH3 | H | OCH3 | OCH3 | CH | |
| H | H | CO2CH3 | H | CH2CH3 | OCH3 | CH | |
| H | CH2CH3 | CO2CH3 | H | CH3 | Br | CH | |
| H | (CH2)2CH3 | CO2CH3 | H | CH3 | OCH2CH3 | CH | |
| H | H | CO2CH3 | H | CH3 | CH2CH3 | CH | |
| H | CH2CH3 | CO2CH3 | H | OCH3 | Cl | CH | |
| H | H | SO2N(CH3)2 | H | CH3 | CH3 | CH | |
| H | CH2CH3 | CH3 | H | CH3 | OCH3 | CH | |
| H | H | Br | H | OCH3 | CH3 | CH | |
| H | CH2CH3 | SO2CH3 | H | CH3 | Cl | CH | |
| H | H | OCF2H | H | CH3 | OCH3 | N | |
| H | (CH2)2CH3 | OCH3 | H | CH3 | OCH2CH3 | N | |
| H | CH(CH3)2 | CO2CH3 | H | OCH3 | Cl | CH | |

TABLE 11

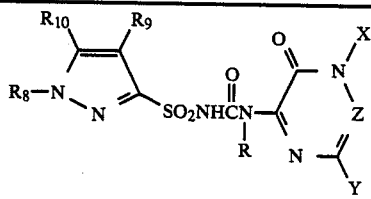

| R | R8 | R9 | R10 | X | Y | Z | m.p. (°C.) |
|---|---|---|---|---|---|---|---|
| H | CH3 | CO2CH3 | H | H | OCH3 | CH | |
| H | CH3 | CO2CH3 | H | CH3 | Cl | CH | |
| H | CH3 | CO2CH3 | H | CH3 | Br | CH | |
| H | CH3 | CO2CH3 | H | CH3 | OCH3 | CH | |
| H | CH3 | CO2CH3 | H | CH3 | OCH2CH3 | CH | |
| H | CH3 | CO2CH3 | H | CH3 | O(CH2)2CH3 | CH | |
| H | CH3 | CO2CH3 | H | CH3 | CH3 | CH | |
| H | CH3 | CO2CH3 | H | CH3 | CH2CH3 | CH | |
| H | CH3 | CO2CH3 | H | CH3 | (CH2)2CH3 | CH | |
| H | CH3 | CO2CH3 | H | CH2CH3 | Cl | CH | |
| H | CH3 | CO2CH3 | H | CH2CH3 | OCH3 | CH | |
| H | CH3 | CO2CH3 | H | (CH2)2CH3 | Cl | CH | |
| H | CH3 | CO2CH3 | H | (CH2)2CH3 | OCH3 | CH | |
| H | CH3 | CO2CH3 | H | OCH3 | H | CH | |
| H | CH3 | CO2CH3 | H | OCH3 | CH3 | CH | |
| H | CH3 | CO2CH3 | H | OCH3 | CH2CH3 | CH | |
| H | CH3 | CO2CH3 | H | OCH3 | (CH2)2CH3 | CH | |
| H | CH3 | CO2CH3 | H | OCH3 | OCH3 | CH | |
| H | CH3 | CO2CH3 | H | OCH3 | OCH2CH3 | CH | |
| H | CH3 | CO2CH3 | H | OCH3 | O(CH2)2CH3 | CH | |
| H | CH3 | CO2CH3 | H | CH3 | SCH3 | CH | |
| H | CH3 | CO2CH3 | H | OCH3 | SCH3 | CH | |
| H | CH3 | CO2CH3 | H | CH2CH3 | SCH3 | CH | |
| H | CH3 | CO2CH3 | H | CH3 | SCH3 | N | |
| H | CH3 | CO2CH3 | H | CH3 | SCH2CH3 | CH | |
| H | CH3 | CO2CH3 | H | NHCH3 | SCH3 | N | |
| H | CH3 | CO2CH3 | H | OCH3 | Cl | CH | |
| H | CH3 | CO2CH3 | H | OCH3 | Br | CH | |
| H | CH3 | CO2CH3 | H | OCH2CH3 | Cl | CH | |
| H | CH3 | CO2CH3 | H | OCH2CH3 | CH3 | CH | |
| H | CH3 | CO2CH3 | H | OCH2CH3 | OCH3 | CH | |
| H | CH3 | CO2CH3 | H | O(CH2)2CH3 | Cl | CH | |
| H | CH3 | CO2CH3 | H | O(CH2)2CH3 | CH3 | CH | |
| H | CH3 | CO2CH3 | H | O(CH2)2CH3 | OCH3 | CH | |
| H | CH3 | CO2CH3 | H | NH2 | Cl | CH | |

TABLE 11-continued

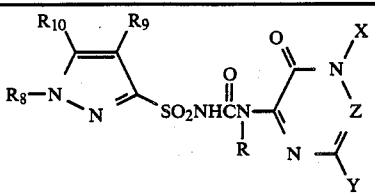

| R | R8 | R9 | R10 | X | Y | Z | m.p. (°C.) |
|---|---|---|---|---|---|---|---|
| H | CH3 | CO2CH3 | H | NH2 | CH3 | CH | |
| H | CH3 | CO2CH3 | H | NH2 | OCH3 | CH | |
| H | CH3 | CO2CH3 | H | NHCH3 | Cl | CH | |
| H | CH3 | CO2CH3 | H | NHCH3 | CH3 | CH | |
| H | CH3 | CO2CH3 | H | NHCH3 | OCH3 | CH | |
| H | CH3 | CO2CH3 | H | N(CH3)2 | Cl | CH | |
| H | CH3 | CO2CH3 | H | N(CH3)2 | CH3 | CH | |
| H | CH3 | CO2CH3 | H | N(CH3)2 | OCH3 | CH | |
| H | CH3 | CO2CH3 | H | NHCH3 | OCH2CH3 | CH | |
| CH3 | CH3 | CO2CH3 | H | CH3 | Cl | CH | |
| CH3 | CH3 | CO2CH3 | H | OCH3 | Cl | CH | |
| CH3 | CH3 | CO2CH3 | H | CH3 | OCH3 | CH | |
| CH3 | CH3 | CO2CH3 | H | OCH3 | CH3 | CH | |
| CH3 | CH3 | CO2CH3 | H | OCH3 | OCH3 | CH | |
| H | CH3 | CO2CH3 | H | CH3 | Cl | CF | |
| H | CH3 | CO2CH3 | H | CH3 | OCH3 | CF | |
| H | CH3 | CO2CH3 | H | OCH3 | OCH3 | CF | |
| H | CH3 | CO2CH3 | H | OCH3 | CH3 | CF | |
| H | CH3 | CO2CH3 | H | CH3 | Cl | CCl | |
| H | CH3 | CO2CH3 | H | CH3 | OCH3 | CCl | |
| H | CH3 | CO2CH3 | H | CH3 | Br | CBr | |
| H | CH3 | CO2CH3 | H | CH3 | Cl | CBr | |
| H | CH3 | CO2CH3 | H | CH3 | OCH3 | CBr | |
| H | CH3 | CO2CH3 | H | H | OCH3 | N | |
| H | CH3 | CO2CH3 | H | CH3 | Cl | N | |
| H | CH3 | CO2CH3 | H | CH3 | Br | N | |
| H | CH3 | CO2CH3 | H | CH3 | OCH3 | N | |
| H | CH3 | CO2CH3 | H | CH3 | OCH2CH3 | N | |
| H | CH3 | CO2CH3 | H | CH3 | O(CH2)2CH3 | N | |
| H | CH3 | CO2CH3 | H | CH3 | CH3 | N | |
| H | CH3 | CO2CH3 | H | CH3 | CH2CH3 | N | |
| H | CH3 | CO2CH3 | H | CH3 | (CH2)2CH3 | N | |
| H | CH3 | CO2CH3 | H | CH2CH3 | Cl | N | |
| H | CH3 | CO2CH3 | H | CH2CH3 | OCH3 | N | |
| H | CH3 | CO2CH3 | H | (CH2)2CH3 | Cl | N | |
| H | CH3 | CO2CH3 | H | (CH2)2CH3 | OCH3 | N | |
| H | CH3 | CO2CH3 | H | OCH3 | H | N | |
| H | CH3 | CO2CH3 | H | OCH3 | CH3 | N | |
| H | CH3 | CO2CH3 | H | OCH3 | CH2CH3 | N | |
| H | CH3 | CO2CH3 | H | OCH3 | (CH2)2CH3 | N | |
| H | CH3 | CO2CH3 | H | OCH3 | OCH3 | N | |
| H | CH3 | CO2CH3 | H | OCH3 | OCH2CH3 | N | |
| H | CH3 | CO2CH3 | H | OCH3 | O(CH2)2CH3 | N | |
| H | CH3 | CO2CH3 | H | OCH3 | Cl | N | |
| H | CH3 | CO2CH3 | H | OCH3 | Br | N | |
| H | CH3 | CO2CH3 | H | OCH2CH3 | Cl | N | |
| H | CH3 | CO2CH3 | H | OCH2CH3 | CH3 | N | |
| H | CH3 | CO2CH3 | H | OCH2CH3 | OCH3 | N | |
| H | CH3 | CO2CH3 | H | O(CH2)2CH3 | Cl | N | |
| H | CH3 | CO2CH3 | H | O(CH2)2CH3 | CH3 | N | |
| H | CH3 | CO2CH3 | H | O(CH2)2CH3 | OCH3 | N | |
| H | CH3 | CO2CH3 | H | NH2 | Cl | N | |
| H | CH3 | CO2CH3 | H | NH2 | CH3 | N | |
| H | CH3 | CO2CH3 | H | NH2 | OCH3 | N | |
| H | CH3 | CO2CH3 | H | NHCH3 | Cl | N | |
| H | CH3 | CO2CH3 | H | NHCH3 | CH3 | N | |
| H | CH3 | CO2CH3 | H | NHCH3 | OCH3 | N | |
| H | CH3 | CO2CH3 | H | N(CH3)2 | Cl | N | |
| H | CH3 | CO2CH3 | H | N(CH3)2 | CH3 | N | |
| H | CH3 | CO2CH3 | H | N(CH3)2 | OCH3 | N | |
| H | CH3 | CO2CH3 | H | NHCH3 | OCH2CH3 | N | |
| CH3 | CH3 | CO2CH3 | H | CH3 | Cl | N | |
| CH3 | CH3 | CO2CH3 | H | OCH3 | Cl | N | |
| CH3 | CH3 | CO2CH3 | H | CH3 | OCH3 | N | |
| CH3 | CH3 | CO2CH3 | H | CH2CH3 | OCH3 | N | |
| CH3 | CH3 | CO2CH3 | H | OCH3 | CH3 | N | |
| CH3 | CH3 | CO2CH3 | H | OCH3 | OCH3 | N | |
| H | CH3 | CO2CH3 | Cl | OCH3 | Cl | CH | |
| H | CH3 | CO2CH3 | F | CH3 | CH3 | CH | |
| H | CH3 | CO2CH3 | Br | CH3 | OCH3 | CH | |
| H | CH3 | CO2CH3 | CH3 | OCH3 | CH3 | CH | |

TABLE 11-continued

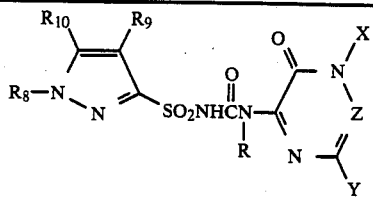

| R | $R_8$ | $R_9$ | $R_{10}$ | X | Y | Z | m.p. (°C.) |
|---|---|---|---|---|---|---|---|
| H | $CH_3$ | $CO_2CH_3$ | $CH_2CH_3$ | $CH_3$ | Cl | Cl | |
| H | $CH_3$ | $CO_2CH_3$ | $(CH_2)_2CH_3$ | $CH_3$ | $OCH_3$ | N | |
| H | $CH_3$ | $CO_2CH_3$ | $CH(CH_3)_2$ | $CH_3$ | $OCH_2CH_3$ | N | |
| H | $CH_3$ | $CO_2CH_3$ | Br | $OCH_3$ | Cl | CH | |
| H | $CH_3$ | $CO_2CH_3$ | $OCH_3$ | $CH_3$ | $CH_3$ | CH | |
| H | $CH_3$ | $CO_2CH_3$ | $OCH_2CH_3$ | $CH_3$ | $OCH_3$ | CH | |
| H | $CH_3$ | $CO_2CH_2CH_3$ | H | $OCH_3$ | Cl | CH | |
| H | $CH_3$ | $CO_2CH_2CH_3$ | H | $CH_3$ | $CH_3$ | CH | |
| H | $CH_3$ | $CO_2CH_2CH_3$ | H | $OCH_3$ | $OCH_3$ | CH | |
| H | $CH_3$ | $CO_2CH_2CH_3$ | H | $OCH_3$ | $CH_3$ | CH | |
| H | $CH_3$ | $CO_2CH_2CH_3$ | H | $CH_3$ | Cl | CH | |
| H | $CH_3$ | $CO_2CH_2CH_3$ | H | $CH_3$ | $OCH_3$ | CH | |
| H | $CH_3$ | $CO_2CH_2CH_3$ | H | $CH_3$ | $OCH_3$ | N | |
| H | $CH_3$ | $CO_2CH_2CH_3$ | H | $CH_3$ | $OCH_2CH_3$ | N | |
| H | $CH_3$ | $CO_2CH_2CH_3$ | H | $OCH_2CH_3$ | $CH_3$ | CH | |
| H | $CH_3$ | $CO_2CH_2CH_3$ | H | $OCH_3$ | $OCH_3$ | CH | |
| H | $CH_3$ | $CO_2CH_2CH_3$ | H | $CH_2CH_3$ | $OCH_3$ | CH | |
| H | $CH_3$ | $CO_2CH_2CH_3$ | H | $CH_3$ | Br | CH | |
| H | $CH_3$ | $CO_2CH_2CH_3$ | H | $CH_3$ | $OCH_2CH_3$ | CH | |
| H | $CH_3$ | $CO_2CH_2CH_3$ | H | $CH_3$ | $CH_2CH_3$ | CH | |
| H | $CH_3$ | $CO_2CH_2CH=CH_3$ | H | $OCH_3$ | Cl | CH | |
| H | $CH_3$ | $CO_2CH_2C\equiv CH$ | H | $CH_3$ | $CH_3$ | CH | |
| H | $CH_3$ | $CO_2CH(CH_3)_2$ | H | $CH_3$ | $OCH_3$ | CH | |
| H | $CH_3$ | $CO_2(CH_2)_2CH_3$ | H | $OCH_3$ | $CH_3$ | CH | |
| H | $CH_3$ | $CO_2(CH_2)_2OCH_3$ | H | $CH_3$ | Cl | CH | |
| H | $CH_3$ | $CO_2(CH_2)_2OCH_2CH_3$ | H | $CH_3$ | $OCH_3$ | N | |
| H | $CH_3$ | $CO_2CH_2OCH_3$ | H | $CH_3$ | $OCH_2CH_3$ | N | |
| H | $CH_3$ | $CO_2(CH_2)_2Cl$ | H | $OCH_2CH_3$ | $CH_3$ | CH | |
| H | $CH_3$ | $CO_2(CH_2)_2F$ | H | $OCH_3$ | $OCH_3$ | CH | |
| H | $CH_3$ | $CO_2(CH_2)_2Br$ | H | $CH_2CH_3$ | $OCH_3$ | CH | |
| H | $CH_3$ | $CO_2(CH_2)_2I$ | H | $CH_3$ | Br | CH | |
| H | $CH_3$ | $CO_2CH_2CF_3$ | H | $CH_3$ | $OCH_2CH_3$ | CH | |
| H | $CH_3$ | $CO_2CH_2CH_2CN$ | H | $CH_3$ | $CH_2CH_3$ | CH | |
| $CH_3$ | $CH_3$ | $CO_2CH_2CH_3$ | H | $OCH_3$ | Cl | CH | |
| H | $CH_3$ | $CO_2CH_2CH_3$ | $OCH_3$ | $CH_3$ | $OCH_3$ | CH | |
| H | $CH_3$ | F | H | $OCH_3$ | $CH_3$ | CH | |
| H | $CH_3$ | Cl | H | $CH_3$ | $OCH_2CH_3$ | N | |
| H | $CH_3$ | Br | H | $CH_3$ | $OCH_3$ | N | |
| H | $CH_3$ | $NO_2$ | H | $CH_3$ | Cl | CH | |
| H | $CH_3$ | $CH_3$ | H | $OCH_3$ | $CH_3$ | CH | |
| H | $CH_3$ | $CH_2CH_3$ | H | $CH_3$ | $OCH_3$ | CH | |
| H | $CH_3$ | $(CH_2)_2CH_3$ | H | $CH_3$ | $CH_3$ | CH | |
| H | $CH_3$ | $CH(CH_3)_2$ | H | $OCH_2CH_3$ | $CH_3$ | CH | |
| H | $CH_3$ | $CH=CF_2$ | H | $CH_3$ | $OCH_3$ | CH | |
| H | $CH_3$ | $CCl=CCl_2$ | H | $OCH_3$ | $CH_3$ | CH | |
| H | $CH_3$ | $CH_2CH=CHCCl_3$ | H | $CH_3$ | Cl | CH | |
| H | $CH_3$ | $CH=CHCl$ | H | $CH_3$ | $OCH_3$ | N | |
| H | $CH_3$ | $CH=CHI$ | H | $CH_3$ | $OCH_2CH_3$ | N | |
| H | $CH_3$ | $CH=CBr_2$ | H | $OCH_2CH_3$ | $CH_3$ | CH | |
| H | $CH_3$ | $CF=CFH$ | H | $OCH_3$ | $OCH_3$ | CH | |
| H | $CH_3$ | $CH_2CH=CF_2$ | H | $CH_2CH_3$ | $OCH_3$ | CH | |
| H | $CH_3$ | $CH=CHCF_3$ | H | $CH_3$ | Br | CH | |
| H | $CH_3$ | $CF=CFCH_3$ | H | $CH_3$ | $OCH_2CH_3$ | H | |
| H | $CH_3$ | $OCH_3$ | H | $CH_3$ | $CH_2CH_3$ | CH | |
| H | $CH_3$ | $OCH_3$ | $CH_3$ | $OCH_3$ | Cl | CH | |
| H | $CH_3$ | $OCH_2CH_3$ | H | $CH_3$ | $CH_3$ | CH | |
| H | $CH_3$ | $C(O)N(CH_3)_2$ | H | $CH_3$ | $OCH_2CH_3$ | N | |
| H | $CH_3$ | $C(O)NHCH_2CH_3$ | H | $OCH_3$ | Cl | CH | |
| H | $CH_3$ | $C(O)N(CH_3)OCH_3$ | H | $CH_3$ | $CH_3$ | CH | |
| H | $CH_3$ | $C(O)NHOCH_2CH_3$ | H | $CH_3$ | $OCH_3$ | CH | |
| H | $CH_3$ | $C(O)NH(CH_2)_2CH_3$ | H | $OCH_3$ | $CH_3$ | CH | |
| H | $CH_3$ | $SO_2N(CH_3)_2$ | H | $OCH_3$ | Cl | CH | |
| H | $CH_3$ | $SO_2NH$—cyclopropyl | H | $OCH_3$ | Cl | CH | |
| $CH_3$ | $CH_3$ | $SO_2N(CH_3)_2$ | H | $CH_3$ | $CH_3$ | CH | |
| H | $CH_3$ | $SO_2N(CH_3)_2$ | $CH_3$ | $CH_3$ | $OCH_3$ | CH | |
| H | $CH_3$ | $SO_2N(CH_3)CH_2CH=CH_2$ | H | $OCH_3$ | $CH_3$ | CH | |
| H | $CH_3$ | $SO_2N((CH_2)_2CH_3)_2$ | H | $CH_3$ | Cl | CH | |
| H | $CH_3$ | $SO_2NH_2$ | H | $CH_3$ | $OCH_3$ | N | |
| H | $CH_3$ | $SO_2N(CH_3)OCH_3$ | H | $CH_3$ | $OCH_2CH_3$ | N | |
| H | $CH_3$ | $SO_2N(CH_3)OCH_2CH_3$ | H | $OCH_2CH_3$ | $CH_3$ | CH | |
| H | $CH_3$ | $SCH_3$ | H | $OCH_3$ | $OCH_3$ | CH | |

TABLE 11-continued

| R | R$_8$ | R$_9$ | R$_{10}$ | X | Y | Z | m.p. (°C.) |
|---|---|---|---|---|---|---|---|
| H | CH$_3$ | SCH$_2$CH=CH$_2$ | H | CH$_2$CH$_3$ | OCH$_3$ | CH | |
| H | CH$_3$ | SCH$_2$C≡CH | H | CH$_3$ | Br | CH | |
| H | CH$_3$ | S(CH$_2$)$_2$CH$_3$ | H | CH$_3$ | OCH$_2$CH$_3$ | CH | |
| H | CH$_3$ | S(O)CH$_3$ | H | CH$_3$ | CH$_2$CH$_3$ | CH | |
| H | CH$_3$ | SCF$_2$H | H | OCH$_3$ | Cl | CH | |
| H | CH$_3$ | SCF$_2$CF$_2$H | H | CH$_3$ | CH$_3$ | CH | |
| H | CH$_3$ | S(CH$_2$)$_2$Cl | H | CH$_3$ | OCH$_3$ | CH | |
| H | CH$_3$ | S(CH$_2$)$_2$I | H | OCH$_3$ | CH$_3$ | CH | |
| H | CH$_3$ | S(CH$_2$)$_3$Br | H | CH$_3$ | Cl | CH | |
| H | CH$_3$ | S(O)CF$_2$CF$_2$H | H | CH$_3$ | OCH$_3$ | N | |
| H | CH$_3$ | S(O)(CH$_2$)$_2$I | H | CH$_3$ | OCH$_2$CH$_3$ | N | |
| H | CH$_3$ | S(O)$_2$CH$_3$ | H | OCH$_3$ | Cl | CH | |
| H | CH$_3$ | S(O)$_2$CH$_2$CH$_3$ | H | CH$_3$ | CH$_3$ | CH | |
| H | CH$_3$ | S(O)$_2$CH$_2$CH=CH$_2$ | H | CH$_3$ | OCH$_3$ | CH | |
| H | CH$_3$ | S(O)$_2$CH$_2$C≡CH | H | OCH$_3$ | CH$_3$ | CH | |
| H | CH$_3$ | S(O)$_2$CF$_2$H | H | CH$_3$ | Cl | CH | |
| H | CH$_3$ | S(O)$_2$CF$_2$CF$_2$H | H | CH$_3$ | OCH$_3$ | N | |
| H | CH$_3$ | S(O)$_2$(CH$_2$)$_2$I | H | CH$_3$ | OCH$_2$CH$_3$ | N | |
| H | CH$_3$ | C(O)CH$_3$ | H | OCH$_3$ | Cl | CH | |
| H | CH$_3$ | C(O)(CH$_2$)$_3$CH$_3$ | H | CH$_3$ | CH$_3$ | CH | |
| H | CH$_3$ | C(O)CH$_2$CH$_3$ | H | CH$_3$ | OCH$_3$ | CH | |
| H | CH$_3$ | C(O)—cyclo-C$_3$H$_5$ | H | OCH$_3$ | CH$_3$ | CH | |
| H | CH$_3$ | C(O)—cyclo-C$_4$H$_7$ | H | CH$_3$ | Cl | CH | |
| H | CH$_3$ | C(O)—cyclo-C$_5$H$_9$ | H | OCH$_3$ | Cl | CH | |
| H | CH$_3$ | C(O)—cyclo-C$_3$F$_5$ | H | CH$_3$ | CH$_3$ | CH | |
| H | CH$_3$ | C(O)CF$_3$ | H | CH$_3$ | OCH$_3$ | CH | |
| H | CH$_3$ | C(O)(CH$_2$)$_3$CCl$_2$H | H | OCH$_3$ | CH$_3$ | CH | |
| H | CH$_3$ | C(O)(CH$_2$)$_4$F | H | CH$_3$ | Cl | CH | |
| H | CH$_3$ | C(O)—cyclo-(CHCH$_2$CCl$_2$) | H | CH$_3$ | OCH$_3$ | N | |
| H | CH$_3$ | OCF$_2$H | H | CH$_3$ | OCH$_2$CH$_3$ | N | |
| H | CH$_3$ | L-1, R$_h$ = H | H | OCH$_2$CH$_3$ | CH$_3$ | CH | |
| H | CH$_3$ | L-1, R$_h$ = CH$_3$ | H | OCH$_3$ | OCH$_3$ | CH | |
| H | CH$_3$ | L-2, R$_h$ = H | H | CH$_2$CH$_3$ | OCH$_3$ | CH | |
| H | CH$_3$ | L-2, R$_h$ = CH$_3$ | H | CH$_3$ | Br | CH | |
| H | CH$_3$ | L-3 | H | CH$_3$ | OCH$_2$CH$_3$ | CH | |
| H | CH$_3$ | L-4 | H | CH$_3$ | CH$_2$CH$_3$ | CH | |
| H | CH$_3$ | L-5 | H | OCH$_3$ | Cl | CH | |
| H | CH$_3$ | L-6 | H | CH$_3$ | CH$_3$ | CH | |
| H | CH$_3$ | L-7 | H | CH$_3$ | OCH$_3$ | CH | |
| H | CH$_3$ | L-8 | H | OCH$_3$ | CH$_3$ | CH | |
| H | CH$_3$ | L-9 | H | CH$_3$ | Cl | CH | |
| H | CH$_3$ | L-10 | H | CH$_3$ | OCH$_3$ | N | |
| H | CH$_3$ | L-11 | H | CH$_3$ | OCH$_2$CH$_3$ | N | |
| H | CH$_3$ | L-12 | H | OCH$_3$ | Cl | CH | |
| H | CH$_3$ | L-13 | H | CH$_3$ | CH$_3$ | CH | |
| H | CH$_3$ | L-14 | H | CH$_3$ | OCH$_3$ | CH | |
| H | CH$_3$ | L-15 | H | OCH$_3$ | CH$_3$ | CH | |
| H | CH$_3$ | L-16, R$_i$ = H | H | CH$_3$ | Cl | CH | |
| H | CH$_3$ | L-16, R$_i$ = CH$_3$ | H | CH$_3$ | OCH$_3$ | N | |
| H | CH$_3$ | L-17 | H | CH$_3$ | OCH$_2$CH$_3$ | N | |
| H | CH$_3$ | L-18 | H | OCH$_3$ | Cl | CH | |
| H | CH$_3$ | L-19 | H | CH$_3$ | CH$_3$ | CH | |
| H | CH$_3$ | L-20 | H | CH$_3$ | OCH$_3$ | CH | |
| H | CH$_3$ | L-21 | H | OCH$_3$ | CH$_3$ | CH | |
| H | CH$_3$ | L-22 | H | CH$_3$ | Cl | CH | |
| H | CH$_3$ | L-23 | H | OCH$_3$ | Cl | CH | |
| H | CH$_3$ | L-24 | H | CH$_3$ | CH$_3$ | CH | |
| H | CH$_3$ | L-25 | H | CH$_3$ | OCH$_3$ | CH | |
| H | CH$_3$ | L-26, R$_j$ = H | H | OCH$_3$ | CH$_3$ | CH | |
| H | CH$_3$ | L-26, R$_j$ = CH$_3$ | H | CH$_3$ | Cl | CH | |
| H | CH$_3$ | L-26, R$_j$ = CH$_2$CH$_3$ | H | CH$_3$ | OCH$_3$ | CH | |
| H | CH$_3$ | L-27, R$_j$ = H | H | CH$_3$ | OCH$_2$CH$_3$ | N | |
| H | CH$_3$ | L-27, R$_j$ = CH$_3$ | H | OCH$_2$CH$_3$ | CH$_3$ | CH | |
| H | CH$_3$ | L-27, R$_j$ = CH$_2$CH$_3$ | H | OCH$_3$ | OCH$_3$ | CH | |
| H | CH$_3$ | L-28, R$_k$ = H | H | CH$_2$CH$_3$ | OCH$_3$ | CH | |
| H | CH$_3$ | L-28, R$_k$ = CH$_3$ | H | CH$_3$ | Br | CH | |
| H | CH$_3$ | L-28, R$_k$ = CH$_2$CH$_3$ | H | CH$_3$ | OCH$_2$CH$_3$ | CH | |
| H | CH$_3$ | L-28, R$_k$ = OCH$_3$ | H | CH$_3$ | CH$_2$CH$_3$ | CH | |
| H | CH$_3$ | L-28, R$_k$ = OCH$_2$CH$_3$ | H | OCH$_3$ | Cl | CH | |
| H | CH$_3$ | L-28, R$_k$ = SCH$_3$ | H | CH$_3$ | CH$_3$ | CH | |
| H | CH$_3$ | L-28, R$_k$ = SCH$_2$CH$_3$ | H | CH$_3$ | OCH$_3$ | CH | |

TABLE 12-continued

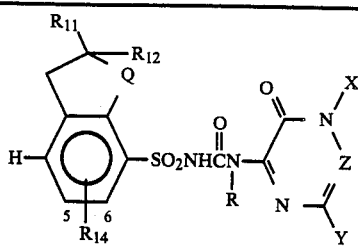

| R | Q | R11 | R12 | R14 | X | Y | Z | m.p. (°C.) |
|---|---|-----|-----|-----|---|---|---|-----------|
| H | O | CH3 | H | H | OCH3 | CH3 | CH | |
| H | O | CH3 | H | H | OCH3 | CH2CH3 | CH | |
| H | O | CH3 | H | H | OCH3 | (CH2)2CH3 | CH | |
| H | O | CH3 | H | H | OCH3 | OCH3 | CH | |
| H | O | CH3 | H | H | OCH3 | OCH2CH3 | CH | |
| H | O | CH3 | H | H | CH3 | SCH3 | CH | |
| H | O | CH3 | H | H | OCH3 | SCH3 | CH | |
| H | O | CH3 | H | H | CH3 | SCH3 | N | |
| H | O | CH2 | H | H | CH3 | SCH2CH3 | CH | |
| H | O | CH2 | H | H | OCH2CH3 | SCH3 | N | |
| H | O | CH2 | H | H | N(CH3)2 | SCH3 | CH | |
| H | O | CH3 | H | H | OCH3 | O(CH2)2CH3 | CH | |
| H | O | CH3 | H | H | OCH3 | Cl | CH | |
| H | O | CH3 | H | H | OCH3 | Br | CH | |
| H | O | CH3 | H | H | OCH2CH3 | Cl | CH | |
| H | O | CH3 | H | H | OCH2CH3 | CH3 | CH | |
| H | O | CH3 | H | H | OCH2CH3 | OCH3 | CH | |
| H | O | CH3 | H | H | O(CH2)2CH3 | Cl | CH | |
| H | O | CH3 | H | H | O(CH2)2CH3 | CH3 | CH | |
| H | O | CH3 | H | H | O(CH2)2CH3 | OCH3 | CH | |
| H | O | CH3 | H | H | NH2 | Cl | CH | |
| H | O | CH3 | H | H | NH2 | CH3 | CH | |
| H | O | CH3 | H | H | NH2 | OCH3 | CH | |
| H | O | CH3 | H | H | NHCH3 | Cl | CH | |
| H | O | CH3 | H | H | NHCH3 | CH3 | CH | |
| H | O | CH3 | H | H | NHCH3 | OCH3 | CH | |
| H | O | CH3 | H | H | N(CH3)2 | Cl | CH | |
| H | O | CH3 | H | H | N(CH3)2 | CH3 | CH | |
| H | O | CH3 | H | H | N(CH3)2 | OCH3 | CH | |
| H | O | CH3 | H | H | NHCH3 | OCH2CH3 | CH | |
| CH3 | O | CH3 | H | H | CH3 | Cl | CH | |
| CH3 | O | CH3 | H | H | OCH3 | Cl | CH | |
| CH3 | O | CH3 | H | H | CH3 | OCH3 | CH | |
| CH3 | O | CH3 | H | H | OCH3 | CH3 | CH | |
| CH3 | O | CH3 | H | H | OCH3 | OCH3 | CH | |
| H | O | CH3 | H | H | CH3 | Cl | CF | |
| H | O | CH3 | H | H | CH3 | OCH3 | CF | |
| H | O | CH3 | H | H | OCH3 | OCH3 | CF | |
| H | O | CH3 | H | H | OCH3 | CH3 | CF | |
| H | O | CH3 | H | H | CH3 | Cl | CCl | |
| H | O | CH3 | H | H | CH3 | OCH3 | CCl | |
| H | O | CH3 | H | H | CH3 | Br | CBr | |
| H | O | CH3 | H | H | CH3 | Cl | CBr | |
| H | O | CH3 | H | H | CH3 | OCH3 | CBr | |
| H | O | CH3 | H | H | H | OCH3 | N | |
| H | O | CH3 | H | H | CH3 | Cl | N | |
| H | O | CH3 | H | H | CH3 | Br | N | |
| H | O | CH3 | H | H | CH3 | OCH3 | N | |
| H | O | CH3 | H | H | CH3 | OCH2CH3 | N | |
| H | O | CH3 | H | H | CH3 | O(CH2)2CH3 | N | |
| H | O | CH3 | H | H | CH3 | CH3 | N | |
| H | O | CH3 | H | H | CH3 | CH2CH3 | N | |
| H | O | CH3 | H | H | CH3 | (CH2)2CH3 | N | |
| H | O | CH3 | H | H | CH2CH3 | Cl | N | |
| H | O | CH3 | H | H | CH2CH3 | OCH3 | N | |
| H | O | CH3 | H | H | (CH2)2CH3 | Cl | N | |
| H | O | CH3 | H | H | (CH2)2CH3 | OCH3 | N | |
| H | O | CH3 | H | H | OCH3 | H | N | |
| H | O | CH3 | H | H | OCH3 | CH3 | N | |
| H | O | CH3 | H | H | OCH3 | CH2CH3 | N | |
| H | O | CH3 | H | H | OCH3 | (CH2)2CH3 | N | |
| H | O | CH3 | H | H | OCH3 | OCH3 | N | |
| H | O | CH3 | H | H | OCH3 | OCH2CH3 | N | |
| H | O | CH3 | H | H | OCH3 | O(CH2)2CH3 | N | |
| H | O | CH3 | H | H | OCH3 | Cl | N | |
| H | O | CH3 | H | H | OCH3 | Br | N | |
| H | O | CH3 | H | H | OCH2CH3 | Cl | N | |
| H | O | CH3 | H | H | OCH2CH3 | CH3 | N | |
| H | O | CH3 | H | H | OCH2CH3 | OCH3 | N | |

TABLE 11-continued

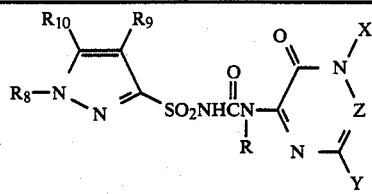

| R | R8 | R9 | R10 | X | Y | Z | m.p. (°C.) |
|---|---|---|---|---|---|---|---|
| H | CH3 | L-29, Rk = H | H | OCH3 | CH3 | CH | |
| H | CH3 | L-29, Rk = CH3 | H | CH3 | Cl | CH | |
| H | CH3 | L-29, Rk = CH2CH3 | H | CH3 | OCH3 | N | |
| H | CH3 | L-29, Rk = OCH3 | H | CH3 | OCH2CH3 | N | |
| H | CH3 | L-29, Rk = OCH2CH3 | H | OCH3 | Cl | CH | |
| H | CH3 | L-29, Rk = SCH3 | H | CH3 | CH3 | CH | |
| H | CH3 | L-29, Rk = SCH2CH3 | H | CH3 | OCH3 | CH | |
| H | CH3 | L-30, Rm = H | H | OCH3 | CH3 | CH | |
| H | CH3 | L-30, Rm = CH3 | H | CH3 | Cl | CH | |
| H | CH3 | L-30, Rm = CH2CH3 | H | CH3 | OCH3 | N | |
| H | CH3 | L-31, Rm = H | H | CH3 | OCH2CH3 | N | |
| H | CH3 | L-31, Rm = CH3 | H | OCH3 | Cl | CH | |
| H | CH3 | L-31, Rm = CH2CH3 | H | CH3 | CH3 | CH | |
| H | CH3 | L-32, Rm = H | H | CH3 | OCH3 | CH | |
| H | CH3 | L-32, Rm = CH3 | H | OCH3 | CH3 | CH | |
| H | CH3 | L-32, Rm = CH2CH3 | H | CH3 | Cl | CH | |
| H | CH3 | L-33, Rn = H | H | CH3 | CH3 | N | |
| H | CH3 | L-33, Rn = CH3 | H | CH3 | OCH3 | CH | |
| H | H | CO2CH3 | H | OCH3 | Cl | CH | |
| H | CH2CH3 | CO2CH3 | H | CH3 | CH3 | CH | |
| H | (CH2)2CH3 | CO2CH3 | H | CH3 | OCH3 | CH | |
| H | H | CO2CH2CH3 | H | OCH3 | CH3 | CH | |
| H | CH2CH3 | CO2CH2CH3 | H | CH3 | Cl | CH | |
| H | (CH2)2CH3 | CO2CH2CH3 | H | CH3 | OCH3 | N | |
| CH3 | CH2CH3 | CO2CH3 | H | CH3 | OCH2CH3 | N | |
| CH3 | (CH2)2CH3 | CO2CH3 | H | OCH2CH3 | CH3 | CH | |
| CH3 | H | CO2CH3 | H | OCH3 | OCH3 | CH | |
| H | H | CO2CH3 | H | CH2CH3 | OCH3 | CH | |
| H | CH2CH3 | CO2CH3 | H | CH3 | Br | CH | |
| H | (CH2)2CH3 | CO2CH3 | H | CH3 | OCH2CH3 | CH | |
| H | H | CO2CH3 | H | CH3 | CH2CH3 | CH | |
| H | CH2CH3 | CO2CH3 | H | OCH3 | Cl | CH | |
| H | H | SO2N(CH3)2 | H | CH3 | CH3 | CH | |
| H | CH2CH3 | CH3 | H | CH3 | OCH3 | CH | |
| H | H | Br | H | OCH3 | CH3 | CH | |
| H | CH2CH3 | SO2CH3 | H | CH3 | Cl | CH | |
| H | H | OCF2H | H | CH3 | OCH3 | N | |
| H | (CH2)2CH3 | OCH3 | H | CH3 | OCH2CH3 | N | |
| H | CH(CH3)2 | CO2CH3 | H | OCH3 | Cl | CH | |

TABLE 12

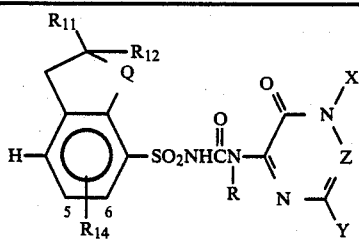

| R | Q | R11 | R12 | R14 | X | Y | Z | m.p. (°C.) |
|---|---|---|---|---|---|---|---|---|
| H | O | CH3 | H | H | H | OCH3 | CH | |
| H | O | CH3 | H | H | CH3 | Cl | CH | |
| H | O | CH3 | H | H | CH3 | Br | CH | |
| H | O | CH3 | H | H | CH3 | OCH3 | CH | |
| H | O | CH3 | H | H | CH3 | OCH2CH3 | CH | |
| H | O | CH3 | H | H | CH3 | O(CH2)2CH3 | CH | |
| H | O | CH3 | H | H | CH3 | CH3 | CH | |
| H | O | CH3 | H | H | CH3 | CH2CH3 | CH | |
| H | O | CH3 | H | H | CH3 | (CH2)2CH3 | CH | |
| H | O | CH3 | H | H | CH2CH3 | Cl | CH | |
| H | O | CH3 | H | H | CH2CH3 | OCH3 | CH | |
| H | O | CH3 | H | H | (CH2)2CH3 | Cl | CH | |
| H | O | CH3 | H | H | (CH2)2CH3 | OCH3 | CH | |
| H | O | CH3 | H | H | OCH3 | H | CH | |

TABLE 12-continued

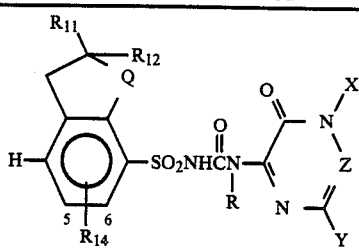

| R | Q | R11 | R12 | R14 | X | Y | Z | m.p. (°C.) |
|---|---|---|---|---|---|---|---|---|
| H | S | CH3 | H | H | OCH3 | O(CH2)2CH3 | CH | |
| H | S | CH3 | H | H | OCH3 | Cl | CH | |
| H | S | CH3 | H | H | OCH3 | Br | CH | |
| H | S | CH3 | H | H | OCH2CH3 | Cl | CH | |
| H | S | CH3 | H | H | OCH2CH3 | CH3 | CH | |
| H | S | CH3 | H | H | OCH2CH3 | OCH3 | CH | |
| H | S | CH3 | H | H | O(CH2)2CH3 | Cl | CH | |
| H | S | CH3 | H | H | O(CH2)2CH3 | CH3 | CH | |
| H | S | CH3 | H | H | O(CH2)2CH3 | OCH3 | CH | |
| H | S | CH3 | H | H | NH2 | Cl | CH | |
| H | S | CH3 | H | H | NH2 | CH3 | CH | |
| H | S | CH3 | H | H | NH2 | OCH3 | CH | |
| H | S | CH3 | H | H | NHCH3 | Cl | CH | |
| H | S | CH3 | H | H | NHCH3 | CH3 | CH | |
| H | S | CH3 | H | H | NHCH3 | OCH3 | CH | |
| H | S | CH3 | H | H | N(CH3)2 | Cl | CH | |
| H | S | CH3 | H | H | N(CH3)2 | CH3 | CH | |
| H | S | CH3 | H | H | N(CH3)2 | OCH3 | CH | |
| H | S | CH3 | H | H | NHCH3 | OCH2CH3 | CH | |
| CH3 | S | CH3 | H | H | CH3 | Cl | CH | |
| CH3 | S | CH3 | H | H | OCH3 | Cl | CH | |
| CH3 | S | CH3 | H | H | CH3 | OCH3 | CH | |
| CH3 | S | CH3 | H | H | OCH3 | CH3 | CH | |
| CH3 | S | CH3 | H | H | OCH3 | OCH3 | CH | |
| H | S | CH3 | H | H | CH3 | Cl | CF | |
| H | S | CH3 | H | H | CH3 | OCH3 | CF | |
| H | S | CH3 | H | H | OCH3 | OCH3 | CF | |
| H | S | CH3 | H | H | OCH3 | CH3 | CF | |
| H | S | CH3 | H | H | CH3 | Cl | CCl | |
| H | S | CH3 | H | H | CH3 | OCH3 | CCl | |
| H | S | CH3 | H | H | CH3 | Br | CBr | |
| H | S | CH3 | H | H | CH3 | Cl | CBr | |
| H | S | CH3 | H | H | CH3 | OCH3 | CBr | |
| H | S | CH3 | H | H | H | OCH3 | N | |
| H | S | CH3 | H | H | CH3 | Cl | N | |
| H | S | CH3 | H | H | CH3 | Br | N | |
| H | S | CH3 | H | H | CH3 | OCH3 | N | |
| H | S | CH3 | H | H | CH3 | OCH2CH3 | N | |
| H | S | CH3 | H | H | CH3 | O(CH2)2CH3 | N | |
| H | S | CH3 | H | H | CH3 | CH3 | N | |
| H | S | CH3 | H | H | CH3 | CH2CH3 | N | |
| H | S | CH3 | H | H | CH3 | (CH2)2CH3 | N | |
| H | S | CH3 | H | H | CH2CH3 | Cl | N | |
| H | S | CH3 | H | H | CH2CH3 | OCH3 | N | |
| H | S | CH3 | H | H | (CH2)2CH3 | Cl | N | |
| H | S | CH3 | H | H | (CH2)2CH3 | OCH3 | N | |
| H | S | CH3 | H | H | OCH3 | H | N | |
| H | S | CH3 | H | H | OCH3 | CH3 | N | |
| H | S | CH3 | H | H | OCH3 | CH2CH3 | N | |
| H | S | CH3 | H | H | OCH3 | (CH2)2CH3 | N | |
| H | S | CH3 | H | H | OCH3 | OCH3 | N | |
| H | S | CH3 | H | H | OCH3 | OCH2CH3 | N | |
| H | S | CH3 | H | H | OCH3 | O(CH2)2CH3 | N | |
| H | S | CH3 | H | H | OCH3 | Cl | N | |
| H | S | CH3 | H | H | OCH3 | Br | N | |
| H | S | CH3 | H | H | OCH2CH3 | Cl | N | |
| H | S | CH3 | H | H | OCH2CH3 | CH3 | N | |
| H | S | CH3 | H | H | OCH2CH3 | OCH3 | N | |
| H | S | CH3 | H | H | O(CH2)2CH3 | Cl | N | |
| H | S | CH3 | H | H | O(CH2)2CH3 | CH3 | N | |
| H | S | CH3 | H | H | O(CH2)2CH3 | OCH3 | N | |
| H | S | CH3 | H | H | NH2 | Cl | N | |
| H | S | CH3 | H | H | NH2 | CH3 | N | |
| N | S | CH3 | H | H | NH2 | OCH3 | N | |
| H | S | CH3 | H | H | NHCH3 | Cl | N | |
| H | S | CH3 | H | H | NHCH3 | CH3 | N | |
| H | S | CH3 | H | H | NHCH3 | OCH3 | N | |
| H | S | CH3 | H | H | N(CH3)2 | Cl | N | |
| H | S | CH3 | H | H | N(CH3)2 | CH3 | N | |

TABLE 12-continued

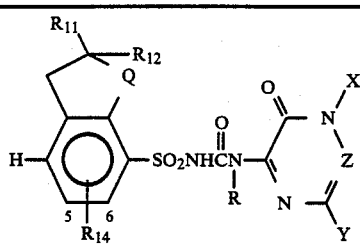

| R | Q | $R_{11}$ | $R_{12}$ | $R_{14}$ | X | Y | Z | m.p. (°C.) |
|---|---|---|---|---|---|---|---|---|
| H | O | $CH_3$ | H | H | $O(CH_2)_2CH_3$ | Cl | N | |
| H | O | $CH_3$ | H | H | $O(CH_2)_2CH_3$ | $CH_3$ | N | |
| H | O | $CH_3$ | H | H | $O(CH_2)_2CH_3$ | $OCH_3$ | N | |
| H | O | $CH_3$ | H | H | $NH_2$ | Cl | N | |
| H | O | $CH_3$ | H | H | $NH_2$ | $CH_3$ | N | |
| H | O | $CH_3$ | H | H | $NH_2$ | $OCH_3$ | N | |
| H | O | $CH_3$ | H | H | $NHCH_3$ | Cl | N | |
| H | O | $CH_3$ | H | H | $NHCH_3$ | $CH_3$ | N | |
| H | O | $CH_3$ | H | H | $NHCH_3$ | $OCH_3$ | N | |
| H | O | $CH_3$ | H | H | $N(CH_3)_2$ | Cl | N | |
| H | O | $CH_3$ | H | H | $N(CH_3)_2$ | $CH_3$ | N | |
| H | O | $CH_3$ | H | H | $N(CH_3)_2$ | $OCH_3$ | N | |
| H | O | $CH_3$ | H | H | $NHCH_3$ | $OCH_2CH_3$ | N | |
| $CH_3$ | O | $CH_3$ | H | H | $CH_3$ | Cl | N | |
| $CH_3$ | O | $CH_3$ | H | H | $OCH_3$ | Cl | N | |
| $CH_3$ | O | $CH_3$ | H | H | $OCH_3$ | $OCH_3$ | N | |
| $CH_3$ | O | $CH_3$ | H | H | $CH_2CH_3$ | $OCH_3$ | N | |
| $CH_3$ | O | $CH_3$ | H | H | $OCH_3$ | $CH_3$ | N | |
| $CH_3$ | O | $CH_3$ | H | H | $OCH_3$ | $OCH_3$ | N | |
| H | O | H | H | H | $OCH_3$ | Cl | CH | |
| H | O | $CH_3$ | $CH_3$ | H | $CH_3$ | $CH_3$ | CH | |
| H | O | $CH_3$ | $CH_2CH_3$ | H | $CH_3$ | $OCH_3$ | CH | |
| H | O | $CH_2CH_3$ | $CH_3$ | H | $OCH_3$ | $CH_3$ | CH | |
| H | O | $CH_2CH_3$ | H | H | $CH_3$ | Cl | CH | |
| H | O | $CH_2CH_3$ | $CH_2CH_3$ | H | $CH_3$ | $OCH_3$ | N | |
| H | O | H | $CH_3$ | H | $CH_3$ | $OCH_2CH_3$ | N | |
| $CH_3$ | O | H | H | H | $OCH_2CH_3$ | $CH_3$ | CH | |
| H | O | H | H | 5-F | $OCH_3$ | $OCH_3$ | CH | |
| H | O | $CH_3$ | H | 6-F | $CH_2CH_3$ | $OCH_3$ | CH | |
| H | O | H | $CH_3$ | 5-Cl | $CH_3$ | Br | CH | |
| H | O | $CH_3$ | $CH_3$ | 6-Cl | $CH_3$ | $OCH_2CH_3$ | CH | |
| H | O | H | H | 5-Br | $CH_3$ | $CH_2CH_3$ | CH | |
| H | O | $CH_3$ | H | 6-Br | $OCH_3$ | Cl | CH | |
| H | O | H | $CH_3$ | 5-CN | $CH_3$ | $CH_3$ | CH | |
| H | O | $CH_3$ | $CH_3$ | 6-CN | $CH_3$ | $OCH_3$ | CH | |
| H | O | H | H | 5-$CH_3$ | $OCH_3$ | $CH_3$ | CH | |
| H | O | $CH_3$ | H | 6-$CH_3$ | $CH_3$ | Cl | CH | |
| H | O | H | $CH_3$ | 5-$OCH_3$ | $CH_3$ | $OCH_3$ | N | |
| H | O | $CH_3$ | $CH_3$ | 6-$OCH_3$ | $CH_3$ | $OCH_2CH_3$ | N | |
| H | O | H | $CH_3$ | 5-$SCH_3$ | $OCH_3$ | Cl | CH | |
| H | O | $CH_3$ | H | 6-$SCH_3$ | $CH_3$ | $CH_3$ | CH | |
| H | O | H | $CH_3$ | 5-$OCF_2H$ | $CH_3$ | $OCH_3$ | CH | |
| H | O | $CH_3$ | $CH_3$ | 6-$OCF_2H$ | $OCH_3$ | $CH_3$ | CH | |
| $CH_3$ | O | $CH_3$ | H | 6-Cl | $CH_3$ | Cl | CH | |
| H | S | $CH_3$ | H | H | H | $OCH_3$ | CH | |
| H | S | $CH_3$ | H | H | $CH_3$ | Cl | CH | |
| H | S | $CH_3$ | H | H | $CH_3$ | Br | CH | |
| H | S | $CH_3$ | H | H | $CH_3$ | $OCH_3$ | CH | |
| H | S | $CH_3$ | H | H | $CH_3$ | $OCH_2CH_3$ | CH | |
| H | S | $CH_3$ | H | H | $CH_3$ | $O(CH_2)_2CH_3$ | CH | |
| H | S | $CH_3$ | H | H | $CH_3$ | $CH_3$ | CH | |
| H | S | $CH_3$ | H | H | $CH_3$ | $CH_2CH_3$ | CH | |
| H | S | $CH_3$ | H | H | $CH_3$ | $(CH_2)_2CH_3$ | CH | |
| H | S | $CH_3$ | H | H | $CH_2CH_3$ | Cl | CH | |
| H | S | $CH_3$ | H | H | $CH_2CH_3$ | $OCH_3$ | CH | |
| H | S | $CH_3$ | H | H | $CH_3$ | $SCH_3$ | CH | |
| H | S | $CH_3$ | H | H | $OCH_3$ | $SCH_3$ | CH | |
| H | S | $CH_3$ | H | H | $CH_2CH_3$ | $SCH_3$ | CH | |
| H | S | $CH_3$ | H | H | $CH_3$ | $SCH_2CH_3$ | N | |
| H | S | $CH_3$ | H | H | $CH_3$ | $SCH_2CH_3$ | CH | |
| H | S | $CH_3$ | H | H | $NHCH_3$ | $SCH_3$ | N | |
| H | S | $CH_3$ | H | H | $(CH_2)_2CH_3$ | Cl | CH | |
| H | S | $CH_3$ | H | H | $(CH_2)_2CH_3$ | $OCH_3$ | CH | |
| H | S | $CH_3$ | H | H | $OCH_3$ | H | CH | |
| H | S | $CH_3$ | H | H | $OCH_3$ | $CH_3$ | CH | |
| H | S | $CH_3$ | H | H | $OCH_3$ | $CH_2CH_3$ | CH | |
| H | S | $CH_3$ | H | H | $OCH_3$ | $(CH_2)_2CH_3$ | CH | |
| H | S | $CH_3$ | H | H | $OCH_3$ | $OCH_3$ | CH | |
| H | S | $CH_3$ | H | H | $OCH_3$ | $OCH_2CH_3$ | CH | |

TABLE 12-continued

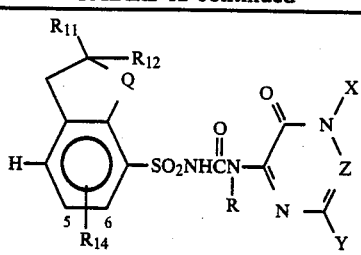

| R | Q | R11 | R12 | R14 | X | Y | Z | m.p. (°C.) |
|---|---|-----|-----|-----|---|---|---|-----------|
| H | S | CH3 | H | H | N(CH3)2 | OCH3 | N | |
| H | S | CH3 | H | H | NHCH3 | OCH2CH3 | N | |
| CH3 | S | CH3 | H | H | CH3 | Cl | N | |
| CH3 | S | CH3 | H | H | OCH3 | Cl | N | |
| CH3 | S | CH3 | H | H | CH3 | OCH3 | N | |
| CH3 | S | CH3 | H | H | CH2CH3 | OCH3 | N | |
| CH3 | S | CH3 | H | H | OCH3 | CH3 | N | |
| CH3 | S | CH3 | H | H | OCH3 | OCH3 | N | |
| H | S | H | H | H | OCH3 | Cl | CH | |
| H | S | CH3 | CH3 | H | CH3 | CH3 | CH | |
| H | S | CH3 | CH2CH3 | H | CH3 | OCH3 | CH | |
| H | S | CH2CH3 | CH3 | H | OCH3 | CH3 | CH | |
| H | S | CH2CH3 | H | H | CH3 | Cl | CH | |
| H | S | CH2CH3 | CH2CH3 | H | CH3 | OCH3 | N | |
| H | S | H | CH3 | H | CH3 | OCH2CH3 | N | |
| CH3 | S | H | H | H | OCH2CH3 | CH3 | CH | |
| H | S | H | H | 5-F | OCH3 | OCH3 | CH | |
| H | S | CH3 | H | 6-F | CH2CH3 | OCH3 | CH | |
| H | S | H | CH3 | 5-Cl | CH3 | Br | CH | |
| H | S | CH3 | CH3 | 6-Cl | CH3 | OCH2CH3 | CH | |
| H | S | H | H | 5-Br | CH3 | CH2CH3 | CH | |
| H | S | CH3 | H | 6-Br | OCH3 | Cl | CH | |
| H | S | H | CH3 | 5-CN | CH3 | CH3 | CH | |
| H | S | CH3 | CH3 | 6-CN | CH3 | OCH3 | CH | |
| H | S | H | H | 5-CH3 | OCH3 | CH3 | CH | |
| H | S | CH3 | H | 6-CH3 | CH3 | Cl | CH | |
| H | S | H | CH3 | 5-OCH3 | CH3 | OCH3 | N | |
| H | S | CH3 | CH3 | 6-OCH3 | CH3 | OCH2CH3 | N | |
| H | S | H | H | 5-SCH3 | OCH3 | Cl | CH | |
| H | S | CH3 | H | 6-SCH3 | CH3 | CH3 | CH | |
| H | S | H | CH3 | 5-OCF2H | CH3 | OCH3 | CH | |
| H | S | CH3 | CH3 | 6-OCF2H | OCH3 | CH3 | CH | |
| CH3 | S | CH3 | H | 6-Cl | CH3 | Cl | CH | |
| H | SO | CH3 | H | H | H | OCH3 | CH | |
| H | SO | CH3 | H | H | CH3 | Cl | CH | |
| H | SO | CH3 | H | H | CH3 | SCH3 | CH | |
| H | SO | CH3 | H | H | OCH3 | SCH3 | CH | |
| H | SO | CH3 | H | H | OCH3 | SCH3 | N | |
| H | SO | CH3 | H | H | CH3 | SCH2CH3 | CH | |
| H | SO | CH3 | H | H | CH3 | SCH3 | N | |
| H | SO | CH3 | H | H | NH2 | SCH3 | CH | |
| H | SO | CH3 | H | H | CH3 | Br | CH | |
| H | SO | CH3 | H | H | CH3 | OCH3 | CH | |
| H | SO | CH3 | H | H | CH3 | OCH2CH3 | CH | |
| H | SO | CH3 | H | H | CH3 | O(CH2)2CH3 | CH | |
| H | SO | CH3 | H | H | CH3 | CH3 | CH | |
| H | SO | CH3 | H | H | CH3 | CH2CH3 | CH | |
| H | SO | CH3 | H | H | CH3 | (CH2)2CH3 | CH | |
| H | SO | CH3 | H | H | CH2CH3 | Cl | CH | |
| H | SO | CH3 | H | H | CH2CH3 | OCH3 | CH | |
| H | SO | CH3 | H | H | (CH2)2CH3 | Cl | CH | |
| H | SO | CH3 | H | H | (CH2)2CH3 | OCH3 | CH | |
| H | SO | CH3 | H | H | OCH3 | H | CH | |
| H | SO | CH3 | H | H | OCH3 | CH3 | CH | |
| H | SO | CH3 | H | H | OCH3 | CH2CH3 | CH | |
| H | SO | CH3 | H | H | OCH3 | (CH2)2CH3 | CH | |
| H | SO | CH3 | H | H | OCH3 | OCH3 | CH | |
| H | SO | CH3 | H | H | OCH3 | OCH2CH3 | CH | |
| H | SO | CH3 | H | H | OCH3 | O(CH2)2CH3 | CH | |
| H | SO | CH3 | H | H | OCH3 | Cl | CH | |
| H | SO | CH3 | H | H | OCH3 | Br | CH | |
| H | SO | CH3 | H | H | OCH2CH3 | Cl | CH | |
| H | SO | CH3 | H | H | OCH2CH3 | CH3 | CH | |
| H | SO | CH3 | H | H | OCH2CH3 | OCH3 | CH | |
| H | SO | CH3 | H | H | O(CH2)2CH3 | Cl | CH | |
| H | SO | CH3 | H | H | O(CH2)2CH3 | CH3 | CH | |
| H | SO | CH3 | H | H | O(CH2)2CH3 | OCH3 | CH | |
| H | SO | CH3 | H | H | NH2 | Cl | CH | |
| H | SO | CH3 | H | H | NH2 | CH3 | CH | |

TABLE 12-continued

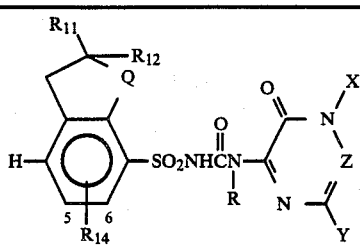

| R | Q | R11 | R12 | R14 | X | Y | Z | m.p. (°C.) |
|---|---|---|---|---|---|---|---|---|
| H | SO | CH3 | H | H | NH2 | OCH3 | CH | |
| H | SO | CH3 | H | H | NHCH3 | Cl | CH | |
| H | SO | CH3 | H | H | NHCH3 | CH3 | CH | |
| H | SO | CH3 | H | H | NHCH3 | OCH3 | CH | |
| H | SO | CH3 | H | H | N(CH3)2 | Cl | CH | |
| H | SO | CH3 | H | H | N(CH3)2 | CH3 | CH | |
| H | SO | CH3 | H | H | N(CH3)2 | OCH3 | CH | |
| H | SO | CH3 | H | H | NHCH3 | OCH2CH3 | CH | |
| CH3 | SO | CH3 | H | H | CH3 | Cl | CH | |
| CH3 | SO | CH3 | H | H | OCH3 | Cl | CH | |
| CH3 | SO | CH3 | H | H | CH3 | OCH3 | CH | |
| CH3 | SO | CH3 | H | H | OCH3 | CH3 | CH | |
| CH3 | SO | CH3 | H | H | OCH3 | OCH3 | CH | |
| H | SO | CH3 | H | H | CH3 | Cl | CF | |
| H | SO | CH3 | H | H | CH3 | OCH3 | CF | |
| H | SO | CH3 | H | H | OCH3 | OCH3 | CF | |
| H | SO | CH3 | H | H | OCH3 | CH3 | CF | |
| H | SO | CH3 | H | H | CH3 | Cl | CCl | |
| H | SO | CH3 | H | H | CH3 | OCH3 | CCl | |
| H | SO | CH3 | H | H | CH3 | Br | CBr | |
| H | SO | CH3 | H | H | CH3 | Cl | CBr | |
| H | SO | CH3 | H | H | CH3 | OCH3 | CBr | |
| H | SO | CH3 | H | H | H | OCH3 | N | |
| H | SO | CH3 | H | H | CH3 | Cl | N | |
| H | SO | CH3 | H | H | CH3 | Br | N | |
| H | SO | CH3 | H | H | CH3 | OCH3 | N | |
| H | SO | CH3 | H | H | CH3 | OCH2CH3 | N | |
| H | SO | CH3 | H | H | CH3 | O(CH2)2CH3 | N | |
| H | SO | CH3 | H | H | CH3 | CH3 | N | |
| H | SO | CH3 | H | H | CH3 | CH2CH3 | N | |
| H | SO | CH3 | H | H | CH3 | (CH2)2CH3 | N | |
| H | SO | CH3 | H | H | CH2CH3 | Cl | N | |
| H | SO | CH3 | H | H | CH2CH3 | OCH3 | N | |
| H | SO | CH3 | H | H | (CH2)2CH3 | Cl | N | |
| H | SO | CH3 | H | H | (CH2)2CH3 | OCH3 | N | |
| H | SO | CH3 | H | H | OCH3 | H | N | |
| H | SO | CH3 | H | H | OCH3 | CH3 | N | |
| H | SO | CH3 | H | H | OCH3 | CH2CH3 | N | |
| H | SO | CH3 | H | H | OCH3 | (CH2)2CH3 | N | |
| H | SO | CH3 | H | H | OCH3 | OCH3 | N | |
| H | SO | CH3 | H | H | OCH3 | OCH2CH3 | N | |
| H | SO | CH3 | H | H | OCH3 | O(CH2)2CH3 | N | |
| H | SO | CH3 | H | H | OCH3 | Cl | N | |
| H | SO | CH3 | H | H | OCH3 | Br | N | |
| H | SO | CH3 | H | H | OCH2CH3 | Cl | N | |
| H | SO | CH3 | H | H | OCH2CH3 | CH3 | N | |
| H | SO | CH3 | H | H | OCH2CH3 | OCH3 | N | |
| H | SO | CH3 | H | H | O(CH2)2CH3 | Cl | N | |
| H | SO | CH3 | H | H | O(CH2)2CH3 | CH3 | N | |
| H | SO | CH3 | H | H | O(CH2)2CH3 | OCH3 | N | |
| H | SO | CH3 | H | H | NH2 | Cl | N | |
| H | SO | CH3 | H | H | NH2 | CH3 | N | |
| H | SO | CH3 | H | H | NH2 | OCH3 | N | |
| H | SO | CH3 | H | H | NHCH3 | Cl | N | |
| H | SO | CH3 | H | H | NHCH3 | CH3 | N | |
| H | SO | CH3 | H | H | NHCH3 | OCH3 | N | |
| H | SO | CH3 | H | H | N(CH3)2 | Cl | N | |
| H | SO | CH3 | H | H | N(CH3)2 | CH3 | N | |
| H | SO | CH3 | H | H | N(CH3)2 | OCH3 | N | |
| H | SO | CH3 | H | H | NHCH3 | OCH2CH3 | N | |
| CH3 | SO | CH3 | H | H | CH3 | Cl | N | |
| CH3 | SO | CH3 | H | H | OCH3 | Cl | N | |
| CH3 | SO | CH3 | H | H | CH3 | OCH3 | N | |
| CH3 | SO | CH3 | H | H | CH2CH3 | OCH3 | N | |
| CH3 | SO | CH3 | H | H | OCH3 | CH3 | N | |
| CH3 | SO | CH3 | H | H | OCH3 | OCH3 | N | |
| H | SO | H | H | H | OCH3 | Cl | CH | |
| H | SO | CH3 | CH3 | H | CH3 | CH3 | CH | |
| H | SO | CH3 | CH2CH3 | H | CH3 | OCH3 | CH | |

TABLE 12-continued

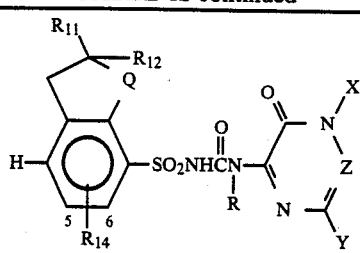

| R | Q | R11 | R12 | R14 | X | Y | Z | m.p. (°C.) |
|---|---|---|---|---|---|---|---|---|
| H | SO | CH2CH3 | CH3 | H | OCH3 | CH3 | CH | |
| H | SO | CH2CH3 | H | H | CH3 | Cl | CH | |
| H | SO | CH2CH3 | CH2CH3 | H | CH3 | OCH3 | N | |
| H | SO | H | CH3 | H | CH3 | OCH2CH3 | N | |
| CH3 | SO | H | H | H | OCH2CH3 | CH3 | CH | |
| H | SO | H | H | 5-F | OCH3 | OCH3 | CH | |
| H | SO | CH3 | H | 6-F | CH2CH3 | OCH3 | CH | |
| H | SO | H | CH3 | 5-Cl | CH3 | Br | CH | |
| H | SO | CH3 | CH3 | 6-Cl | CH3 | OCH2CH3 | CH | |
| H | SO | H | H | 5-Br | CH3 | CH2CH3 | CH | |
| H | SO | CH3 | H | 6-Br | OCH3 | Cl | CH | |
| H | SO | H | CH3 | 5-CN | CH3 | CH3 | CH | |
| H | SO | CH3 | CH3 | 6-CN | CH3 | OCH3 | CH | |
| H | SO | H | H | 5-CH3 | OCH3 | CH3 | CH | |
| H | SO | CH3 | H | 6-CH3 | CH3 | Cl | CH | |
| H | SO | H | CH3 | 5-OCH3 | CH3 | OCH3 | N | |
| H | SO | CH3 | CH3 | 6-OCH3 | CH3 | OCH2CH3 | N | |
| H | SO | H | H | 5-SCH3 | OCH3 | Cl | CH | |
| H | SO | CH3 | H | 6-SCH3 | CH3 | CH3 | CH | |
| H | SO | H | CH3 | 5-OCF2H | OCH3 | OCH3 | CH | |
| H | SO | CH3 | CH3 | 6-OCF2H | OCH3 | CH3 | CH | |
| CH3 | SO | CH3 | H | 6-Cl | CH3 | Cl | CH | |
| H | SO2 | CH3 | H | H | H | OCH3 | CH | |
| H | SO2 | CH3 | H | H | CH3 | Cl | CH | 240-250 |
| H | SO2 | CH3 | H | H | CH3 | Br | CH | |
| H | SO2 | CH3 | H | H | CH3 | OCH3 | CH | |
| H | SO2 | CH3 | H | H | CH3 | OCH2CH3 | CH | |
| H | SO2 | CH3 | H | H | CH3 | O(CH2)2CH3 | CH | |
| H | SO2 | CH3 | H | H | CH3 | CH3 | CH | |
| H | SO2 | CH3 | H | H | CH3 | CH2CH3 | CH | |
| H | SO2 | CH3 | H | H | CH3 | (CH2)2CH3 | CH | |
| H | SO2 | CH3 | H | H | CH2CH3 | Cl | CH | |
| H | SO2 | CH3 | H | H | CH2CH3 | OCH3 | CH | |
| H | SO2 | CH3 | H | H | (CH2)2CH3 | Cl | CH | |
| H | SO2 | CH3 | H | H | (CH2)2CH3 | OCH3 | CH | |
| H | SO2 | SO3 | H | H | OCH3 | H | CH | |
| H | SO2 | CH3 | H | H | OCH3 | CH3 | CH | |
| H | SO2 | CH3 | H | H | OCH3 | CH2CH3 | CH | |
| H | SO2 | CH3 | H | H | OCH3 | (CH2)2CH3 | CH | |
| H | SO2 | CH3 | H | H | OCH3 | OCH3 | CH | |
| H | SO2 | CH3 | H | H | CH3 | SCH3 | CH | |
| H | SO2 | CH3 | H | H | OCH3 | SCH3 | CH | |
| H | SO2 | CH3 | H | H | CH3 | SCH3 | N | |
| H | SO2 | CH3 | H | H | CH3 | SCH2CH3 | N | |
| H | SO2 | CH3 | H | H | CH3 | SCH2CH3 | CH | |
| H | SO2 | CH3 | H | H | N(CH3)2 | SCH3 | N | |
| H | SO2 | CH3 | H | H | OCH3 | OCH2CH3 | CH | |
| H | SO2 | CH3 | H | H | OCH3 | O(CH2)2CH3 | CH | |
| H | SO2 | CH3 | H | H | OCH3 | Cl | CH | |
| H | SO2 | CH3 | H | H | OCH3 | Br | CH | |
| H | SO2 | CH3 | H | H | OCH2CH3 | Cl | CH | |
| H | SO2 | CH3 | H | H | OCH2CH3 | CH3 | CH | |
| H | SO2 | CH3 | H | H | OCH2CH3 | OCH3 | CH | |
| H | SO2 | CH3 | H | H | O(CH2)2CH3 | Cl | CH | |
| H | SO2 | CH3 | H | H | O(CH2)2CH3 | CH3 | CH | |
| H | SO2 | CH3 | H | H | O(CH2)2CH3 | OCH3 | CH | |
| H | SO2 | CH3 | H | H | NH2 | Cl | CH | |
| H | SO2 | CH3 | H | H | NH2 | CH3 | CH | |
| H | SO2 | CH3 | H | H | NH2 | OCH3 | CH | |
| H | SO2 | CH3 | H | H | NHCH3 | Cl | CH | |
| H | SO2 | CH3 | H | H | NHCH3 | CH3 | CH | |
| H | SO2 | CH3 | H | H | NHCH3 | OCH3 | CH | |
| H | SO2 | CH3 | H | H | N(CH3)2 | Cl | CH | |
| H | SO2 | CH3 | H | H | N(CH3)2 | CH3 | CH | |
| H | SO2 | CH3 | H | H | N(CH3)2 | OCH3 | CH | |
| H | SO2 | CH3 | H | H | NHCH3 | OCH2CH3 | CH | |
| CH3 | SO2 | CH3 | H | H | CH3 | Cl | CH | |
| CH3 | SO2 | CH3 | H | H | OCH3 | Cl | CH | |
| CH3 | SO2 | CH3 | H | H | CH3 | OCH3 | CH | |

TABLE 12-continued

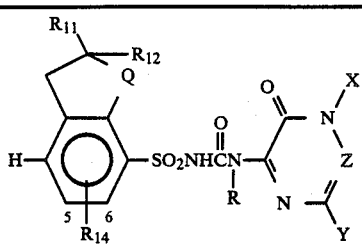

| R | Q | R11 | R12 | R14 | X | Y | Z | m.p. (°C.) |
|---|---|---|---|---|---|---|---|---|
| CH3 | SO2 | CH3 | H | H | OCH3 | CH3 | CH | |
| CH3 | SO2 | CH3 | H | H | OCH3 | OCH3 | CH | |
| H | SO2 | CH3 | H | H | CH3 | Cl | CF | |
| H | SO2 | CH3 | H | H | CH3 | OCH3 | CF | |
| H | SO2 | CH3 | H | H | OCH3 | OCH3 | CF | |
| H | SO2 | CH3 | H | H | OCH3 | CH3 | CF | |
| H | SO2 | CH3 | H | H | CH3 | Cl | CCl | |
| H | SO2 | CH3 | H | H | CH3 | OCH3 | CCl | |
| H | SO2 | CH3 | H | H | CH3 | Br | CBr | |
| H | SO2 | CH3 | H | H | CH3 | Cl | CBr | |
| H | SO2 | CH3 | H | H | CH3 | OCH3 | CBr | |
| H | SO2 | CH3 | H | H | H | OCH3 | N | |
| H | SO2 | CH3 | H | H | CH3 | Cl | N | |
| H | SO2 | CH3 | H | H | CH3 | Br | N | |
| H | SO2 | CH3 | H | H | CH3 | OCH3 | N | |
| H | SO2 | CH3 | H | H | CH3 | OCH2CH3 | N | |
| H | SO2 | CH3 | H | H | CH3 | O(CH2)2CH3 | N | |
| H | SO2 | CH3 | H | H | CH3 | CH3 | N | |
| H | SO2 | CH3 | H | H | CH3 | CH2CH3 | N | |
| H | SO2 | CH3 | H | H | CH3 | (CH2)2CH3 | N | |
| H | SO2 | CH3 | H | H | CH2CH3 | Cl | N | |
| H | SO2 | CH3 | H | H | CH2CH3 | OCH3 | N | |
| H | SO2 | CH3 | H | H | (CH2)2CH3 | Cl | N | |
| H | SO2 | CH3 | H | H | (CH2)2CH3 | OCH3 | N | |
| H | SO2 | CH3 | H | H | OCH3 | H | N | |
| H | SO2 | CH3 | H | H | OCH3 | CH3 | N | |
| H | SO2 | CH3 | H | H | OCH3 | CH2CH3 | N | |
| H | SO2 | CH3 | H | H | OCH3 | (CH2)2CH3 | N | |
| H | SO2 | CH3 | H | H | OCH3 | OCH3 | N | |
| H | SO2 | CH3 | H | H | OCH3 | OCH2CH3 | N | |
| H | SO2 | CH3 | H | H | OCH3 | O(CH2)2CH3 | N | |
| H | SO2 | CH3 | H | H | OCH3 | Cl | N | |
| H | SO2 | CH3 | H | H | OCH3 | Br | N | |
| H | SO2 | CH3 | H | H | OCH2CH3 | Cl | N | |
| H | SO2 | CH3 | H | H | OCH2CH3 | CH3 | N | |
| H | SO2 | CH3 | H | H | OCH2CH3 | OCH3 | N | |
| H | SO2 | CH3 | H | H | O(CH2)2CH3 | Cl | N | |
| H | SO2 | CH3 | H | H | O(CH2)2CH3 | CH3 | N | |
| H | SO2 | CH3 | H | H | O(CH2)2CH3 | OCH3 | N | |
| H | SO2 | CH3 | H | H | NH2 | Cl | N | |
| H | SO2 | CH3 | H | H | NH2 | CH3 | N | |
| H | SO2 | CH3 | H | H | NH2 | OCH3 | N | |
| H | SO2 | CH3 | H | H | NHCH3 | Cl | N | |
| H | SO2 | CH3 | H | H | NHCH3 | CH3 | N | |
| H | SO2 | CH3 | H | H | NHCH3 | OCH3 | N | |
| H | SO2 | CH3 | H | H | N(CH3)2 | Cl | N | |
| H | SO2 | CH3 | H | H | N(CH3)2 | CH3 | N | |
| H | SO2 | CH3 | H | H | N(CH3)2 | OCH3 | N | |
| H | SO2 | CH3 | H | H | NHCH3 | OCH2CH3 | N | |
| CH3 | SO2 | CH3 | H | H | CH3 | Cl | N | |
| CH3 | SO2 | CH3 | H | H | OCH3 | Cl | N | |
| CH3 | SO2 | CH3 | H | H | CH3 | OCH3 | N | |
| CH3 | SO2 | CH3 | H | H | CH2CH3 | OCH3 | N | |
| CH3 | SO2 | CH3 | H | H | OCH3 | CH3 | N | |
| CH3 | SO2 | CH3 | H | H | OCH3 | OCH3 | N | |
| H | SO2 | H | H | H | OCH3 | Cl | CH | |
| H | SO2 | CH3 | CH3 | H | CH3 | CH3 | CH | |
| H | SO2 | CH3 | CH2CH3 | H | CH3 | OCH3 | CH | |
| H | SO2 | CH2CH3 | CH3 | H | OCH3 | CH3 | CH | |
| H | SO2 | CH2CH3 | H | H | CH3 | Cl | CH | |
| H | SO2 | CH2CH3 | CH2CH3 | H | CH3 | OCH3 | N | |
| H | SO2 | H | CH3 | H | CH3 | OCH2CH3 | N | |
| CH3 | SO2 | H | H | H | OCH2CH3 | CH3 | CH | |
| H | SO2 | H | H | 5-F | OCH3 | OCH3 | CH | |
| H | SO2 | H | CH3 | 6-F | CH2CH3 | OCH3 | CH | |
| H | SO2 | CH3 | H | 5-Cl | CH3 | Br | CH | |
| H | SO2 | CH3 | CH3 | 6-Cl | CH3 | OCH2CH3 | CH | |
| H | SO2 | H | H | 5-Br | CH3 | CH2CH3 | CH | |
| H | SO2 | CH3 | H | 6-Br | OCH3 | Cl | CH | |

TABLE 12-continued

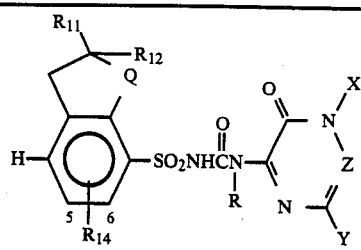

| R | Q | R11 | R12 | R14 | X | Y | Z | m.p. (°C.) |
|---|---|---|---|---|---|---|---|---|
| H | SO2 | H | CH3 | 5-CN | CH3 | CH3 | CH | |
| H | SO2 | CH3 | CH3 | 6-CN | CH3 | OCH3 | CH | |
| H | SO2 | H | H | 5-CH3 | OCH3 | CH3 | CH | |
| H | SO2 | CH3 | H | 6-CH3 | CH3 | Cl | CH | |
| H | SO2 | H | CH3 | 5-OCH3 | CH3 | OCH3 | N | |
| H | SO2 | CH3 | CH3 | 6-OCH3 | CH3 | OCH2CH3 | N | |
| H | SO2 | H | H | 5-SCH3 | OCH3 | Cl | CH | |
| H | SO2 | CH3 | H | 6-SCH3 | CH3 | CH3 | CH | |
| H | SO2 | H | CH3 | 5-OCF2H | CH3 | OCH3 | CH | |
| H | SO2 | CH3 | CH3 | 6-OCF2H | OCH3 | CH3 | CH | |
| CH3 | SO2 | CH3 | H | 6-Cl | CH3 | Cl | CH | |
| H | C(O) | CH3 | H | H | H | OCH3 | CH | |
| H | C(O) | CH3 | H | H | CH3 | Cl | CH | |
| H | C(O) | CH3 | H | H | CH3 | Br | CH | |
| H | C(O) | CH3 | H | H | CH3 | OCH3 | CH | |
| H | C(O) | CH3 | H | H | CH3 | OCH2CH3 | CH | |
| H | C(O) | CH3 | H | H | CH3 | O(CH2)2CH3 | CH | |
| H | C(O) | CH3 | H | H | CH3 | CH3 | CH | |
| H | C(O) | CH3 | H | H | CH3 | CH2CH3 | CH | |
| H | C(O) | CH3 | H | H | CH3 | (CH2)2CH3 | CH | |
| H | C(O) | CH3 | H | H | CH2CH3 | Cl | CH | |
| H | C(O) | CH3 | H | H | CH3 | SCH3 | CH | |
| H | C(O) | CH3 | H | H | CH3 | SCH3 | N | |
| H | C(O) | CH3 | H | H | CH2CH3 | SCH3 | CH | |
| H | C(O) | CH3 | H | H | OCH3 | SCH3 | CH | |
| H | C(O) | CH3 | H | H | CH3 | SCH2CH3 | CH | |
| H | C(O) | CH3 | H | H | OCH3 | SCH2CH3 | N | |
| H | C(O) | CH3 | H | H | CH2CH3 | OCH3 | CH | |
| H | C(O) | CH3 | H | H | (CH2)2CH3 | Cl | CH | |
| H | C(O) | CH3 | H | H | (CH2)2CH3 | OCH3 | CH | |
| H | C(O) | CH3 | H | H | OCH3 | H | CH | |
| H | C(O) | CH3 | H | H | OCH3 | CH3 | CH | |
| H | C(O) | CH3 | H | H | OCH3 | CH2CH3 | CH | |
| H | C(O) | CH3 | H | H | OCH3 | (CH2)2CH3 | CH | |
| H | C(O) | CH3 | H | H | OCH3 | OCH3 | CH | |
| H | C(O) | CH3 | H | H | OCH3 | OCH2CH3 | CH | |
| H | C(O) | CH3 | H | H | OCH3 | O(CH2)2CH3 | CH | |
| H | C(O) | CH3 | H | H | OCH3 | Cl | CH | |
| H | C(O) | CH3 | H | H | OCH3 | Br | CH | |
| H | C(O) | CH3 | H | H | OCH2CH3 | Cl | CH | |
| H | C(O) | CH3 | H | H | OCH2CH3 | CH3 | CH | |
| H | C(O) | CH3 | H | H | OCH2CH3 | OCH3 | CH | |
| H | C(O) | CH3 | H | H | O(CH2)2CH3 | Cl | CH | |
| H | C(O) | CH3 | H | H | O(CH2)2CH3 | CH3 | CH | |
| H | C(O) | CH3 | H | H | O(CH2)2CH3 | OCH3 | CH | |
| H | C(O) | CH3 | H | H | NH2 | Cl | CH | |
| H | C(O) | CH3 | H | H | NH2 | CH3 | CH | |
| H | C(O) | CH3 | H | H | NH2 | OCH3 | CH | |
| H | C(O) | CH3 | H | H | NHCH3 | Cl | CH | |
| H | C(O) | CH3 | H | H | NHCH3 | CH3 | CH | |
| H | C(O) | CH3 | H | H | NHCH3 | OCH3 | CH | |
| H | C(O) | CH3 | H | H | N(CH3)2 | Cl | CH | |
| H | C(O) | CH3 | H | H | N(CH3)2 | CH3 | CH | |
| H | C(O) | CH3 | H | H | N(CH3)2 | OCH3 | CH | |
| H | C(O) | CH3 | H | H | NHCH3 | OCH2CH3 | CH | |
| CH3 | C(O) | CH3 | H | H | CH3 | Cl | CH | |
| CH3 | C(O) | CH3 | H | H | OCH3 | Cl | CH | |
| CH3 | C(O) | CH3 | H | H | CH3 | OCH3 | CH | |
| CH3 | C(O) | CH3 | H | H | OCH3 | CH3 | CH | |
| CH3 | C(O) | CH3 | H | H | OCH3 | OCH3 | CH | |
| H | C(O) | CH3 | H | H | CH3 | Cl | CF | |
| H | C(O) | CH3 | H | H | CH3 | OCH3 | CF | |
| H | C(O) | CH3 | H | H | OCH3 | OCH3 | CF | |
| H | C(O) | CH3 | H | H | OCH3 | CH3 | CF | |
| H | C(O) | CH3 | H | H | CH3 | Cl | CCl | |
| H | C(O) | CH3 | H | H | CH3 | OCH3 | CCl | |
| H | C(O) | CH3 | H | H | CH3 | Br | CBr | |
| H | C(O) | CH3 | H | H | CH3 | Cl | CBr | |
| H | C(O) | CH3 | H | H | CH3 | OCH3 | CBr | |

TABLE 12-continued

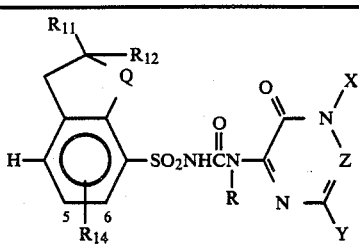

| R | Q | R₁₁ | R₁₂ | R₁₄ | X | Y | Z | m.p. (°C.) |
|---|---|---|---|---|---|---|---|---|
| H | C(O) | CH₃ | H | H | H | OCH₃ | N | |
| H | C(O) | CH₃ | H | H | CH₃ | Cl | N | |
| H | C(O) | CH₃ | H | H | CH₃ | Br | N | |
| H | C(O) | CH₃ | H | H | CH₃ | OCH₃ | N | |
| H | C(O) | CH₃ | H | H | CH₃ | OCH₂CH₃ | N | |
| H | C(O) | CH₃ | H | H | CH₃ | O(CH₂)₂CH₃ | N | |
| H | C(O) | CH₃ | H | H | CH₃ | CH₃ | N | |
| H | C(O) | CH₃ | H | H | CH₃ | CH₂CH₃ | N | |
| H | C(O) | CH₃ | H | H | CH₃ | (CH₂)₂CH₃ | N | |
| H | C(O) | CH₃ | H | H | CH₂CH₃ | Cl | N | |
| H | C(O) | CH₃ | H | H | CH₂CH₃ | OCH₃ | N | |
| H | C(O) | CH₃ | H | H | (CH₂)₂CH₃ | Cl | N | |
| H | C(O) | CH₃ | H | H | (CH₂)₂CH₃ | OCH₃ | N | |
| H | C(O) | CH₃ | H | H | OCH₃ | H | N | |
| H | C(O) | CH₃ | H | H | OCH₃ | CH₃ | N | |
| H | C(O) | CH₃ | H | H | OCH₃ | CH₂CH₃ | N | |
| H | C(O) | CH₃ | H | H | OCH₃ | (CH₂)₂CH₃ | N | |
| H | C(O) | CH₃ | H | H | OCH₃ | OCH₃ | N | |
| H | C(O) | CH₃ | H | H | OCH₃ | OCH₂CH₃ | N | |
| H | C(O) | CH₃ | H | H | OCH₃ | O(CH₂)₂CH₃ | N | |
| H | C(O) | CH₃ | H | H | OCH₃ | Cl | N | |
| H | C(O) | CH₃ | H | H | OCH₃ | Br | N | |
| H | C(O) | CH₃ | H | H | OCH₂CH₃ | Cl | N | |
| H | C(O) | CH₃ | H | H | OCH₂CH₃ | CH₃ | N | |
| H | C(O) | CH₃ | H | H | OCHCH₃ | Cl | N | |
| H | C(O) | CH₃ | H | H | O(CH₂)₃CH₃ | Cl | N | |
| H | C(O) | CH₃ | H | H | O(CH₂)₃CH₃ | CH₃ | N | |
| H | C(O) | CH₃ | H | H | O(CH₂)₃CH₃ | OCH₃ | N | |
| H | C(O) | CH₃ | H | H | NH₂ | Cl | N | |
| H | C(O) | CH₃ | H | H | NH₂ | CH₃ | N | |
| H | C(O) | CH₃ | H | H | NH₂ | OCH₃ | N | |
| H | C(O) | CH₃ | H | H | NHCH₃ | Cl | N | |
| H | C(O) | CH₃ | H | H | NHCH₃ | CH₃ | N | |
| H | C(O) | CH₃ | H | H | NHCH₃ | OCH₃ | N | |
| H | C(O) | CH₃ | H | H | N(CH₃)₂ | Cl | N | |
| H | C(O) | CH₃ | H | H | N(CH₃)₂ | CH₃ | N | |
| H | C(O) | CH₃ | H | H | N(CH₃)₂ | OCH₃ | N | |
| H | C(O) | CH₃ | H | H | NHCH₃ | OCH₂CH₃ | N | |
| CH₃ | C(O) | CH₃ | H | H | CH₃ | Cl | N | |
| CH₃ | C(O) | CH₃ | H | H | OCH₃ | Cl | N | |
| CH₃ | C(O) | CH₃ | H | H | CH₃ | OCH₃ | N | |
| CH₃ | C(O) | CH₃ | H | H | CH₂CH₃ | OCH₃ | N | |
| CH₃ | C(O) | CH₃ | H | H | OCH₃ | CH₃ | N | |
| CH₃ | C(O) | CH₃ | H | H | OCH₃ | OCH₃ | N | |
| H | C(O) | H | H | H | OCH₃ | Cl | CH | |
| H | C(O) | CH₃ | CH₃ | H | CH₃ | CH₃ | CH | |
| H | C(O) | CH₃ | CH₂CH₃ | H | CH₃ | OCH₃ | CH | |
| H | C(O) | CH₂CH₃ | CH₃ | H | OCH₃ | CH₃ | CH | |
| H | C(O) | CH₂CH₃ | H | H | CH₃ | Cl | CH | |
| H | C(O) | CH₂CH₃ | CH₂CH₃ | H | CH₃ | OCH₃ | N | |
| H | C(O) | H | CH₃ | H | CH₃ | OCH₂CH₃ | N | |
| CH₃ | C(O) | H | H | H | OCH₂CH₃ | CH₃ | CH | |
| H | C(O) | H | H | 5-F | OCH₃ | OCH₃ | CH | |
| H | C(O) | CH₃ | H | 6-F | CH₂CH₃ | OCH₃ | CH | |
| H | C(O) | H | CH₃ | 5-Cl | CH₃ | Br | CH | |
| H | C(O) | CH₃ | CH₃ | 6-Cl | CH₃ | OCH₂CH₃ | CH | |
| H | C(O) | H | H | 5-Br | CH₃ | CH₂CH₃ | CH | |
| H | C(O) | CH₃ | H | 6-Br | OCH₃ | Cl | CH | |
| H | C(O) | H | CH₃ | 5-CN | CH₃ | CH₃ | CH | |
| H | C(O) | CH₃ | CH₃ | 6-CN | CH₃ | OCH₃ | CH | |
| H | C(O) | H | H | 5-CH₃ | OCH₃ | CH₃ | CH | |
| H | C(O) | CH₃ | H | 6-CH₃ | CH₃ | Cl | CH | |
| H | C(O) | H | CH₃ | 5-OCH₃ | CH₃ | OCH₃ | N | |
| H | C(O) | CH₃ | CH₃ | 6-OCH₃ | CH₃ | OCH₂CH₃ | N | |
| H | C(O) | H | H | 5-SCH₃ | OCH₃ | Cl | CH | |
| H | C(O) | CH₃ | H | 6-SCH₃ | CH₃ | CH₃ | CH | |
| H | C(O) | H | CH₃ | 5-OCF₂H | CH₃ | OCH₃ | CH | |
| H | C(O) | CH₃ | CH₃ | 6-OCF₂H | OCH₃ | CH₃ | CH | |

TABLE 12-continued

| R | Q | $R_{11}$ | $R_{12}$ | $R_{14}$ | X | Y | Z | m.p. (°C.) |
|---|---|---|---|---|---|---|---|---|
| $CH_3$ | C(O) | $CH_3$ | H | 6-Cl | $CH_3$ | Cl | CH | |

TABLE 13

| R | $R_{11}$ | $R_{12}$ | $R_{14}$ | X | Y | Z | m.p. (°C.) |
|---|---|---|---|---|---|---|---|
| H | $CH_3$ | H | H | H | $OCH_3$ | CH | |
| H | $CH_3$ | H | H | $CH_3$ | Cl | CH | |
| H | $CH_3$ | H | H | $CH_3$ | Br | CH | |
| H | $CH_3$ | H | H | $CH_3$ | $OCH_3$ | CH | |
| H | $CH_3$ | H | H | $CH_3$ | $OCH_2CH_3$ | CH | |
| H | $CH_3$ | H | H | $CH_3$ | $O(CH_2)_2CH_3$ | CH | |
| H | $CH_3$ | H | H | $CH_3$ | $CH_3$ | CH | |
| H | $CH_3$ | H | H | $CH_3$ | $CH_2CH_3$ | CH | |
| H | $CH_3$ | H | H | $CH_3$ | $(CH_2)_2CH_3$ | CH | |
| H | $CH_3$ | H | H | $CH_2CH_3$ | Cl | CH | |
| H | $CH_3$ | H | H | $CH_2CH_3$ | $OCH_3$ | CH | |
| H | $CH_3$ | H | H | $(CH_2)_2CH_3$ | Cl | CH | |
| H | $CH_3$ | H | H | $(CH_2)_2CH_3$ | $OCH_3$ | CH | |
| H | $CH_3$ | H | H | $OCH_3$ | H | CH | |
| H | $CH_3$ | H | H | $OCH_3$ | $CH_3$ | CH | |
| H | $CH_3$ | H | H | $OCH_3$ | $CH_2CH_3$ | CH | |
| H | $CH_3$ | H | H | $OCH_3$ | $(CH_2)_2CH_3$ | CH | |
| H | $CH_3$ | H | H | $OCH_3$ | $OCH_3$ | CH | |
| H | $CH_3$ | H | H | $OCH_3$ | $OCH_2CH_3$ | CH | |
| H | $CH_3$ | H | H | $CH_3$ | $SCH_3$ | CH | |
| H | $CH_3$ | H | H | $CH_3$ | $SCH_3$ | N | |
| H | $CH_3$ | H | H | $OCH_3$ | $SCH_3$ | CH | |
| H | $CH_3$ | H | H | $CH_3$ | $SCH_2CH_3$ | CH | |
| H | CH | H | H | $CH_2CH_3$ | $SCH_3$ | CH | |
| H | $CH_3$ | H | H | $N(CH_3)_2$ | $SCH_3$ | CH | |
| H | $CH_3$ | H | H | $NHCH_3$ | $SCH_3$ | N | |
| H | $CH_3$ | H | H | $OCH_3$ | $O(CH_2)_2CH_3$ | CH | |
| H | $CH_3$ | H | H | $OCH_3$ | Cl | CH | |
| H | $CH_3$ | H | H | $OCH_3$ | Br | CH | |
| H | $CH_3$ | H | H | $OCH_2CH_3$ | Cl | CH | |
| H | $CH_3$ | H | H | $OCH_2CH_3$ | $CH_3$ | CH | |
| H | $CH_3$ | H | H | $OCH_2CH_3$ | $OCH_3$ | CH | |
| H | $CH_3$ | H | H | $O(CH_2)_2CH_3$ | Cl | CH | |
| H | $CH_3$ | H | H | $O(CH_2)_2CH_3$ | $CH_3$ | CH | |
| H | $CH_3$ | H | H | $O(CH_2)_2CH_3$ | $OCH_3$ | CH | |
| H | $CH_3$ | H | H | $NH_2$ | Cl | CH | |
| H | $CH_3$ | H | H | $NH_2$ | $CH_3$ | CH | |
| H | $CH_3$ | H | H | $NH_2$ | $OCH_3$ | CH | |
| H | $CH_3$ | H | H | $NHCH_3$ | Cl | CH | |
| H | $CH_3$ | H | H | $NHCH_3$ | $CH_3$ | CH | |
| H | $CH_3$ | H | H | $NHCH_3$ | $OCH_3$ | CH | |
| H | $CH_3$ | H | H | $N(CH_3)_2$ | Cl | CH | |
| H | $CH_3$ | H | H | $N(CH_3)_2$ | $CH_3$ | CH | |
| H | $CH_3$ | H | H | $N(CH_3)_2$ | $OCH_3$ | CH | |
| H | $CH_3$ | H | H | $NHCH_3$ | $OCH_2CH_3$ | CH | |
| $CH_3$ | $CH_3$ | H | H | $CH_3$ | Cl | CH | |
| $CH_3$ | $CH_3$ | H | H | $OCH_3$ | Cl | CH | |
| $CH_3$ | $CH_3$ | H | H | $CH_3$ | $OCH_3$ | CH | |
| $CH_3$ | $CH_3$ | H | H | $OCH_3$ | $CH_3$ | CH | |

TABLE 13-continued

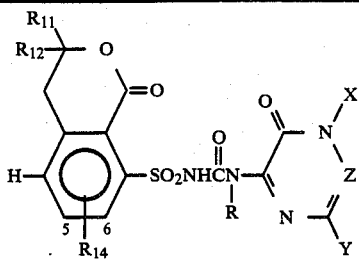

| R | $R_{11}$ | $R_{12}$ | $R_{14}$ | X | Y | Z | m.p. (°C.) |
|---|---|---|---|---|---|---|---|
| CH₃ | CH₃ | H | H | OCH₃ | OCH₃ | CH | |
| H | CH₃ | H | H | CH₃ | Cl | CF | |
| H | CH₃ | H | H | CH₃ | OCH₃ | CF | |
| H | CH₃ | H | H | OCH₃ | OCH₃ | CF | |
| H | CH₃ | H | H | OCH₃ | CH₃ | CF | |
| H | CH₃ | H | H | CH₃ | Cl | CCl | |
| H | CH₃ | H | H | CH₃ | OCH₃ | CCl | |
| H | CH₃ | H | H | CH₃ | Br | CBr | |
| H | CH₃ | H | H | CH₃ | Cl | CBr | |
| H | CH₃ | H | H | CH₃ | OCH₃ | CBr | |
| H | CH₃ | H | H | H | OCH₃ | N | |
| H | CH₃ | H | H | CH₃ | Cl | N | |
| H | CH₃ | H | H | CH₃ | Br | N | |
| H | CH₃ | H | H | CH₃ | OCH₃ | N | |
| H | CH₃ | H | H | CH₃ | OCH₂CH₃ | N | |
| H | CH₃ | H | H | CH₃ | O(CH₂)₂CH₃ | N | |
| H | CH₃ | H | H | CH₃ | CH₃ | N | |
| H | CH₃ | H | H | CH₃ | CH₂CH₃ | N | |
| H | CH₃ | H | H | CH₃ | (CH₂)₂CH₃ | N | |
| H | CH₃ | H | H | CH₂CH₃ | Cl | N | |
| H | CH₃ | H | H | CH₂CH₃ | OCH₃ | N | |
| H | CH₃ | H | H | (CH₂)₂CH₃ | Cl | N | |
| H | CH₃ | H | H | (CH₂)₂CH₃ | OCH₃ | N | |
| H | CH₃ | H | H | OCH₃ | H | N | |
| H | CH₃ | H | H | OCH₃ | CH₃ | N | |
| H | CH₃ | H | H | OCH₃ | CH₂CH₃ | N | |
| H | CH₃ | H | H | OCH₃ | (CH₂)₂CH₃ | N | |
| H | CH₃ | H | H | OCH₃ | OCH₃ | N | |
| H | CH₃ | H | H | OCH₃ | OCH₂CH₃ | N | |
| H | CH₃ | H | H | OCH₃ | O(CH₂)₂CH₃ | N | |
| H | CH₃ | H | H | OCH₃ | Cl | N | |
| H | CH₃ | H | H | OCH₃ | Br | N | |
| H | CH₃ | H | H | OCH₂CH₃ | Cl | N | |
| H | CH₃ | H | H | OCH₂CH₃ | CH₃ | N | |
| H | CH₃ | H | H | OCH₂CH₃ | OCH₃ | N | |
| H | CH₃ | H | H | O(CH₂)₂CH₃ | Cl | N | |
| H | CH₃ | H | H | O(CH₂)₂CH₃ | CH₃ | N | |
| H | CH₃ | H | H | O(CH₂)₂CH₃ | OCH₃ | N | |
| H | CH₃ | H | H | NH₂ | Cl | N | |
| H | CH₃ | H | H | NH₂ | CH₃ | N | |
| H | CH₃ | H | H | NH₂ | OCH₃ | N | |
| H | CH₃ | H | H | NHCH₃ | Cl | N | |
| H | CH₃ | H | H | NHCH₃ | CH₃ | N | |
| H | CH₃ | H | H | NHCH₃ | OCH₃ | N | |
| H | CH₃ | H | H | N(CH₃)₂ | Cl | N | |
| H | CH₃ | H | H | N(CH₃)₂ | CH₃ | N | |
| H | CH₃ | H | H | N(CH₃)₂ | OCH₃ | N | |
| H | CH₃ | H | H | NHCH₃ | OCH₂CH₃ | N | |
| CH₃ | CH₃ | H | H | CH₃ | Cl | N | |
| CH₃ | CH₃ | H | H | OCH₃ | Cl | N | |
| CH₃ | CH₃ | H | H | CH₃ | OCH₃ | N | |
| CH₃ | CH₃ | H | H | CH₂CH₃ | OCH₃ | N | |
| CH₃ | CH₃ | H | H | OCH₃ | CH₃ | N | |
| CH₃ | CH₃ | H | H | OCH₃ | OCH₃ | N | |
| H | H | H | H | OCH₃ | Cl | CH | |
| H | CH₃ | CH₃ | H | CH₃ | CH₃ | CH | |
| H | CH₃ | CH₂CH₃ | H | CH₃ | OCH₃ | CH | |
| H | CH₂CH₃ | CH₃ | H | OCH₃ | CH₃ | CH | |
| H | CH₂CH₃ | H | H | CH₃ | Cl | CH | |
| H | CH₂CH₃ | CH₂CH₃ | H | CH₃ | OCH₃ | N | |
| H | H | CH₃ | H | CH₃ | OCH₂CH₃ | N | |
| H | H | H | H | OCH₂CH₃ | CH₃ | CH | |
| H | H | H | 5-F | OCH₃ | OCH₃ | CH | |
| H | CH₃ | H | 6-F | CH₂CH₃ | OCH₃ | CH | |
| H | H | CH₃ | 5-Cl | CH₃ | Br | CH | |
| H | CH₃ | CH₃ | 6-Cl | CH₃ | OCH₂CH₃ | CH | |
| H | H | H | 5-Br | CH₃ | CH₂CH₃ | CH | |
| H | CH₃ | H | 6-Br | OCH₃ | Cl | CH | |

TABLE 13-continued

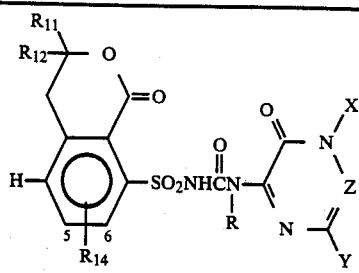

| R | R$_{11}$ | R$_{12}$ | R$_{14}$ | X | Y | Z | m.p. (°C.) |
|---|---|---|---|---|---|---|---|
| H | H | CH$_3$ | 5-CN | CH$_3$ | CH$_3$ | CH | |
| H | CH$_3$ | CH$_3$ | 6-CN | CH$_3$ | OCH$_3$ | CH | |
| H | H | H | 5-CH$_3$ | OCH$_3$ | CH$_3$ | CH | |
| H | CH$_3$ | H | 6-CH$_3$ | CH$_3$ | Cl | CH | |
| H | H | CH$_3$ | 5-OCH$_3$ | CH$_3$ | OCH$_3$ | N | |
| H | CH$_3$ | CH$_3$ | 6-OCH$_3$ | CH$_3$ | OCH$_2$CH$_3$ | N | |
| H | H | H | 5-SCH$_3$ | OCH$_3$ | Cl | CH | |
| H | CH$_3$ | H | 6-SCH$_3$ | CH$_3$ | CH$_3$ | CH | |
| H | H | CH$_3$ | 5-OCF$_2$H | CH$_3$ | OCH$_3$ | CH | |
| H | CH$_3$ | CH$_3$ | 6-OCF$_2$H | OCH$_3$ | CH$_3$ | CH | |
| CH$_3$ | CH$_3$ | H | 6-Cl | CH$_3$ | Cl | CH | |

TABLE 14

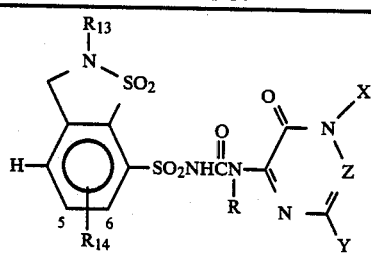

| R | R$_{13}$ | R$_{14}$ | X | Y | Z | m.p. (°C.) |
|---|---|---|---|---|---|---|
| H | CH$_3$ | H | H | OCH$_3$ | CH | |
| H | CH$_3$ | H | CH$_3$ | Cl | CH | |
| H | CH$_3$ | H | CH$_3$ | Br | CH | |
| H | CH$_3$ | H | CH$_3$ | OCH$_3$ | CH | |
| H | CH$_3$ | H | CH$_3$ | OCH$_2$CH$_3$ | CH | |
| H | CH$_3$ | H | CH$_3$ | O(CH$_2$)$_2$CH$_3$ | CH | |
| H | CH$_3$ | H | CH$_3$ | CH$_3$ | CH | |
| H | CH$_3$ | H | CH$_3$ | CH$_2$CH$_3$ | CH | |
| H | CH$_3$ | H | CH$_3$ | (CH$_2$)$_2$CH$_3$ | CH | |
| H | CH$_3$ | H | CH$_2$CH$_3$ | Cl | CH | |
| H | CH$_3$ | H | CH$_2$CH$_3$ | OCH$_3$ | CH | |
| H | CH$_3$ | H | (CH$_2$)$_2$CH$_3$ | Cl | CH | |
| H | CH$_3$ | H | (CH$_2$)$_2$CH$_3$ | OCH$_3$ | CH | |
| H | CH$_3$ | H | OCH$_3$ | H | CH | |
| H | CH$_3$ | H | OCH$_3$ | CH$_3$ | CH | |
| H | CH$_3$ | H | OCH$_3$ | CH$_2$CH$_3$ | CH | |
| H | CH$_3$ | H | OCH$_3$ | (CH$_2$)$_2$CH$_3$ | CH | |
| H | CH$_3$ | H | OCH$_3$ | OCH$_3$ | CH | |
| H | CH$_3$ | H | OCH$_3$ | OCH$_2$CH$_3$ | CH | |
| H | CH$_3$ | H | CH$_3$ | SCH$_3$ | CH | |
| H | CH$_3$ | H | CH$_3$ | SCH$_3$ | N | |
| H | CH$_3$ | H | CH$_2$CH$_3$ | SCH$_3$ | CH | |
| H | CH$_3$ | H | CH$_3$ | SCH$_2$CH$_3$ | CH | |
| H | CH$_3$ | H | OCH$_3$ | SCH$_3$ | CH | |
| H | CH$_3$ | H | OCH$_3$ | SCH$_3$ | N | |
| H | CH$_3$ | H | N(CH$_3$)$_2$ | SCH$_3$ | N | |
| H | CH$_3$ | H | OCH$_3$ | O(CH$_2$)$_2$CH$_3$ | CH | |
| H | CH$_3$ | H | OCH$_3$ | Cl | CH | |
| H | CH$_3$ | H | OCH$_3$ | Br | CH | |
| H | CH$_3$ | H | OCH$_2$CH$_3$ | Cl | CH | |
| H | CH$_3$ | H | OCH$_2$CH$_3$ | CH$_3$ | CH | |
| H | CH$_3$ | H | OCH$_2$CH$_3$ | OCH$_3$ | CH | |
| H | CH$_3$ | H | O(CH$_2$)$_2$CH$_3$ | Cl | CH | |
| H | CH$_3$ | H | O(CH$_2$)$_2$CH$_3$ | CH$_3$ | CH | |
| H | CH$_3$ | H | O(CH$_2$)$_2$CH$_3$ | OCH$_3$ | CH | |
| H | CH$_3$ | H | NH$_2$ | Cl | CH | |
| H | CH$_3$ | H | NH$_2$ | CH$_3$ | CH | |
| H | CH$_3$ | H | NH$_2$ | OCH$_3$ | CH | |
| H | CH$_3$ | H | NHCH$_3$ | Cl | CH | |

TABLE 14-continued

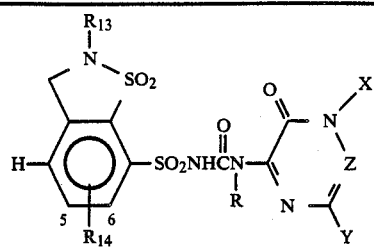

| R | R13 | R14 | X | Y | Z | m.p. (°C.) |
|---|---|---|---|---|---|---|
| H | CH3 | H | NHCH3 | CH3 | CH | |
| H | CH3 | H | NHCH3 | OCH3 | CH | |
| H | CH3 | H | N(CH3)2 | Cl | CH | |
| H | CH3 | H | N(CH3)2 | CH3 | CH | |
| H | CH3 | H | N(CH3)2 | OCH3 | CH | |
| H | CH3 | H | NHCH3 | OCH2CH3 | CH | |
| CH3 | CH3 | H | CH3 | Cl | CH | |
| CH3 | CH3 | H | OCH3 | Cl | CH | |
| CH3 | CH3 | H | CH3 | OCH3 | CH | |
| CH3 | CH3 | H | OCH3 | CH3 | CH | |
| CH3 | CH3 | H | OCH3 | OCH3 | CH | |
| H | CH3 | H | CH3 | Cl | CF | |
| H | CH3 | H | CH3 | OCH3 | CF | |
| H | CH3 | H | OCH3 | OCH3 | CF | |
| H | CH3 | H | OCH3 | CH3 | CF | |
| H | CH3 | H | CH3 | Cl | CCl | |
| H | CH3 | H | CH3 | OCH3 | CCl | |
| H | CH3 | H | CH3 | Br | CBr | |
| H | CH3 | H | CH3 | Cl | CBr | |
| H | CH3 | H | CH3 | OCH3 | CBr | |
| H | CH3 | H | H | OCH3 | N | |
| H | CH3 | H | CH3 | Cl | N | |
| H | CH3 | H | CH3 | Br | N | |
| H | CH3 | H | CH3 | OCH3 | N | |
| H | CH3 | H | CH3 | OCH2CH3 | N | |
| H | CH3 | H | CH3 | O(CH2)2CH3 | N | |
| H | CH3 | H | CH3 | CH3 | N | |
| H | CH3 | H | CH3 | CH2CH3 | N | |
| H | CH3 | H | CH3 | (CH2)2CH3 | N | |
| H | CH3 | H | CH2CH3 | Cl | N | |
| H | CH3 | H | CH2CH3 | OCH3 | N | |
| H | CH3 | H | (CH2)2CH3 | Cl | N | |
| H | CH3 | H | (CH2)2CH3 | OCH3 | N | |
| H | CH3 | H | OCH3 | H | N | |
| H | CH3 | H | OCH3 | CH3 | N | |
| H | CH3 | H | OCH3 | CH2CH3 | N | |
| H | CH3 | H | OCH3 | (CH2)2CH3 | N | |
| H | CH3 | H | OCH3 | OCH3 | N | |
| H | CH3 | H | OCH3 | OCH2CH3 | N | |
| H | CH3 | H | OCH3 | O(CH2)2CH3 | N | |
| H | CH3 | H | OCH3 | Cl | N | |
| H | CH3 | H | OCH3 | Br | N | |
| H | CH3 | H | OCH2CH3 | Cl | N | |
| H | CH3 | H | OCH2CH3 | CH3 | N | |
| H | CH3 | H | OCH2CH3 | OCH3 | N | |
| H | CH3 | H | O(CH2)2CH3 | Cl | N | |
| H | CH3 | H | O(CH2)2CH3 | CH3 | N | |
| H | CH3 | H | O(CH2)2CH3 | OCH3 | N | |
| H | CH3 | H | NH2 | Cl | N | |
| H | CH3 | H | NH2 | CH3 | N | |
| H | CH3 | H | NH2 | OCH3 | N | |
| H | CH3 | H | NHCH3 | Cl | N | |
| H | CH3 | H | NHCH3 | CH3 | N | |
| H | CH3 | H | NHCH3 | OCH3 | N | |
| H | CH3 | H | N(CH3)2 | Cl | N | |
| H | CH3 | H | N(CH3)2 | CH3 | N | |
| H | CH3 | H | N(CH3)2 | OCH3 | N | |
| H | CH3 | H | NHCH3 | OCH2CH3 | N | |
| CH3 | CH3 | H | CH3 | Cl | N | |
| CH3 | CH3 | H | OCH3 | Cl | N | |
| CH3 | CH3 | H | CH3 | OCH3 | N | |
| CH3 | CH3 | H | CH2CH3 | OCH3 | N | |
| CH3 | CH3 | H | OCH3 | CH3 | N | |
| CH3 | CH3 | H | OCH3 | OCH3 | N | |
| H | CH2CH3 | H | OCH3 | Cl | CH | |
| H | (CH2)2CH3 | H | CH3 | CH3 | CH | |
| H | (CH2)3CH3 | H | CH3 | OCH3 | CH | |
| H | (CH2)4CH3 | H | OCH3 | CH3 | CH | |

TABLE 14-continued

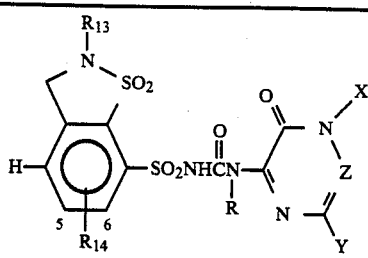

| R | R13 | R14 | X | Y | Z | m.p. (°C.) |
|---|---|---|---|---|---|---|
| H | (CH2)5CH3 | H | CH3 | Cl | CH | |
| H | CF2H | CH3 | OCH3 | N | | |
| H | (CH2)2Br | H | CH3 | OCH2CH3 | N | |
| H | (CH2)4F | H | OCH2CH3 | CH3 | CH | |
| H | (CH2)3Cl | H | OCH3 | OCH3 | CH | |
| H | CF2CF2H | H | CH2CH3 | OCH3 | CH | |
| H | CH2OCH3 | H | CH3 | Br | CH | |
| H | (CH2)2OCH3 | H | CH3 | OCH2CH3 | CH | |
| H | (CH2)2OCH2CH3 | H | CH3 | CH2CH3 | CH | |
| H | CH2O(CH2)2CH3 | H | OCH3 | Cl | CH | |
| H | cyclopropyl | H | CH3 | CH3 | CH | |
| H | cyclobutyl | H | CH3 | OCH3 | CH | |
| H | cyclomethyl | H | OCH3 | CH3 | CH | |
| H | cyclopropylmethyl | H | CH3 | Cl | CH | |
| H | cyclobutylmethyl | H | CH3 | OCH3 | N | |
| H | cyclopentylmethyl | H | CH3 | OCH2CH3 | N | |
| H | 2-cyclopropylethyl | H | OCH3 | Cl | CH | |
| CH3 | (CH2)2OCH2CH3 | H | CH3 | CH3 | CH | |
| H | H | 5-F | CH3 | OCH3 | CH | |
| H | CH3 | 6-F | OCH3 | CH3 | CH | |
| H | (CH2)2OCH3 | 5-Cl | CH3 | Cl | CH | |
| H | cyclopropylmethyl | 6-Cl | CH3 | OCH3 | N | |
| H | CH2CH3 | 5-Br | CH3 | OCH2CH3 | N | |
| H | CF2CF2H | 6-Br | OCH3 | Cl | CH | |
| H | H | 5-CN | CH3 | CH3 | CH | |
| H | CH3 | 6-CN | CH3 | OCH3 | CH | |
| H | CH2CH3 | 5-CH3 | OCH3 | CH3 | CH | |
| H | CH3 | 6-CH3 | CH3 | Cl | CH | |
| H | (CH2)2Cl | 5-OCH3 | OCH3 | Cl | CH | |
| H | CH3 | 6-OCH3 | CH3 | CH3 | CH | |
| H | H | 5-SCH3 | CH3 | OCH3 | CH | |
| H | CH3 | 6-SCH3 | OCH3 | CH3 | CH | |
| H | H | 5-OCF2H | CH3 | Cl | CH | |
| H | CH3 | 6-OCF2H | CH3 | OCH3 | N | |
| H | H | H | CH3 | OCH2CH3 | N | |
| CH3 | H | H | OCH2CH3 | CH3 | CH | |
| CH3 | CH3 | 6-Br | OCH3 | OCH3 | CH | |
| CH3 | (CH2)2OCH3 | 5-F | CH2CH3 | OCH3 | CH | |

TABLE 15

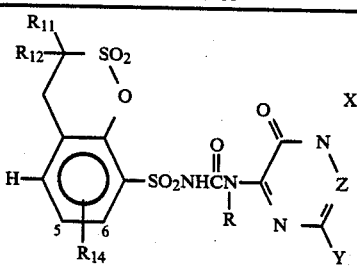

| R | R11 | R12 | R14 | X | Y | Z | m.p. (°C.) |
|---|---|---|---|---|---|---|---|
| H | CH3 | H | H | H | OCH3 | CH | |
| H | CH3 | H | H | CH3 | Cl | CH | |
| H | CH3 | H | H | CH3 | Br | CH | |
| H | CH3 | H | H | CH3 | OCH3 | CH | |
| H | CH3 | H | H | CH3 | OCH2CH3 | CH | |
| H | CH3 | H | H | CH3 | O(CH2)2CH3 | CH | |
| H | CH3 | H | H | CH3 | CH3 | CH | |
| H | CH3 | H | H | CH3 | CH2CH3 | CH | |
| H | CH3 | H | H | CH3 | (CH2)2CH3 | CH | |
| H | CH3 | H | H | CH2CH3 | Cl | CH | |
| H | CH3 | H | H | CH2CH3 | OCH3 | CH | |
| H | CH3 | H | H | (CH2)2CH3 | Cl | CH | |

TABLE 15-continued

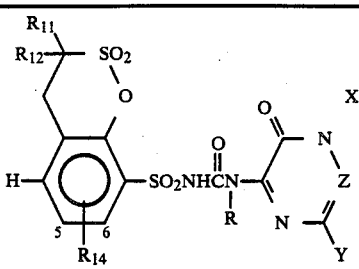

| R | R11 | R12 | R14 | X | Y | Z | m.p. (°C.) |
|---|-----|-----|-----|---|---|---|-----------|
| H | CH3 | H | H | (CH2)2CH3 | OCH3 | CH | |
| H | CH3 | H | H | OCH3 | H | CH | |
| H | CH3 | H | H | OCH3 | CH3 | CH | |
| H | CH3 | H | H | OCH3 | CH2CH3 | CH | |
| H | CH3 | H | H | OCH3 | (CH2)2CH3 | CH | |
| H | CH3 | H | H | OCH3 | OCH3 | CH | |
| H | CH3 | H | H | OCH3 | OCH2CH3 | CH | |
| H | CH3 | H | H | CH3 | SCH3 | CH | |
| H | CH3 | H | H | CH3 | SCH3 | N | |
| H | CH3 | H | H | CH3 | SCH2CH3 | CH | |
| H | CH3 | H | H | OCH3 | SCH3 | CH | |
| H | CH3 | H | H | OCH3 | SCH2CH3 | CH | |
| H | CH3 | H | H | NHCH3 | SCH3 | CH | |
| H | CH3 | H | H | OCH3 | O(CH2)2CH3 | CH | |
| H | CH3 | H | H | OCH3 | Cl | CH | |
| H | CH3 | H | H | OCH3 | Br | CH | |
| H | CH3 | H | H | OCH2CH3 | Cl | CH | |
| H | CH3 | H | H | OCH2CH3 | CH3 | CH | |
| H | CH3 | H | H | OCH2CH3 | OCH3 | CH | |
| H | CH3 | H | H | O(CH2)2CH3 | Cl | CH | |
| H | CH3 | H | H | O(CH2)2CH3 | CH3 | CH | |
| H | CH3 | H | H | O(CH2)2CH3 | OCH3 | CH | |
| H | CH3 | H | H | NH2 | Cl | CH | |
| H | CH3 | H | H | NH2 | CH3 | CH | |
| H | CH3 | H | H | NH2 | OCH3 | CH | |
| H | CH3 | H | H | NHCH3 | Cl | CH | |
| H | CH3 | H | H | NHCH3 | CH3 | CH | |
| H | CH3 | H | H | NHCH3 | OCH3 | CH | |
| H | CH3 | H | H | N(CH3)2 | Cl | CH | |
| H | CH3 | H | H | N(CH3)2 | CH3 | CH | |
| H | CH3 | H | H | N(CH3)2 | OCH3 | CH | |
| H | CH3 | H | H | NHCH3 | OCH2CH3 | CH | |
| CH3 | CH3 | H | H | CH3 | Cl | CH | |
| CH3 | CH3 | H | H | OCH3 | Cl | CH | |
| CH3 | CH3 | H | H | CH3 | OCH3 | CH | |
| CH3 | CH3 | H | H | OCH3 | CH3 | CH | |
| CH3 | CH3 | H | H | OCH3 | OCH3 | CH | |
| H | CH3 | H | H | CH3 | Cl | CF | |
| H | CH3 | H | H | CH3 | OCH3 | CF | |
| H | CH3 | H | H | OCH3 | OCH3 | CF | |
| H | CH3 | H | H | OCH3 | CH3 | CF | |
| H | CH3 | H | H | CH3 | Cl | CCl | |
| H | CH3 | H | H | CH3 | OCH3 | CCl | |
| H | CH3 | H | H | CH3 | Br | CBr | |
| H | CH3 | H | H | CH3 | Cl | CBr | |
| H | CH3 | H | H | CH3 | OCH3 | CBr | |
| H | CH3 | H | H | H | OCH3 | N | |
| H | CH3 | H | H | CH3 | Cl | N | |
| H | CH3 | H | H | CH3 | Br | N | |
| H | CH3 | H | H | CH3 | OCH3 | N | |
| H | CH3 | H | H | CH3 | OCH2CH3 | N | |
| H | CH3 | H | H | CH3 | O(CH2)2CH3 | N | |
| H | CH3 | H | H | CH3 | CH3 | N | |
| H | CH3 | H | H | CH3 | CH2CH3 | N | |
| H | CH3 | H | H | CH3 | (CH2)2CH3 | N | |
| H | CH3 | H | H | CH2CH3 | Cl | N | |
| H | CH3 | H | H | CH2CH3 | OCH3 | N | |
| H | CH3 | H | H | (CH2)2CH3 | Cl | N | |
| H | CH3 | H | H | (CH2)2CH3 | OCH3 | N | |
| H | CH3 | H | H | OCH3 | H | N | |
| H | CH3 | H | H | OCH3 | CH3 | N | |
| H | CH3 | H | H | OCH3 | CH2CH3 | N | |
| H | CH3 | H | H | OCH3 | (CH2)2CH3 | N | |
| H | CH3 | H | H | OCH3 | OCH3 | N | |
| H | CH3 | H | H | OCH3 | OCH2CH3 | N | |
| H | CH3 | H | H | OCH3 | O(CH2)2CH3 | N | |
| H | CH3 | H | H | OCH3 | Cl | N | |
| H | CH3 | H | H | OCH3 | Br | N | |

EXAMPLE 18

| Oil Suspension | |
|---|---|
| 2-[[(6-chloro-3,4-dihydro-4-methyl-3-oxo-2-pyrazinyl-amino)carbonylamino]sulfonyl]benzoic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 19

| Dust | |
|---|---|
| 2-[[(6-chloro-3,4-dihydro-4-methyl-3-oxo-2-pyrazinyl-amino)carbonylamino]sulfonyl]benzoic acid, methyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 20

| Oil Suspension | |
|---|---|
| 2-[[(6-chloro-3,4-dihydro-4-methyl-3-oxo-2-pyrazinyl-amino)carbonylamino]sulfonyl]benzoic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 21

| Wettable Powder | |
|---|---|
| 2-[[(6-chloro-3,4-dihydro-4-methyl-3-oxo-2-pyrazinyl-amino)carbonylamino]sulfonyl]benzoic acid, methyl ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

Utility

Test results indicate that the compounds of the present invention are active preemergent or postemergent herbicides or plant growth regulants. Some of them have utility for broad-spectrum pre- and/or postemergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat and barley. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.004 to 10 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, sulfonylurea, uracil, urea, amide, diphenylether, carbamate and bipyridylium types.

The herbicidal properties of the subject compounds were discovered in a number of greenhouse tests. The test procedures and results follow.

Compounds

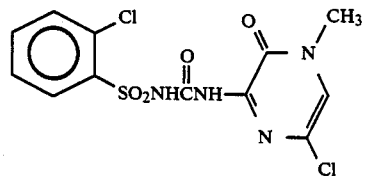
Compound 1

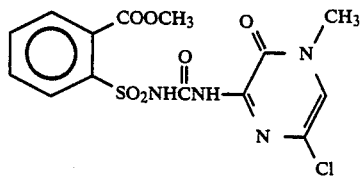
Compound 2

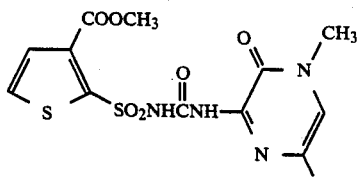
Compound 3

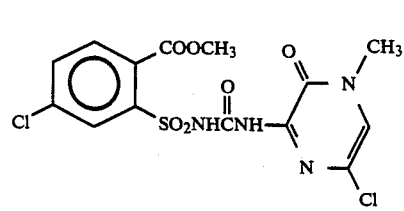
Compound 4 mm openings) may be packaged for use and the fines recycled.

EXAMPLE 10

| Low Strength Granule | |
|---|---|
| 2-[[(6-chloro-3,4-dihydro-4-methyl-3-oxo-2-pyrazinyl-amino)carbonylamino]sulfonyl]benzoic acid, methyl ester | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 11

| Granule | |
|---|---|
| 2-[[(6-chloro-3,4-dihydro-4-methyl-3-oxo-2-pyrazinyl-amino)carbonylamino]sulfonyl]benzoic acid, methyl ester | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410-149 microns), and packaged for use.

EXAMPLE 12

| Low Strength Granule | |
|---|---|
| 2-[[(6-chloro-3,4-dihydro-4-methyl-3-oxo-2-pyrazinyl-amino)carbonylamino]sulfonyl]benzoic acid, methyl ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 13

| Aqueous Suspension | |
|---|---|
| 2-[[(6-chloro-3,4-dihydro-4-methyl-3-oxo-2-pyrazinyl-amino)carbonylamino]sulfonyl]benzoic acid, methyl ester | 40% |
| polyacrylic acid thickener | 0.3% |
| dodecylphenol polyethylene glycol ether | 0.5% |
| disodium phosphate | 1% |
| monosodium phosphate | 0.5% |

-continued

| Aqueous Suspension | |
|---|---|
| polyvinyl alcohol | 1.0% |
| water | 56.7% |

The ingredients are blended and ground together in a sand mill to produce particles essentially all under 5 microns in size.

EXAMPLE 14

| Solution | |
|---|---|
| 2-[[(6-chloro-3,4-dihydro-4-methyl-3-oxo-2-pyrazinyl-amino)carbonylamino]sulfonyl]benzoic acid, methyl ester, ammonium salt | 5% |
| water | 95% |

The salt is added directly to the water with stirring to produce the solution, which may then be packaged for use.

EXAMPLE 15

| High Strength Concentrate | |
|---|---|
| 2-[[(6-chloro-3,4-dihydro-4-methyl-3-oxo-2-pyrazinyl-amino)carbonylamino]sulfonyl]benzoic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 16

| Wettable Powder | |
|---|---|
| 2-[[(6-chloro-3,4-dihydro-4-methyl-3-oxo-2-pyrazinyl-amino)carbonylamino]sulfonyl]benzoic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 17

| Wettable Powder | |
|---|---|
| 2-[[(6-chloro-3,4-dihydro-4-methyl-3-oxo-2-pyrazinyl-amino)carbonylamino]sulfonyl]benzoic acid, methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

(a) about 0.1% to 20% surfactant(s) and (b) about 1% to 99.9% solid or liquid inert diluent(s). More specifically, they will contain these ingredients in the following approximate proportions:

|  | Active Ingredient | Weight Percent* | |
|---|---|---|---|
|  |  | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 6

| Wettable Powder | |
|---|---|
| 2-[[(6-chloro-3,4-dihydro-4-methyl-3-oxo-2-pyrazinyl-amino)carbonylamino]sulfonyl]benzoic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 7

| Wettable Powder | |
|---|---|
| 2-[[(6-chloro-3,4-dihydro-4-methyl-3-oxo-2-pyrazinyl-amino)carbonylamino]sulfonyl]benzoic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 8

| Granule | |
|---|---|
| Wettable Powder of Example 7 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 9

| Extruded Pellet | |
|---|---|
| 2-[[(6-chloro-3,4-dihydro-4-methyl-3-oxo-2-pyrazinyl-amino)carbonylamino]sulfonyl]benzoic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42

TABLE 16-continued

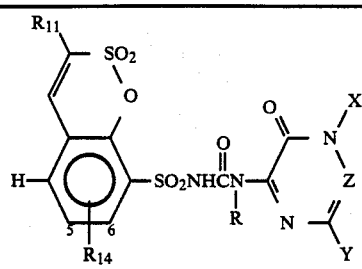

| R | R11 | R14 | X | Y | Z | m.p. (°C.) |
|---|-----|-----|---|---|---|------------|
| H | CH3 | H | (CH2)2CH3 | Cl | N | |
| H | CH3 | H | (CH2)2CH3 | OCH3 | N | |
| H | CH3 | H | OCH3 | H | N | |
| H | CH3 | H | OCH3 | CH3 | N | |
| H | CH3 | H | OCH3 | CH2CH3 | N | |
| H | CH3 | H | OCH3 | (CH2)2CH3 | N | |
| H | CH3 | H | OCH3 | OCH3 | N | |
| H | CH3 | H | OCH3 | OCH2CH3 | N | |
| H | CH3 | H | OCH3 | O(CH2)2CH3 | N | |
| H | CH3 | H | OCH3 | Cl | N | |
| H | CH3 | H | OCH3 | Br | N | |
| H | CH3 | H | OCH2CH3 | Cl | N | |
| H | CH3 | H | OCH2CH3 | CH3 | N | |
| H | CH3 | H | OCH2CH3 | OCH3 | N | |
| H | CH3 | H | O(CH2)2CH3 | Cl | N | |
| H | CH3 | H | O(CH2)2CH3 | CH3 | N | |
| H | CH3 | H | O(CH2)2CH3 | OCH3 | N | |
| H | CH3 | H | NH2 | Cl | N | |
| H | CH3 | H | NH2 | CH3 | N | |
| H | CH3 | H | NH2 | OCH3 | N | |
| H | CH3 | H | NHCH3 | Cl | N | |
| H | CH3 | H | NHCH3 | CH3 | N | |
| H | CH3 | H | NHCH3 | OCH3 | N | |
| H | CH3 | H | N(CH3)2 | Cl | N | |
| H | CH3 | H | N(CH3)2 | CH3 | N | |
| H | CH3 | H | N(CH3)2 | OCH3 | N | |
| H | CH3 | H | NHCH3 | OCH2CH3 | N | |
| CH3 | CH3 | H | CH3 | Cl | N | |
| CH3 | CH3 | H | OCH3 | Cl | N | |
| CH3 | CH3 | H | CH3 | OCH3 | N | |
| CH3 | CH3 | H | CH2CH3 | OCH3 | N | |
| CH3 | CH3 | H | OCH3 | CH3 | N | |
| CH3 | CH3 | H | OCH3 | OCH3 | N | |
| H | H | H | OCH3 | Cl | CH | |
| H | CH3 | H | CH3 | CH3 | CH | |
| H | CH3 | H | CH3 | OCH3 | CH | |
| H | CH2CH3 | H | OCH3 | CH3 | CH | |
| H | CH2CH3 | H | CH3 | Cl | CH | |
| H | CH2CH3 | H | CH3 | OCH3 | N | |
| H | H | H | CH3 | OCH2CH3 | N | |
| H | H | H | OCH2CH3 | CH3 | CH | |
| H | H | 5-F | OCH3 | OCH3 | CH | |
| H | CH3 | 6-F | CH2CH3 | OCH3 | CH | |
| H | H | 5-Cl | CH3 | Br | CH | |
| H | CH3 | 6-Cl | CH3 | OCH2CH3 | CH | |
| H | H | 5-Br | CH3 | CH2CH3 | CH | |
| H | CH3 | 6-Br | OCH3 | Cl | CH | |
| H | H | 5-CN | CH3 | CH3 | CH | |
| H | CH3 | 6-CN | CH3 | OCH3 | CH | |
| H | H | 5-CH3 | OCH3 | CH3 | CH | |
| H | CH3 | 6-CH3 | CH3 | Cl | CH | |
| H | H | 5-OCH3 | CH3 | OCH3 | N | |
| H | CH3 | 6-OCH3 | CH3 | OCH2CH3 | N | |
| H | H | 5-SCH3 | OCH3 | Cl | CH | |
| H | CH3 | 6-SCH3 | CH3 | CH3 | CH | |
| H | H | 5-OCF2H | CH3 | OCH3 | CH | |
| H | CH3 | 6-OCF2H | OCH3 | CH3 | CH | |
| CH3 | CH3 | 6-Cl | CH3 | Cl | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of TABLE 16-continued

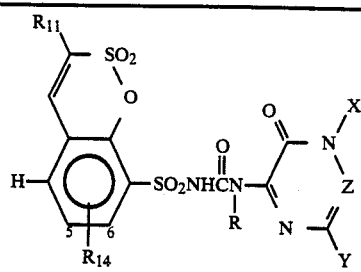

| R | R₁₁ | R₁₄ | X | Y | Z | m.p. (°C.) |
|---|---|---|---|---|---|---|
| H | CH₃ | H | CH₃ | Br | CH | |
| H | CH₃ | H | CH₃ | OCH₃ | CH | |
| H | CH₃ | H | CH₃ | OCH₂CH₃ | CH | |
| H | CH₃ | H | CH₃ | O(CH₂)₂CH₃ | CH | |
| H | CH₃ | H | CH₃ | CH₃ | CH | |
| H | CH₃ | H | CH₃ | CH₂CH₃ | CH | |
| H | CH₃ | H | CH₃ | (CH₂)₂CH₃ | CH | |
| H | CH₃ | H | CH₂CH₃ | Cl | CH | |
| H | CH₃ | H | CH₂CH₃ | OCH₃ | CH | |
| H | CH₃ | H | (CH₂)₂CH₃ | Cl | CH | |
| H | CH₃ | H | (CH₂)₂CH₃ | OCH₃ | CH | |
| H | CH₃ | H | OCH₃ | H | CH | |
| H | CH₃ | H | OCH₃ | CH₃ | CH | |
| H | CH₃ | H | OCH₃ | CH₂CH₃ | CH | |
| H | CH₃ | H | OCH₃ | (CH₂)₂CH₃ | CH | |
| H | CH₃ | H | OCH₃ | OCH₃ | CH | |
| H | CH₃ | H | OCH₃ | OCH₂CH₃ | CH | |
| H | CH₃ | H | CH₃ | SCH₃ | CH | |
| H | CH₃ | H | OCH₃ | SCH₃ | CH | |
| H | CH₃ | H | CH₃ | SCH₃ | N | |
| H | CH₃ | H | CH₃ | SCH₂CH₃ | CH | |
| H | CH₃ | H | CH₂CH₃ | SCH₃ | CH | |
| H | CH₃ | H | CH₃ | SCH₂CH₃ | N | |
| H | CH₃ | H | NHCH₃ | SCH₃ | N | |
| H | CH₃ | H | OCH₃ | O(CH₂)₂CH₃ | CH | |
| H | CH₃ | H | OCH₃ | Cl | CH | |
| H | CH₃ | H | OCH₃ | Br | CH | |
| H | CH₃ | H | OCH₂CH₃ | Cl | CH | |
| H | CH₃ | H | OCH₂CH₃ | CH₃ | CH | |
| H | CH₃ | H | OCH₂CH₃ | OCH₃ | CH | |
| H | CH₃ | H | O(CH₂)₂CH₃ | Cl | CH | |
| H | CH₃ | H | O(CH₂)₂CH₃ | CH₃ | CH | |
| H | CH₃ | H | O(CH₂)₂CH₃ | OCH₃ | CH | |
| H | CH₃ | H | NH₂ | Cl | CH | |
| H | CH₃ | H | NH₂ | CH₃ | CH | |
| H | CH₃ | H | NH₂ | OCH₃ | CH | |
| H | CH₃ | H | NHCH₃ | Cl | CH | |
| H | CH₃ | H | NHCH₃ | CH₃ | CH | |
| H | CH₃ | H | NHCH₃ | OCH₃ | CH | |
| H | CH₃ | H | N(CH₃)₂ | Cl | CH | |
| H | CH₃ | H | N(CH₃)₂ | CH₃ | CH | |
| H | CH₃ | H | N(CH₃)₂ | OCH₃ | CH | |
| H | CH₃ | H | NHCH₃ | OCH₂CH₃ | CH | |
| CH₃ | CH₃ | H | CH₃ | Cl | CH | |
| CH₃ | CH₃ | H | OCH₃ | Cl | CH | |
| CH₃ | CH₃ | H | CH₃ | OCH₃ | CH | |
| CH₃ | CH₃ | H | OCH₃ | CH₃ | CH | |
| CH₃ | CH₃ | H | OCH₃ | OCH₃ | CH | |
| H | CH₃ | H | CH₃ | Cl | CF | |
| H | CH₃ | H | CH₃ | OCH₃ | CF | |
| H | CH₃ | H | OCH₃ | OCH₃ | CF | |
| H | CH₃ | H | OCH₃ | CH₃ | CF | |
| H | CH₃ | H | CH₃ | Cl | CCl | |
| H | CH₃ | H | CH₃ | OCH₃ | CCl | |
| H | CH₃ | H | CH₃ | Br | CBr | |
| H | CH₃ | H | CH₃ | Cl | CBr | |
| H | CH₃ | H | CH₃ | OCH₃ | CBr | |
| H | CH₃ | H | H | OCH₃ | N | |
| H | CH₃ | H | CH₃ | Cl | N | |
| H | CH₃ | H | CH₃ | Br | N | |
| H | CH₃ | H | CH₃ | OCH₃ | N | |
| H | CH₃ | H | CH₃ | OCH₂CH₃ | N | |
| H | CH₃ | H | CH₃ | O(CH₂)₂CH₃ | N | |
| H | CH₃ | H | CH₃ | CH₃ | N | |
| H | CH₃ | H | CH₃ | CH₂CH₃ | N | |
| H | CH₃ | H | CH₃ | (CH₂)₂CH₃ | N | |
| H | CH₃ | H | CH₂CH₃ | Cl | N | |
| H | CH₃ | H | CH₂CH₃ | OCH₃ | N | |

TABLE 15-continued

[Structure: benzene ring with R11, R12, SO2, O substituents forming a ring, H at position, R14 at position 5/6, SO2NHC(O)N(R) connected to C(=O)N(X)-pyrimidine/triazine with Y, Z]

| R | R11 | R12 | R14 | X | Y | Z | m.p. (°C.) |
|---|---|---|---|---|---|---|---|
| H | CH3 | H | H | OCH2CH3 | Cl | N | |
| H | CH3 | H | H | OCH2CH3 | CH3 | N | |
| H | CH3 | H | H | OCH2CH3 | OCH3 | N | |
| H | CH3 | H | H | O(CH2)2CH3 | Cl | N | |
| H | CH3 | H | H | O(CH2)2CH3 | CH3 | N | |
| H | CH3 | H | H | O(CH2)2CH3 | OCH3 | N | |
| H | CH3 | H | H | NH2 | Cl | N | |
| H | CH3 | H | H | NH2 | CH3 | N | |
| H | CH3 | H | H | NH2 | OCH3 | N | |
| H | CH3 | H | H | NHCH3 | Cl | N | |
| H | CH3 | H | H | NHCH3 | CH3 | N | |
| H | CH3 | H | H | NHCH3 | OCH3 | N | |
| H | CH3 | H | H | N(CH3)2 | Cl | N | |
| H | CH3 | H | H | N(CH3)2 | CH3 | N | |
| H | CH3 | H | H | N(CH3)2 | OCH3 | N | |
| H | CH3 | H | H | NHCH3 | OCH2CH3 | N | |
| CH3 | CH3 | H | H | CH3 | Cl | N | |
| CH3 | CH3 | H | H | OCH3 | Cl | N | |
| CH3 | CH3 | H | H | CH3 | OCH3 | N | |
| CH3 | CH3 | H | H | CH2CH3 | OCH3 | N | |
| CH3 | CH3 | H | H | OCH3 | CH3 | N | |
| CH3 | CH3 | H | H | OCH3 | OCH3 | N | |
| H | H | H | H | OCH3 | Cl | CH | |
| H | CH3 | CH3 | H | CH3 | CH3 | CH | |
| H | CH3 | CH2CH3 | H | CH3 | OCH3 | CH | |
| H | CH2CH3 | CH3 | H | OCH3 | CH3 | CH | |
| H | CH2CH3 | H | H | CH3 | Cl | CH | |
| H | CH2CH3 | CH2CH3 | H | CH3 | OCH3 | N | |
| H | H | CH3 | H | CH3 | OCH2CH3 | N | |
| H | H | H | H | OCH2CH3 | CH3 | CH | |
| H | H | H | 5-F | OCH3 | OCH3 | CH | |
| H | CH3 | H | 6-F | CH2CH3 | OCH3 | CH | |
| H | H | CH3 | 5-Cl | CH3 | Br | CH | |
| H | CH3 | CH3 | 6-Cl | CH3 | OCH2CH3 | CH | |
| H | H | H | 5-Br | CH3 | CH2CH3 | CH | |
| H | CH3 | H | 6-Br | OCH3 | Cl | CH | |
| H | H | CH3 | 5-CN | CH3 | CH3 | CH | |
| H | CH3 | CH3 | 6-CN | CH3 | OCH3 | CH | |
| H | H | H | 5-CH3 | OCH3 | CH3 | CH | |
| H | CH3 | H | 6-CH3 | CH3 | Cl | CH | |
| H | H | CH3 | 5-OCH3 | CH3 | OCH3 | N | |
| H | CH3 | CH3 | 6-OCH3 | CH3 | OCH2CH3 | N | |
| H | H | H | 5-SCH3 | OCH3 | Cl | CH | |
| H | CH3 | H | 6-SCH3 | CH3 | CH3 | CH | |
| H | H | CH3 | 5-OCF2H | CH3 | OCH3 | CH | |
| H | CH3 | CH3 | 6-OCF2H | OCH3 | CH3 | CH | |
| CH3 | CH3 | H | 6-Cl | CH3 | Cl | CH | |

TABLE 16

[Structure with R11, SO2, O forming ring on benzene, H and R14 substituents, SO2NHC(O)N(R) linked to heterocycle with X, Y, Z]

| R | R11 | R14 | X | Y | Z | m.p. (°C.) |
|---|---|---|---|---|---|---|
| H | CH3 | H | H | OCH3 | CH | |
| H | CH3 | H | CH3 | Cl | CH | |

-continued
Compounds

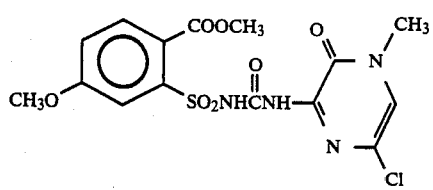
Compound 5

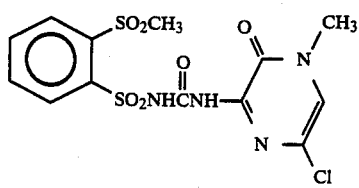
Compound 6

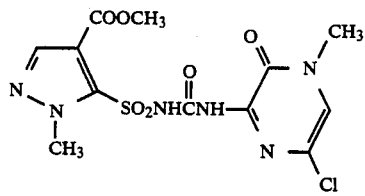
Compound 7

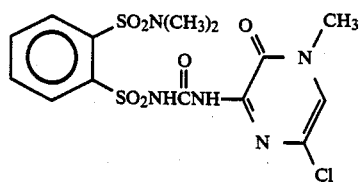
Compound 8

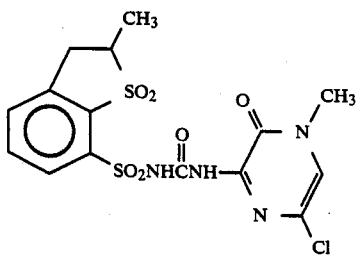
Compound 9

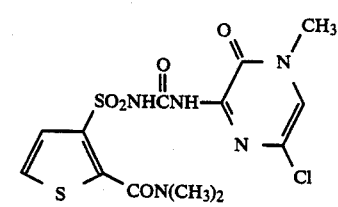
Compound 10

-continued
Compounds

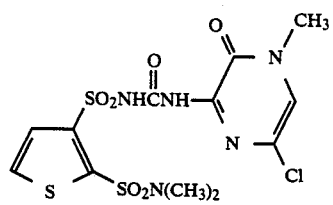
Compound 11

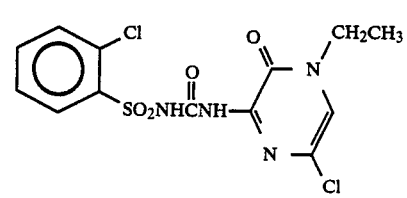
Compound 12

TEST A

Seeds of crabgrass (Digitaria sp.), barnyardgrass (Echinochloa crusgalli), wild oats (Avena fatua), cheatgrass (Bromus secalinus), velvetleaf (Abutilon theophrasti), morningglory (Ipomoea spp.), cocklebur (Xanthium pensylvanicum), sorghum, corn, soybean, sugarbeet, cotton, rice, wheat, barley and purple nutsedge (Cyperus rotundus) tubers were planted and treated preemergence with the test chemicals dissolved in a nonphytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

TABLE A

| | Compound 1 | | Compound 2 | | Compound 3 | | CMPD 4 | | CMPD 5 | | CMPD 6 | | CMPD 7 | |
|---|---|---|---|---|---|---|---|---|---|---|---|---|---|---|
| Rate kg/ha | 0.05 | 0.4 | 0.05 | 0.4 | 0.05 | 0.4 | 0.05 | 0.4 | 0.05 | 0.4 | 0.05 | 0.4 | 0.05 | 0.4 |
| POSTEMERGENCE | | | | | | | | | | | | | | |
| Cotton | 6G | 9C | 9C | 10C | 3C,6G | 9C | 6G | 10C | 8G | 9C | 2G | 3C,8G | 0 | 0 |
| Morningglory | 3C,8G | 10C | 4C,9G | 10C | 3C,7G | 2C,9G | 3C,7G | 9C | 2C,8G | 9C | 2G | 3C,8G | 0 | 0 |
| Cocklebur | 5G | 10C | 5C,9G | 10C | 2H,7G | 10C | 8G | 10C | 8G | 10C | 4G | 5H | 0 | 2G |
| Nutsedge | 3C,8G | 9C | 9C | 9C | 0 | 2C,5G | 3G | 2C,9G | 2G | 9C | 0 | 7G | 0 | 0 |
| Crabgrass | 5G | 9G | 6G | 4C,8G | 0 | 3C,7G | 4G | 2C,8G | 0 | 9C | 0 | 3C,9G | 0 | 0 |
| Barnyardgrass | 3C,8H | 6C,9H | 4C,8H | 9C | 2C,5H | 4C,9G | 9C | 5C,9G | 2G | 9C | 2H | 5C,9G | 0 | 0 |
| Wild Oats | 3G | 2C,8G | 3C,9G | 4C,9G | 0 | 9G | 9G | 3C,9G | 2C,9G | 2C,9G | 2C,9G | 9C | 0 | 0 |
| Wheat | 2G | 2C,9G | 5C,9G | 9C | 8G | 9G | 5G | 7G | 7G | 2C,9G | 9G | 9C | 0 | 0 |
| Corn | 8H | 9G | 2U,9G | 10C | 2U,9G | 3U,9G | 4G | 7G | 6G | 7G | 3G | 3C,9G | 0 | 3G |
| Soybean | 4C,9G | 5C,9G | 9C | 9C | 4C,9G | 5C,9G | 4C,9G | 9C | 4C,9G | 6C,9G | 3C,8G | 4C,9G | 0 | 1C |

TABLE A-continued

| | | | | | | | | | | | | | |
|---|---|---|---|---|---|---|---|---|---|---|---|---|---|
| Rice | 5C,9G | 6C,9G | 5C,9G | 9C | 9C | 9C | 5C,9G | 10C | 4C,9G | 5C,9G | 5C,9G | 9C | 0 | 0 |
| Sorghum | 3C,9G | 3C,9G | 9C | 9C | 4C,9G | 4C,9G | 3C,9G | 4C,9G | 4C,9H | 9C | 2C,5G | 4C,8H | 0 | 0 |
| Cheatgrass | 4C,9G | 9C | 10C | 9C | 3C,9G | 9C | 2C,8G | 9C | 8G | 9C | 9G | 9C | 0 | 6G |
| Sugar beet | 3C,8G | 10C | 10C | 10C | 3C,8H | 10C | 6G | 9C | 3C,8H | 9C | 2C,2H | 9C | 0 | 0 |
| Velvetleaf | 8G | 10C | 7G | 4C,9G | 4G | 2C,8G | 5G | 6C,9G | 7G | 8G | 2G | 3G | 0 | 0 |
| Giant Foxtail | 3C,6G | 6C,9G | 3C,5G | 9C | 0 | 5G | 4G | 7G | 0 | 5G | 6G | 10C | 0 | 0 |
| Barley | 0 | 6G | 9C | 6C,9G | 0 | 4G | 8G | 8G | 7G | 4C,9G | 3C,7G | 3C,9G | 0 | 0 |

PREEMERGENCE

| | | | | | | | | | | | | | |
|---|---|---|---|---|---|---|---|---|---|---|---|---|---|
| Cotton | 7G | 9G | 9G | 9G | 5G | 7G | 5G | 9G | 2C,5G | 9G | 2G | 7G | 0 | 2G |
| Morningglory | 5G | 9G | 9H | 9G | 3C,6G | 8G | 8G | 10E | 8G | 9G | 3G | 5G | 0 | 0 |
| Cocklebur | 0 | 7G | 4G | 9H | 1H | 8H | 2H | 9H | 9H | 9H | — | 3G | 0 | — |
| Nutsedge | 9G | 10E | 10E | 10E | 10E | 10E | 9G | 10E | 9G | 10E | 0 | 10E | 0 | 0 |
| Crabgrass | 2G | 8G | 7G | 10E | 0 | 3C,7G | 2G | 2C,5G | 0 | 2C,8G | 0 | 4G | 0 | 0 |
| Barnyardgrass | 3C,8H | 3C,9H | 7H | 9H | 1C | 9H | 7G | 9H | 5G | 9H | 2G | 8H | 0 | 0 |
| Wild Oats | 5G | 2C,7G | 4C,8G | 3C,9H | 0 | 2C,6G | 2C,6G | 2C,8G | 5G | 3C,7H | 0 | 2C,6G | 0 | 0 |
| Wheat | 5G | 3C,8G | 2C,8G | 3C,9H | 0 | 3C,8H | 2G | 2C,7G | 5G | 9H | 0 | 9H | 0 | 0 |
| Corn | 3C,8G | 9H | 3C,9H | 10E | 3C,9G | 9G | 2C,6G | 2C,9G | 3C,3G | 9G | 3C,5G | 9G | 0 | 0 |
| Soybean | 3C,3G | 4C,9H | 9H | 9H | 2H | 3C,7H | 9H | 9H | 8H | 9H | 2C | 3C,7H | 0 | 0 |
| Rice | 10E | 10E | 10E | 10E | 10E | 10E | 9H | 10E | 10E | 10E | 9H | 10E | 0 | 0 |
| Sorghum | 4C,9H | 10H | 5C,9H | 10E | 9H | 10E | 3C,8H | 4C,9H | 3C,9H | 5C,9H | 2C | 3C,8H | 0 | 0 |
| Cheatgrass | 9H | 10E | 9H | 9H | 9H | 9H | 8H | 9H | 9H | 9H | 5G | 10E | 0 | 0 |
| Sugar beet | 8G | 9G | 9G | 3C,9G | 9G | 9G | 9G | 9G | 9G | 9G | 3H | 2C,8G | 0 | 5G |
| Velvetleaf | 1H | 3C,8G | 7G | 3C,9G | 3G | 3G | 2G | 8G | 3G | 8G | 0 | 2C | 0 | 0 |
| Giant Foxtail | 4G | 3C,8G | 3G | 8H | 0 | 0 | 0 | 2G | 0 | 3G | 0 | 8H | 0 | 0 |
| Barley | 2G | 3C,7G | 3C,9H | 4C,9H | 1C | 9G | 8G | 2C,9H | 8G | 3C,9H | 2C | 9H | 0 | 0 |

| | | CMPD 8 | | CMPD 9 | | CMPD 10 | | CMPD 11 | | CMPD 12 | |
|---|---|---|---|---|---|---|---|---|---|---|---|
| | Rate kg/ha | 0.05 | 0.4 | 0.05 | 0.4 | 0.05 | 0.4 | 0.05 | 0.4 | 0.05 | 0.4 |

POSTEMERGENCE

| | | | | | | | | | | | |
|---|---|---|---|---|---|---|---|---|---|---|---|
| Cotton | 2C,8G | 4C,9G | 0 | 0 | 0 | 5G | 2C,5G | 10C | 0 | 0 |
| Morningglory | 3C,8H | 9C | 0 | 2G | 0 | 0 | 2H | 5C,9G | 0 | 0 |
| Cocklebur | 8H | 10C | 0 | 2G | 0 | 1C | 2H | 4C,8H | 0 | 0 |
| Nutsedge | 5G | 3C,9G | 0 | 0 | 0 | 0 | 0 | 3G | 0 | — |
| Crabgrass | 8G | 9G | 0 | 0 | 0 | 2G | 0 | 3G | 0 | 0 |
| Barnyardgrass | 5C,9G | 9C | 0 | 0 | 0 | 0 | 5H | 9C | 0 | 0 |
| Wild Oats | 2C,8G | 5C,9G | 0 | 6G | 0 | 0 | 3G | 8G | 0 | 0 |
| Wheat | 8G | 6C,9G | 0 | 4G | 0 | 0 | 9G | 9C | 0 | 0 |
| Corn | 9H | 3U,9G | 0 | 2G | 0 | 0 | 2G | 2C,8G | 0 | 0 |
| Soybean | 4C,9G | 9C | 0 | 2G | 0 | 2C,5G | 3C,9G | 5C,9G | 0 | 2C,5H |
| Rice | 9C | 9C | 0 | 2C,3G | 0 | 8G | 3C,6G | 5C,9G | 0 | 5G |
| Sorghum | 3C,9G | 6C,9G | 0 | 0 | 0 | 5G | 2C,7G | 2C,9G | 0 | 0 |
| Cheatgrass | 9C | 9C | 0 | 3G | 0 | 3G | 9G | 5C,9G | 0 | 0 |
| Sugar beet | 3C,7G | 9C | 0 | 3G | 0 | 2H | 3C,6G | 9C | 0 | 3G |
| Velvetleaf | 4G | 4C,9G | 0 | 0 | 0 | 0 | 0 | 6G | 0 | 3G |
| Giant Foxtail | 3C,8G | 9C | 0 | 0 | 0 | 6G | 3G | 2C,7G | 0 | 2G |
| Barley | 4C,9G | 6C,9G | 0 | 0 | 0 | 0 | 3G | 2C,8G | 0 | 0 |

PREEMERGENCE

| | | | | | | | | | | | |
|---|---|---|---|---|---|---|---|---|---|---|---|
| Cotton | 7G | 9G | 0 | 0 | 0 | 2G | 8G | 4G | 0 | 0 |
| Morningglory | 9G | 9G | 0 | 0 | 0 | 0 | 0 | 8G | 0 | 0 |
| Cocklebur | 8G | — | 0 | 0 | — | 2G | 0 | 5G | 0 | 0 |
| Nutsedge | 9G | 10E | 0 | 0 | 0 | 0 | 4G | 9G | 0 | 0 |
| Crabgrass | 3G | 3C,6G | 0 | 0 | 0 | 0 | 0 | 4G | 0 | 0 |
| Barnyardgrass | 7H | 9H | 0 | 0 | 0 | 2C | 1C | 9H | 0 | 0 |
| Wild Oats | 2G | 3C,7H | 0 | 0 | 0 | 0 | 3G | 2C,6G | 0 | 0 |
| Wheat | 8H | 9H | 0 | 0 | 0 | 0 | 0 | 7G | 0 | 0 |
| Corn | 9G | 9H | 0 | 0 | 0 | 0 | 2C,4G | 8G | 0 | 0 |
| Soybean | 9H | 9H | 0 | 0 | 0 | 3G | 2C,2H | 8H | 0 | 0 |
| Rice | 10H | 10E | 0 | 0 | 0 | 0 | 2C,8G | 10E | 0 | 3G |
| Sorghum | 3C,9H | 5C,9H | 0 | 0 | 0 | 0 | 3C,3G | 3C,9H | 0 | 0 |
| Cheatgrass | 8H | 9H | 0 | 0 | 0 | 2G | 7G | 10E | 0 | 0 |
| Sugar beet | 8G | 9G | 0 | 0 | 0 | 0 | 7G | 9G | 0 | 3G |
| Velvetleaf | 0 | 2C,8G | 0 | 0 | 0 | 0 | 0 | 5G | 0 | 2G |
| Giant Foxtail | 0 | 6G | 0 | 0 | 0 | 0 | 0 | 3C,6G | 0 | 0 |
| Barley | 9H | 5C,9H | 0 | 0 | 0 | 0 | 5G | 8G | 0 | 0 |

TEST B

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanquinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*) and teaweed (*Sida spinosa*). The second pot was planted with green foxtail (*Setaria viridis*), cocklebur (*Xantium pensylvanicum*), morningglory (*Ipomoea hederacea*), cotton (*Gossypium hirsutum*), johnsongrass (*Sorghum halepense*), barnyardgrass (*Echinochloa crusgalli*), corn (*Zea mays*), soybean (*Glycine max*) and giant foxtail (*Setaria faberi*). The third pot was planted with wheat (*Triticum aestivum*), barley (*Hordeum vulgare*), wild buckwheat (*Polgonum convolvulus* L.), cheatgrass (*Bromus secalinus* L.), sugarbeet (*Beta vulgaris*), wild oats (*Avena fatua*), viola (*Viola arvensis*), blackgrass (*Alopecurus myosuroides*), and rape (*Brassica napus*). The plants were grown for approximately fourteen days, then sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf,, lambsquarters, rice and teaweed. The second pot was planted with green foxtail, cocklebur, morningglory, cotton, johnsongrass, barnyardgrass, corn, soybean and giant foxtail. The third pot was planted with wheat, barley, wild buckwheat, cheatgrass, sugarbeet, wild oat, viola, blackgrass and rape. The three pans were sprayed preemergence with the chemicals dissolved in a non-phytotoxic solvent.

Treated plants and controls were maintained in the greenhouse for 24 days, then all rated plants were compared to controls and visually rated for plant response.

Response ratings are based on a scale of 0 to 100 where 0=no effect and 100=complete control. A dash (—) response means no test.

Response ratings are contained in Table B.

TABLE B

| RATE RATE = G/HA | CMPD 1 | | | CMPD 2 | | | |
|---|---|---|---|---|---|---|---|
| | 0016 | 0062 | 0250 | 0004 | 0016 | 0062 | 0250 |
| POSTEMERGENCE | | | | | | | |
| GIANT FOXTAIL | 30 | 40 | | 0 | 0 | 30 | |
| VELVETLEAF | 30 | 50 | 70 | 30 | 50 | 70 | 100 |
| SUGAR BEETS | 50 | 70 | | 50 | 70 | 100 | |
| CRABGRASS | 50 | 60 | 70 | 50 | 60 | 70 | 90 |
| TEAWEED | 30 | 40 | 50 | 30 | 50 | 70 | 90 |
| JIMSONWEED | 30 | 50 | 70 | 30 | 50 | 70 | 100 |
| RICE | 90 | 100 | 100 | 80 | 90 | 100 | 100 |
| COCKLEBUR | 20 | 30 | 40 | 30 | 50 | 70 | 90 |
| COTTON | 0 | 30 | 40 | 20 | 30 | 60 | 80 |
| SOYBEAN | 30 | 50 | | 60 | 70 | 80 | |
| BARNYARD GRASS | 30 | 40 | 50 | 30 | 50 | 70 | 90 |
| WILD OATS | 0 | 30 | | 30 | 50 | 60 | |
| MORNINGGLORY | 0 | 0 | 0 | 30 | 50 | 70 | 100 |
| WHEAT | 0 | 30 | | 20 | 40 | 100 | |
| CASSIA | 40 | 50 | 60 | 30 | 60 | 100 | 100 |
| JOHNSONGRASS | 50 | 60 | 70 | 80 | 90 | 100 | 100 |
| NUTSEDGE | 30 | 50 | 70 | 0 | 30 | 70 | 100 |
| CORN | 20 | 30 | | 0 | 20 | 60 | |
| WILD BUCKWHEAT | 0 | 30 | | 0 | 30 | 60 | |
| BLACK GRASS | 0 | 30 | | 30 | 50 | 70 | |
| RAPESEED | 30 | 50 | | 50 | 70 | 100 | |
| BARLEY | 0 | 30 | | 20 | 60 | 100 | |
| GREEN FOXTAIL | 30 | 40 | 60 | 0 | 30 | 50 | 80 |
| CHEAT GRASS | 30 | 50 | | 50 | 70 | 100 | |
| BUCKWHEAT | | | | | | | |
| VIOLA | 0 | 0 | | 0 | 30 | 40 | |
| LAMBSQUARTER | 50 | 60 | 70 | 50 | 70 | 90 | 100 |

| RATE RATE = G/HA | CMPD 1 | | | | | CMPD 2 | | | |
|---|---|---|---|---|---|---|---|---|---|
| | 0016 | 0062 | 0250 | 0500 | 1000 | 0004 | 0016 | 0062 | 0250 |
| PREEMERGENCE | | | | | | | | | |
| GIANT FOXTAIL | 0 | 30 | 50 | 70 | 80 | 0 | 0 | 30 | 70 |
| VELVETLEAF | 30 | 50 | 70 | 80 | 90 | 30 | 50 | 60 | 80 |
| SUGAR BEETS | 80 | 90 | 100 | 100 | 100 | 70 | 80 | 90 | 100 |
| CRABGRASS | 30 | 50 | 70 | 90 | 90 | 30 | 50 | 70 | 90 |
| TEAWEED | 40 | 50 | 60 | 70 | 80 | 30 | 50 | 70 | 90 |
| JIMSONWEED | 90 | 90 | 100 | 100 | 100 | 50 | 70 | 80 | 90 |
| RICE | 100 | 100 | 100 | 100 | 100 | 100 | 100 | 100 | 100 |
| COCKLEBUR | 0 | 0 | 20 | 40 | 60 | 30 | 50 | 60 | 80 |
| COTTON | 0 | 20 | 40 | 50 | 60 | 20 | 30 | 50 | 80 |
| SOYBEAN | 0 | 30 | 60 | 70 | 80 | 40 | 60 | 80 | 90 |
| BARNYARD GRASS | 30 | 50 | 60 | 70 | 80 | 30 | 60 | 90 | 100 |
| WILD OATS | 0 | 30 | 50 | 60 | 70 | 30 | 50 | 70 | 90 |
| MORNINGGLORY | 0 | 20 | 30 | 40 | 50 | 30 | 50 | 70 | 100 |
| WHEAT | 20 | 30 | 40 | 60 | 80 | 30 | 50 | 70 | 100 |
| CASSIA | 70 | 80 | 100 | 100 | 100 | 70 | 80 | 90 | 100 |
| JOHNSONGRASS | 30 | 40 | 50 | 60 | 70 | 30 | 60 | 90 | 100 |
| NUTSEDGE | 30 | 50 | 70 | 90 | 100 | 100 | 100 | 100 | 100 |
| CORN | 0 | 20 | 60 | 70 | 80 | 30 | 60 | 80 | 100 |
| WILD BUCKWHEAT | 30 | 40 | 50 | 60 | 70 | 30 | 50 | 70 | 90 |
| BLACK GRASS | 40 | 50 | 60 | 70 | 80 | 50 | 70 | 90 | 100 |
| RAPESEED | 70 | 80 | 90 | 100 | 100 | 90 | 100 | 100 | 100 |
| BARLEY | 0 | 20 | 40 | 60 | 80 | 50 | 70 | 90 | 100 |
| GREEN FOXTAIL | 0 | 30 | 50 | 70 | 100 | 0 | 30 | 60 | 90 |
| CHEAT GRASS | 40 | 50 | 70 | 80 | 90 | 50 | 70 | 90 | 100 |
| BUCKWHEAT | | | | | | | | | |
| VIOLA | 30 | 50 | 70 | 90 | 100 | 0 | 30 | 50 | 80 |
| LAMBSQUARTER | 50 | 60 | 70 | 80 | 90 | 30 | 50 | 70 | 90 |

What is claimed is:

1. A compound of the formula:

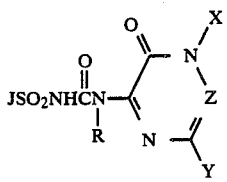

I wherein

R is H or CH₃;

X is H, $C_1$-$C_3$ alkyl, $C_1$-$C_3$ alkoxy, $NH_2$, $NHCH_3$ or $N(CH_3)_2$;

Y is H, $C_1$-$C_3$ alkyl, $C_1$-$C_3$ alkoxy, $C_1$-$C_2$ alkylthio, Cl or Br;

Z is CH, CF, CCl or CBr;

J is

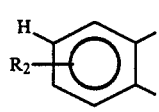 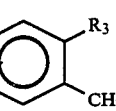 

J-1  J-2  J-3

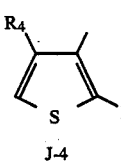 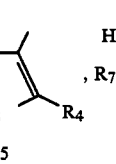 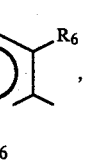

J-4  J-5  J-6

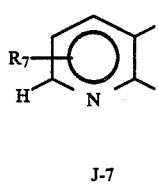 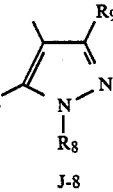 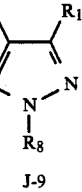

J-7  J-8  J-9

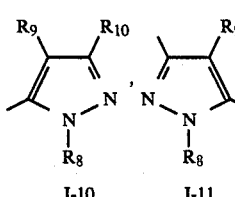 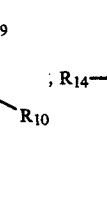 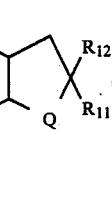

J-10  J-11  J-12

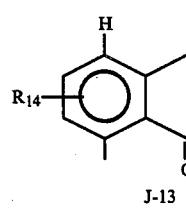 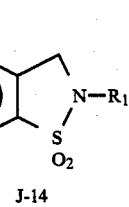

J-13  J-14

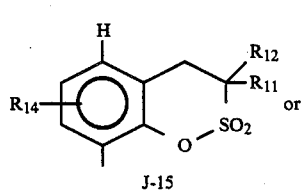

J-15

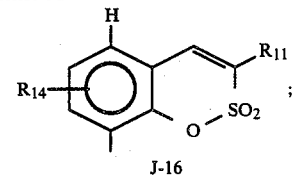

J-16

$R_1$ is F, Cl, Br, $NO_2$, $C_1$-$C_4$ alkyl, $C_1$-$C_4$ haloalkyl, $C_3$-$C_4$ cycloalkyl, $C_2$-$C_4$ haloalkenyl, $C_1$-$C_4$ alkoxy, $C_1$-$C_4$ haloalkoxy, $C_2$-$C_4$ alkoxyalkoxy, $CO_2R_a$, $C(O)NR_bR_c$, $SO_2NR_dR_e$, $S(O)_nR_f$, $C(O)R_g$, $CH_2CN$ or L;

$R_2$ is H, F, Cl, Br, CN, $CH_3$, $OCH_3$, $SCH_3$ or $OCF_2H$;

$R_3$ is Cl, $NO_2$, $CO_2CH_3$, $CO_2CH_2CH_3$, $SO_2N(CH_3)_2$, $SO_2CH_3$, $SO_2CH_2CH_3$, $OCH_3$ or $OCH_2CH_3$;

$R_a$ is $C_1$-$C_3$ alkyl optionally substituted by halogen, $C_1$-$C_2$ alkoxy or CN, allyl or propargyl;

$R_b$ is H, $C_1$-$C_3$ alkyl or $C_1$-$C_2$ alkoxy;

$R_c$ is $C_1$-$C_2$ alkyl;

$R_d$ is H, $C_1$-$C_3$ alkyl, $C_1$-$C_2$ alkoxy, allyl or cyclopropyl;

$R_e$ is H or $C_1$-$C_3$ alkyl;

$R_f$ is $C_1$-$C_3$ alkyl, $C_1$-$C_3$ haloalkyl, allyl or propargyl;

$R_g$ is $C_1$-$C_4$ alkyl, $C_1$-$C_4$ haloalkyl or $C_3$-$C_5$ cycloalkyl optionally substituted by halogen;

n is 0, 1 or 2;

L is

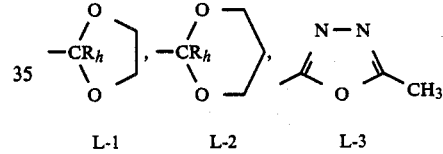

L-1  L-2  L-3

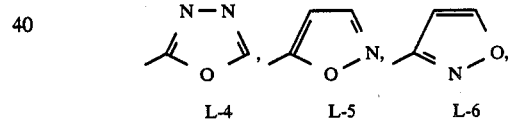

L-4  L-5  L-6

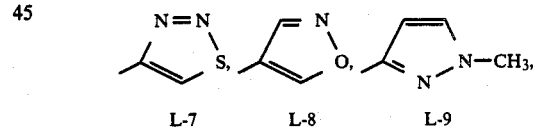

L-7  L-8  L-9

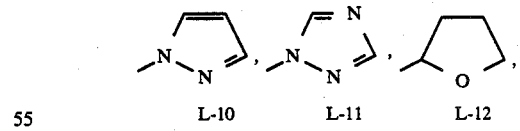

L-10  L-11  L-12

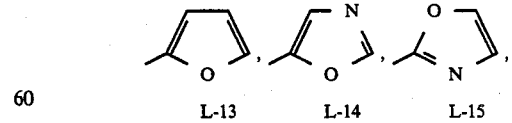

L-13  L-14  L-15

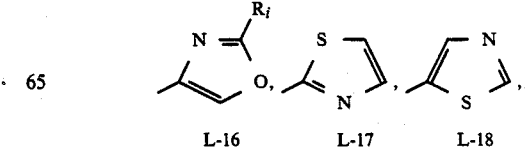

L-16  L-17  L-18

-continued

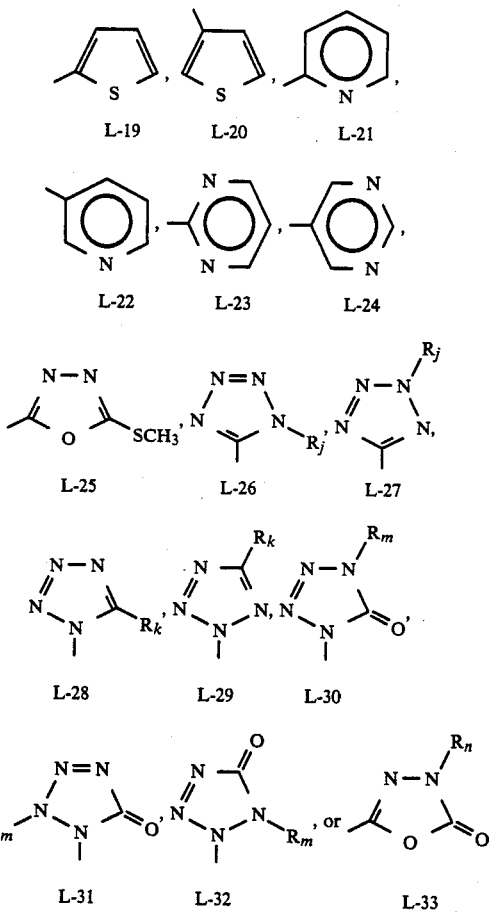

$R_h$ is H or $CH_3$;
$R_i$ is H or $CH_3$;
$R_j$ is H, $CH_3$ or $CH_2CH_3$;
$R_k$ is H, $CH_3$, $CH_2CH_3$, $OCH_3$, $OCH_2CH_3$, $SCH_3$ or $SCH_2CH_3$;
$R_m$ is H, $CH_3$ or $CH_2CH_3$;
$R_n$ is H or $CH_3$;
$R_4$ is $C_1$-$C_3$ alkyl, $C_1$-$C_2$ haloalkyl, $C_1$-$C_2$ alkoxy, $C_2$-$C_4$ haloalkenyl, F, Cl, Br, $NO_2$, $CO_2R_a$, $C(O)NR_bR_c$, $SO_2NR_dR_e$, $S(O)_nR_f$, $C(O)R_g$ or L;
$R_5$ is H, F, Cl, Br or $CH_3$;
$R_6$ is $C_1$-$C_3$ alkyl, $C_1$-$C_2$ alkoxy, $C_2$-$C_4$ haloalkenyl, F, Cl, Br, $CO_2R_a$, $C(O)NR_bR_c$, $SO_2NR_dR_e$, $S(O)_nR_f$, $C(O)R_g$ or L;
$R_7$ is H, F, Cl or $CH_3$;
$R_8$ is H or $C_1$-$C_3$ alkyl;
$R_9$ is $C_1$-$C_3$ alkyl, $C_1$-$C_2$ alkoxy, F, Cl, Br, $NO_2$, $CO_2R_a$, $SO_2NR_dR_e$, $S(O)_nR_f$, $OCF_2H$, $C(O)R_g$, $C_2$-$C_4$ haloalkenyl or L;
$R_{10}$ is H, Cl, F, Br, $C_1$-$C_3$ alkyl or $C_1$-$C_2$ alkoxy;
$R_{11}$ is H or $C_1$-$C_2$ alkyl;
$R_{12}$ is H or $C_1$-$C_2$ alkyl;
$R_{13}$ is H, $C_1$-$C_6$ alkyl, $C_1$-$C_4$ haloalkyl, $C_2$-$C_4$ alkoxyalkyl, $C_3$-$C_5$ cycloalkyl or $C_4$-$C_6$ cycloalkylalkyl;
$R_{14}$ is H, F, Cl, Br, CN, $CH_3$, $OCH_3$, $SCH_3$ or $OCF_2H$; and
Q is O, S, SO, $SO_2$ or C(O);
and their agriculturally suitable salts; provided that X and Y are not simultaneously H.

2. The compounds of claim 1 where
X is $CH_3$, $CH_2CH_3$, $OCH_3$ or $OCH_2CH_3$; and
Y is $CH_3$, $CH_2CH_3$, $OCH_3$, $OCH_2CH_3$, $SCH_3$, $SCH_2CH_3$, Cl or Br.

3. The compounds of claim 2 where
$R_1$ is Cl, $NO_2$, $CH_3$, $CH_2CH_3$, $C_1$-$C_2$ haloalkyl, cyclopropyl, $C_2$-$C_3$ haloalkenyl, $OCH_3$, $OCH_2CH_3$, $C_1$-$C_2$ haloalkoxy, $CO_2R_a$, $C(O)NR_bR_c$, $SO_2NR_dR_e$, $S(O)_nR_f$, $C(O)R_g$, $CH_2CN$ or L;
$R_b$ is H, $CH_3$ or $OCH_3$;
$R_c$ is $CH_3$;
$R_d$ is H, $CH_3$ or $OCH_3$;
$R_e$ is $CH_3$;
$R_f$ is $CH_3$ or $CH_2CH_3$;
$R_g$ is $CH_3$, $CH_2CH_3$ or cyclopropyl;
n is 0 or 2;
$R_4$ is $CH_3$, $CH_2CH_3$, Cl, Br, $NO_2$, $CO_2R_a$, $C(O)NR_bR_c$, $SO_2NR_dR_e$, $S(O)_nR_f$ or $C(O)R_g$;
$R_5$ is H;
$R_6$ is $CH_3$, $CH_2CH_3$, $OCH_3$, Cl, Br, $CO_2R_a$, $C(O)NR_bR_c$, $SO_2NR_dR_e$, $S(O)_nR_f$ or $C(O)R_g$;
$R_7$ is H;
$R_8$ is $CH_3$;
$R_9$ is $CH_3$, $CH_2CH_3$, $OCH_3$, $OCH_2CH_3$, Cl, Br, $NO_2$, $CO_2R_a$, $SO_2NR_dR_e$ or $S(O)_nR_f$;
$R_{10}$ is H, Cl, $CH_3$ or $OCH_3$;
$R_{11}$ is H or $CH_3$;
$R_{12}$ is H; and
$R_{13}$ is H or $C_1$-$C_4$ alkyl.

4. Compounds of claim 3 where J is J-1.
5. Compounds of claim 3 where J is J-2.
6. Compounds of claim 3 where J is J-3.
7. Compounds of claim 3 where J is J-4.
8. Compounds of claim 3 where J is J-5.
9. Compounds of claim 3 where J is J-6.
10. Compounds of claim 3 where J is J-7.
11. Compounds of claim 3 where J is J-8.
12. Compounds of claim 3 where J is J-9.
13. Compounds of claim 3 where J is J-10.
14. Compounds of claim 3 where J is J-11.
15. Compounds of claim 3 where J is J-12.
16. Compounds of claim 3 where J is J-13.
17. Compounds of claim 3 where J is J-14.
18. Compounds of claim 3 where J is J-15.
19. Compounds of claim 3 where J is J-16.
20. The compound of claim 1 which is 2-[[(6-chloro-3,4-dihydro-4-methyl-3-oxo-2-pyrazinylamino)carbonylamino]sulfonyl]benzoic acid, methyl ester.
21. The compound of claim 1 which is 2-chloro-N-[(6-chloro-3,4-dihydro-4-methyl-3-oxo-2-pyrazinyl)aminocarbonyl]benzenesulfonamide.
22. A composition suitable for controlling the growth of undesired vegetation which comprises an effective amount of a compound of claim 1 and at least one of the following: surfactant, solid or liquid diluent.
23. A composition suitable for controlling the growth of undesired vegetation which comprises an effective amount of a compound of claim 2 and at least one of the following: surfactant, solid or liquid diluent.
24. A composition suitable for controlling the growth of undesired vegetation which comprises an effective amount of a compound of claim 3 and at least one of the following: surfactant, solid or liquid diluent.
25. A composition suitable for controlling the growth of undesired vegetation which comprises an effective amount of a compound of claim 4 and at least one of the following: surfactant, solid or liquid diluent.
26. A composition suitable for controlling the growth of undesired vegetation which comprises an effective amount of a compound of claim 5 and at least one of the following: surfactant, solid or liquid diluent.

27. A composition suitable for controlling the growth of undesired vegetation which comprises an effective amount of a compound of claim 6 and at least one of the following: surfactant, solid or liquid diluent.

28. A composition suitable for controlling the growth of undesired vegetation which comprises an effective amount of a compound of claim 7 and at least one of the following: surfactant, solid or liquid diluent.

29. A method for controlling the growth of undesired vegetation which comprises applying to the locus to be protected an effective amount of a compound of claim 1.

30. A method for controlling the growth of undesired vegetation which comprises applying to the locus to be protected an effective amount of a compound of claim 2.

31. A method for controlling the growth of undesired vegetation which comprises applying to the locus to be protected an effective amount of a compound of claim 3.

32. A method for controlling the growth of undesired vegetation which comprises applying to the locus to be protected an effective amount of a compound of claim 4.

33. A method for controlling the growth of undesired vegetation which comprises applying to the locus to be protected an effective amount of a compound of claim 5.

34. A method for controlling the growth of undesired vegetation which comprises applying to the locus to be protected an effective amount of a compound of claim 6.

35. A method for controlling the growth of undesired vegetation which comprises applying to the locus to be protected an effective amount of a compound of claim 7.

* * * * *